United States Patent
De Groot et al.

(10) Patent No.: US 11,911,414 B2
(45) Date of Patent: Feb. 27, 2024

(54) REGULATORY T CELL EPITOPES

(71) Applicant: EpiVax Inc., Providence, RI (US)

(72) Inventors: Anne De Groot, Providence, RI (US); William Martin, Providence, RI (US)

(73) Assignee: EpiVax Inc., Providence, RI (US)

( * ) Notice: Subject to any disclaimer, the term of this patent is extended or adjusted under 35 U.S.C. 154(b) by 302 days.

(21) Appl. No.: 17/214,061

(22) Filed: Mar. 26, 2021

(65) Prior Publication Data

US 2021/0308182 A1 Oct. 7, 2021

Related U.S. Application Data

(60) Provisional application No. 63/077,253, filed on Sep. 11, 2020, provisional application No. 63/000,630, filed on Mar. 27, 2020.

(51) Int. Cl.
*A61K 35/17* (2015.01)
*A61K 35/12* (2015.01)
*C07K 7/08* (2006.01)
*C12N 5/0783* (2010.01)

(52) U.S. Cl.
CPC ............... *A61K 35/17* (2013.01); *C07K 7/08* (2013.01); *C12N 5/0637* (2013.01); *A61K 2035/122* (2013.01)

(58) Field of Classification Search
None
See application file for complete search history.

(56) References Cited

U.S. PATENT DOCUMENTS

2009/0018067 A1  1/2009  De Groot et al.

OTHER PUBLICATIONS

Aguirre, D., Deletion of antibody encoded tolerogenic signals to improve a dendritic cell targeted vaccine delivery platform system, Master of Science Thesis of University of Rhode Island, pp. 1-98, 2014.
Cousens, L. et al., Application of IgG-derived natural Treg epitopes (IgG Tregitopes) to antigen-specific tolerance Induction in a murine model of type I diabetes, Journal of Diabetes Research, vol. 2013, Article ID 621693: 1-17, 2013.
De Groot, A. et al., Therapeutic administration of tregitope-human albumin fusion with insulin peptides to promote antigen-specific adaptive tolerance induction, Scientific Reports, 9(16103): 1-12, 2019.
De Groot, A. et al., Identification of a potent regulatory T cell epitope in factor V that modulates CD4+ and CD8+ memory T cell responses, Clinical Immunology, 224(108661): 1-14, Jan. 4, 2021.
Sordé, L. et al., Tregitopes and impaired antigen presentation: drivers of the immunomodulatory effects of IVIg?, Immunity, Inflammation and Disease, 5(4): 400-4 15, 2017.

*Primary Examiner* — Amy E Juedes
(74) *Attorney, Agent, or Firm* — Weston R. Gould; Dinsmore & Shohl LLP

(57) ABSTRACT

The present is directed to compositions comprising regulatory T cell epitopes, wherein said epitopes comprises a polypeptide comprising at least a portion of SEQ NOS: 1-124 (and/or fragments and variants thereof), and optionally 1 to 12 additional amino acids distributed in any ratio on the N-terminus and/or C-terminus of the polypeptide of SEQ ID NOS: 1-124, as well as methods of producing and using the same.

9 Claims, 23 Drawing Sheets

Specification includes a Sequence Listing.

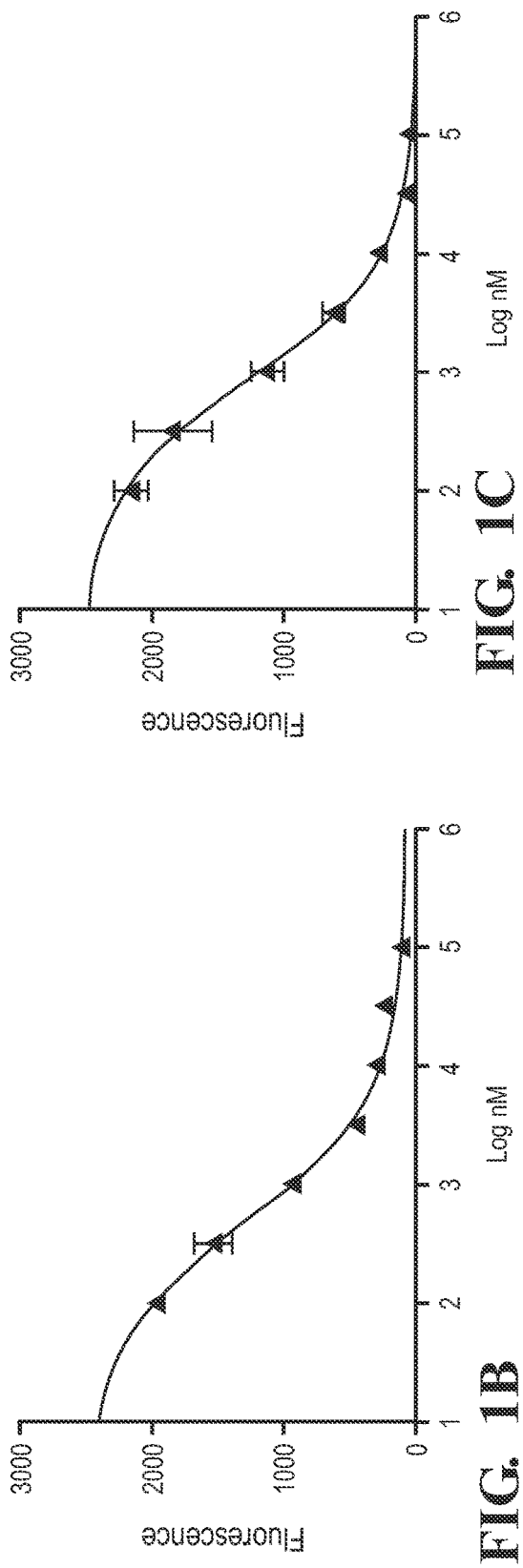

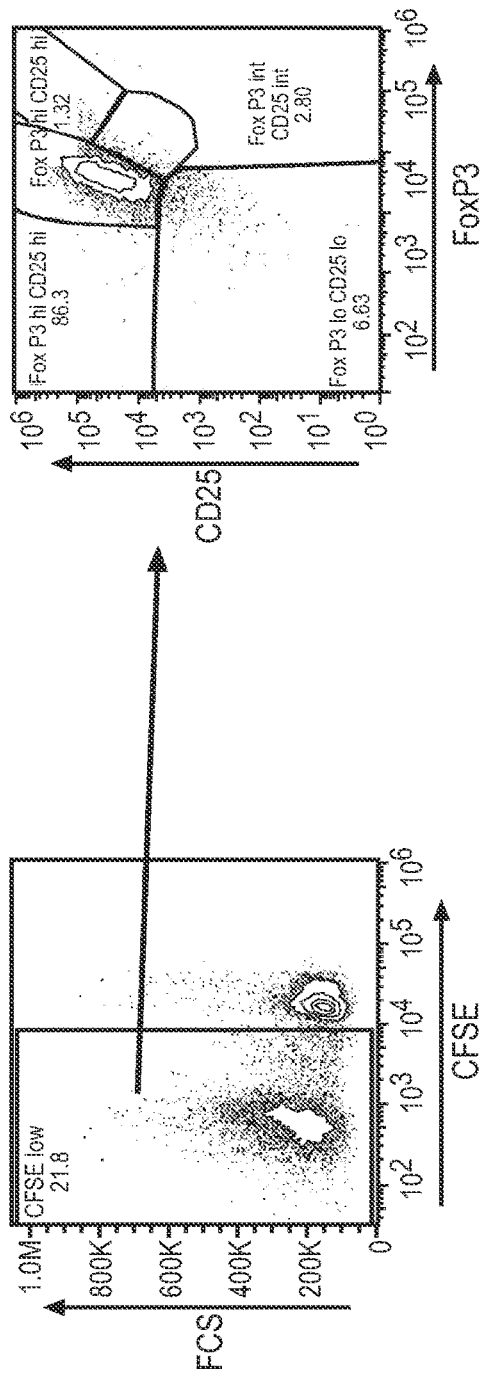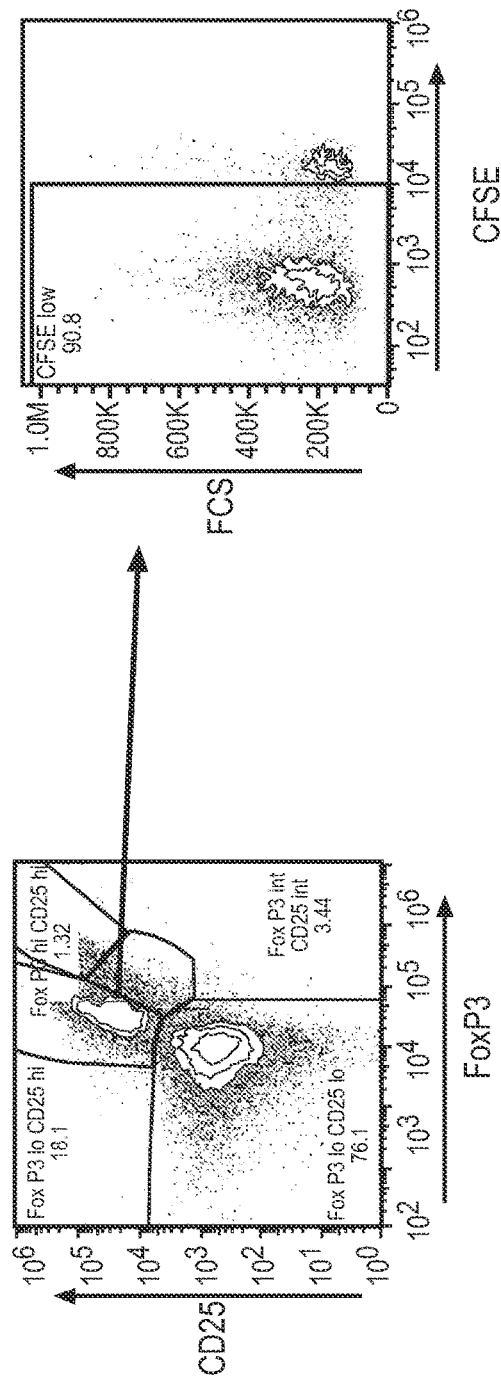
FIG. 2C

FIG. 3A
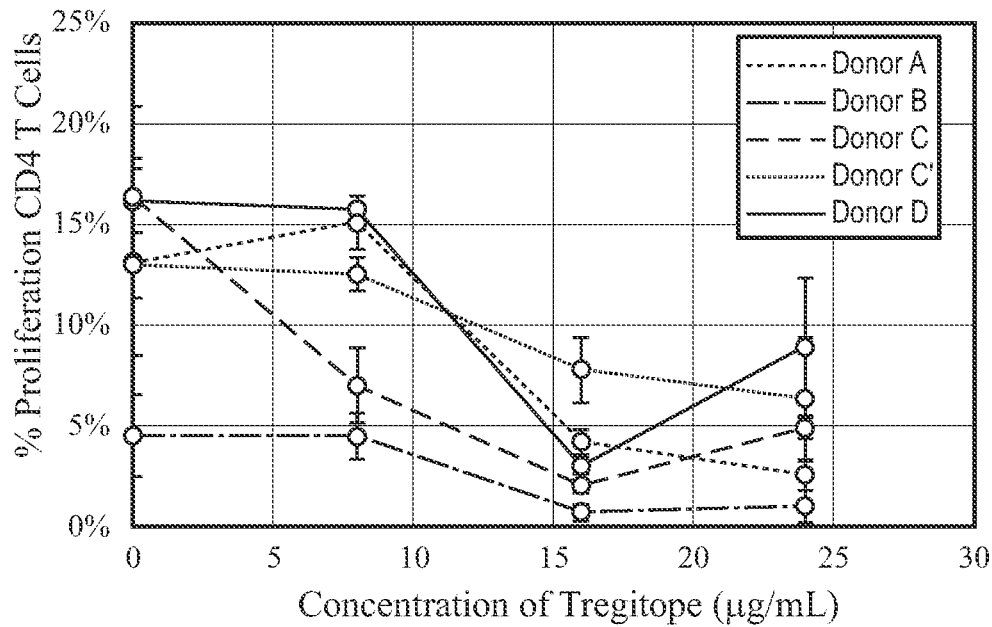
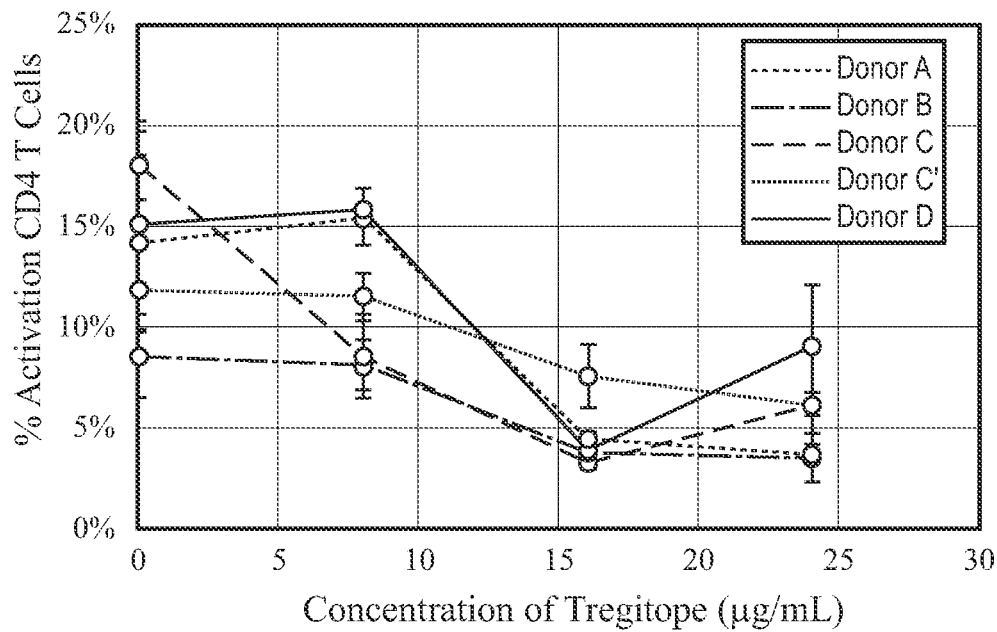
FIG. 3B

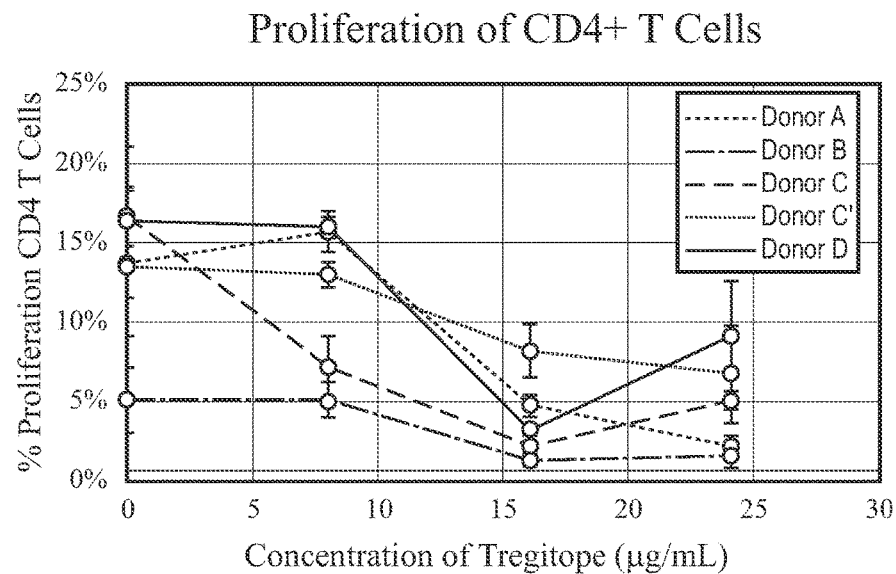
FIG. 5A
FIG. 5B
| Donor | A | B | C | C' | D |
|---|---|---|---|---|---|
| Media Only | 0.60% | 0.63% | 0.21% | 0.45% | 0.23% |
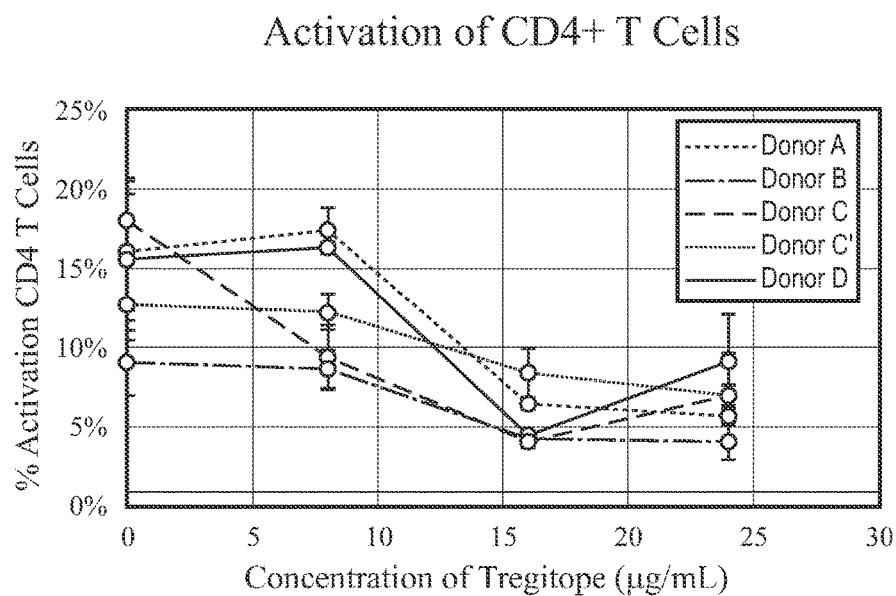
FIG. 5C
FIG. 5D
| Donor | A | B | C | C' | D |
|---|---|---|---|---|---|
| Media Only | 1.92% | 0.47% | 0.75% | 0.75% | 0.49% |

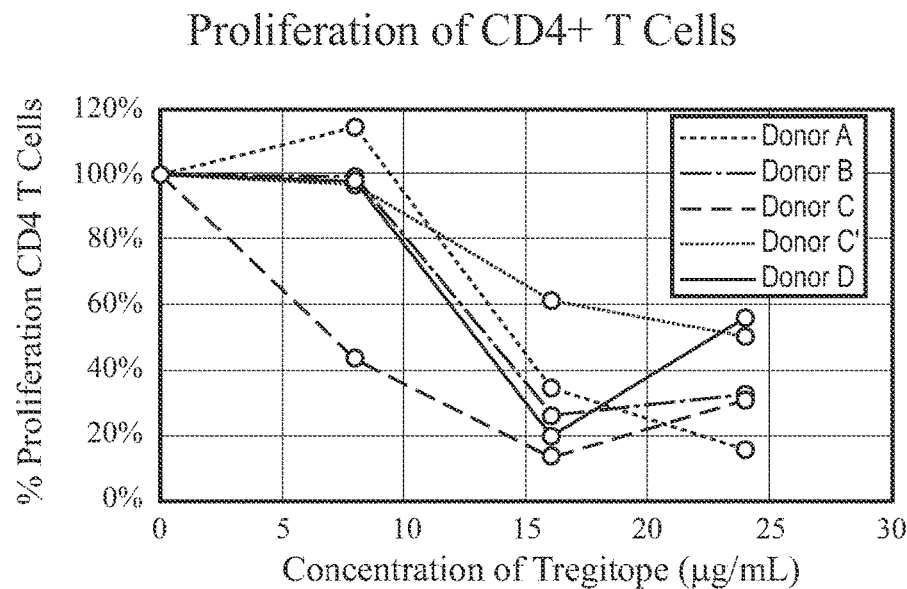
FIG. 6A
FIG. 6B
| Donor | A | B | C | C' | D |
|---|---|---|---|---|---|
| Media Only | 0.60% | 0.63% | 0.21% | 0.45% | 0.23% |
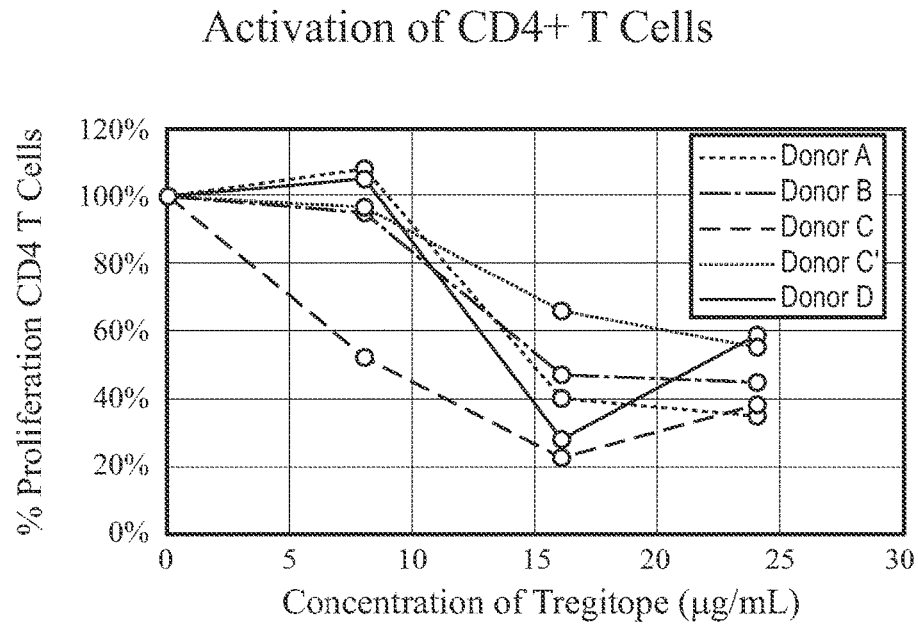
FIG. 6C
FIG. 6D
| Donor | A | B | C | C' | D |
|---|---|---|---|---|---|
| Media Only | 1.92% | 0.47% | 0.75% | 0.75% | 0.49% |

Example EpiBar
Accession: Influenza - Sequence: HA306-318

| Frame Start | AA Sequence | Frame Stop | DRB1*0101 Z Score | DRB1*0301 Z Score | DRB1*0401 Z Score | DRB1*0701 Z Score | DRB1*0801 Z Score | DRB1*1101 Z Score | DRB1*1301 Z Score | DRB1*1501 Z Score | HITS |
|---|---|---|---|---|---|---|---|---|---|---|---|
| 306 | PRYVKQNTL | 314 | 1.34 | 1.40 | | | | | | 1.28 | 1 |
| 307 | RYVKQNTLK | 315 | | | | 2.06 | | | | | |
| 308 | YVKQNTLKL | 316 | 3.33 | 1.97 | 3.15 | 3.27 | 1.96 | 1.99 | 2.37 | 2.36 | 8 |
| 309 | VKQNTLKLA | 317 | | | | | | 1.59 | 1.67 | | 1 |
| 310 | KQNTLKLAT | 318 | | | | | | | | | |

Z score indicates the potential of a 9-mer frame to bind to a given HLA allele; the strength of the score is indicated by the blue shading as shown below:

| Cluster Regions Outlined | Z Scores in Top 1% | Z Scores in Top 5% | Z Scores in Top 10% | Remaining Scores Masked |

Assessments Performed: 40    Deviation from Expectation: 17.62

FIG. 7

EpiMatrix Cluster Detail Report

File: TREGITOPE_OPT Sequence: TREGITOPE_88X Cluster: 88

| Frame Start | Frame Stop | AA Sequence | Hydro-phobicity | DRB1*0101 Z Score | DRB1*0301 Z Score | DRB1*0401 Z Score | DRB1*0701 Z Score | DRB1*0801 Z Score | DRB1*1101 Z Score | DRB1*1301 Z Score | DRB1*1501 Z Score | HITS |
|---|---|---|---|---|---|---|---|---|---|---|---|---|
| 88 | 96 | KTLYLQMNS | -0.1 | -0.38 | -0.44 | -0.2 | -0.61 | 0.78 | 0.5 | -0.05 | 0.53 | 0 |
| 89 | 97 | TLYLQMNSL | 0.08 | 0.73 | 0.04 | 0.28 | 0.98 | 0.28 | 0.58 | -0.51 | 0.34 | 0 |
| 90 | 98 | LYLQMNSLR | -0.01 | 1.92 | 2.33 | 1.89 | 1.08 | 2.02 | 1.57 | 2.91 | 1.9 | 6 |
| 91 | 99 | YLQMNSLRA | -0.26 | 3.3 | 2.01 | 3.41 | 2.9 | 2.23 | 3.43 | 1.97 | 2.82 | 8 |
| 92 | 100 | LQMNSLRAE | -0.5 | 0.03 | 1.72 | 0.08 | 0.03 | 1.89 | 1.52 | 1.24 | 0.33 | 2 |
| 93 | 101 | QMNSLRAED | -1.31 | -0.09 | 0.15 | -0.98 | -0.19 | 0.93 | 0.35 | 0.04 | -0.82 | 0 |
| 94 | 102 | MNSLRAEDT | -1 | 2.01 | 0.53 | 1.62 | 1.66 | 1.39 | 1.52 | 0.29 | 1.42 | 2 |
| 95 | 103 | NSLRAEDTA | -0.22 | -0.93 | -1.69 | -1.57 | -1.3 | -1.33 | -0.87 | -1.12 | -1.51 | 0 |
| 96 | 104 | SLRAEDTAK | -0.23 | -0.53 | 0.16 | 0.74 | -0.56 | -0.06 | -0.86 | 0.14 | 0.57 | 0 |
| 97 | 105 | LRAEDTAKH | -0.28 | 1.17 | 1.1 | 2.25 | 0.09 | 0.89 | 1.46 | 1.08 | -0.31 | 1 |

| Summarized Results | DRB1*0101 | DRB1*0301 | DRB1*0401 | DRB1*0701 | DRB1*0801 | DRB1*1101 | DRB1*1301 | DRB1*1501 | Total |
|---|---|---|---|---|---|---|---|---|---|
| Maximum Single Z Score | 3.3 | 2.33 | 3.41 | 2.9 | 2.23 | 3.43 | 2.91 | 2.82 | -- |
| Sum of Significant Z Scores | 7.23 | 6.06 | 7.55 | 4.55 | 6.14 | 3.43 | 4.88 | 4.71 | 44.55 |
| Count of Significant Z Scores | 3 | 3 | 3 | 2 | 3 | 1 | 2 | 2 | 19 |

| Total Assessments Performed: 80 | Hydrophobicity: -0.89 | EpiMatrix Score: 36.32 | EpiMatrix Score (w/o flanks): 26.05 |
|---|---|---|---|
| Scores Adjusted for Tregitope: | -- | EpiMatrix Score: -2.32 | EpiMatrix Score (w/o flanks): 0.37 |

FIG. 8

EpiMatrix Cluster Detail Report

File: TREGITOPE_OPT_NZ3 Sequence: TREGITOPE_88X Cluster: 88

| Frame Start | AA Sequence | Frame Stop | Hydro-phobicity | DRB1*0101 Z Score | DRB1*0301 Z Score | DRB1*0401 Z Score | DRB1*0701 Z Score | DRB1*0801 Z Score | DRB1*1101 Z Score | DRB1*1301 Z Score | DRB1*1501 Z Score | HITS |
|---|---|---|---|---|---|---|---|---|---|---|---|---|
| 88 | ETLYLQMNS | 96 | -0.09 | -0.57 | -0.84 | -0.38 | -0.79 | 0.58 | 0.32 | -0.44 | 0.15 | 0 |
| 89 | TLYLQMNSL | 97 | 0.08 | 0.73 | 0.04 | 0.28 | 0.98 | 0.28 | 0.58 | -0.51 | 0.34 | 0 |
| 90 | LYLQMNSLR | 98 | -0.01 | 1.92 | 2.33 | 1.89 | 1.08 | 2.02 | 1.57 | 2.91 | 1.90 | 6 |
| 91 | YLQMNSLRA | 99 | -0.26 | 3.3 | 2.01 | 3.41 | 2.9 | 2.23 | 3.43 | 1.97 | 2.82 | 8 |
| 92 | LQMNSLRAE | 100 | -0.50 | 0.03 | 1.72 | 0.08 | 0.03 | 1.89 | 1.52 | 1.24 | 0.33 | 2 |
| 93 | QMNSLRAED | 101 | -1.31 | -0.09 | 0.15 | -0.98 | -0.19 | 0.93 | 0.35 | 0.04 | -0.82 | 0 |
| 94 | MNSLRAEDT | 102 | -1.00 | 2.01 | 0.53 | 1.62 | 1.66 | 1.39 | 1.52 | 0.29 | 1.42 | 2 |
| 95 | NSLRAEDTA | 103 | -0.22 | -0.93 | -1.69 | -1.57 | -1.30 | -1.33 | -0.87 | -1.12 | -1.51 | 0 |
| 96 | SLRAEDTAV | 104 | -0.03 | 0.00 | 0.49 | 0.65 | 0.48 | -0.39 | -0.95 | 0.46 | 1.09 | 0 |
| 97 | LRAEDTAVY | 105 | -0.05 | 1.03 | 1.50 | 1.47 | -0.31 | -0.67 | 0.65 | 1.48 | -0.44 | 0 |

| Summarized Results | DRB1*0101 | DRB1*0301 | DRB1*0401 | DRB1*0701 | DRB1*0801 | DRB1*1101 | DRB1*1301 | DRB1*1501 | Total |
|---|---|---|---|---|---|---|---|---|---|
| Maximum Single Z Score | 3.3 | 2.33 | 3.41 | 2.9 | 2.23 | 3.43 | 2.91 | 2.82 | -- |
| Sum of Significant Z Scores | 7.23 | 6.06 | 7.55 | 4.55 | 6.14 | 3.43 | 4.88 | 4.71 | 42.30 |
| Count of Significant Z Scores | 3.00 | 3.00 | 3.00 | 2.00 | 3.00 | 1.00 | 2.00 | 2.00 | 18.00 |

| Total Assessments Performed: 80 | Hydrophobicity: -0.32 | EpiMatrix Score: 34.07 | EpiMatrix Score (w/o flanks): 26.05 |
|---|---|---|---|
| Scores Adjusted for Tregitope: | -- | EpiMatrix Score: -4.57 | EpiMatrix Score (w/o flanks): 0.37 |

FIG. 9

| Input Sequence | Cluster Address (w/Flanks) | Cluster Sequence | EpiMatrix Cluster Score (w/o Flanks) | Treg-Adj Cluster Score (w/o Flanks) | Number of HUMAN Matches | Janus Homology Score |
|---|---|---|---|---|---|---|
| SEQNO_1 | 1 - 21 | KTLYLQMNSLRAEDTAKHYCA | 34.84 | -6.14 | 89 | 19.60 |
| SEQNO_10 | 1 - 15 | YNSTYRVVSVLTVLH | 27.91 | 3.26 | 38 | 7.24 |
| SEQNO_11 | 1 - 15 | YQSTYRVVSVLTVLH | 28.26 | 3.61 | 36 | 6.59 |
| SEQNO_12 | 1 - 9 | FTLTISSLQ | 18.64 | -0.93 | 33 | 28.75 |
| SEQNO_13 | 1 - 18 | FYPREAKVQWKVDNALQS | 3.38 | -9.27 | 4 | 2.50 |
| SEQNO_14 | 1 - 18 | ETLYLQMNSLRAEDTAVY | 35.38 | -5.60 | 89 | 20.63 |
| SEQNO_15 | 1 - 12 | YLQMNSLRAEDT | 27.94 | -0.04 | 66 | 20.54 |
| SEQNO_2 | 1 - 21 | EEQYQSTYRVVSVLTVLHQDW | 26.18 | 1.52 | 39 | 6.21 |
| SEQNO_3 | 1 - 15 | VQPGGSLRLSCAASG | 16.78 | -6.49 | 45 | 24.40 |
| SEQNO_4 | 1 - 10 | WVRQAPGKGL | 18.14 | -1.85 | 53 | 24.56 |
| SEQNO_5 | 1 - 9 | VRQAPGKGL | 7.64 | -0.93 | 28 | 26.25 |
| SEQNO_6 | 1 - 15 | YLQMNSLRAEDTAVY | 25.19 | -2.82 | 66 | 20.54 |
| SEQNO_7 | 1 - 18 | KTLYLQMNSLRAEDTAKH | 37.62 | -3.35 | 89 | 19.60 |
| SEQNO_8 | 1 - 15 | YLQMNSLRAEDTAKH | 27.44 | -0.57 | 66 | 19.07 |
| SEQNO_9 | 1 - 20 | LQSSGLYSLSSVVTVPSSSL | 35.33 | 8.69 | 50 | 5.35 |

FIG. 11

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_1 | | | | | | | DB Ver. March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| | | 1-21 | KTLYLQMNSLRAEDTAKYHYCA | 27.91 | 89 | 19.60 | | | | | | | | | |
| 16 | | 1 | KTLYLQMNS | | 0 | | -0.38 | -0.44 | -0.20 | -0.61 | 0.78 | 0.49 | 0.50 | -0.05 | 0.53 |
| 17 | | 2 | TLYLQMNSL | | 0 | | 0.73 | 0.04 | 0.28 | 0.98 | 0.28 | 0.52 | 0.58 | -0.51 | 0.34 |
| 18 | | 3 | LYLQMNSLR | | 23 | | 1.92 | 2.33 | 1.89 | 1.08 | 2.02 | 1.41 | 1.57 | 2.91 | 1.90 |
| 19 | | 4 | YLQMNSLRA | | 32 | | 3.30 | 2.01 | 3.41 | 2.90 | 2.23 | 2.34 | 3.43 | 1.97 | 2.82 |
| 20 | | 5 | LQMNSLRAE | | 18 | | 0.03 | 1.72 | 0.08 | 0.03 | 1.89 | 0.33 | 1.52 | 1.24 | 0.33 |
| 21 | | 6 | QMNSLRAED | | 0 | | -0.09 | 0.15 | -0.98 | -0.19 | 0.93 | 0.54 | 0.35 | 0.04 | -0.82 |
| 22 | | 7 | MNSLRAEDT | | 16 | | 2.01 | 0.53 | 1.62 | 1.66 | 1.39 | 0.51 | 1.52 | 0.29 | 1.42 |
| 23 | | 8 | NSLRAEDTA | | 0 | | -0.93 | -1.69 | -1.57 | -1.30 | -1.33 | -1.21 | -0.87 | -1.12 | -1.51 |
| 24 | | 9 | SLRAEDTAK | | 0 | | -0.53 | 0.16 | -0.74 | -0.56 | -0.06 | -0.29 | -0.86 | 0.14 | 0.57 |
| 25 | | 10 | LRAEDTAKH | | 0 | | 1.17 | 1.10 | 2.25 | 0.09 | 0.89 | 1.02 | 1.46 | 1.08 | -0.31 |
| 26 | | 11 | RAEDTAKHY | | 0 | | -0.70 | 0.71 | -0.43 | -1.46 | -1.64 | -0.52 | -1.76 | -0.17 | -1.12 |
| 27 | | 12 | AEDTAKHYC | | 0 | | -1.60 | -2.09 | -2.29 | -1.68 | -1.54 | -1.27 | -1.98 | -1.21 | -1.56 |
| 28 | | 13 | EDTAKHYCA | | 0 | | -0.58 | -0.22 | -0.01 | -0.49 | -0.23 | -0.81 | 0.02 | -0.36 | 0.40 |

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver March 01, 2020 | EpiMatrix Ver. 1.2 with DR9 | | | | | | JMX Hit Threshold: 1.64 | |
| SEQNO_10 | | 1-15 | YNSTYRWSVLTVLH | 27.91 | 38 | 7.24 | 1.90 | 1.42 | 1.22 | 1.38 | 2.26 | 1.73 | 1.41 | 2.20 | 1.41 |
| 87 | | 1 | YNSTYRWS | | 3 | | -0.46 | -0.95 | -0.34 | 0.30 | -0.29 | -0.50 | -1.09 | 0.38 | -0.52 |
| 88 | | 2 | NSTYRWSV | | 0 | | 0.34 | -0.34 | -0.47 | 0.67 | -0.00 | -0.20 | -0.46 | 0.63 | -0.18 |
| 89 | | 3 | STYRWSVL | | 0 | | -1.49 | -0.11 | 1.19 | 1.66 | 0.50 | 1.39 | 0.56 | 0.09 | 1.19 |
| 90 | | 4 | TYRWSVLT | | 2 | | 1.94 | 1.24 | 2.03 | 2.63 | 1.05 | 2.43 | 2.00 | 1.57 | 1.31 |
| 91 | | 5 | YRWSVLTV | | 14 | | -0.32 | 1.09 | -0.79 | 0.21 | -0.64 | 0.79 | -0.82 | 0.74 | 0.74 |
| 92 | | 6 | RWSVLTVL | | 0 | | 1.68 | 1.85 | 2.42 | 1.38 | 2.10 | 1.90 | 1.67 | 2.02 | 1.52 |
| 93 | | 7 | WSVLTVLH | | 19 | | | | | | | | | | |

FIG. 14

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver March 01, 2020 | EpiMatrix Ver. 1.2 with DR9 | | | | | | JMX Hit Threshold: 1.64 | |
| SEQNO_11 | | 1-15 | YQSTYRWSVLTVLH | 28.26 | 36 | 6.59 | 1.98 | 1.50 | 1.30 | 1.47 | 2.35 | 1.82 | 1.50 | 2.28 | 1.49 |
| 94 | | 1 | YQSTYRWS | | 1 | | -0.32 | -1.04 | -0.20 | 0.44 | -0.15 | -0.35 | -0.95 | 0.30 | -0.60 |
| 95 | | 2 | NSTYRWSV | | 0 | | 0.34 | -0.34 | -0.47 | 0.67 | -0.00 | -0.20 | -0.46 | 0.63 | -0.18 |
| 96 | | 3 | STYRWSVL | | 0 | | -1.49 | -0.11 | 1.19 | 1.66 | 0.50 | 1.39 | 0.56 | 0.09 | 1.19 |
| 97 | | 4 | TYRWSVLT | | 2 | | 1.94 | 1.24 | 2.03 | 2.63 | 1.05 | 2.43 | 2.00 | 1.57 | 1.31 |
| 98 | | 5 | YRWSVLTV | | 14 | | -0.32 | 1.09 | -0.79 | 0.21 | -0.64 | 0.79 | -0.82 | 0.74 | 0.74 |
| 99 | | 6 | RWSVLTVL | | 0 | | 1.68 | 1.85 | 2.42 | 1.38 | 2.10 | 1.90 | 1.67 | 2.02 | 1.52 |
| 100 | | 7 | WSVLTVLH | | 19 | | | | | | | | | | |

FIG. 15

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver: March 01, 2020 | EpiMatrix Ver: 1.2 with DR9 | JMX Hit Threshold: 1.64 | | | | | | |
| SEQNO_12 | | 1-9 | FTLTSSLQ | 18.64 | 33 | 28.75 | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 12 | | 1 | FTLTSSLQ | | 33 | | 2.40 | 1.44 | 2.80 | 3.11 | 2.41 | 2.35 | 1.96 | 2.13 | 2.39 |

FIG. 16

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver: March 01, 2020 | EpiMatrix Ver: 1.2 with DR9 | JMX Hit Threshold: 1.64 | | | | | | |
| SEQNO_13 | | 1-18 | FYPREAKVQWKVDNALQS | 3.38 | 4 | 2.50 | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 101 | | 1 | FYPREAKVQ | | 0 | | 1.27 | -0.44 | 0.75 | 1.42 | 1.58 | 0.14 | 1.24 | 0.85 | 0.63 |
| 102 | | 2 | YPREAKVQW | | 0 | | 0.07 | 0.54 | -0.30 | 0.04 | -0.49 | 0.71 | -0.20 | 0.31 | -0.94 |
| 103 | | 3 | PREAKVQWK | | 0 | | -0.20 | 0.08 | 0.37 | -0.18 | 0.03 | -0.23 | -0.43 | -1.13 | -0.61 |
| 104 | | 4 | REAKVQWKV | | 0 | | -0.59 | -0.39 | -1.98 | 0.18 | -1.16 | -0.39 | -0.27 | -0.47 | -0.82 |
| 105 | | 5 | EAKVQWKVD | | 0 | | -1.18 | -2.08 | -1.51 | 0.28 | -0.48 | -0.79 | -1.37 | -1.62 | -0.86 |
| 106 | | 6 | AKVQWKVDN | | 0 | | -0.31 | -0.12 | -0.75 | -1.49 | 0.56 | -0.91 | -0.09 | 0.59 | -0.08 |
| 107 | | 7 | KVQWKVDNA | | 0 | | -0.24 | -0.73 | 0.93 | -0.27 | -1.49 | -0.44 | -0.09 | -0.25 | -1.19 |
| 108 | | 8 | VQWKVDNAL | | 0 | | 0.28 | 1.41 | 0.61 | 1.56 | 1.31 | 0.63 | 0.89 | 1.06 | 1.20 |
| 109 | | 9 | QWKVDNALQ | | 0 | | 0.49 | -0.37 | 1.08 | 0.10 | 0.38 | 0.77 | 1.19 | 0.06 | -0.07 |
| 110 | | 10 | WKVDNALQS | | 4 | | 2.12 | 2.04 | 3.16 | 1.07 | 1.83 | 1.72 | 1.79 | 1.07 | 0.84 |

FIG. 17

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_14 | | 1-18 | ETLYLQMNSLRAEDTAVY | 35.38 | 89 | 20.63 | DB Ver: March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 111 | | 1 | ETLYLQMNS | | 0 | | -0.57 | -0.84 | -0.38 | -0.79 | 0.58 | 0.30 | 0.32 | -0.44 | 0.15 |
| 112 | | 2 | TLYLQMNSL | | 0 | | 0.73 | 0.04 | 0.28 | 0.98 | 0.28 | 0.52 | 0.58 | -0.51 | 0.34 |
| 113 | | 3 | LYLQMNSLR | | 23 | | 1.92 | 2.33 | 1.89 | 1.08 | 2.02 | 1.41 | 1.57 | 2.91 | 1.90 |
| 114 | | 4 | YLQMNSLRA | | 32 | | 3.30 | 2.01 | 3.41 | 2.90 | 2.23 | 2.34 | 3.43 | 1.97 | 2.82 |
| 115 | | 5 | LQMNSLRAE | | 18 | | 0.03 | 1.72 | 0.08 | 0.03 | 1.89 | 0.33 | 1.52 | 1.24 | 0.33 |
| 116 | | 6 | QMNSLRAED | | 0 | | -0.09 | 0.15 | -0.98 | -0.19 | 0.93 | 0.54 | 0.35 | 0.04 | -0.82 |
| 117 | | 7 | MNSLRAEDT | | 16 | | 2.01 | 0.53 | 1.62 | 1.66 | 1.39 | 0.51 | 1.52 | 0.29 | 1.42 |
| 118 | | 8 | NSLRAEDTA | | 0 | | -0.93 | -1.69 | -1.57 | -1.30 | -1.33 | -1.21 | -0.87 | -1.12 | -1.51 |
| 119 | | 9 | SLRAEDTAV | | 0 | | 0.00 | 0.49 | 0.65 | 0.48 | -0.39 | 0.68 | -0.95 | 0.46 | 1.09 |
| 120 | | 10 | LRAEDTAVY | | 0 | | 1.03 | 1.50 | 1.47 | -0.31 | -0.67 | 1.09 | 0.65 | 1.48 | -0.44 |

FIG. 18

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_15 | | 1-18 | YLQMNSLRAEDT | 27.97 | 66 | 20.54 | DB Ver: March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 121 | | 1 | YLQMNSLRA | | 32 | | 3.30 | 2.01 | 3.41 | 2.90 | 2.23 | 2.34 | 3.43 | 1.97 | 2.82 |
| 122 | | 2 | LQMNSLRAE | | 18 | | 0.03 | 1.72 | 0.08 | 0.03 | 1.89 | 0.33 | 1.52 | 1.24 | 0.33 |
| 123 | | 3 | QMNSLRAED | | 0 | | -0.09 | 0.15 | -0.98 | -0.19 | 0.93 | 0.54 | 0.35 | 0.04 | -0.82 |
| 124 | | 4 | MNSLRAEDT | | 16 | | 2.01 | 0.53 | 1.62 | 1.66 | 1.39 | 0.51 | 1.52 | 0.29 | 1.42 |

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver. March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| SEQNO_2 | | 1-21 | EEQYQSTYRVVSVLTVLHQDW | 26.81 | 39 | 6.21 | | | | | | | | | |
| 29 | | 1 | EEQYQSTYR | | 0 | | -0.55 | -0.60 | -0.49 | -0.32 | 0.28 | -0.22 | -1.47 | 0.72 | 0.11 |
| 30 | | 2 | EQYQSTYRV | | 0 | | 1.02 | 0.19 | 1.29 | 0.84 | 0.43 | -0.38 | 0.96 | 0.77 | 0.70 |
| 31 | | 3 | QYQSTYRVV | | 0 | | 0.55 | -0.52 | -0.74 | 0.90 | -1.44 | 1.01 | -0.09 | -1.30 | -0.41 |
| 32 | | 4 | YQSTYRVVS | | 1 | | 1.98 | 1.50 | 1.30 | 1.47 | 2.35 | 1.82 | 1.50 | 2.28 | 1.49 |
| 33 | | 5 | QSTYRVVSV | | 0 | | -0.32 | -1.04 | -0.20 | 0.44 | -0.15 | -0.35 | -0.95 | 0.30 | -0.60 |
| 34 | | 6 | STYRVVSVL | | 0 | | 0.34 | -0.34 | -0.47 | 0.67 | -0.00 | -0.20 | -0.46 | 0.63 | -0.29 |
| 35 | | 7 | TYRVVSVLT | | 2 | | 1.49 | -0.11 | 1.19 | 1.66 | 0.50 | 1.39 | 0.56 | 0.09 | 1.19 |
| 36 | | 8 | YRVVSVLTV | | 14 | | 1.94 | 1.24 | 2.03 | 2.63 | 1.05 | 2.43 | 2.00 | 1.57 | 1.31 |
| 37 | | 9 | RVVSVLTVL | | 0 | | -0.32 | 1.09 | -0.79 | 0.21 | -0.64 | 0.79 | -0.82 | 0.74 | 0.74 |
| 38 | | 10 | VVSVLTVLH | | 19 | | 1.68 | 1.85 | 2.42 | 1.38 | 2.10 | 1.90 | 1.67 | 2.02 | 1.52 |
| 39 | | 11 | VSVLTVLHQ | | 3 | | 1.01 | 0.50 | 1.82 | 1.04 | 1.10 | 0.40 | 1.66 | 0.86 | 0.54 |
| 40 | | 12 | SVLTVLHQD | | 0 | | -0.93 | -0.69 | -1.07 | -0.14 | 0.26 | -0.38 | -1.18 | 0.17 | -0.52 |
| 41 | | 13 | VLTVLHQDW | | 0 | | -0.06 | 0.81 | -0.31 | 1.18 | -0.07 | 0.57 | 0.15 | -0.20 | 1.05 |

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver. March 01, 2020 | EpiMatrix Ver. 1.2 with DR9 | JMX Hit Threshold: 1.64 | | | | | | |
| SEQNO_3 | | 1-15 | VQPGGSLRLSCAASG | 16.78 | 45 | 24.40 | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 42 | | 1 | VQPGGSLRL | | 15 | | 1.49 | 1.56 | 1.45 | 1.88 | 0.45 | 0.44 | 0.82 | 1.23 | 2.24 |
| 43 | | 2 | QPGGSLRLS | | 0 | | -1.18 | -0.51 | -0.92 | -1.74 | -0.87 | -1.19 | 0.08 | -1.41 | -0.77 |
| 44 | | 3 | PGGSLRLSC | | 0 | | -0.10 | -0.09 | -1.01 | 0.10 | -0.37 | 0.08 | 0.09 | -0.27 | 0.14 |
| 45 | | 4 | GGSLRLSCA | | 0 | | -0.30 | -0.07 | -0.21 | -0.49 | 0.03 | -1.51 | 0.49 | 0.06 | 0.32 |
| 46 | | 5 | GSLRLSCAA | | 0 | | 0.39 | -1.42 | -0.77 | 0.57 | -0.72 | -0.56 | 0.19 | -0.45 | 0.05 |
| 47 | | 6 | SLRLSCAAS | | 0 | | 0.58 | 0.34 | 1.63 | -0.45 | 0.80 | 0.69 | 1.35 | 0.78 | 0.09 |
| 48 | | 7 | LRLSCAASG | | 30 | | 2.44 | 2.45 | 2.40 | 1.32 | 2.15 | 3.06 | 2.51 | 2.29 | 1.84 |

FIG. 21

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver. March 01, 2020 | EpiMatrix Ver. 1.2 with DR9 | JMX Hit Threshold: 1.64 | | | | | | |
| SEQNO_4 | | 1-10 | WVRQAPGKGL | 18.14 | 53 | 24.56 | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 49 | | 1 | WVRQAPGKG | | 25 | | 2.40 | 1.37 | 2.07 | 1.38 | 2.73 | 1.79 | 2.45 | 0.98 | 1.35 |
| 50 | | 2 | VRQAPGKGL | | 28 | | 2.09 | 1.08 | 1.16 | 2.22 | 0.92 | 2.47 | 0.57 | 1.26 | 1.78 |

FIG. 22

| Protein ID [+]Show Matches | Protein Description | Start Position | Sequence | Cluster Score | Number of HUMAN Matches* | Janus HMLGY Score*** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver. March 01, 2020 | EpiMatrix Ver. 1.2 with DR9 | | | | | | JMX Hit Threshold: 1.64 | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| SEQNO_5 | | 1-9 | VRQAPGKGL | 7.64 | 28 | 26.25 | 2.09 | 1.08 | 1.16 | 2.22 | 0.92 | 2.47 | 0.57 | 1.26 | 1.78 |
| 50 | | 1 | VRQAPGKGL | | | | | | | | | | | | |

FIG. 23

| Protein ID [+]Show Matches | Protein Description | Start Position | Sequence | Cluster Score | Number of HUMAN Matches* | Janus HMLGY Score*** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| | | | | | | | DB Ver. March 01, 2020 | EpiMatrix Ver. 1.2 with DR9 | | | | | | JMX Hit Threshold: 1.64 | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| SEQNO_6 | | 1-15 | YLQMNSLRAEDTAVY | 25.19 | 66 | 20.54 | 3.30 | 2.01 | 3.41 | 2.90 | 2.23 | 2.34 | 3.43 | 1.97 | 2.82 |
| 51 | | 1 | YLQMNSLRA | | 32 | | 0.03 | 1.72 | 0.08 | 0.03 | 1.89 | 0.33 | 1.52 | 1.24 | 0.33 |
| 52 | | 2 | LQMNSLRAE | | 18 | | -0.09 | 0.15 | -0.98 | -0.19 | 0.93 | 0.54 | 0.35 | 0.04 | -0.82 |
| 53 | | 3 | QMNSLRAED | | 0 | | 2.01 | 0.53 | 1.62 | 1.66 | 1.39 | 0.51 | 1.52 | 0.29 | 1.42 |
| 54 | | 4 | MNSLRAEDT | | 16 | | -0.93 | -1.69 | -1.57 | -1.30 | -1.33 | -1.21 | -0.87 | -1.12 | -1.51 |
| 55 | | 5 | NSLRAEDTA | | 0 | | 0.00 | 0.49 | 0.65 | 0.48 | -0.39 | 0.68 | -0.95 | 0.46 | 1.09 |
| 56 | | 6 | SLRAEDTAV | | 0 | | 1.03 | 1.50 | 1.47 | -0.31 | -0.67 | 1.09 | 0.65 | 1.48 | -0.44 |
| 57 | | 7 | LRAEDTAVY | | 0 | | | | | | | | | | |

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_7 | | 1-18 | KTLYLQMNSLRAEDTAKH | 37.62 | 89 | 19.60 | | | | | | | | | |
| | | | | | | | DB Ver. March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 58 | | 1 | KTLYLQMNS | | 0 | | -0.38 | -0.44 | -0.20 | -0.61 | 0.78 | 0.49 | 0.50 | -0.05 | 0.53 |
| 59 | | 2 | TLYLQMNSL | | 0 | | 0.73 | 0.04 | 0.28 | 0.98 | 0.28 | 0.52 | 0.58 | -0.51 | 0.34 |
| 60 | | 3 | LYLQMNSLR | | 23 | | 1.92 | 2.33 | 1.89 | 1.08 | 2.02 | 1.41 | 1.57 | 2.91 | 1.90 |
| 61 | | 4 | YLQMNSLRA | | 32 | | 3.30 | 2.01 | 3.41 | 2.90 | 2.23 | 2.34 | 3.43 | 1.97 | 2.82 |
| 62 | | 5 | LQMNSLRAE | | 18 | | 0.03 | 1.72 | 0.08 | 0.03 | 1.89 | 0.33 | 1.52 | 1.24 | 0.33 |
| 63 | | 6 | QMNSLRAED | | 0 | | -0.09 | 0.15 | -0.98 | -0.19 | 0.93 | 0.54 | 0.35 | 0.04 | -0.82 |
| 64 | | 7 | MNSLRAEDT | | 16 | | -2.01 | 0.53 | -1.62 | -1.66 | 1.39 | 0.51 | 1.52 | 0.29 | 1.42 |
| 65 | | 8 | NSLRAEDTA | | 0 | | -0.93 | -1.69 | -1.57 | -1.30 | -1.33 | -1.21 | -0.87 | -1.12 | -1.51 |
| 66 | | 9 | SLRAEDTAK | | 0 | | -0.53 | 0.16 | 0.74 | -0.56 | -0.06 | -0.29 | -0.86 | 0.14 | 0.57 |
| 67 | | 10 | LRAEDTAKH | | 0 | | 1.17 | 1.10 | 2.25 | 0.09 | 0.89 | 1.02 | 1.46 | 1.08 | -0.31 |

FIG. 24

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_8 | | 1-15 | YLQMNSLRAEDTAKH | 27.44 | 66 | 19.07 | DB Ver. March 01, 2020 | EpiMatrix Ver. 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 68 | | 1 | YLQMNSLRA | | 32 | | 3.30 | 2.01 | 3.41 | 2.90 | 2.23 | 2.34 | 3.43 | 1.97 | 2.82 |
| 69 | | 2 | LQMNSLRAE | | 18 | | 0.03 | 1.72 | 0.08 | 0.03 | 1.89 | 0.33 | 1.52 | 1.24 | 0.33 |
| 70 | | 3 | QMNSLRAED | | 0 | | -0.09 | 0.15 | -0.98 | -0.19 | 0.93 | 0.54 | 0.35 | 0.04 | -0.82 |
| 71 | | 4 | MNSLRAEDT | | 16 | | 2.01 | 0.53 | 1.62 | 1.66 | 1.39 | 0.51 | 1.52 | 0.29 | 1.42 |
| 72 | | 5 | NSLRAEDTA | | 0 | | -0.93 | -1.69 | -1.57 | -1.30 | -1.33 | -1.21 | -0.87 | -1.12 | -1.51 |
| 73 | | 6 | SLRAEDTAK | | 0 | | -0.53 | 0.16 | 0.74 | -0.56 | -0.06 | 0.29 | -0.86 | 0.14 | 0.57 |
| 74 | | 7 | SLRAEDTAKH | | 0 | | 1.17 | 1.10 | 2.25 | 0.09 | 0.89 | 1.02 | 1.46 | 1.08 | -0.31 |

FIG. 25

| Protein ID [+]Show Matches | Protein Description | Start Position | Sequence | Cluster Score | Number of HUMAN Matches* | Janus HMLGY Score** | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
|---|---|---|---|---|---|---|---|---|---|---|---|---|---|---|---|
| SEQNO_9 | | 1-20 | LQSSGLYSLSSVVTVPSSSL | 35.33 | 50 | 5.35 | DB Ver: March 01, 2020 | EpiMatrix Ver 1.2 with DR9 | JMX Hit Threshold: 1.64 | | | | | | |
| | | | | | | | DRB1 *0101 | DRB1 *0301 | DRB1 *0401 | DRB1 *0701 | DRB1 *0801 | DRB1 *0901 | DRB1 *1101 | DRB1 *1301 | DRB1 *1501 |
| 75 | | 1 | LQSSGLYSL | | 7 | | 1.05 | 2.07 | 0.75 | 1.81 | 1.15 | 1.85 | 1.63 | 1.52 | 2.14 |
| 76 | | 2 | QSSGLYSLS | | 0 | | 0.51 | -0.13 | 0.13 | -0.13 | -0.55 | 0.13 | -0.24 | -0.67 | 0.32 |
| 77 | | 3 | SSGLYSLSS | | 7 | | 1.34 | 0.63 | 1.66 | 0.74 | 0.83 | 0.53 | 1.44 | 1.00 | 1.57 |
| 78 | | 4 | SGLYSLSSV | | 0 | | -1.20 | -0.47 | -1.19 | -0.08 | -0.16 | 0.20 | -0.51 | 0.76 | 0.80 |
| 79 | | 5 | GLYSLSSVV | | 8 | | 0.94 | 0.80 | 0.64 | 1.80 | -0.48 | 1.62 | 0.21 | 0.36 | 0.91 |
| 80 | | 6 | LYSLSSVVT | | 4 | | 2.41 | 0.67 | 2.03 | 2.08 | 1.58 | 1.60 | 1.32 | 0.88 | 2.05 |
| 81 | | 7 | YSLSSVVTV | | 9 | | 1.95 | 1.66 | 1.78 | 2.46 | 0.81 | 2.56 | 1.02 | 1.29 | 0.56 |
| 82 | | 8 | SLSSVVTVP | | 0 | | -0.12 | 0.44 | 0.42 | 0.31 | -0.55 | 1.46 | -0.59 | 0.10 | -0.86 |
| 83 | | 9 | LSSVVTVPS | | 8 | | 1.80 | 1.74 | 2.23 | 1.15 | 1.36 | 1.54 | 1.48 | 1.91 | 1.57 |
| 84 | | 10 | SSVVTVPSS | | 0 | | 0.03 | -0.02 | 0.39 | -0.71 | -0.04 | -0.23 | 0.67 | 0.29 | -0.13 |
| 85 | | 11 | SVVTVPSSS | | 0 | | 0.67 | 0.19 | 0.68 | 0.55 | 0.38 | 0.80 | 0.03 | 0.90 | 0.68 |
| 86 | | 12 | VVTVPSSSL | | 7 | | 1.77 | 1.46 | 1.22 | 2.44 | 0.69 | 2.11 | 1.02 | 1.55 | 2.18 |

FIG. 26

SEQUENCE LISTING

```
<160> NUMBER OF SEQ ID NOS: 138

<210> SEQ ID NO 1
<211> LENGTH: 21
<212> TYPE: PRT
<213> ORGANISM: Homo sapiens

<400> SEQUENCE: 1

Lys Thr Leu Tyr Leu Gln Met Asn Ser Leu Arg Ala Glu Asp Thr Ala
1               5                   10                  15

Lys His Tyr Cys Ala
            20

<210> SEQ ID NO 2
<211> LENGTH: 21
<212> TYPE: PRT
<213> ORGANISM: Homo sapiens

<400> SEQUENCE: 2

Glu Glu Gln Tyr Gln Ser Thr Tyr Arg Val Val Ser Val Leu Thr Val
1               5                   10                  15

Leu His Gln Asp Trp
            20

<210> SEQ ID NO 3
<211> LENGTH: 15
<212> TYPE: PRT
<213> ORGANISM: Homo sapiens

<400> SEQUENCE: 3

Val Gln Pro Gly Gly Ser Leu Arg Leu Ser Cys Ala Ala Ser Gly
1               5                   10                  15

<210> SEQ ID NO 4
<211> LENGTH: 10
<212> TYPE: PRT
<213> ORGANISM: Homo sapiens

<400> SEQUENCE: 4

Trp Val Arg Gln Ala Pro Gly Lys Gly Leu
1               5                   10

<210> SEQ ID NO 5
<211> LENGTH: 9
<212> TYPE: PRT
<213> ORGANISM: Homo sapiens

<400> SEQUENCE: 5

Val Arg Gln Ala Pro Gly Lys Gly Leu
1               5
```

```
<210> SEQ ID NO 6
<211> LENGTH: 15
<212> TYPE: PRT
<213> ORGANISM: Homo sapiens

<400> SEQUENCE: 6

Tyr Leu Gln Met Asn Ser Leu Arg Ala Glu Asp Thr Ala Val Tyr
1               5                   10                  15

<210> SEQ ID NO 7
<211> LENGTH: 18
<212> TYPE: PRT
<213> ORGANISM: Homo sapiens

<400> SEQUENCE: 7

Lys Thr Leu Tyr Leu Gln Met Asn Ser Leu Arg Ala Glu Asp Thr Ala
1               5                   10                  15

Lys His

<210> SEQ ID NO 8
<211> LENGTH: 15
<212> TYPE: PRT
<213> ORGANISM: Homo sapiens

<400> SEQUENCE: 8

Tyr Leu Gln Met Asn Ser Leu Arg Ala Glu Asp Thr Ala Lys His
1               5                   10                  15

<210> SEQ ID NO 9
<211> LENGTH: 20
<212> TYPE: PRT
<213> ORGANISM: Homo sapiens

<400> SEQUENCE: 9

Leu Gln Ser Ser Gly Leu Tyr Ser Leu Ser Ser Val Val Thr Val Pro
1               5                   10                  15

Ser Ser Ser Leu
            20

<210> SEQ ID NO 10
<211> LENGTH: 15
<212> TYPE: PRT
<213> ORGANISM: Homo sapiens

<400> SEQUENCE: 10

Tyr Asn Ser Thr Tyr Arg Val Val Ser Val Leu Thr Val Leu His
1               5                   10                  15

<210> SEQ ID NO 11
<211> LENGTH: 15
<212> TYPE: PRT
<213> ORGANISM: Homo sapiens

<400> SEQUENCE: 11

Tyr Gln Ser Thr Tyr Arg Val Val Ser Val Leu Thr Val Leu His
1               5                   10                  15

<210> SEQ ID NO 12
<211> LENGTH: 9
<212> TYPE: PRT
<213> ORGANISM: Homo sapiens

<400> SEQUENCE: 12

Phe Thr Leu Thr Ile Ser Ser Leu Gln
```

```
1               5

<210> SEQ ID NO 13
<211> LENGTH: 18
<212> TYPE: PRT
<213> ORGANISM: Homo sapiens

<400> SEQUENCE: 13

Phe Tyr Pro Arg Glu Ala Lys Val Gln Trp Lys Val Asp Asn Ala Leu
1               5                   10                  15

Gln Ser

<210> SEQ ID NO 14
<211> LENGTH: 18
<212> TYPE: PRT
<213> ORGANISM: Homo sapiens

<400> SEQUENCE: 14

Glu Thr Leu Tyr Leu Gln Met Asn Ser Leu Arg Ala Glu Asp Thr Ala
1               5                   10                  15

Val Tyr

<210> SEQ ID NO 15
<211> LENGTH: 12
<212> TYPE: PRT
<213> ORGANISM: Homo sapiens

<400> SEQUENCE: 15

Tyr Leu Gln Met Asn Ser Leu Arg Ala Glu Asp Thr
1               5                   10

<210> SEQ ID NO 16
<211> LENGTH: 9
<212> TYPE: PRT
<213> ORGANISM: Homo sapiens

<400> SEQUENCE: 16

Lys Thr Leu Tyr Leu Gln Met Asn Ser
1               5

<210> SEQ ID NO 17
<211> LENGTH: 9
<212> TYPE: PRT
<213> ORGANISM: Homo sapiens

<400> SEQUENCE: 17

Thr Leu Tyr Leu Gln Met Asn Ser Leu
1               5

<210> SEQ ID NO 18
<211> LENGTH: 9
<212> TYPE: PRT
<213> ORGANISM: Homo sapiens

<400> SEQUENCE: 18

Leu Tyr Leu Gln Met Asn Ser Leu Arg
1               5

<210> SEQ ID NO 19
<211> LENGTH: 9
<212> TYPE: PRT
<213> ORGANISM: Homo sapiens

<400> SEQUENCE: 19
```

```
Tyr Leu Gln Met Asn Ser Leu Arg Ala
1               5

<210> SEQ ID NO 20
<211> LENGTH: 9
<212> TYPE: PRT
<213> ORGANISM: Homo sapiens

<400> SEQUENCE: 20

Leu Gln Met Asn Ser Leu Arg Ala Glu
1               5

<210> SEQ ID NO 21
<211> LENGTH: 9
<212> TYPE: PRT
<213> ORGANISM: Homo sapiens

<400> SEQUENCE: 21

Gln Met Asn Ser Leu Arg Ala Glu Asp
1               5

<210> SEQ ID NO 22
<211> LENGTH: 9
<212> TYPE: PRT
<213> ORGANISM: Homo sapiens

<400> SEQUENCE: 22

Met Asn Ser Leu Arg Ala Glu Asp Thr
1               5

<210> SEQ ID NO 23
<211> LENGTH: 9
<212> TYPE: PRT
<213> ORGANISM: Homo sapiens

<400> SEQUENCE: 23

Asn Ser Leu Arg Ala Glu Asp Thr Ala
1               5

<210> SEQ ID NO 24
<211> LENGTH: 9
<212> TYPE: PRT
<213> ORGANISM: Homo sapiens

<400> SEQUENCE: 24

Ser Leu Arg Ala Glu Asp Thr Ala Lys
1               5

<210> SEQ ID NO 25
<211> LENGTH: 9
<212> TYPE: PRT
<213> ORGANISM: Homo sapiens

<400> SEQUENCE: 25

Leu Arg Ala Glu Asp Thr Ala Lys His
1               5

<210> SEQ ID NO 26
<211> LENGTH: 9
<212> TYPE: PRT
<213> ORGANISM: Homo sapiens

<400> SEQUENCE: 26

Arg Ala Glu Asp Thr Ala Lys His Tyr
```

```
<210> SEQ ID NO 27
<211> LENGTH: 9
<212> TYPE: PRT
<213> ORGANISM: Homo sapiens

<400> SEQUENCE: 27

Ala Glu Asp Thr Ala Lys His Tyr Cys
1               5

<210> SEQ ID NO 28
<211> LENGTH: 9
<212> TYPE: PRT
<213> ORGANISM: Homo sapiens

<400> SEQUENCE: 28

Glu Asp Thr Ala Lys His Tyr Cys Ala
1               5

<210> SEQ ID NO 29
<211> LENGTH: 9
<212> TYPE: PRT
<213> ORGANISM: Homo sapiens

<400> SEQUENCE: 29

Glu Glu Gln Tyr Gln Ser Thr Tyr Arg
1               5

<210> SEQ ID NO 30
<211> LENGTH: 9
<212> TYPE: PRT
<213> ORGANISM: Homo sapiens

<400> SEQUENCE: 30

Glu Gln Tyr Gln Ser Thr Tyr Arg Val
1               5

<210> SEQ ID NO 31
<211> LENGTH: 9
<212> TYPE: PRT
<213> ORGANISM: Homo sapiens

<400> SEQUENCE: 31

Gln Tyr Gln Ser Thr Tyr Arg Val Val
1               5

<210> SEQ ID NO 32
<211> LENGTH: 9
<212> TYPE: PRT
<213> ORGANISM: Homo sapiens

<400> SEQUENCE: 32

Tyr Gln Ser Thr Tyr Arg Val Val Ser
1               5

<210> SEQ ID NO 33
<211> LENGTH: 9
<212> TYPE: PRT
<213> ORGANISM: Homo sapiens

<400> SEQUENCE: 33

Gln Ser Thr Tyr Arg Val Val Ser Val
1               5
```

```
<210> SEQ ID NO 34
<211> LENGTH: 9
<212> TYPE: PRT
<213> ORGANISM: Homo sapiens

<400> SEQUENCE: 34

Ser Thr Tyr Arg Val Val Ser Val Leu
1               5

<210> SEQ ID NO 35
<211> LENGTH: 9
<212> TYPE: PRT
<213> ORGANISM: Homo sapiens

<400> SEQUENCE: 35

Thr Tyr Arg Val Val Ser Val Leu Thr
1               5

<210> SEQ ID NO 36
<211> LENGTH: 9
<212> TYPE: PRT
<213> ORGANISM: Homo sapiens

<400> SEQUENCE: 36

Tyr Arg Val Val Ser Val Leu Thr Val
1               5

<210> SEQ ID NO 37
<211> LENGTH: 9
<212> TYPE: PRT
<213> ORGANISM: Homo sapiens

<400> SEQUENCE: 37

Arg Val Val Ser Val Leu Thr Val Leu
1               5

<210> SEQ ID NO 38
<211> LENGTH: 9
<212> TYPE: PRT
<213> ORGANISM: Homo sapiens

<400> SEQUENCE: 38

Val Val Ser Val Leu Thr Val Leu His
1               5

<210> SEQ ID NO 39
<211> LENGTH: 9
<212> TYPE: PRT
<213> ORGANISM: Homo sapiens

<400> SEQUENCE: 39

Val Ser Val Leu Thr Val Leu His Gln
1               5

<210> SEQ ID NO 40
<211> LENGTH: 9
<212> TYPE: PRT
<213> ORGANISM: Homo sapiens

<400> SEQUENCE: 40

Ser Val Leu Thr Val Leu His Gln Asp
1               5

<210> SEQ ID NO 41
```

```
<211> LENGTH: 9
<212> TYPE: PRT
<213> ORGANISM: Homo sapiens

<400> SEQUENCE: 41

Val Leu Thr Val Leu His Gln Asp Trp
1               5

<210> SEQ ID NO 42
<211> LENGTH: 9
<212> TYPE: PRT
<213> ORGANISM: Homo sapiens

<400> SEQUENCE: 42

Val Gln Pro Gly Gly Ser Leu Arg Leu
1               5

<210> SEQ ID NO 43
<211> LENGTH: 9
<212> TYPE: PRT
<213> ORGANISM: Homo sapiens

<400> SEQUENCE: 43

Gln Pro Gly Gly Ser Leu Arg Leu Ser
1               5

<210> SEQ ID NO 44
<211> LENGTH: 9
<212> TYPE: PRT
<213> ORGANISM: Homo sapiens

<400> SEQUENCE: 44

Pro Gly Gly Ser Leu Arg Leu Ser Cys
1               5

<210> SEQ ID NO 45
<211> LENGTH: 9
<212> TYPE: PRT
<213> ORGANISM: Homo sapiens

<400> SEQUENCE: 45

Gly Gly Ser Leu Arg Leu Ser Cys Ala
1               5

<210> SEQ ID NO 46
<211> LENGTH: 9
<212> TYPE: PRT
<213> ORGANISM: Homo sapiens

<400> SEQUENCE: 46

Gly Ser Leu Arg Leu Ser Cys Ala Ala
1               5

<210> SEQ ID NO 47
<211> LENGTH: 9
<212> TYPE: PRT
<213> ORGANISM: Homo sapiens

<400> SEQUENCE: 47

Ser Leu Arg Leu Ser Cys Ala Ala Ser
1               5

<210> SEQ ID NO 48
<211> LENGTH: 9
<212> TYPE: PRT
```

<213> ORGANISM: Homo sapiens

<400> SEQUENCE: 48

Leu Arg Leu Ser Cys Ala Ala Ser Gly
1               5

<210> SEQ ID NO 49
<211> LENGTH: 9
<212> TYPE: PRT
<213> ORGANISM: Homo sapiens

<400> SEQUENCE: 49

Trp Val Arg Gln Ala Pro Gly Lys Gly
1               5

<210> SEQ ID NO 50
<211> LENGTH: 9
<212> TYPE: PRT
<213> ORGANISM: Homo sapiens

<400> SEQUENCE: 50

Val Arg Gln Ala Pro Gly Lys Gly Leu
1               5

<210> SEQ ID NO 51
<211> LENGTH: 9
<212> TYPE: PRT
<213> ORGANISM: Homo sapiens

<400> SEQUENCE: 51

Tyr Leu Gln Met Asn Ser Leu Arg Ala
1               5

<210> SEQ ID NO 52
<211> LENGTH: 9
<212> TYPE: PRT
<213> ORGANISM: Homo sapiens

<400> SEQUENCE: 52

Leu Gln Met Asn Ser Leu Arg Ala Glu
1               5

<210> SEQ ID NO 53
<211> LENGTH: 9
<212> TYPE: PRT
<213> ORGANISM: Homo sapiens

<400> SEQUENCE: 53

Gln Met Asn Ser Leu Arg Ala Glu Asp
1               5

<210> SEQ ID NO 54
<211> LENGTH: 9
<212> TYPE: PRT
<213> ORGANISM: Homo sapiens

<400> SEQUENCE: 54

Met Asn Ser Leu Arg Ala Glu Asp Thr
1               5

<210> SEQ ID NO 55
<211> LENGTH: 9
<212> TYPE: PRT
<213> ORGANISM: Homo sapiens

```
<400> SEQUENCE: 55

Asn Ser Leu Arg Ala Glu Asp Thr Ala
1               5

<210> SEQ ID NO 56
<211> LENGTH: 9
<212> TYPE: PRT
<213> ORGANISM: Homo sapiens

<400> SEQUENCE: 56

Ser Leu Arg Ala Glu Asp Thr Ala Val
1               5

<210> SEQ ID NO 57
<211> LENGTH: 9
<212> TYPE: PRT
<213> ORGANISM: Homo sapiens

<400> SEQUENCE: 57

Leu Arg Ala Glu Asp Thr Ala Val Tyr
1               5

<210> SEQ ID NO 58
<211> LENGTH: 9
<212> TYPE: PRT
<213> ORGANISM: Homo sapiens

<400> SEQUENCE: 58

Lys Thr Leu Tyr Leu Gln Met Asn Ser
1               5

<210> SEQ ID NO 59
<211> LENGTH: 9
<212> TYPE: PRT
<213> ORGANISM: Homo sapiens

<400> SEQUENCE: 59

Thr Leu Tyr Leu Gln Met Asn Ser Leu
1               5

<210> SEQ ID NO 60
<211> LENGTH: 9
<212> TYPE: PRT
<213> ORGANISM: Homo sapiens

<400> SEQUENCE: 60

Leu Tyr Leu Gln Met Asn Ser Leu Arg
1               5

<210> SEQ ID NO 61
<211> LENGTH: 9
<212> TYPE: PRT
<213> ORGANISM: Homo sapiens

<400> SEQUENCE: 61

Tyr Leu Gln Met Asn Ser Leu Arg Ala
1               5

<210> SEQ ID NO 62
<211> LENGTH: 9
<212> TYPE: PRT
<213> ORGANISM: Homo sapiens

<400> SEQUENCE: 62
```

-continued

```
Leu Gln Met Asn Ser Leu Arg Ala Glu
1               5

<210> SEQ ID NO 63
<211> LENGTH: 9
<212> TYPE: PRT
<213> ORGANISM: Homo sapiens

<400> SEQUENCE: 63

Gln Met Asn Ser Leu Arg Ala Glu Asp
1               5

<210> SEQ ID NO 64
<211> LENGTH: 9
<212> TYPE: PRT
<213> ORGANISM: Homo sapiens

<400> SEQUENCE: 64

Met Asn Ser Leu Arg Ala Glu Asp Thr
1               5

<210> SEQ ID NO 65
<211> LENGTH: 9
<212> TYPE: PRT
<213> ORGANISM: Homo sapiens

<400> SEQUENCE: 65

Asn Ser Leu Arg Ala Glu Asp Thr Ala
1               5

<210> SEQ ID NO 66
<211> LENGTH: 9
<212> TYPE: PRT
<213> ORGANISM: Homo sapiens

<400> SEQUENCE: 66

Ser Leu Arg Ala Glu Asp Thr Ala Lys
1               5

<210> SEQ ID NO 67
<211> LENGTH: 9
<212> TYPE: PRT
<213> ORGANISM: Homo sapiens

<400> SEQUENCE: 67

Leu Arg Ala Glu Asp Thr Ala Lys His
1               5

<210> SEQ ID NO 68
<211> LENGTH: 9
<212> TYPE: PRT
<213> ORGANISM: Homo sapiens

<400> SEQUENCE: 68

Tyr Leu Gln Met Asn Ser Leu Arg Ala
1               5

<210> SEQ ID NO 69
<211> LENGTH: 9
<212> TYPE: PRT
<213> ORGANISM: Homo sapiens

<400> SEQUENCE: 69

Leu Gln Met Asn Ser Leu Arg Ala Glu
1               5
```

<210> SEQ ID NO 70
<211> LENGTH: 9
<212> TYPE: PRT
<213> ORGANISM: Homo sapiens

<400> SEQUENCE: 70

Gln Met Asn Ser Leu Arg Ala Glu Asp
1               5

<210> SEQ ID NO 71
<211> LENGTH: 9
<212> TYPE: PRT
<213> ORGANISM: Homo sapiens

<400> SEQUENCE: 71

Met Asn Ser Leu Arg Ala Glu Asp Thr
1               5

<210> SEQ ID NO 72
<211> LENGTH: 9
<212> TYPE: PRT
<213> ORGANISM: Homo sapiens

<400> SEQUENCE: 72

Asn Ser Leu Arg Ala Glu Asp Thr Ala
1               5

<210> SEQ ID NO 73
<211> LENGTH: 9
<212> TYPE: PRT
<213> ORGANISM: Homo sapiens

<400> SEQUENCE: 73

Ser Leu Arg Ala Glu Asp Thr Ala Lys
1               5

<210> SEQ ID NO 74
<211> LENGTH: 9
<212> TYPE: PRT
<213> ORGANISM: Homo sapiens

<400> SEQUENCE: 74

Leu Arg Ala Glu Asp Thr Ala Lys His
1               5

<210> SEQ ID NO 75
<211> LENGTH: 9
<212> TYPE: PRT
<213> ORGANISM: Homo sapiens

<400> SEQUENCE: 75

Leu Gln Ser Ser Gly Leu Tyr Ser Leu
1               5

<210> SEQ ID NO 76
<211> LENGTH: 9
<212> TYPE: PRT
<213> ORGANISM: Homo sapiens

<400> SEQUENCE: 76

Gln Ser Ser Gly Leu Tyr Ser Leu Ser
1               5

<210> SEQ ID NO 77
<211> LENGTH: 9
<212> TYPE: PRT
<213> ORGANISM: Homo sapiens

<400> SEQUENCE: 77

Ser Ser Gly Leu Tyr Ser Leu Ser Ser
1               5

<210> SEQ ID NO 78
<211> LENGTH: 9
<212> TYPE: PRT
<213> ORGANISM: Homo sapiens

<400> SEQUENCE: 78

Ser Gly Leu Tyr Ser Leu Ser Ser Val
1               5

<210> SEQ ID NO 79
<211> LENGTH: 9
<212> TYPE: PRT
<213> ORGANISM: Homo sapiens

<400> SEQUENCE: 79

Gly Leu Tyr Ser Leu Ser Ser Val Val
1               5

<210> SEQ ID NO 80
<211> LENGTH: 9
<212> TYPE: PRT
<213> ORGANISM: Homo sapiens

<400> SEQUENCE: 80

Leu Tyr Ser Leu Ser Ser Val Val Thr
1               5

<210> SEQ ID NO 81
<211> LENGTH: 9
<212> TYPE: PRT
<213> ORGANISM: Homo sapiens

<400> SEQUENCE: 81

Tyr Ser Leu Ser Ser Val Val Thr Val
1               5

<210> SEQ ID NO 82
<211> LENGTH: 9
<212> TYPE: PRT
<213> ORGANISM: Homo sapiens

<400> SEQUENCE: 82

Ser Leu Ser Ser Val Val Thr Val Pro
1               5

<210> SEQ ID NO 83
<211> LENGTH: 9
<212> TYPE: PRT
<213> ORGANISM: Homo sapiens

<400> SEQUENCE: 83

Leu Ser Ser Val Val Thr Val Pro Ser
1               5

<210> SEQ ID NO 84
<211> LENGTH: 9

```
<212> TYPE: PRT
<213> ORGANISM: Homo sapiens

<400> SEQUENCE: 84

Ser Ser Val Val Thr Val Pro Ser Ser
1               5

<210> SEQ ID NO 85
<211> LENGTH: 9
<212> TYPE: PRT
<213> ORGANISM: Homo sapiens

<400> SEQUENCE: 85

Ser Val Val Thr Val Pro Ser Ser Ser
1               5

<210> SEQ ID NO 86
<211> LENGTH: 9
<212> TYPE: PRT
<213> ORGANISM: Homo sapiens

<400> SEQUENCE: 86

Val Val Thr Val Pro Ser Ser Ser Leu
1               5

<210> SEQ ID NO 87
<211> LENGTH: 9
<212> TYPE: PRT
<213> ORGANISM: Homo sapiens

<400> SEQUENCE: 87

Tyr Asn Ser Thr Tyr Arg Val Val Ser
1               5

<210> SEQ ID NO 88
<211> LENGTH: 9
<212> TYPE: PRT
<213> ORGANISM: Homo sapiens

<400> SEQUENCE: 88

Asn Ser Thr Tyr Arg Val Val Ser Val
1               5

<210> SEQ ID NO 89
<211> LENGTH: 9
<212> TYPE: PRT
<213> ORGANISM: Homo sapiens

<400> SEQUENCE: 89

Ser Thr Tyr Arg Val Val Ser Val Leu
1               5

<210> SEQ ID NO 90
<211> LENGTH: 9
<212> TYPE: PRT
<213> ORGANISM: Homo sapiens

<400> SEQUENCE: 90

Thr Tyr Arg Val Val Ser Val Leu Thr
1               5

<210> SEQ ID NO 91
<211> LENGTH: 9
<212> TYPE: PRT
<213> ORGANISM: Homo sapiens
```

<400> SEQUENCE: 91

Tyr Arg Val Val Ser Val Leu Thr Val
1               5

<210> SEQ ID NO 92
<211> LENGTH: 9
<212> TYPE: PRT
<213> ORGANISM: Homo sapiens

<400> SEQUENCE: 92

Arg Val Val Ser Val Leu Thr Val Leu
1               5

<210> SEQ ID NO 93
<211> LENGTH: 9
<212> TYPE: PRT
<213> ORGANISM: Homo sapiens

<400> SEQUENCE: 93

Val Val Ser Val Leu Thr Val Leu His
1               5

<210> SEQ ID NO 94
<211> LENGTH: 9
<212> TYPE: PRT
<213> ORGANISM: Homo sapiens

<400> SEQUENCE: 94

Tyr Gln Ser Thr Tyr Arg Val Val Ser
1               5

<210> SEQ ID NO 95
<211> LENGTH: 9
<212> TYPE: PRT
<213> ORGANISM: Homo sapiens

<400> SEQUENCE: 95

Gln Ser Thr Tyr Arg Val Val Ser Val
1               5

<210> SEQ ID NO 96
<211> LENGTH: 9
<212> TYPE: PRT
<213> ORGANISM: Homo sapiens

<400> SEQUENCE: 96

Ser Thr Tyr Arg Val Val Ser Val Leu
1               5

<210> SEQ ID NO 97
<211> LENGTH: 9
<212> TYPE: PRT
<213> ORGANISM: Homo sapiens

<400> SEQUENCE: 97

Thr Tyr Arg Val Val Ser Val Leu Thr
1               5

<210> SEQ ID NO 98
<211> LENGTH: 9
<212> TYPE: PRT
<213> ORGANISM: Homo sapiens

<400> SEQUENCE: 98

Tyr Arg Val Val Ser Val Leu Thr Val
1               5

<210> SEQ ID NO 99
<211> LENGTH: 9
<212> TYPE: PRT
<213> ORGANISM: Homo sapiens

<400> SEQUENCE: 99

Arg Val Val Ser Val Leu Thr Val Leu
1               5

<210> SEQ ID NO 100
<211> LENGTH: 9
<212> TYPE: PRT
<213> ORGANISM: Homo sapiens

<400> SEQUENCE: 100

Val Val Ser Val Leu Thr Val Leu His
1               5

<210> SEQ ID NO 101
<211> LENGTH: 9
<212> TYPE: PRT
<213> ORGANISM: Homo sapiens

<400> SEQUENCE: 101

Phe Tyr Pro Arg Glu Ala Lys Val Gln
1               5

<210> SEQ ID NO 102
<211> LENGTH: 9
<212> TYPE: PRT
<213> ORGANISM: Homo sapiens

<400> SEQUENCE: 102

Tyr Pro Arg Glu Ala Lys Val Gln Trp
1               5

<210> SEQ ID NO 103
<211> LENGTH: 9
<212> TYPE: PRT
<213> ORGANISM: Homo sapiens

<400> SEQUENCE: 103

Pro Arg Glu Ala Lys Val Gln Trp Lys
1               5

<210> SEQ ID NO 104
<211> LENGTH: 9
<212> TYPE: PRT
<213> ORGANISM: Homo sapiens

<400> SEQUENCE: 104

Arg Glu Ala Lys Val Gln Trp Lys Val
1               5

<210> SEQ ID NO 105
<211> LENGTH: 9
<212> TYPE: PRT
<213> ORGANISM: Homo sapiens

<400> SEQUENCE: 105

Glu Ala Lys Val Gln Trp Lys Val Asp

```
1               5

<210> SEQ ID NO 106
<211> LENGTH: 9
<212> TYPE: PRT
<213> ORGANISM: Homo sapiens

<400> SEQUENCE: 106

Ala Lys Val Gln Trp Lys Val Asp Asn
1               5

<210> SEQ ID NO 107
<211> LENGTH: 9
<212> TYPE: PRT
<213> ORGANISM: Homo sapiens

<400> SEQUENCE: 107

Lys Val Gln Trp Lys Val Asp Asn Ala
1               5

<210> SEQ ID NO 108
<211> LENGTH: 9
<212> TYPE: PRT
<213> ORGANISM: Homo sapiens

<400> SEQUENCE: 108

Val Gln Trp Lys Val Asp Asn Ala Leu
1               5

<210> SEQ ID NO 109
<211> LENGTH: 9
<212> TYPE: PRT
<213> ORGANISM: Homo sapiens

<400> SEQUENCE: 109

Gln Trp Lys Val Asp Asn Ala Leu Gln
1               5

<210> SEQ ID NO 110
<211> LENGTH: 9
<212> TYPE: PRT
<213> ORGANISM: Homo sapiens

<400> SEQUENCE: 110

Trp Lys Val Asp Asn Ala Leu Gln Ser
1               5

<210> SEQ ID NO 111
<211> LENGTH: 9
<212> TYPE: PRT
<213> ORGANISM: Homo sapiens

<400> SEQUENCE: 111

Glu Thr Leu Tyr Leu Gln Met Asn Ser
1               5

<210> SEQ ID NO 112
<211> LENGTH: 9
<212> TYPE: PRT
<213> ORGANISM: Homo sapiens

<400> SEQUENCE: 112

Thr Leu Tyr Leu Gln Met Asn Ser Leu
1               5
```

```
<210> SEQ ID NO 113
<211> LENGTH: 9
<212> TYPE: PRT
<213> ORGANISM: Homo sapiens

<400> SEQUENCE: 113

Leu Tyr Leu Gln Met Asn Ser Leu Arg
1               5

<210> SEQ ID NO 114
<211> LENGTH: 9
<212> TYPE: PRT
<213> ORGANISM: Homo sapiens

<400> SEQUENCE: 114

Tyr Leu Gln Met Asn Ser Leu Arg Ala
1               5

<210> SEQ ID NO 115
<211> LENGTH: 9
<212> TYPE: PRT
<213> ORGANISM: Homo sapiens

<400> SEQUENCE: 115

Leu Gln Met Asn Ser Leu Arg Ala Glu
1               5

<210> SEQ ID NO 116
<211> LENGTH: 9
<212> TYPE: PRT
<213> ORGANISM: Homo sapiens

<400> SEQUENCE: 116

Gln Met Asn Ser Leu Arg Ala Glu Asp
1               5

<210> SEQ ID NO 117
<211> LENGTH: 9
<212> TYPE: PRT
<213> ORGANISM: Homo sapiens

<400> SEQUENCE: 117

Met Asn Ser Leu Arg Ala Glu Asp Thr
1               5

<210> SEQ ID NO 118
<211> LENGTH: 9
<212> TYPE: PRT
<213> ORGANISM: Homo sapiens

<400> SEQUENCE: 118

Asn Ser Leu Arg Ala Glu Asp Thr Ala
1               5

<210> SEQ ID NO 119
<211> LENGTH: 9
<212> TYPE: PRT
<213> ORGANISM: Homo sapiens

<400> SEQUENCE: 119

Ser Leu Arg Ala Glu Asp Thr Ala Val
1               5

<210> SEQ ID NO 120
```

```
<211> LENGTH: 9
<212> TYPE: PRT
<213> ORGANISM: Homo sapiens

<400> SEQUENCE: 120

Leu Arg Ala Glu Asp Thr Ala Val Tyr
1               5

<210> SEQ ID NO 121
<211> LENGTH: 9
<212> TYPE: PRT
<213> ORGANISM: Homo sapiens

<400> SEQUENCE: 121

Tyr Leu Gln Met Asn Ser Leu Arg Ala
1               5

<210> SEQ ID NO 122
<211> LENGTH: 9
<212> TYPE: PRT
<213> ORGANISM: Homo sapiens

<400> SEQUENCE: 122

Leu Gln Met Asn Ser Leu Arg Ala Glu
1               5

<210> SEQ ID NO 123
<211> LENGTH: 9
<212> TYPE: PRT
<213> ORGANISM: Homo sapiens

<400> SEQUENCE: 123

Gln Met Asn Ser Leu Arg Ala Glu Asp
1               5

<210> SEQ ID NO 124
<211> LENGTH: 9
<212> TYPE: PRT
<213> ORGANISM: Homo sapiens

<400> SEQUENCE: 124

Met Asn Ser Leu Arg Ala Glu Asp Thr
1               5

<210> SEQ ID NO 125
<211> LENGTH: 9
<212> TYPE: PRT
<213> ORGANISM: Human Influenza A virus

<400> SEQUENCE: 125

Pro Arg Tyr Val Lys Gln Asn Thr Leu
1               5

<210> SEQ ID NO 126
<211> LENGTH: 9
<212> TYPE: PRT
<213> ORGANISM: Human Influenza A virus

<400> SEQUENCE: 126

Arg Tyr Val Lys Gln Asn Thr Leu Lys
1               5

<210> SEQ ID NO 127
<211> LENGTH: 9
<212> TYPE: PRT
```

<213> ORGANISM: Human Influenza A virus

<400> SEQUENCE: 127

Tyr Val Lys Gln Asn Thr Leu Lys Leu
1               5

<210> SEQ ID NO 128
<211> LENGTH: 9
<212> TYPE: PRT
<213> ORGANISM: Human Influenza A virus

<400> SEQUENCE: 128

Val Lys Gln Asn Thr Leu Lys Leu Ala
1               5

<210> SEQ ID NO 129
<211> LENGTH: 9
<212> TYPE: PRT
<213> ORGANISM: Human Influenza A virus

<400> SEQUENCE: 129

Lys Gln Asn Thr Leu Lys Leu Ala Thr
1               5

<210> SEQ ID NO 130
<211> LENGTH: 32
<212> TYPE: DNA
<213> ORGANISM: Artificial Sequence
<220> FEATURE:
<223> OTHER INFORMATION: Synthetic primer

<400> SEQUENCE: 130
gttaactagt tcagctggac cacagccgca gc                                    32

<210> SEQ ID NO 131
<211> LENGTH: 40
<212> TYPE: DNA
<213> ORGANISM: Artificial Sequence
<220> FEATURE:
<223> OTHER INFORMATION: Synthetic primer

<400> SEQUENCE: 131
cgggttaact agttcagaaa tcctttctct tgaccatggc                            40

<210> SEQ ID NO 132
<211> LENGTH: 25
<212> TYPE: DNA
<213> ORGANISM: Artificial Sequence
<220> FEATURE:
<223> OTHER INFORMATION: Synthetic primer

<400> SEQUENCE: 132
ctagcctctg gaatcctttc tcttg                                            25

<210> SEQ ID NO 133
<211> LENGTH: 21
<212> TYPE: PRT
<213> ORGANISM: Homo sapiens

<400> SEQUENCE: 133

Arg Ile His Met Val Tyr Ser Lys Arg Ser Gly Lys Pro Arg Gly Tyr
1               5                   10                  15

Ala Phe Ile Glu Tyr
            20

```
<210> SEQ ID NO 134
<211> LENGTH: 28
<212> TYPE: PRT
<213> ORGANISM: Homo sapiens

<400> SEQUENCE: 134

Pro Ala Val Leu Gln Ser Ser Gly Leu Tyr Ser Leu Ser Leu Ser Ser
1               5                   10                  15

Val Val Thr Val Pro Ser Ser Ser Leu Gly Thr Gln
            20                  25

<210> SEQ ID NO 135
<211> LENGTH: 2372
<212> TYPE: PRT
<213> ORGANISM: Artificial Sequence
<220> FEATURE:
<223> OTHER INFORMATION: Synthetic construct

<400> SEQUENCE: 135

Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
    50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
    130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
    210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Thr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
```

```
                290             295             300
Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Cys Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asn Ser
    370                 375                 380

Pro Ser Phe Ile Gln Ile Arg Ser Val Ala Lys Lys His Pro Lys Thr
385                 390                 395                 400

Trp Val His Tyr Ile Ala Ala Glu Glu Asp Trp Asp Tyr Ala Pro
                405                 410                 415

Leu Val Leu Ala Pro Asp Asp Arg Ser Tyr Lys Ser Gln Tyr Leu Asn
                420                 425                 430

Asn Gly Pro Gln Arg Ile Gly Arg Lys Tyr Lys Lys Val Arg Phe Met
                435                 440                 445

Ala Tyr Thr Asp Glu Thr Phe Lys Thr Arg Glu Ala Ile Gln His Glu
                450                 455                 460

Ser Gly Ile Leu Gly Pro Leu Leu Tyr Gly Glu Val Gly Asp Thr Leu
465                 470                 475                 480

Leu Ile Ile Phe Lys Asn Gln Ala Ser Arg Pro Tyr Asn Ile Tyr Pro
                485                 490                 495

His Gly Ile Thr Asp Val Arg Pro Leu Tyr Ser Arg Arg Leu Pro Lys
                500                 505                 510

Gly Val Lys His Leu Lys Asp Phe Pro Ile Leu Pro Gly Glu Ile Phe
                515                 520                 525

Lys Tyr Lys Trp Thr Val Thr Val Glu Asp Gly Pro Thr Lys Ser Asp
                530                 535                 540

Pro Arg Cys Leu Thr Arg Tyr Tyr Ser Ser Phe Val Asn Met Glu Arg
545                 550                 555                 560

Asp Leu Ala Ser Gly Leu Ile Gly Pro Leu Leu Ile Cys Tyr Lys Glu
                565                 570                 575

Ser Val Asp Gln Arg Gly Asn Gln Ile Met Ser Asp Lys Arg Asn Val
                580                 585                 590

Ile Leu Phe Ser Val Phe Asp Glu Asn Arg Ser Trp Tyr Leu Thr Glu
                595                 600                 605

Asn Ile Gln Arg Phe Leu Pro Asn Pro Ala Gly Val Gln Leu Glu Asp
                610                 615                 620

Pro Glu Phe Gln Ala Ser Asn Ile Met His Ser Ile Asn Gly Tyr Val
625                 630                 635                 640

Phe Asp Ser Leu Gln Leu Ser Val Cys Leu His Glu Val Ala Tyr Trp
                645                 650                 655

Tyr Ile Leu Ser Ile Gly Ala Gln Thr Asp Phe Leu Ser Val Phe Phe
                660                 665                 670

Ser Gly Tyr Thr Phe Lys His Lys Met Val Tyr Glu Asp Thr Leu Thr
                675                 680                 685

Leu Phe Pro Phe Ser Gly Glu Thr Val Phe Met Ser Met Glu Asn Pro
                690                 695                 700

Gly Leu Trp Ile Leu Gly Cys His Asn Ser Asp Phe Arg Asn Arg Gly
705                 710                 715                 720
```

-continued

Met Thr Ala Leu Leu Lys Val Ser Ser Cys Asp Lys Asn Thr Gly Asp
                725                 730                 735

Tyr Tyr Glu Asp Ser Tyr Glu Asp Ile Ser Ala Tyr Leu Leu Ser Lys
            740                 745                 750

Asn Asn Ala Ile Glu Pro Arg Ser Phe Ser Gln Asn Ser Arg His Pro
            755                 760                 765

Ser Thr Arg Gln Lys Gln Phe Asn Ala Thr Thr Ile Pro Glu Asn Asp
        770                 775                 780

Ile Glu Lys Thr Asp Pro Trp Phe Ala His Arg Thr Pro Met Pro Lys
785                 790                 795                 800

Ile Gln Asn Val Ser Ser Asp Leu Leu Met Leu Leu Arg Gln Ser
                805                 810                 815

Pro Thr Pro His Gly Leu Ser Leu Ser Asp Leu Gln Glu Ala Lys Tyr
                820                 825                 830

Glu Thr Phe Ser Asp Asp Pro Ser Pro Gly Ala Ile Asp Ser Asn Asn
            835                 840                 845

Ser Leu Ser Glu Met Thr His Phe Arg Pro Gln Leu His His Ser Gly
        850                 855                 860

Asp Met Val Phe Thr Pro Glu Ser Gly Leu Gln Leu Arg Leu Asn Glu
865                 870                 875                 880

Lys Leu Gly Thr Thr Ala Ala Thr Glu Leu Lys Lys Leu Asp Phe Lys
                885                 890                 895

Val Ser Ser Thr Ser Asn Asn Leu Ile Ser Thr Ile Pro Ser Asp Asn
                900                 905                 910

Leu Ala Ala Gly Thr Asp Asn Thr Ser Ser Leu Gly Pro Pro Ser Met
                915                 920                 925

Pro Val His Tyr Asp Ser Gln Leu Asp Thr Thr Leu Phe Gly Lys Lys
            930                 935                 940

Ser Ser Pro Leu Thr Glu Ser Gly Gly Pro Leu Ser Leu Ser Glu Glu
945                 950                 955                 960

Asn Asn Asp Ser Lys Leu Leu Glu Ser Gly Leu Met Asn Ser Gln Glu
                965                 970                 975

Ser Ser Trp Gly Lys Asn Val Ser Ser Thr Glu Ser Gly Arg Leu Phe
            980                 985                 990

Lys Gly Lys Arg Ala His Gly Pro Ala Leu Leu Thr Lys Asp Asn Ala
            995                 1000                1005

Leu Phe Lys Val Ser Ile Ser Leu Leu Lys Thr Asn Lys Thr Ser
        1010                1015                1020

Asn Asn Ser Ala Thr Asn Arg Lys Thr His Ile Asp Gly Pro Ser
        1025                1030                1035

Leu Leu Ile Glu Asn Ser Pro Ser Val Trp Gln Asn Ile Leu Glu
        1040                1045                1050

Ser Asp Thr Glu Phe Lys Lys Val Thr Pro Leu Ile His Asp Arg
        1055                1060                1065

Met Leu Met Asp Lys Asn Ala Thr Ala Leu Arg Leu Asn His Met
        1070                1075                1080

Ser Asn Lys Thr Thr Ser Ser Lys Asn Met Glu Met Val Gln Gln
        1085                1090                1095

Lys Lys Glu Gly Pro Ile Pro Pro Asp Ala Gln Asn Pro Asp Met
        1100                1105                1110

Ser Phe Phe Lys Met Leu Phe Leu Pro Glu Ser Ala Arg Trp Ile
        1115                1120                1125

-continued

Gln Arg Thr His Gly Lys Asn Ser Leu Asn Ser Gly Gln Gly Pro
1130                1135                1140

Ser Pro Lys Gln Leu Val Ser Leu Gly Pro Glu Lys Ser Val Glu
1145                1150                1155

Gly Gln Asn Phe Leu Ser Glu Lys Asn Lys Val Val Val Gly Lys
1160                1165                1170

Gly Glu Phe Thr Lys Asp Val Gly Leu Lys Glu Met Val Phe Pro
1175                1180                1185

Ser Ser Arg Asn Leu Phe Leu Thr Asn Leu Asp Asn Leu His Glu
1190                1195                1200

Asn Asn Thr His Asn Gln Glu Lys Lys Ile Gln Glu Glu Ile Glu
1205                1210                1215

Lys Lys Glu Thr Leu Ile Gln Glu Asn Val Val Leu Pro Gln Ile
1220                1225                1230

His Thr Val Thr Gly Thr Lys Asn Phe Met Lys Asn Leu Phe Leu
1235                1240                1245

Leu Ser Thr Arg Gln Asn Val Glu Gly Ser Tyr Asp Gly Ala Tyr
1250                1255                1260

Ala Pro Val Leu Gln Asp Phe Arg Ser Leu Asn Asp Ser Thr Asn
1265                1270                1275

Arg Thr Lys Lys His Thr Ala His Phe Ser Lys Lys Gly Glu Glu
1280                1285                1290

Glu Asn Leu Glu Gly Leu Gly Asn Gln Thr Lys Gln Ile Val Glu
1295                1300                1305

Lys Tyr Ala Cys Thr Thr Arg Ile Ser Pro Asn Thr Ser Gln Gln
1310                1315                1320

Asn Phe Val Thr Gln Arg Ser Lys Arg Ala Leu Lys Gln Phe Arg
1325                1330                1335

Leu Pro Leu Glu Glu Thr Glu Leu Glu Lys Arg Ile Ile Val Asp
1340                1345                1350

Asp Thr Ser Thr Gln Trp Ser Lys Asn Met Lys His Leu Thr Pro
1355                1360                1365

Ser Thr Leu Thr Gln Ile Asp Tyr Asn Glu Lys Glu Lys Gly Ala
1370                1375                1380

Ile Thr Gln Ser Pro Leu Ser Asp Cys Leu Thr Arg Ser Glu Ser
1385                1390                1395

Ile Pro Gln Ala Asn Arg Ser Pro Leu Pro Ile Ala Lys Val Ser
1400                1405                1410

Ser Phe Pro Ser Ile Arg Pro Ile Tyr Leu Thr Arg Val Leu Phe
1415                1420                1425

Gln Asp Asn Ser Ser Asn Leu Pro Ala Ala Ser Tyr Arg Lys Lys
1430                1435                1440

Asp Ser Gly Val Gln Glu Ser Ser His Phe Leu Gln Gly Ala Lys
1445                1450                1455

Lys Asn Asn Leu Ser Leu Ala Ile Leu Thr Leu Glu Met Thr Gly
1460                1465                1470

Asp Gln Arg Glu Val Gly Ser Leu Gly Thr Ser Ala Thr Asn Ser
1475                1480                1485

Val Thr Tyr Lys Lys Val Glu Asn Thr Val Leu Pro Lys Pro Asp
1490                1495                1500

Leu Pro Lys Thr Ser Gly Lys Val Glu Leu Leu Pro Lys Val His
1505                1510                1515

Ile Tyr Gln Lys Asp Leu Phe Pro Thr Glu Thr Ser Asn Gly Ser

```
                1520                1525                1530
Pro Gly His Leu Asp Leu Val Glu Gly Ser Leu Leu Gln Gly Thr
    1535                1540                1545
Glu Gly Ala Ile Lys Trp Asn Glu Ala Asn Arg Pro Gly Lys Val
    1550                1555                1560
Pro Phe Leu Arg Val Ala Thr Glu Ser Ser Ala Lys Thr Pro Ser
    1565                1570                1575
Lys Leu Leu Asp Pro Leu Ala Trp Asp Asn His Tyr Gly Thr Gln
    1580                1585                1590
Ile Pro Lys Glu Glu Trp Lys Ser Gln Glu Lys Ser Pro Glu Lys
    1595                1600                1605
Thr Ala Phe Lys Lys Lys Asp Thr Ile Leu Ser Leu Asn Ala Cys
    1610                1615                1620
Glu Ser Asn His Ala Ile Ala Ile Asn Glu Gly Gln Asn Lys
    1625                1630                1635
Pro Glu Ile Glu Val Thr Trp Ala Lys Gln Gly Arg Thr Glu Arg
    1640                1645                1650
Leu Cys Ser Gln Asn Pro Pro Val Leu Lys Arg His Gln Arg Glu
    1655                1660                1665
Ile Thr Arg Thr Thr Leu Gln Ser Asp Gln Glu Glu Ile Asp Tyr
    1670                1675                1680
Asp Asp Thr Ile Ser Val Glu Met Lys Lys Glu Asp Phe Asp Ile
    1685                1690                1695
Tyr Asp Glu Asp Glu Asn Gln Ser Pro Arg Ser Phe Gln Lys Lys
    1700                1705                1710
Thr Arg His Tyr Phe Ile Ala Ala Val Glu Arg Leu Trp Asp Tyr
    1715                1720                1725
Gly Met Ser Ser Ser Pro His Val Leu Arg Asn Arg Ala Gln Ser
    1730                1735                1740
Gly Ser Val Pro Gln Phe Lys Lys Val Val Phe Gln Glu Phe Thr
    1745                1750                1755
Asp Gly Ser Phe Thr Gln Pro Leu Tyr Arg Gly Glu Leu Asn Glu
    1760                1765                1770
His Leu Gly Leu Leu Gly Pro Tyr Ile Arg Ala Glu Val Glu Asp
    1775                1780                1785
Asn Ile Met Val Thr Phe Arg Asn Gln Ala Ser Arg Pro Tyr Ser
    1790                1795                1800
Phe Tyr Ser Ser Leu Ile Ser Tyr Glu Glu Asp Gln Arg Gln Gly
    1805                1810                1815
Ala Glu Pro Arg Lys Asn Phe Val Lys Pro Asn Glu Thr Lys Thr
    1820                1825                1830
Tyr Phe Trp Lys Val Gln His His Met Ala Pro Thr Lys Asp Glu
    1835                1840                1845
Phe Asp Cys Lys Ala Trp Ala Tyr Phe Ser Asp Val Asp Leu Glu
    1850                1855                1860
Lys Asp Val His Ser Gly Leu Ile Gly Pro Leu Leu Val Cys His
    1865                1870                1875
Thr Asn Thr Leu Asn Pro Ala His Gly Arg Gln Val Thr Val Gln
    1880                1885                1890
Glu Phe Ala Leu Phe Phe Thr Ile Phe Asp Glu Thr Lys Ser Trp
    1895                1900                1905
Tyr Phe Thr Glu Asn Met Glu Arg Asn Cys Arg Ala Pro Ser Asn
    1910                1915                1920
```

```
Ile Gln Met Glu Asp Pro Thr Phe Lys Glu Asn Tyr Arg Phe His
    1925                1930                1935

Ala Ile Asn Gly Tyr Ile Met Asp Thr Leu Phe Gly Leu Val Met
    1940                1945                1950

Ala Gln Asp Gln Arg Ile Arg Trp Tyr Leu Leu Ser Met Gly Ser
    1955                1960                1965

Asn Glu Asn Ile His Ser Ile His Phe Ser Gly His Val Phe Thr
    1970                1975                1980

Val Arg Lys Lys Glu Glu Tyr Lys Met Ala Leu Tyr Asn Leu Tyr
    1985                1990                1995

Pro Gly Val Phe Glu Thr Val Glu Met Leu Pro Ser Lys Ala Gly
    2000                2005                2010

Ile Trp Arg Val Glu Cys Leu Ile Gly Glu His Leu His Ala Gly
    2015                2020                2025

Met Ser Thr Leu Phe Leu Val Tyr Ser Asn Lys Cys Gln Thr Pro
    2030                2035                2040

Leu Gly Met Ala Ser Gly His Ile Arg Asp Phe Gln Ile Thr Ala
    2045                2050                2055

Ser Gly Gln Tyr Gly Gln Trp Ala Pro Lys Leu Ala Arg Leu His
    2060                2065                2070

Tyr Ser Gly Ser Ile Asn Ala Trp Ser Thr Lys Glu Pro Phe Ser
    2075                2080                2085

Trp Ile Lys Val Asp Leu Leu Ala Pro Met Ile Ile His Gly Ile
    2090                2095                2100

Lys Thr Gln Gly Ala Arg Gln Lys Phe Ser Ser Leu Tyr Ile Ser
    2105                2110                2115

Gln Phe Ile Ile Met Tyr Ser Leu Asp Gly Lys Lys Trp Gln Thr
    2120                2125                2130

Tyr Arg Gly Asn Ser Thr Gly Thr Leu Met Val Phe Phe Gly Asn
    2135                2140                2145

Val Asp Ser Ser Gly Ile Lys His Asn Ile Phe Asn Pro Pro Ile
    2150                2155                2160

Ile Ala Arg Tyr Ile Arg Leu His Pro Thr His Tyr Ser Ile Arg
    2165                2170                2175

Ser Thr Leu Arg Met Glu Leu Met Gly Cys Asp Leu Asn Ser Cys
    2180                2185                2190

Ser Met Pro Leu Gly Met Glu Ser Lys Ala Ile Ser Asp Ala Gln
    2195                2200                2205

Ile Thr Ala Ser Ser Tyr Phe Thr Asn Met Phe Ala Thr Trp Ser
    2210                2215                2220

Pro Ser Lys Ala Arg Leu His Leu Gln Gly Arg Ser Asn Ala Trp
    2225                2230                2235

Arg Pro Gln Val Asn Asn Pro Lys Glu Trp Leu Gln Val Asp Phe
    2240                2245                2250

Gln Lys Thr Met Lys Val Thr Gly Val Thr Thr Gln Gly Val Lys
    2255                2260                2265

Ser Leu Leu Thr Ser Met Tyr Val Lys Glu Phe Leu Ile Ser Ser
    2270                2275                2280

Ser Gln Asp Gly His Gln Trp Thr Leu Phe Phe Gln Asn Gly Lys
    2285                2290                2295

Val Lys Val Phe Gln Gly Asn Gln Asp Ser Phe Thr Pro Val Val
    2300                2305                2310
```

Asn Ser Leu Asp Pro Pro Leu Leu Thr Arg Tyr Leu Arg Ile His
2315                2320                2325

Pro Gln Ser Trp Val His Gln Ile Ala Leu Arg Met Glu Val Leu
2330                2335                2340

Gly Cys Glu Ala Gln Asp Leu Tyr Lys Thr Leu Tyr Leu Gln Met
2345                2350                2355

Asn Ser Leu Arg Ala Glu Asp Thr Ala Lys His Tyr Cys Ala
2360                2365                2370

<210> SEQ ID NO 136
<211> LENGTH: 2371
<212> TYPE: PRT
<213> ORGANISM: Artificial Sequence
<220> FEATURE:
<223> OTHER INFORMATION: Synthetic construct

<400> SEQUENCE: 136

Lys Thr Leu Tyr Leu Gln Met Asn Ser Leu Arg Ala Glu Asp Thr Ala
1               5                   10                  15

Lys His Tyr Cys Ala Gln Ile Glu Leu Ser Thr Cys Phe Phe Leu Cys
                20                  25                  30

Leu Leu Arg Phe Cys Phe Ser Ala Thr Arg Arg Tyr Tyr Leu Gly Ala
            35                  40                  45

Val Glu Leu Ser Trp Asp Tyr Met Gln Ser Asp Leu Gly Glu Leu Pro
50                  55                  60

Val Asp Ala Arg Phe Pro Pro Arg Val Pro Lys Ser Phe Pro Phe Asn
65                  70                  75                  80

Thr Ser Val Val Tyr Lys Lys Thr Leu Phe Val Glu Phe Thr Asp His
                85                  90                  95

Leu Phe Asn Ile Ala Lys Pro Arg Pro Pro Trp Met Gly Leu Leu Gly
            100                 105                 110

Pro Thr Ile Gln Ala Glu Val Tyr Asp Thr Val Val Ile Thr Leu Lys
        115                 120                 125

Asn Met Ala Ser His Pro Val Ser Leu His Ala Val Gly Val Ser Tyr
    130                 135                 140

Trp Lys Ala Ser Glu Gly Ala Glu Tyr Asp Asp Gln Thr Ser Gln Arg
145                 150                 155                 160

Glu Lys Glu Asp Asp Lys Val Phe Pro Gly Gly Ser His Thr Tyr Val
                165                 170                 175

Trp Gln Val Leu Lys Glu Asn Gly Pro Met Ala Ser Asp Pro Leu Cys
            180                 185                 190

Leu Thr Tyr Ser Tyr Leu Ser His Val Asp Leu Val Lys Asp Leu Asn
        195                 200                 205

Ser Gly Leu Ile Gly Ala Leu Leu Val Cys Arg Glu Gly Ser Leu Ala
    210                 215                 220

Lys Glu Lys Thr Gln Thr Leu His Lys Phe Ile Leu Leu Phe Ala Val
225                 230                 235                 240

Phe Asp Glu Gly Lys Ser Trp His Ser Glu Thr Lys Asn Ser Leu Met
                245                 250                 255

Gln Asp Arg Asp Ala Ala Ser Ala Arg Ala Trp Pro Lys Met His Thr
            260                 265                 270

Val Asn Gly Thr Val Asn Arg Ser Leu Pro Gly Leu Ile Gly Cys His
        275                 280                 285

Arg Lys Ser Val Tyr Trp His Val Ile Gly Met Gly Thr Thr Pro Glu
    290                 295                 300

```
Val His Ser Ile Phe Leu Glu Gly His Thr Phe Leu Val Arg Asn His
305                 310                 315                 320

Arg Gln Ala Ser Leu Glu Ile Ser Pro Ile Thr Phe Leu Thr Ala Gln
                325                 330                 335

Thr Leu Leu Met Asp Leu Gly Gln Phe Leu Leu Phe Cys His Ile Ser
            340                 345                 350

Ser His Gln His Asp Gly Met Glu Ala Tyr Val Lys Cys Asp Ser Cys
        355                 360                 365

Pro Glu Glu Pro Gln Leu Arg Met Lys Asn Asn Glu Ala Glu Asp
    370                 375                 380

Tyr Asp Asp Leu Thr Asp Ser Glu Met Asp Val Arg Phe Asp
385                 390                 395                 400

Asp Asp Asn Ser Pro Ser Phe Ile Gln Ile Arg Ser Val Ala Lys Lys
                405                 410                 415

His Pro Lys Thr Trp Val His Tyr Ile Ala Ala Glu Glu Asp Trp
            420                 425                 430

Asp Tyr Ala Pro Leu Val Leu Ala Pro Asp Asp Arg Ser Tyr Lys Ser
        435                 440                 445

Gln Tyr Leu Asn Asn Gly Pro Gln Arg Ile Gly Arg Lys Tyr Lys Lys
    450                 455                 460

Val Arg Phe Met Ala Tyr Thr Asp Glu Thr Phe Lys Thr Arg Glu Ala
465                 470                 475                 480

Ile Gln His Glu Ser Gly Ile Leu Gly Pro Leu Leu Tyr Gly Glu Val
                485                 490                 495

Gly Asp Thr Leu Leu Ile Ile Phe Lys Asn Gln Ala Ser Arg Pro Tyr
        500                 505                 510

Asn Ile Tyr Pro His Gly Ile Thr Asp Val Arg Pro Leu Tyr Ser Arg
    515                 520                 525

Arg Leu Pro Lys Gly Val Lys His Leu Lys Asp Phe Pro Ile Leu Pro
530                 535                 540

Gly Glu Ile Phe Lys Tyr Lys Trp Thr Val Thr Val Glu Asp Gly Pro
545                 550                 555                 560

Thr Lys Ser Asp Pro Arg Cys Leu Thr Arg Tyr Tyr Ser Ser Phe Val
                565                 570                 575

Asn Met Glu Arg Asp Leu Ala Ser Gly Leu Ile Gly Pro Leu Leu Ile
            580                 585                 590

Cys Tyr Lys Glu Ser Val Asp Gln Arg Gly Asn Gln Ile Met Ser Asp
        595                 600                 605

Lys Arg Asn Val Ile Leu Phe Ser Val Phe Asp Glu Asn Arg Ser Trp
    610                 615                 620

Tyr Leu Thr Glu Asn Ile Gln Arg Phe Leu Pro Asn Pro Ala Gly Val
625                 630                 635                 640

Gln Leu Glu Asp Pro Glu Phe Gln Ala Ser Asn Ile Met His Ser Ile
                645                 650                 655

Asn Gly Tyr Val Phe Asp Ser Leu Gln Leu Ser Val Cys Leu His Glu
            660                 665                 670

Val Ala Tyr Trp Tyr Ile Leu Ser Ile Gly Ala Gln Thr Asp Phe Leu
        675                 680                 685

Ser Val Phe Phe Ser Gly Tyr Thr Phe Lys His Lys Met Val Tyr Glu
    690                 695                 700

Asp Thr Leu Thr Leu Phe Pro Phe Ser Gly Glu Thr Val Phe Met Ser
705                 710                 715                 720

Met Glu Asn Pro Gly Leu Trp Ile Leu Gly Cys His Asn Ser Asp Phe
```

-continued

```
            725                 730                 735
Arg Asn Arg Gly Met Thr Ala Leu Leu Lys Val Ser Ser Cys Asp Lys
            740                 745                 750

Asn Thr Gly Asp Tyr Tyr Glu Asp Ser Tyr Glu Asp Ile Ser Ala Tyr
            755                 760                 765

Leu Leu Ser Lys Asn Asn Ala Ile Glu Pro Arg Ser Phe Ser Gln Asn
            770                 775                 780

Ser Arg His Pro Ser Thr Arg Gln Lys Gln Phe Asn Ala Thr Thr Ile
785                 790                 795                 800

Pro Glu Asn Asp Ile Glu Lys Thr Asp Pro Trp Phe Ala His Arg Thr
                805                 810                 815

Pro Met Pro Lys Ile Gln Asn Val Ser Ser Ser Asp Leu Leu Met Leu
                820                 825                 830

Leu Arg Gln Ser Pro Thr Pro His Gly Leu Ser Leu Ser Asp Leu Gln
                835                 840                 845

Glu Ala Lys Tyr Glu Thr Phe Ser Asp Asp Pro Ser Pro Gly Ala Ile
850                 855                 860

Asp Ser Asn Asn Ser Leu Ser Glu Met Thr His Phe Arg Pro Gln Leu
865                 870                 875                 880

His His Ser Gly Asp Met Val Phe Thr Pro Glu Ser Gly Leu Gln Leu
                885                 890                 895

Arg Leu Asn Glu Lys Leu Gly Thr Thr Ala Ala Thr Glu Leu Lys Lys
                900                 905                 910

Leu Asp Phe Lys Val Ser Ser Thr Ser Asn Asn Leu Ile Ser Thr Ile
                915                 920                 925

Pro Ser Asp Asn Leu Ala Ala Gly Thr Asp Asn Thr Ser Ser Leu Gly
930                 935                 940

Pro Pro Ser Met Pro Val His Tyr Asp Ser Gln Leu Asp Thr Thr Leu
945                 950                 955                 960

Phe Gly Lys Lys Ser Ser Pro Leu Thr Glu Ser Gly Gly Pro Leu Ser
                965                 970                 975

Leu Ser Glu Glu Asn Asn Asp Ser Lys Leu Leu Glu Ser Gly Leu Met
                980                 985                 990

Asn Ser Gln Glu Ser Ser Trp Gly Lys Asn Val Ser Ser Thr Glu Ser
                995                1000                1005

Gly Arg Leu Phe Lys Gly Lys Arg Ala His Gly Pro Ala Leu Leu
                1010                1015                1020

Thr Lys Asp Asn Ala Leu Phe Lys Val Ser Ile Ser Leu Leu Lys
                1025                1030                1035

Thr Asn Lys Thr Ser Asn Asn Ser Ala Thr Asn Arg Lys Thr His
                1040                1045                1050

Ile Asp Gly Pro Ser Leu Leu Ile Glu Asn Ser Pro Ser Val Trp
                1055                1060                1065

Gln Asn Ile Leu Glu Ser Asp Thr Glu Phe Lys Lys Val Thr Pro
                1070                1075                1080

Leu Ile His Asp Arg Met Leu Met Asp Lys Asn Ala Thr Ala Leu
                1085                1090                1095

Arg Leu Asn His Met Ser Asn Lys Thr Thr Ser Ser Lys Asn Met
                1100                1105                1110

Glu Met Val Gln Gln Lys Lys Glu Gly Pro Ile Pro Pro Asp Ala
                1115                1120                1125

Gln Asn Pro Asp Met Ser Phe Phe Lys Met Leu Phe Leu Pro Glu
                1130                1135                1140
```

```
Ser Ala Arg Trp Ile Gln Arg Thr His Gly Lys Asn Ser Leu Asn
1145                1150                1155

Ser Gly Gln Gly Pro Ser Pro Lys Gln Leu Val Ser Leu Gly Pro
1160                1165                1170

Glu Lys Ser Val Glu Gly Gln Asn Phe Leu Ser Glu Lys Asn Lys
1175                1180                1185

Val Val Val Gly Lys Gly Glu Phe Thr Lys Asp Val Gly Leu Lys
1190                1195                1200

Glu Met Val Phe Pro Ser Ser Arg Asn Leu Phe Leu Thr Asn Leu
1205                1210                1215

Asp Asn Leu His Glu Asn Asn Thr His Asn Gln Glu Lys Lys Ile
1220                1225                1230

Gln Glu Glu Ile Glu Lys Lys Glu Thr Leu Ile Gln Glu Asn Val
1235                1240                1245

Val Leu Pro Gln Ile His Thr Val Thr Gly Thr Lys Asn Phe Met
1250                1255                1260

Lys Asn Leu Phe Leu Leu Ser Thr Arg Gln Asn Val Glu Gly Ser
1265                1270                1275

Tyr Asp Gly Ala Tyr Ala Pro Val Leu Gln Asp Phe Arg Ser Leu
1280                1285                1290

Asn Asp Ser Thr Asn Arg Thr Lys Lys His Thr Ala His Phe Ser
1295                1300                1305

Lys Lys Gly Glu Glu Glu Asn Leu Glu Gly Leu Gly Asn Gln Thr
1310                1315                1320

Lys Gln Ile Val Glu Lys Tyr Ala Cys Thr Thr Arg Ile Ser Pro
1325                1330                1335

Asn Thr Ser Gln Gln Asn Phe Val Thr Gln Arg Ser Lys Arg Ala
1340                1345                1350

Leu Lys Gln Phe Arg Leu Pro Leu Glu Glu Thr Glu Leu Glu Lys
1355                1360                1365

Arg Ile Ile Val Asp Asp Thr Ser Thr Gln Trp Ser Lys Asn Met
1370                1375                1380

Lys His Leu Thr Pro Ser Thr Leu Thr Gln Ile Asp Tyr Asn Glu
1385                1390                1395

Lys Glu Lys Gly Ala Ile Thr Gln Ser Pro Leu Ser Asp Cys Leu
1400                1405                1410

Thr Arg Ser Glu Ser Ile Pro Gln Ala Asn Arg Ser Pro Leu Pro
1415                1420                1425

Ile Ala Lys Val Ser Ser Phe Pro Ser Ile Arg Pro Ile Tyr Leu
1430                1435                1440

Thr Arg Val Leu Phe Gln Asp Asn Ser Ser Asn Leu Pro Ala Ala
1445                1450                1455

Ser Tyr Arg Lys Lys Asp Ser Gly Val Gln Glu Ser Ser His Phe
1460                1465                1470

Leu Gln Gly Ala Lys Lys Asn Asn Leu Ser Leu Ala Ile Leu Thr
1475                1480                1485

Leu Glu Met Thr Gly Asp Gln Arg Glu Val Gly Ser Leu Gly Thr
1490                1495                1500

Ser Ala Thr Asn Ser Val Thr Tyr Lys Lys Val Glu Asn Thr Val
1505                1510                1515

Leu Pro Lys Pro Asp Leu Pro Lys Thr Ser Gly Lys Val Glu Leu
1520                1525                1530
```

-continued

Leu Pro Lys Val His Ile Tyr Gln Lys Asp Leu Phe Pro Thr Glu
1535                1540                1545

Thr Ser Asn Gly Ser Pro Gly His Leu Asp Leu Val Glu Gly Ser
1550                1555                1560

Leu Leu Gln Gly Thr Glu Gly Ala Ile Lys Trp Asn Glu Ala Asn
1565                1570                1575

Arg Pro Gly Lys Val Pro Phe Leu Arg Val Ala Thr Glu Ser Ser
1580                1585                1590

Ala Lys Thr Pro Ser Lys Leu Leu Asp Pro Leu Ala Trp Asp Asn
1595                1600                1605

His Tyr Gly Thr Gln Ile Pro Lys Glu Glu Trp Lys Ser Gln Glu
1610                1615                1620

Lys Ser Pro Glu Lys Thr Ala Phe Lys Lys Lys Asp Thr Ile Leu
1625                1630                1635

Ser Leu Asn Ala Cys Glu Ser Asn His Ala Ile Ala Ala Ile Asn
1640                1645                1650

Glu Gly Gln Asn Lys Pro Glu Ile Glu Val Thr Trp Ala Lys Gln
1655                1660                1665

Gly Arg Thr Glu Arg Leu Cys Ser Gln Asn Pro Pro Val Leu Lys
1670                1675                1680

Arg His Gln Arg Glu Ile Thr Arg Thr Thr Leu Gln Ser Asp Gln
1685                1690                1695

Glu Glu Ile Asp Tyr Asp Asp Thr Ile Ser Val Glu Met Lys Lys
1700                1705                1710

Glu Asp Phe Asp Ile Tyr Asp Glu Asp Glu Asn Gln Ser Pro Arg
1715                1720                1725

Ser Phe Gln Lys Lys Thr Arg His Tyr Phe Ile Ala Ala Val Glu
1730                1735                1740

Arg Leu Trp Asp Tyr Gly Met Ser Ser Ser Pro His Val Leu Arg
1745                1750                1755

Asn Arg Ala Gln Ser Gly Ser Val Pro Gln Phe Lys Lys Val Val
1760                1765                1770

Phe Gln Glu Phe Thr Asp Gly Ser Phe Thr Gln Pro Leu Tyr Arg
1775                1780                1785

Gly Glu Leu Asn Glu His Leu Gly Leu Leu Gly Pro Tyr Ile Arg
1790                1795                1800

Ala Glu Val Glu Asp Asn Ile Met Val Thr Phe Arg Asn Gln Ala
1805                1810                1815

Ser Arg Pro Tyr Ser Phe Tyr Ser Ser Leu Ile Ser Tyr Glu Glu
1820                1825                1830

Asp Gln Arg Gln Gly Ala Glu Pro Arg Lys Asn Phe Val Lys Pro
1835                1840                1845

Asn Glu Thr Lys Thr Tyr Phe Trp Lys Val Gln His His Met Ala
1850                1855                1860

Pro Thr Lys Asp Glu Phe Asp Cys Lys Ala Trp Ala Tyr Phe Ser
1865                1870                1875

Asp Val Asp Leu Glu Lys Asp Val His Ser Gly Leu Ile Gly Pro
1880                1885                1890

Leu Leu Val Cys His Thr Asn Thr Leu Asn Pro Ala His Gly Arg
1895                1900                1905

Gln Val Thr Val Gln Glu Phe Ala Leu Phe Phe Thr Ile Phe Asp
1910                1915                1920

Glu Thr Lys Ser Trp Tyr Phe Thr Glu Asn Met Glu Arg Asn Cys

```
            1925                1930                1935

Arg Ala Pro Ser Asn Ile Gln Met Glu Asp Pro Thr Phe Lys Glu
        1940                1945                1950

Asn Tyr Arg Phe His Ala Ile Asn Gly Tyr Ile Met Asp Thr Leu
        1955                1960                1965

Phe Gly Leu Val Met Ala Gln Asp Gln Arg Ile Arg Trp Tyr Leu
        1970                1975                1980

Leu Ser Met Gly Ser Asn Glu Asn Ile His Ser Ile His Phe Ser
        1985                1990                1995

Gly His Val Phe Thr Val Arg Lys Lys Glu Glu Tyr Lys Met Ala
        2000                2005                2010

Leu Tyr Asn Leu Tyr Pro Gly Val Phe Glu Thr Val Glu Met Leu
        2015                2020                2025

Pro Ser Lys Ala Gly Ile Trp Arg Val Glu Cys Leu Ile Gly Glu
        2030                2035                2040

His Leu His Ala Gly Met Ser Thr Leu Phe Leu Val Tyr Ser Asn
        2045                2050                2055

Lys Cys Gln Thr Pro Leu Gly Met Ala Ser Gly His Ile Arg Asp
        2060                2065                2070

Phe Gln Ile Thr Ala Ser Gly Gln Tyr Gly Gln Trp Ala Pro Lys
        2075                2080                2085

Leu Ala Arg Leu His Tyr Ser Gly Ser Ile Asn Ala Trp Ser Thr
        2090                2095                2100

Lys Glu Pro Phe Ser Trp Ile Lys Val Asp Leu Leu Ala Pro Met
        2105                2110                2115

Ile Ile His Gly Ile Lys Thr Gln Gly Ala Arg Gln Lys Phe Ser
        2120                2125                2130

Ser Leu Tyr Ile Ser Gln Phe Ile Ile Met Tyr Ser Leu Asp Gly
        2135                2140                2145

Lys Lys Trp Gln Thr Tyr Arg Gly Asn Ser Thr Gly Thr Leu Met
        2150                2155                2160

Val Phe Phe Gly Asn Val Asp Ser Ser Gly Ile Lys His Asn Ile
        2165                2170                2175

Phe Asn Pro Pro Ile Ile Ala Arg Tyr Ile Arg Leu His Pro Thr
        2180                2185                2190

His Tyr Ser Ile Arg Ser Thr Leu Arg Met Glu Leu Met Gly Cys
        2195                2200                2205

Asp Leu Asn Ser Cys Ser Met Pro Leu Gly Met Glu Ser Lys Ala
        2210                2215                2220

Ile Ser Asp Ala Gln Ile Thr Ala Ser Ser Tyr Phe Thr Asn Met
        2225                2230                2235

Phe Ala Thr Trp Ser Pro Ser Lys Ala Arg Leu His Leu Gln Gly
        2240                2245                2250

Arg Ser Asn Ala Trp Arg Pro Gln Val Asn Asn Pro Lys Glu Trp
        2255                2260                2265

Leu Gln Val Asp Phe Gln Lys Thr Met Lys Val Thr Gly Val Thr
        2270                2275                2280

Thr Gln Gly Val Lys Ser Leu Leu Thr Ser Met Tyr Val Lys Glu
        2285                2290                2295

Phe Leu Ile Ser Ser Ser Gln Asp Gly His Gln Trp Thr Leu Phe
        2300                2305                2310

Phe Gln Asn Gly Lys Val Lys Val Phe Gln Gly Asn Gln Asp Ser
        2315                2320                2325
```

```
Phe Thr Pro Val Val Asn Ser Leu Asp Pro Pro Leu Leu Thr Arg
    2330                2335                2340

Tyr Leu Arg Ile His Pro Gln Ser Trp Val His Gln Ile Ala Leu
    2345                2350                2355

Arg Met Glu Val Leu Gly Cys Glu Ala Gln Asp Leu Tyr
    2360                2365                2370

<210> SEQ ID NO 137
<211> LENGTH: 628
<212> TYPE: PRT
<213> ORGANISM: Artificial Sequence
<220> FEATURE:
<223> OTHER INFORMATION: Synthetic construct

<400> SEQUENCE: 137

Met Val Pro Cys Thr Leu Leu Leu Leu Ala Ala Leu Ala Pro
1               5                   10                  15

Thr Gln Thr Arg Ala Glu Asn Lys Gly Gly Asp Gln Gly Pro Pro Leu
            20                  25                  30

Met Thr Asp Gly Gly Gly Pro Gly Pro Gly Pro Leu Ser Ser Ser
            35                  40                  45

Leu Gly Leu Ala Leu Leu Leu Leu Leu Ala Leu Leu Phe Trp Leu
50                  55                  60

Tyr Ile Val Met Ser Asp Trp Thr Gly Gly Ala Leu Leu Val Leu Tyr
65                  70                  75                  80

Ser Phe Ala Leu Met Leu Ile Ile Ile Leu Ile Ile Phe Ile Phe
                85                  90                  95

Arg Arg Asp Leu Leu Cys Pro Leu Gly Ala Leu Cys Ile Leu Leu Leu
                100                 105                 110

Met Ile Thr Leu Leu Ile Ala Leu Trp Asn Leu His Gly Gln Ala
            115                 120                 125

Leu Phe Leu Gly Ile Val Leu Phe Ile Phe Gly Cys Leu Leu Val Leu
                130                 135                 140

Gly Ile Trp Ile Tyr Leu Leu Glu Met Leu Trp Arg Leu Gly Ala Thr
145                 150                 155                 160

Ile Trp Gln Leu Leu Ala Phe Phe Leu Ala Phe Phe Leu Asp Leu Ile
                165                 170                 175

Leu Leu Ile Ile Ala Leu Tyr Leu Gln Gln Asn Trp Trp Thr Leu Leu
                180                 185                 190

Val Asp Leu Leu Trp Leu Leu Leu Phe Leu Ala Ile Leu Ile Trp Met
                195                 200                 205

Tyr Tyr His Gly Gln Arg His Ser Asp Glu His His Asp Asp Ser
210                 215                 220

Leu Pro His Gly Pro Gly Pro Gly Gly Pro Arg His Arg Asp Gly Val
225                 230                 235                 240

Arg Arg Pro Gln Lys Arg Pro Ser Cys Ile Gly Cys Lys Gly Pro Gly
                245                 250                 255

Pro Gly Ile Ala Glu Gly Leu Arg Ala Leu Leu Ala Arg Ser His Val
                260                 265                 270

Glu Arg Thr Gly Pro Gly Pro Gly Ala Gly Val Phe Val Tyr Gly Gly
                275                 280                 285

Ser Lys Thr Ser Leu Tyr Asn Leu Arg Arg Gly Thr Ala Leu Ala Ile
            290                 295                 300

Gly Pro Gly Pro Gly Thr Ser Leu Tyr Asn Leu Arg Arg Gly Thr Ala
305                 310                 315                 320
```

Leu Ala Ile Pro Gln Cys Arg Leu Thr Pro Leu Ser Arg Leu Gly Pro
            325                 330                 335

Gly Pro Gly Arg Glu Ser Ile Val Cys Tyr Phe Met Val Phe Leu Gln
            340                 345                 350

Thr His Ile Phe Ala Glu Val Leu Gly Pro Gly Pro Gly Ala Ile Lys
            355                 360                 365

Asp Leu Val Met Thr Lys Pro Ala Pro Thr Cys Asn Ile Arg Val Gly
        370                 375                 380

Pro Gly Pro Gly Gly Pro Gln Arg Arg Gly Gly Asp Asn His Gly Arg
385                 390                 395                 400

Gly Arg Asp Lys Thr His Thr Cys Pro Pro Cys Pro Ala Pro Glu Leu
            405                 410                 415

Leu Gly Gly Pro Ser Val Phe Leu Phe Pro Pro Lys Pro Lys Asp Thr
            420                 425                 430

Leu Met Ile Ser Arg Thr Pro Glu Val Thr Cys Val Val Val Asp Val
            435                 440                 445

Ser His Glu Asp Pro Glu Val Lys Phe Asn Trp Tyr Val Asp Gly Val
        450                 455                 460

Glu Val His Asn Ala Lys Thr Lys Pro Arg Glu Glu Gln Asn Asn Ser
465                 470                 475                 480

Thr Asn Arg Ala Val Ser Val Leu Thr Val Leu His Gln Asp Trp Leu
            485                 490                 495

Asn Gly Lys Glu Tyr Lys Cys Lys Val Ser Asn Lys Ala Leu Pro Ala
            500                 505                 510

Pro Ile Glu Lys Thr Ile Ser Lys Ala Lys Gly Gln Pro Arg Glu Pro
            515                 520                 525

Gln Val Tyr Thr Leu Pro Pro Ser Arg Asp Glu Leu Thr Lys Asn Gln
        530                 535                 540

Val Ser Leu Thr Cys Leu Val Lys Gly Phe Tyr Pro Ser Asp Ile Ala
545                 550                 555                 560

Val Glu Trp Glu Ser Asn Gly Gln Pro Glu Asn Asn Tyr Lys Thr Thr
            565                 570                 575

Pro Pro Val Leu Asp Ser Asp Gly Ser Phe Phe Leu Tyr Ser Lys Leu
            580                 585                 590

Thr Val Asp Lys Ser Arg Trp Gln Gln Gly Asn Val Phe Ser Cys Ser
            595                 600                 605

Val Met His Glu Ala Leu His Asn His Tyr Thr Gln Lys Ser Leu Ser
        610                 615                 620

Leu Ser Pro Gly
625

<210> SEQ ID NO 138
<211> LENGTH: 220
<212> TYPE: PRT
<213> ORGANISM: Artificial Sequence
<220> FEATURE:
<223> OTHER INFORMATION: Synthetic construct

<400> SEQUENCE: 138

Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

-continued

```
Glu Asp Pro Glu Val Lys Phe Asn Trp Tyr Val Asp Gly Val Glu Val
    50              55                  60

His Asn Ala Lys Thr Lys Pro Arg Glu Glu Gln Gln Asp Trp Leu Asn
65              70                  75                       80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
                100                 105                 110

Val Tyr Thr Leu Pro Pro Ser Arg Asp Glu Leu Thr Glu Glu Gln Tyr
            115                 120                 125

Gln Ser Thr Tyr Arg Lys Asn Gln Val Ser Leu Thr Cys Leu Val Lys
    130                 135                 140

Gly Phe Tyr Pro Ser Asp Ile Ala Val Glu Trp Glu Ser Asn Gly Gln
145                 150                 155                 160

Pro Glu Asn Asn Tyr Lys Thr Thr Pro Pro Val Leu Asp Ser Asp Gly
                165                 170                 175

Ser Phe Phe Leu Tyr Ser Lys Leu Thr Val Asp Lys Ser Arg Trp Gln
            180                 185                 190

Gln Gly Asn Val Phe Ser Cys Ser Val Met His Glu Ala Leu His Asn
        195                 200                 205

His Tyr Thr Gln Lys Ser Leu Ser Leu Ser Pro Gly
    210                 215                 220
```

REGULATORY T CELL EPITOPES

CROSS-REFERENCE TO RELATED APPLICATION

This application depends from and claims priority to U.S. Provisional Application No. 63/000,630 filed Mar. 27, 2020, and U.S. Provisional Application No. 63/077,253 filed Sep. 11, 2020, the entire contents of each of which are incorporated herein by reference in their entirety.

SEQUENCE LISTING

The instant application contains a Sequence Listing which has been submitted in ASCII format via EFS-Web and is hereby incorporated by reference in its entirety. Said ASCII copy, created on Mar. 24, 2021, is named EPV0007_ST25.txt and is 70 KB in size.

FIELD

The present disclosure generally relates to a novel class of regulatory T cell epitopes (termed "Tregitopes"). The present disclosure provides Tregitope compounds and compositions, including one or more of e.g., polypeptides as disclosed herein (which may be termed herein as "Treg activating regulatory T-cell epitope", "Tregitope", "Tregitope peptide", or "T-cell epitope polypeptide"), including polypeptides having a sequence comprising, consisting of, or consisting essentially of one or more of SEQ ID NOS: 1-124 (and/or fragments and variants thereof), and optionally 1 to 12 additional amino acids distributed in any ratio on the N-terminus and/or C-terminus of the polypeptide of SEQ ID NOS: 1-124 as disclosed herein; concatemeric peptides as disclosed herein; nucleic acids, chimeric or fusion polypeptide compositions as disclosed herein; nucleic acids as disclosed herein, expression cassettes, plasmids, expression vectors, recombinant viruses, or cells as disclosed herein; and/or pharmaceutical compositions or formulations as disclosed herein, as well as methods for their preparation and use of the same.

BACKGROUND

Artificial induction of tolerance to self or to foreign antigens is the goal of therapy for autoimmunity, transplantation, allergy and other diseases. Immune response targeting autologous and non-autologous therapeutic proteins often limits clinical efficacy. Immune-modulating treatments, inducing tolerance to therapeutic proteins compositions, may reduce the formation of anti-drug antibodies (ADA), which improve clinical outcomes. Until recently, therapeutic tolerance induction relied on broad-based immune cell depleting therapies. These broad-based approaches weaken the immune system in general and leave many subjects vulnerable to opportunistic infections, autoimmune attack, and cancer. There is a need in the art for less aggressive and more targeted approaches to the induction of immune tolerance.

Immune tolerance is regulated by a complex interplay between antigen presenting cells (APC), T cells, B cells, cytokines, chemokines, and surface receptors. Initial self/non-self discrimination occurs in the thymus during neonatal development where medullary epithelial cells express specific self-protein epitopes to immature T cells. T cells recognizing self-antigens with high affinity are deleted, but autoreactive T cells with moderate affinity sometimes avoid deletion and can be converted to 'natural' regulatory T cells ($T_{Reg}$) cells. These natural $T_{Reg}$ cells are exported to the periphery and help to control latent autoimmune response.

A second form of tolerance develops in the periphery. In this case activated T cells are converted to an 'adaptive' $T_{Reg}$ phenotype through the action of certain immune-suppressive cytokines and chemokines such as IL-10, TGF-β, and CCL19. The possible roles for these 'adaptive' $T_{Reg}$ cells include dampening immune response following the successful clearance of an invading pathogen, controlling excessive inflammation caused by an allergic reaction, controlling excessive inflammation caused by low level or chronic infection, or possibly controlling inflammatory response targeting beneficial symbiotic bacteria.

Naturally occurring $T_{Regs}$ (including both natural $T_{Regs}$ and adaptive $T_{Regs}$) are a critical component of immune regulation in the periphery. For example, upon activation of natural $T_{Regs}$ through their TCR, natural $T_{Regs}$ express immune-modulating cytokines and chemokines. Activated natural $T_{Regs}$ may suppress nearby effector T cells through contact-dependent and independent mechanisms. In addition, the cytokines released by these cells including, but not limited to, IL-10 and TGF-β, are capable of inducing antigen-specific adaptive $T_{Regs}$. Despite extensive efforts, with few exceptions, the antigen specificity of natural $T_{Regs}$, and more importantly natural $T_{Regs}$ circulating in clinically significant volumes, is still unknown.

There is need in the art for the identification of regulatory T cell epitopes contained in common autologous proteins ("Tregitopes"), compositions containing such Tregitopes, and for methods related to their preparation and use.

SUMMARY

Accordingly, the present disclosure provides novel, therapeutic regulatory T cell epitope compounds and compositions. Such compositions include one or more of e.g., polypeptides as disclosed herein (which may be termed herein as "Treg activating regulatory T-cell epitope", "Tregitope", "Tregitope peptide", or "T-cell epitope polypeptide"), including polypeptides having a sequence comprising, consisting of, or consisting essentially of one or more of SEQ ID NOS: 1-124 (and/or fragments and variants thereof), and optionally 1 to 12 additional amino acids distributed in any ratio on the N-terminus and/or C-terminus of the polypeptide of SEQ ID NOS: 1-124 as disclosed herein; concatemeric peptides as disclosed herein; nucleic acids, chimeric or fusion polypeptide compositions as disclosed herein; nucleic acids as disclosed herein, expression cassettes, plasmids, expression vectors, recombinant viruses, or cells as disclosed herein; expression cassettes, plasmids, expression vectors, recombinant viruses, or cells as disclosed herein; chimeric or fusion polypeptide compositions as disclosed herein; and/or pharmaceutical compositions or formulations as disclosed herein, as well as methods for their preparation and use of the same, e.g., to suppress an immune response in the body or more specifically to suppress an immune response in the body caused by the administration of a therapeutic agent to treat a medical condition.

The selective engagement and activation of naturally occurring $T_{Regs}$ (in aspects, including natural $T_{Regs}$ and/or adaptive $T_{Regs}$) through the use of Tregitope compounds and compositions and Tregitope-antigen compounds and compositions as disclosed herein is therapeutically valuable as a means of treatment for any disease or condition marked by the presence of an unwanted immune response. Examples of such an unwanted immune response include the following: autoimmune disease such as type 1 diabetes, MS, Lupus, and RA; transplant related disorders such as Graft vs. Host disease (GVHD) and Host vs. Graft disease (HVGD); allergic reactions; immune rejection of biologic medicines such as monoclonal antibodies; immune response targeting replacement proteins; immune response targeting therapeutic toxins such as Botulinum toxin; and immune response to infectious disease whether acute or chronic. In aspects, the present disclosure harnesses the functions of naturally occurring $T_{Regs}$ (in aspects, including natural $T_{Regs}$ and/or adaptive $T_{Regs}$), and in particular aspects, those cells that already regulate immune responses to foreign and self-proteins in the periphery (pre-existing or natural $T_{Reg}$). In aspects, a Tregitope composition of the present disclosure may be either covalently bound, non-covalently bound, or in admixture with a specific target antigen.

In aspects, a Tregitope compound or composition of the present disclosure includes one or more peptides or polypeptides a disclosed herein. In aspects, the present disclosure is directed to a peptide or polypeptide having an amino acid sequence comprising, consisting of, or consisting essentially of one or more of SEQ ID NOS: 1-124, or fragments and variants thereof. The phrase "consisting essentially of" is intended to mean that a polypeptide according to the present disclosure, in addition to the sequence according to any of SEQ ID NOS: 1-124 or a fragment or variant thereof, contains additional amino acids or residues that may be present at either terminus of the peptide and/or on a side chain that are not necessarily forming part of the peptide that functions as an WIC ligand and provided they do not substantially impair the activity of the peptide to function as a Tregitope. The polypeptides of the present disclosure may be isolated, synthetic, and/or recombinant, and may comprise post-transcriptional modifications such as glycosylation, added chemical groups, etc. In aspects, the peptides or polypeptides can be either in neutral (uncharged) or salt forms, and may be either free of or include modifications such as glycosylation, side chain oxidation, or phosphorylation. In certain aspects, the Tregitopes can be capped with an N-terminal acetyl and/or C-terminal amino group.

In aspects, the instant disclosure is directed to a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124. In aspects, the instant disclosure is directed to a peptide or polypeptide having a core amino acid sequence comprising, consisting of, or consisting essentially of one or more peptides or polypeptides having an amino acid sequence of SEQ ID NOS: 1-124 (and/or fragments and variants thereof), and optionally having extensions of 1 to 12 amino acids on the C-terminal and/or the N-terminal of the core amino acid sequence, wherein the overall number of these flanking amino acids is 1 to 12, 1 to 3, 2 to 4, 3 to 6, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to 10, or 10 to 12, wherein the flanking amino acids can be distributed in any ratio to the C-terminus and the N-terminus (for example all flanking amino acids can be added to one terminus, or the amino acids can be added equally to both termini or in any other ratio). In aspects, the instant disclosure is directed to a peptide or polypeptide having a core sequence comprising, consisting of, or consisting essentially of one or more peptides or polypeptides having an amino acid sequence of SEQ ID NOS: 1-124 (and/or fragments and variants thereof), optionally with extensions of 1 to 12 amino acids on the C-terminal and/or the N-terminal, wherein the overall number of these flanking amino acids is 1 to 12, 1 to 3, 2 to 4, 3 to 6, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to 10, or 10 to 12, wherein the flanking amino acids can be distributed in any ratio to the C-terminus and the N-terminus (for example all flanking amino acids can be added to one terminus, or the amino acids can be added equally to both termini or in any other ratio), provided that the polypeptide with the flanking amino acids is still able to bind to a same HLA molecule (i.e., retain MEW binding propensity) as said polypeptide core sequence without said flanking amino acids. In aspects, said polypeptide with the flanking amino acids is still able to bind to a same HLA molecule (i.e., retain MHC binding propensity) and/or retain the same TCR specificity as said polypeptide core sequence without said flanking amino acids. In aspects, said polypeptide with the flanking amino acids is still able to bind to a same HLA molecule (i.e., retain MEW binding propensity) and/or retain the same TCR specificity, and/or retain Tregitope activity, as said polypeptide core sequence without said flanking amino acids. In aspects, said flanking amino acid sequences are those that also flank the peptides or polypeptides included therein in a naturally occurring protein. In aspects, said flanking amino acid sequences as described herein may serve as a MHC stabilizing region. In aspects, the use of a longer peptide may allow endogenous processing by patient cells and may lead to more effective antigen presentation and induction of T cell responses. In aspects, the extension(s) may serve to improve the biochemical properties of the peptides or polypeptides (e.g., but not limited to, solubility or stability) or to improve the likelihood for efficient proteasomal processing of the peptide. In aspects, the polypeptides of the present disclosure may be isolated, synthetic, and/or recombinant, and may comprise post-transcriptional modifications such as glycosylation, added chemical groups, etc. In aspects, the peptides or polypeptides can be either in neutral (uncharged) or salt forms, and may be either free of or include modifications such as glycosylation, side chain oxidation, or phosphorylation. In certain aspects, the peptides or polypeptides of the instant disclosure can be capped with an n-terminal acetyl and/or c-terminal amino group.

In aspects, the present disclosure is directed to a concatemeric polypeptide or peptide that comprises at one or more of the instantly-disclosed polypeptides or peptides (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) linked, fused, or joined together (e.g., fused in-frame, chemically linked, or otherwise bound) to an additional peptide or polypeptide. Such additional peptide or polypeptide may be one or more of the instantly disclosed polypeptides or peptides, or may be an additional peptide or polypeptide of interest. In aspects a concatemeric peptide is composed of 1 or more, 2 or more, 3 or more, 4 or more, 5 or more 6 or more 7 or more, 8 or more, 9 or more of the instantly disclosed peptides or polypeptides. In other aspects, the concatemeric peptides or polypeptides include 1000 or more, 1000 or less, 900 or less, 500 or less, 100 or less, or less, 50 or less, 40 or less, 30 or less, 20 or less, or 10 or less peptide epitopes. In yet other embodiments, a concatemeric peptide has 3-100, 5-100, 10-100, 15-100, 20-100, 25-100, 30-100, 40-100, 45-100, 50-100, 55-100, 60-100, 65-100, 70-100, 75-100, 80-100, 90-100, 5-50, 15-50, 20-50, 25-50, 30-50, 35-50, 40-50, 45-50, 100-150, 100-200, 100-300, 100-400, 100-500, 50-500, 50-800, 50-1,000, or 100-1,000 of the instantly-disclosed peptides or polypeptides linked, fused, or joined together. Each peptide or polypeptide of the concatemeric polypeptide may optionally have one or more linkers, which may optionally be cleavage sensitive sites, adjacent to their N-terminal and/or C-terminal end. In such a concatemeric peptide, two or more of the peptide epitopes may have a cleavage sensitive site between them. Alternatively, two or more of the peptide epitopes may be connected directly to one another or through a linker that is not a cleavage sensitive site. In aspects, the instantly-disclosed concatemeric polypeptide or peptide sequences do not correspond to a naturally occurring sequence, i.e., each of the one or more of the instantly-disclosed polypeptides or peptides (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) are linked, fused, or joined together (e.g., fused in-frame, chemically-linked, or otherwise bound) to an additional peptide or polypeptide (which may be one or more of the instantly-disclosed peptides) in such a fashion such that the overall concatemeric polypeptide does not correspond to a naturally occurring IgG sequence. In aspects, the concatemeric polypeptides of the present disclosure may be isolated, synthetic, and/or recombinant, and may comprise post-transcriptional modifications such as glycosylation, added chemical groups, etc. In aspects, the concatemeric polypeptides can be either in neutral (uncharged) or salt forms, and may be either free of or include modifications such as glycosylation, side chain oxidation, or phosphorylation. In certain aspects, the concatemeric polypeptides of the instant disclosure can be capped with an n-terminal acetyl and/or c-terminal amino group.

In aspects, one or more peptides or polypeptides or concatemeric polypeptides of the instant disclosure (e.g., but not limited to, a peptide or polypeptide comprising, consisting, or consisting essentially of an amino acid sequence of SEQ ID NOS. 1-124 (and/or fragments or variants thereof), and optionally 1 to 12 additional amino acids distributed in any ratio on the N terminus and/or C-terminus of the polypeptide of SEQ ID NOS. 1-124) may be joined to, linked to (e.g., fused in-frame, chemically linked, or otherwise bound), and/or inserted into a heterologous polypeptide. In aspects, the one or more peptides or polypeptides or concatemeric polypeptides of the instant disclosure may be joined to, linked to (e.g., fused in-frame, chemically linked, or otherwise bound), and/or inserted into a heterologous polypeptide as a whole, although it may be made up from a joined to, linked to (e.g., fused in-frame, chemically linked, or otherwise bound), and/or inserted amino acid sequence, together with flanking amino acids of the heterologous polypeptide.

In aspects, the present disclosure is directed to polypeptide having a sequence comprising one or more of SEQ ID NOS: 1-124 (and fragments or variants thereof), and optionally 1 to 12 additional amino acids distributed in any ratio on the N terminus and/or C-terminus of the polypeptide of SEQ ID NOS: 1-124, wherein said one or more of SEQ ID NOS: 1-124 is not naturally included in the polypeptide and/or said one or more of SEQ ID NOS: 1-124 is not located at its natural position in the polypeptide. In aspects, one or more Tregitopes of the instant disclosure (which, in aspects, may be an isolated, synthetic, or recombinant) having a sequence comprising one or more of SEQ ID NOS: 1-124 (and fragments or variants thereof), and optionally 1 to 12 additional amino acids distributed in any ratio on the N terminus and/or C-terminus of the polypeptide of SEQ ID NOS: 1-124, may also be fused to or inserted internally within (e.g., but not limited to, site directed mutagenesis or other recombinant techniques) an antibody or fragment thereof, such as in instances where the Tregitope is not located in its natural position within the antibody or fragment thereof or wherein the antibody or fragment thereof is missing such a Tregitope (e.g., if a particular antibody or fragment thereof has a mutated or missing corresponding section). In aspects, such polypeptides of the present disclosure, which are further described below, may be isolated, synthetic, and/or recombinant, and may comprise post-transcriptional modifications such as glycosylation, added chemical groups, etc. In aspects, such polypeptides can be either in neutral (uncharged) or salt forms, and may be either free of or include modifications such as glycosylation, side chain oxidation, or phosphorylation. In certain aspects, such polypeptides can be capped with an n-terminal acetyl and/or c-terminal amino group.

In aspects, a polypeptide has a sequence comprising one or more of SEQ ID NOS: 1, 3-8, 14-15, 16-28, 42-74, and 111-124 (and fragments or variants thereof), and optionally 1 to 12 additional amino acids distributed in any ratio on the N terminus and/or C-terminus of the polypeptide of SEQ ID NOS: 1, 3-8, 14-15, 16-28, 42-74, and 111-124, wherein said polypeptide does not comprise an antibody heavy chain variable region. In aspects, if a polypeptide does comprise an antibody heavy chain variable region then said one or more of SEQ ID NOS: 1, 3-8, 14-15, 16-28, 42-74, and 111-124 (and fragments or variants thereof), and optionally 1 to 12 additional amino acids distributed in any ratio on the N terminus and/or C-terminus of the polypeptide of SEQ ID NOS: 1, 3-8, 14-15, 16-28, 42-74, and 111-124, is not located in its natural position in the antibody heavy chain variable region. In aspects, one or more Tregitopes having a sequence comprising SEQ ID NOS: 1, 3-8, 14-15, 16-28, 42-74, and 111-124 (and fragments or variants thereof), and optionally 1 to 12 additional amino acids distributed in any ratio on the N terminus and/or C-terminus of the polypeptide of SEQ ID NOS: 1, 3-8, 14-15, 16-28, 42-74, and 111-124, may also be fused to or inserted internally within (e.g., but not limited to, using immune engineering techniques such as but not limited to, site directed mutagenesis or other recombinant techniques) an antibody heavy chain variable region or fragment thereof, such as in instances where the Tregitope is not located in its natural position within the antibody heavy chain variable region or fragment thereof or where the antibody heavy chain variable region or fragment thereof is missing such a Tregitope (e.g., if a particular antibody heavy chain variable region or fragment thereof has a mutated or missing corresponding section).

In aspects, a polypeptide has a sequence comprising one or more of SEQ ID NOS: 2, 9-11, 29-41, and 75-100, (and fragments or variants thereof), and optionally 1 to 12 additional amino acids distributed in any ratio on the N terminus and/or C-terminus of the polypeptide of SEQ ID NOS: 2, 9-11, 29-41, and 75-100, wherein said polypeptide does not comprise an antibody heavy chain constant region. In aspects, if a polypeptide does comprise an antibody heavy chain constant region then said one or more of SEQ ID NOS: 2, 9-11, 29-41, and 75-100 (and fragments or variants thereof), and optionally 1 to 12 additional amino acids distributed in any ratio on the N terminus and/or C-terminus of the polypeptide of SEQ ID NOS: 2, 9-11, 29-41, and 75-100, is not located in its natural position of the antibody heavy chain constant region. In aspects, one or more Tregitopes having a sequence comprising SEQ ID NOS: 2, 9-11, 29-41, and 75-100 (and fragments or variants thereof), and optionally 1 to 12 additional amino acids distributed in any ratio on the N terminus and/or C-terminus of the polypeptide of SEQ ID NOS: 2, 9-11, 29-41, and 75-100, may also be fused to or inserted internally within (e.g., but not limited to, using immune engineering techniques such as but not limited to, site directed mutagenesis or other recombinant techniques) an antibody heavy chain constant region or fragment thereof, such as in instances where the Tregitope is not located in its natural position within the antibody heavy chain constant region or fragment thereof or where the antibody heavy chain constant region or fragment thereof is missing such a Tregitope (e.g., if a particular antibody heavy chain constant region or fragment thereof has a mutated or missing corresponding section).

In aspects, a polypeptide (which may be an isolated, synthetic, or recombinant) has a sequence comprising SEQ ID NO: 12 (and fragments or variants thereof), and optionally 1 to 12 additional amino acids distributed in any ratio on the N terminus and/or C-terminus of the polypeptide of SEQ ID NO: 12, wherein said polypeptide does not comprise an antibody light chain variable region. In aspects, if a polypeptide does comprise an antibody light chain variable region, then said SEQ ID NO: 12 (and fragments or variants thereof), and optionally 1 to 12 additional amino acids distributed in any ratio on the N terminus and/or C-terminus of the polypeptide of SEQ ID NO: 12, is not located at its natural position of the antibody light chain variable region. In aspects, one or more Tregitopes having a sequence comprising SEQ ID NO: 12 (and fragments or variants thereof), and optionally 1 to 12 additional amino acids distributed in any ratio on the N terminus and/or C-terminus of the polypeptide of SEQ ID NO: 12, may also be fused to or inserted internally within (e.g., but not limited to, using immune engineering techniques such as site directed mutagenesis or other recombinant techniques) an antibody light chain variable region or fragment thereof, such as in instances where the Tregitope is not located in its natural position within the antibody light chain variable region or fragment thereof or where the antibody light chain variable region or fragment thereof is missing such a Tregitope (e.g., if a particular antibody light chain variable region or fragment thereof has a mutated or missing corresponding section).

In aspects, a polypeptide (which may be an isolated, synthetic, or recombinant) has a sequence comprising one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, wherein said polypeptide does not comprise an antibody light chain constant region. In aspects, if a polypeptide does comprise an antibody light chain constant region, then said one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, is not located at its natural position of the antibody light chain constant region. In aspects, one or more Tregitopes having a sequence comprising one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, may also be fused to or inserted internally within (e.g., but not limited to, using immune engineering techniques such as site directed mutagenesis or other recombinant techniques) an antibody light chain constant region or fragment thereof, such as in instances where the Tregitope is not located in its natural position within the antibody light chain constant region or fragment thereof or where an antibody light chain constant region or fragment thereof is missing such a Tregitope (e.g., if a particular antibody light chain variable region or fragment thereof has a mutated or missing corresponding section).

In aspects, the present disclosure is directed to a chimeric or fusion polypeptide compound or composition (which in aspects may be isolated, synthetic, or recombinant) comprising one or more peptides, polypeptides, or concatemeric peptides of the present disclosure. In aspects, a chimeric or fusion polypeptide compound or composition of the present disclosure comprises one or more peptides, polypeptides, or concatemeric peptides of the present disclosure (e.g., a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) joined to, linked to (e.g., fused in-frame, chemically-linked, or otherwise bound), and/or inserted into a heterologous polypeptide. In aspects, the one or more peptides, polypeptides, and/or concatemeric peptides of the present disclosure may be inserted into the heterologous polypeptide, may be added to the C-terminus (with or without the use of linkers, as is known in the art), and/or added to the N-terminus (with or without the use of linkers, as is known in the art) of the heterologous polypeptide. In aspects of the instantly disclosed chimeric or fusion polypeptide compositions, the one or more peptides, polypeptides, and/or concatemeric peptides of the present disclosure may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, a chimeric or fusion polypeptide composition of the present disclosure comprises a peptide, polypeptide, and/or concatemeric peptide of the present disclosure, wherein said peptide, polypeptide, and/or concatemeric peptide having a sequence that is not naturally included in the heterologous polypeptide and/or is not located at its natural position in the heterologous polypeptide. In aspects of above-described chimeric or fusion polypeptide compositions, the chimeric or fusion polypeptides may be isolated, synthetic, or recombinant. In aspects of the instantly-disclosed chimeric or fusion polypeptide compositions, the heterologous polypeptide or polypeptide comprises a biologically active molecule. In aspects, the biologically active molecule is selected from the group consisting of an immunogenic molecule, a T cell epitope, a viral protein, and a bacterial protein. In aspects, the one or more of Tregitopes of the present disclosure can be joined or linked to (e.g., fused in-frame, chemically linked, or otherwise bound) to a small molecule, drug, or drug fragment. In aspects, the chimeric or fusion polypeptides can be in either neutral (uncharged) or salt forms, and may be either free of or include modifications such as glycosylation, side chain oxidation, or phosphorylation.

In aspects, the present disclosure is directed to a nucleic acid (e.g., DNA or RNA, including mRNA) encoding one or more peptides, polypeptides, concatemeric peptides, and/or chimeric or fusion polypeptides as described herein. For example, in aspects, the instant disclosure is directed to a nucleic acid encoding a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124. In aspects, the present disclosure is directed to a vector, such as an expression vector, comprising such a nucleic acid as described. In aspects, the present disclosure is directed to expression cassettes, plasmids, expression vectors, recombinant viruses, or cells comprising a nucleic acid as described herein. In aspects, the present disclosure is directed to a cell or vaccine comprising such a vector as described. In aspects, the present disclosure is directed to a cell comprising a vector of the present disclosure.

In aspects, the instant disclosure is directed to a pharmaceutical composition, the pharmaceutical composition comprising a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein) and a pharmaceutically acceptable carrier, excipient, and/or adjuvant. In aspects, the one or more nucleic acids encoding said peptides or polypeptides are DNA, RNA, or mRNA. In aspects of the above-described pharmaceutical compositions, the composition comprises at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least at least 30, at least 40, at least 50, at least 100, at least 200, at least 300, at least 400, at least 500, at least 600, at least 700, at least 800, at least 900, or at least 1000, peptides, polypeptides, and/or concatemeric peptides, as disclosed herein, including every value or range therebetween.

In aspects, the present disclosure is directed to a method of stimulating, inducing, and/or expanding regulatory T-cells (in aspects, naturally occurring Tae g s, including natural $T_{Regs}$ and/or adaptive Tae g s) in a subject in need thereof and/or suppressing an immune response in a subject in need thereof by administering to the subject a therapeutically effect amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein). In aspects, the subject is a human.

In aspects, the present disclosure is directed to a method of treating or preventing a medical condition in a subject in need thereof comprising administering a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein). In aspects, the medical condition is selected from the group consisting of: an allergy, an autoimmune disease, a transplant related disorder, graft versus host disease, a blood clotting disorder, an enzyme or protein deficiency disorder, a hemostatic disorder, cancer, infertility; and a viral, bacterial or parasitic infection. In another embodiment, the medical condition is hemophilia A, B, or C. In aspects, the subject is a human.

In aspects, the present disclosure is directed to a method of stimulating, inducing, and/or expanding regulatory T-cells (e.g., naturally occurring $T_{Regs}$ (in aspects, including natural $T_{Regs}$ and/or adaptive $T_{Regs}$)) to suppress an immune response in a subject in need thereof by administering to the subject a therapeutically effect amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein). In aspects, the immune response is the result of one or more therapeutic treatments with at least one therapeutic protein, treatment with a vaccine or treatment with at least one antigen. In another aspect, the administration of a Tregitope compound or composition of the present disclosure shifts one or more antigen presenting cells to a regulatory phenotype, one or more dendritic cells to a regulatory phenotype, decreases CD11c and HLA-DR expression in the dendritic cells or other antigen presenting cells.

In aspects, the present disclosure is directed to a method for expanding a population of regulatory T cells, comprising: (a) providing a biological sample from a subject; (b) isolating regulatory T-cells from the biological sample; (c) contacting the isolated regulatory T-cells with an effective amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein), under conditions wherein the T-regulatory cells increase in number to yield an expanded regulatory T-cell composition, thereby expanding the regulatory T-cells in the biological sample; and, additionally, (d) returning the sample to the subject in need of treatment.

In aspects, the present disclosure is directed to a method for stimulating regulatory T cells in a biological sample, comprising: (a) providing a biological sample from a subject; (b) isolating regulatory T-cells from the biological sample; (c) contacting the isolated regulatory T-cells with an effective amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein), under conditions wherein the T-regulatory cells are stimulated to alter one or more biological function, thereby stimulating the regulatory T-cells in the biological sample; and, additionally, (d) returning cells to the subject in need of treatment.

In aspects, the present disclosure is directed to a method for repressing/suppressing an immune response in a subject, comprising administering a therapeutically effective amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein), wherein the Tregitope compound or composition represses/suppresses the immune response. In aspects, the Tregitope compound or composition represses/suppresses an innate immune response. In aspects, the Tregitope compound or composition represses/suppresses an adaptive immune response. In aspects, the Tregitope compound or composition represses/suppresses an effector T cell response. In aspects, the Tregitope compound or composition represses/suppresses a memory T cell response. In aspects, the Tregitope compound or composition represses/suppresses helper T cell response. In aspects, the Tregitope compound or composition represses/suppresses B cell response. In aspects, the Tregitope compound or composition represses/suppresses an NKT cell (natural killer T cell) response. In another aspect, the administration of a Tregitope compound or composition of the present disclosure shifts one or more antigen presenting cells to a regulatory phenotype, one or more dendritic cells to a regulatory phenotype, decreases CD11c and HLA-DR expression in the dendritic cells or other antigen presenting cells.

In aspects, the present disclosure is directed to a method of suppressing an immune response, specifically an antigen specific immune response in a subject, through the administration of a therapeutically effective amount of a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein), wherein said Tregitope compound or composition activates naturally occurring $T_{Regs}$ (in aspects, including natural $T_{Regs}$ and/or adaptive $T_{Regs}$, and in aspects $CD4^+$/$CD25^+$/$FoxP3^+$ regulatory T-cells) or suppresses the activation of $CD4^+$ T-cells, the proliferation of $CD4^+$ and/or $CD8^+$ T-cells, and/or suppresses the activation or proliferation of β-cells or NKT Cells. In aspects, a Tregitope compound or composition of the present disclosure may be covalently bound, non-covalently bound, or in admixture with a specific target antigen. In aspects, an administered Tregitope compound or composition of the present disclosure that is covalently bound, non-covalently bound, or in admixture with a specific target antigen results in the diminution of immune response against the target antigen.

In aspects, the target antigen may be an autologous protein or protein fragment. In aspects, the target antigen may be an allergen. In aspects, the target antigen may allogenic protein or protein fragments. In aspects, the target antigen may be a biologic medicine or fragments thereof. In aspects, the suppressive effect is mediated by natural $T_{Regs}$. In aspects, the suppressive effect is mediated by an adaptive Tae g s. In aspects, the one or more Tregitope included in the Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) suppresses an effector T cell response. In aspects, the one or more Tregitopes of the presently disclosed Tregitope compounds or compositions suppresses an innate immune response. In aspects, the one or more Tregitopes of the presently disclosed Tregitope compounds and compositions suppresses an adaptive immune response. In aspects, the one or more Tregitopes of the presently disclosed Tregitope compounds and compositions suppresses helper T cell response. In aspects, the one or more Tregitopes of the presently disclosed Tregitope compounds and compositions suppresses a memory T cell response. In aspects, the one or more Tregitopes of the presently disclosed Tregitope compounds and compositions suppresses B cell response. In aspects, the one or more Tregitopes of the presently disclosed Tregitope compounds and compositions suppresses NKT cell response.

In aspects, the present disclosure is directed to a kit for preventing or treating a medical condition, in particular, for the suppression of an immune response in a subject, wherein the kit comprises a Tregitope compound or composition of the instant disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein). In aspects, the kit may further comprise an effective amount of an antigen or allergen or therapeutic agent, such as a replacement protein or peptide.

In aspects, the present disclosure is directed to methods of immune engineering, including removal or insertion of one or more Tregitopes of the instant disclosure, from or into a polypeptide, such as an antibody or fragment thereof. For example, in aspects the present disclosure is directed to a method for enhancing the immunogenicity of a compound or composition comprising an antibody or fragment thereof, which may be particularly useful when an antibody or fragment thereof serves as a vaccine delivery vector for antigen targeting to antigen presenting cells, such as dendritic cells. In aspects, said method comprises identification and removal of one or more regulatory T cell epitopes (e.g., a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) from said antibody or fragment thereof. In aspects, the one or more regulatory T cell epitopes of the antibody or fragment thereof are identified by EpiMatrix and JanusMatrix analysis, such as is described herewithin (for example, in section (1) of the exemplification). In aspects, the one or more regulatory T cell epitopes of an antibody (or fragment thereof) vaccine delivery vector can suppress an antigen-specific immune response to a delivered antigen, and removal of said one or more regulatory T cell epitopes can allow for diminution of tolerogenicity and stimulation of a strong antigen-specific immune response against the delivered antigen. In aspects, said removal of the one or more regulatory T cell epitopes from the vaccine delivery vector comprises deletion of all or some of the amino acids of the one or more regulatory T cell epitopes. In aspects, said removal of the one or more regulatory T cell epitopes from the vaccine delivery vector comprises deletion of some or all of the amino acids of the one or more regulatory T cell epitopes and adding one or more amino acids at the site of deletion of the regulatory T cell epitope amino acids. In aspects, said removal of the one or more regulatory T cell epitopes from the vaccine delivery vector comprises mutating the one or more regulatory T cell epitopes (for example, but not limited to, introduction one or more point mutations into the one or more regulatory T cell epitopes by site-directed mutagenesis or other recombinant techniques). In aspects, said removal of the one or more regulatory T cell epitopes from the vaccine delivery vector comprises introducing one or more amino acids into the one or more regulatory T cell epitope sequences, which in aspects will disrupt the one or more regulatory T cell epitope sequences, such that the previous tolerogenicity of the sequence is removed. In aspects, the number of said added one or more amino acids at the site of removal need not correspond to the number of amino acids deleted from the previously existing regulatory T cell epitope amino acids. In aspects, said removal of one or more regulatory T cell epitopes from the antibody or fragment thereof results in enhancing the immunogenicity of the vaccine delivery vector or target antigen of the vaccine delivery vehicle or vector. In aspects, said removal of one or more regulatory T cell epitopes from the vaccine delivery vector results in a heightened antigen-specific immune response to the vaccine delivery vector or target antigen of the vaccine delivery vehicle or vector. In aspects, the vaccine delivery vector can comprise an antibody, including but not limited to a monoclonal antibody, a polyclonal antibody, a mouse antibody, a human antibody, a humanized antibody, a monospecific antibody, a bispecific antibody, a glycosylated antibody, an Fc-modified antibody, an antibody-drug conjugate, an antibody of a different class of subclass (e.g., IgG (e.g., IgG1, IgG2, IgG3, or IgG4), IgM, IgE, or IgA), or fragments or antigen-specific antibody fragments thereof (including, but not limited to, a Fab, F(ab')$_2$, Fv, disulfide linked Fv, scFv, single domain antibody, closed conformation multispecific antibody, disulfide-linked scfv, diabody). In aspects, the one or more regulatory T cell epitopes have a sequence comprising, consisting of, or consisting essentially of one or more of SEQ ID NOS: 1-124.

Additionally, the present disclosure is directed to a method for decreasing the immunogenicity and/or increasing tolerogenicity of an antibody or fragment thereof, which may be particularly useful when an antibody or fragment thereof serves as a therapeutic protein. In aspects, said method comprises insertion of one or more regulatory T cell epitopes (e.g., a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) into said antibody or fragment thereof. In aspects, the one or more regulatory T cell epitopes of the antibody or fragment suppress an antigen-specific immune response against the antibody or fragment thereof. In aspects, said one or more regulatory T cell epitopes may be fused to or inserted internally within (e.g., but not limited to, site directed mutagenesis or other recombinant techniques) an antibody or fragment thereof, such as in instances where the Tregitope is not located in its natural position within the antibody or fragment thereof or wherein the antibody or fragment thereof is missing such a Tregitope (e.g., if a particular antibody or fragment thereof has a mutated or missing corresponding section). In aspects, said insertion of the one or more regulatory T cell epitopes into the antibody or fragment thereof comprises insertion of all or some of the amino acids of the one or more regulatory T cell epitopes. In aspects, said insertion of the one or more regulatory T cell epitopes into the antibody or fragment thereof comprises insertion of some or all of the amino acids of the one or more regulatory T cell epitopes and removing one or more amino acids at the site of insertion of the regulatory T cell epitope amino acids. In aspects, said insertion of the one or more regulatory T cell epitopes into the antibody or fragment thereof comprises mutating the sequence of the antibody or fragment thereof to include the one or more regulatory T cell epitopes (for example, but not limited to, introduction one or more point mutations into the antibody or fragment thereof by site-directed mutagenesis or other recombinant techniques). In aspects, said insertion of the one or more regulatory T cell epitopes into the antibody or fragment, which in aspects will introduce the one or more regulatory T cell epitope sequences, such that the previous immunogenicity of the sequence is decreased and the tolerogenicity of the new sequence is enhanced. In aspects, the number of said added one or more amino acids at the site of insertion of the regulatory T cell epitope amino acids need not correspond to the number of amino acids deleted from the sequence of the antibody or fragment thereof. In aspects, said insertion of one or more regulatory T cell epitopes into the antibody or fragment thereof results in decreasing the immunogenicity of the antibody or fragment thereof. In aspects, said insertion of one or more regulatory T cell epitopes into the antibody or fragment thereof results in a increasing the tolerogenicity of the antibody or fragment thereof. In aspects, one or more Tregitopes may be incorporated as an internal sequence into an Fc domain as disclosed in U.S. Pat. Nos. 7,442,778, 7,645,861, 7,655,764, 7,655,765, and/or 7,750,128 (each of which are herein incorporated by reference in their entirety). Such an internal sequence may be added by insertion (i.e., between amino acids in the previously existing Fc domain) or by replacement of amino acids in the previously existing Fc domain (i.e., removing amino acids in the previously existing Fc domain and adding peptide amino acids). In the latter case, the number of peptide amino acids added need not correspond to the number of amino acids removed from the previously existing Fc domain; for example, in aspects, the compositions may comprise an added internal sequence of 9-15 amino acids, with a sequence of 1-21 amino acids removed from the native Fc domain. In aspects, the antibody or fragment thereof can comprise, but is not limited to, a monoclonal antibody, a polyclonal antibody, a mouse antibody, a human antibody, a humanized antibody, a monospecific antibody, a bispecific antibody, a glycosylated antibody, an Fc-modified antibody, an antibody-drug conjugate, an such as antibody of a different class of subclass (e.g., IgG (e.g., IgG1, IgG2, IgG3, or IgG4), IgM, IgE, or IgA) molecules, or antigen-specific antibody fragments thereof (including, but not limited to, a Fab, F(ab')2, Fv, disulfide linked Fv, scFv, single domain antibody, closed conformation multispecific antibody, disulfide-linked scfv, diabody). In aspects, the one or more regulatory T cell epitopes have a sequence comprising, consisting of, or consisting essentially of one or more of SEQ ID NOS: 1-124.

For example, in aspects, one or more Tregitopes of the instant disclosure having a sequence comprising one or more of SEQ ID NOS: 1-124 (and fragments or variants thereof), and optionally 1 to 12 additional amino acids distributed in any ratio on the N-terminus and/or C-terminus of the polypeptide of SEQ ID NOS: 1-124), may be fused to or inserted internally within (e.g., but not limited to, site directed mutagenesis or other recombinant techniques) a human IgG or fragment thereof, such as in instances where the Tregitope is not located in its natural position within the human IgG or fragment thereof or where the human IgG or fragment thereof (such as a subject's own human IgG or fragment thereof) is missing such a Tregitope (e.g., if a particular human IgG or fragment thereof has a mutated or missing corresponding section). As described previously, a Tregitope comprising one or more of SEQ ID NOS: 1, 3-8, 14-15, 16-28, 42-74, and 111-124 may be fused to or inserted internally within a polypeptide, e.g., a polypeptide that does not comprise a human IgG heavy chain variable region. In aspects, if a polypeptide does comprise a human IgG heavy chain variable region (such as a human IgG antibody or fragment thereof), then said one or more of SEQ ID NOS: 1, 3-8, 14-15, 16-28, 42-74, and 111-124 may be fused to or inserted internally within (e.g., but not limited to, site directed mutagenesis or other recombinant techniques) a human IgG heavy chain variable region or fragment thereof, such as in instances where the Tregitope is not located in its natural position within the a human IgG heavy chain variable region or fragment thereof or where the human IgG heavy chain variable region or fragment thereof is missing such a Tregitope (e.g., if a particular a human IgG heavy chain variable region or fragment thereof has a mutated or missing corresponding section). In aspects, a Tregitope comprising one or more of SEQ ID NOS: 2, 9-11, 29-41, and 75-100 may be fused to or inserted internally within a polypeptide, e.g., a polypeptide that does not comprise a human IgG heavy chain constant region. In aspects, if a polypeptide does comprise a human IgG heavy chain constant region (such as a human IgG antibody or fragment thereof), then said one or more of SEQ ID NOS: 2, 9-11, 29-41, and 75-100 may be fused to or inserted internally within (e.g., but not limited to, site directed mutagenesis or other recombinant techniques) a human IgG heavy chain constant region or fragment thereof, such as in instances where the Tregitope is not located in its natural position within the human IgG heavy chain constant region or fragment thereof or where the human IgG heavy chain constant region or fragment thereof is missing such a Tregitope (e.g., if a particular a human IgG heavy chain constant region or fragment thereof has a mutated or missing corresponding section). In aspects, a Tregitope comprising one or more of SEQ ID NO: 12 may be fused to or inserted internally within a polypeptide, e.g., a polypeptide that does not comprise a human IgG light chain variable region. In aspects, if a polypeptide does comprise a human IgG light chain variable region (such as a human IgG antibody or fragment thereof), then said one or more of SEQ ID NO: 12 may be fused to or inserted internally within (e.g., but not limited to, site directed mutagenesis or other recombinant techniques) a human IgG light chain variable region or fragment thereof, such as in instances where the Tregitope is not located in its natural position within the human IgG light chain variable region or fragment thereof or where the human IgG light chain variable region or fragment thereof is missing such a Tregitope (e.g., if a particular a human IgG light chain variable region or fragment thereof has a mutated or missing corresponding section). In aspects, a Tregitope comprising one or more of SEQ ID NOS: 13 and 101-110 may be fused to or inserted internally within a polypeptide, e.g., a polypeptide that does not comprise a human IgG light chain constant region. In aspects, if a polypeptide does comprise a human IgG light chain constant region (such as a human IgG antibody or fragment thereof), then said one or more of SEQ ID NOS: 13 and 101-110 may be fused to or inserted internally within (e.g., but not limited to, site directed mutagenesis or other recombinant techniques) a human IgG light chain constant region or fragment thereof, such as in instances where the Tregitope is not located in its natural position within the human IgG light chain constant region or fragment thereof or where the human IgG light chain constant region or fragment thereof is missing such a Tregitope (e.g., if a particular a human IgG light chain constant region or fragment thereof has a mutated or missing corresponding section).

BRIEF DESCRIPTION OF THE DRAWINGS

The present disclosure may be better understood with reference to the following figures.

FIGS. 1A-C are a series of graphs reporting HLA DRB1 competition binding curves. In particular, a summary of HLA binding results for Tregitope (SEQ ID NO: 14) is presented in FIG. 1A. EpiMatrix™ Predictions, calculated $IC_{50}$ values, and results classifications are reported for each HLA allele. FIGS. 1B-C shows the binding curves for Tregitope (SEQ ID NO: 14) against the selected Class II HLA alleles. FIG. 1B summarizes the results for HLA DRB1 *0801 assay, while FIG. 1C summarizes the results for the HLA DRB1 *1501 assay.

FIGS. 2A-C show the gating strategy for highly activated regulatory T cells and effector CD4+ T cells in the disclosed Tetanus Toxoid (TT) assay. As shown in FIG. 2A, cells were first gated to eliminate aggregates and dead cells, and live cells were gated for CD4+ T cells, and all subsequent analysis was done on this population. CD4+ T cells are gated for elevated CD25, FoxP3, and low CFSE (proliferation) (FIG. 2B). FIG. 2B shows the results of a representative assay with no added TT (left side), of a representative assay with 0.5 μg/ml TT (right side). FIG. 2C shows representative results of such an assay, and depicts that proliferating and activated CD4+ T cell populations are highly correlated.

FIGS. 3A-B depicts the proliferation (FIG. 3A,— showing absolute values with media only controls subtracted) and activation (FIG. 3B— showing absolute values with media only controls subtracted) of CD4+ T cells upon stimulation with tetanus toxoid (TT) and suppression by peptide SEQ ID NO: 7. The data collected from inhibition experiments for a Tregitope SEQ ID NO:7 stimulation was aggregated and plotted as % of CD4 proliferation or activation remaining after treatment with the Tregitope at several concentrations (0, 8, 16, 24 μg/mL). The plots shown is in absolute values (±Std.dev). This analysis displays susceptibility of individual donors to inhibition by Tregitope SEQ ID NO:7 stimulation.

FIGS. 4A-B depicts the proliferation (FIG. 4A,— showing normalized values with media only controls subtracted) and activation (FIG. 4B—showing normalized values with media only controls subtracted) of CD4+ T cells upon stimulation with tetanus toxoid (TT) and suppression by peptide SEQ ID NO: 7. The data collected from inhibition experiments for a Tregitope SEQ ID NO: 7 stimulation was aggregated and plotted as % of CD4 proliferation or activation remaining after treatment with the Tregitope at several concentrations (0, 8, 16, 24 μg/mL). Normalized values are used. The plots are represented in normalized values (±Std.dev). This analysis displays susceptibility of individual donors to inhibition by Tregitope SEQ ID NO: 7 stimulation.

FIGS. 5A-D depicts the proliferation (FIG. 5A,— showing absolute values with media only controls not subtracted) and activation (FIG. 5C—showing absolute values with media only controls not subtracted) of CD4+ T cells upon stimulation with tetanus toxoid (TT) and suppression by peptide SEQ ID NO: 7. The data collected from inhibition experiments for a Tregitope SEQ ID NO: 7 stimulation was aggregated and plotted as % of CD4 proliferation or activation remaining after treatment with the Tregitope at several concentrations (0, 8, 16, 24 μg/mL). The plots shown are in absolute values (±Std.dev). This analysis displays susceptibility of individual donors to inhibition by Tregitope SEQ ID NO: 7 stimulation. Media only contribute to negligible levels of proliferation and activation, as shown by the average media bar and specified media % for each donor in FIG. 5B and FIG. 5D.

FIGS. 6A-D depicts the proliferation (FIG. 6A,— showing normalized values with media only controls not subtracted) and activation (FIG. 6C—showing normalized values with media only controls not subtracted) of CD4+ T cells upon stimulation with tetanus toxoid (TT) and suppression by peptide SEQ ID NO: 7. The data collected from inhibition experiments for a Tregitope SEQ ID NO: 7 stimulation was aggregated and plotted as % of CD4 proliferation or activation remaining after treatment with the Tregitope at several concentrations (0, 8, 16, 24 μg/mL). Normalized values are used. The above plots are represented in normalized values (±Std.dev). This analysis displays susceptibility of individual donors to inhibition by Tregitope SEQ ID NO: 7 stimulation. Media only contribute to negligible levels of proliferation and activation, as show by the average media % and specified media % for each donor in tables FIG. 5B and FIG.

FIG. 7 depicts an example of an immunogenic influenza HA peptide that contains an EpiBar and the EpiMatrix analysis of the promiscuous influenza epitope. The influenza HA peptide scores extremely high for all eight alleles in EpiMatrix and has a cluster score of 18. Cluster scores of 10 are considered significant. The band-like EpiBar pattern is characteristic of promiscuous epitopes. Results are shown for PRYVKQNTL (SEQ ID NO: 125), RYVKQNTLK (SEQ ID NO: 126), YVKQNTLKL (SEQ ID NO: 127), VKQNTLKLA (SEQ ID NO: 128) and KQNTLKLAT (SEQ ID NO: 129). Z score indicates the potential of a 9-mer frame to bind to a given HLA allele. All scores in the top 5% are considered "hits", while non-hits (*) below 10% are masked in FIG. 7 for simplicity.

FIG. 8 depicts the EpiMatrix analysis of SEQ ID NO: 7. Results are shown for KTLYLQMNS (SEQ ID NO: 16), TLYLQMNSL (SEQ ID NO: 17), LYLQMNSLR (SEQ ID NO: 18), YLQMNSLRA (SEQ ID NO: 19), LQMNSLRAE (SEQ ID NO: 20), QMNSLRAED (SEQ ID NO: 21), MNSLRAEDT (SEQ ID NO: 22), NSLRAEDTA (SEQ ID NO 23), SLRAEDTAK (SEQ ID NO 24), and LRAEDTAKH (SEQ ID NO 25). Z score indicates the potential of a 9-mer frame to bind to a given HLA allele. All scores in the top 5% are considered "hits", while non-hits (*) below 10% are masked in FIG. 8 for simplicity.

FIG. 9 depicts the EpiMatrix analysis of SEQ ID NO: 14. Results are shown for ETLYLQMNS (SEQ ID NO: 111), TLYLQMNSL (SEQ ID NO: 112), LYLQMNSLR (SEQ ID NO: 113), YLQMNSLRA (SEQ ID NO: 114), LQMNSLRAE (SEQ ID NO: 115), QMNSLRAED (SEQ ID NO: 116), MNSLRAEDT (SEQ ID NO: 117), NSLRAEDTA (SEQ ID NO 118), SLRAEDTAV (SEQ ID NO 119), AND LRAEDTAVY (SEQ ID NO 120). Z score indicates the potential of a 9-mer frame to bind to a given HLA allele. All scores in the top 5% are considered "hits", while non-hits (*) below 10% are masked in FIG. 9 for simplicity.

FIG. 11 is the overview of JanusMatrix results for identified the Tregitopes of SEQ ID NOS: 1-15 of the instant disclosure.

FIG. 12 is the JanusMatrix report for the Tregitope of SEQ ID NO: 1 and the 9-mers contained within SEQ ID NO: 1, including SEQ ID NOS: 16-28.

FIG. 13 is the JanusMatrix report for the Tregitope of SEQ ID NO: 10 and the 9-mers contained within SEQ ID NO: 10, including SEQ ID NOS: 87-93.

FIG. 14 is the JanusMatrix report for the Tregitope of SEQ ID NO: 11 and the 9-mers contained within SEQ ID NO: 11, including SEQ ID NOS: 94-100.

FIG. 15 is the JanusMatrix report for the Tregitope of SEQ ID NO: 12.

FIG. 16 is the JanusMatrix report for the Tregitope of SEQ ID NO: 13 and the 9-mers contained within SEQ ID NO: 13, including SEQ ID NOS: 101-110.

FIG. 17 is the JanusMatrix report for the Tregitope of SEQ ID NO: 14 and the 9-mers contained within SEQ ID NO: 14, including SEQ ID NOS: 111-120.

FIG. 18 is the JanusMatrix report for the Tregitope of SEQ ID NO: 15 and the 9-mers contained within SEQ ID NO: 15, including SEQ ID NOS: 121-124.

FIG. 19 is the JanusMatrix report for the Tregitope of SEQ ID NO: 10 and the 9-mers contained within SEQ ID NO: 2, including SEQ ID NOS: 29-41.

FIG. 20 is the JanusMatrix report for the Tregitope of SEQ ID NO: 3 and the 9-mers contained within SEQ ID NO: 3, including SEQ ID NOS: 42-48.

FIG. 21 is the JanusMatrix report for the Tregitope of SEQ ID NO: 4 and the 9-mers contained within SEQ ID NO: 4, including SEQ ID NOS: 49-50.

FIG. 22 is the JanusMatrix report for the Tregitope of SEQ ID NO: 50.

FIG. 23 is the JanusMatrix report for the Tregitope of SEQ ID NO: 6 and the 9-mers contained within SEQ ID NO: 6, including SEQ ID NOS: 51-57.

FIG. 24 is the JanusMatrix report for the Tregitope of SEQ ID NO: 10 and the 9-mers contained within SEQ ID NO: 7, including SEQ ID NOS: 58-67.

FIG. 25 is the JanusMatrix report for the Tregitope of SEQ ID NO: 8 and the 9-mers contained within SEQ ID NO: 8, including SEQ ID NOS: 68-74.

FIG. 26 is the JanusMatrix report for the Tregitope of SEQ ID NO: 9 and the 9-mers contained within SEQ ID NO: 9, including SEQ ID NOS: 87-93.

DETAILED DESCRIPTION OF THE INVENTION

General

Figure 2A:
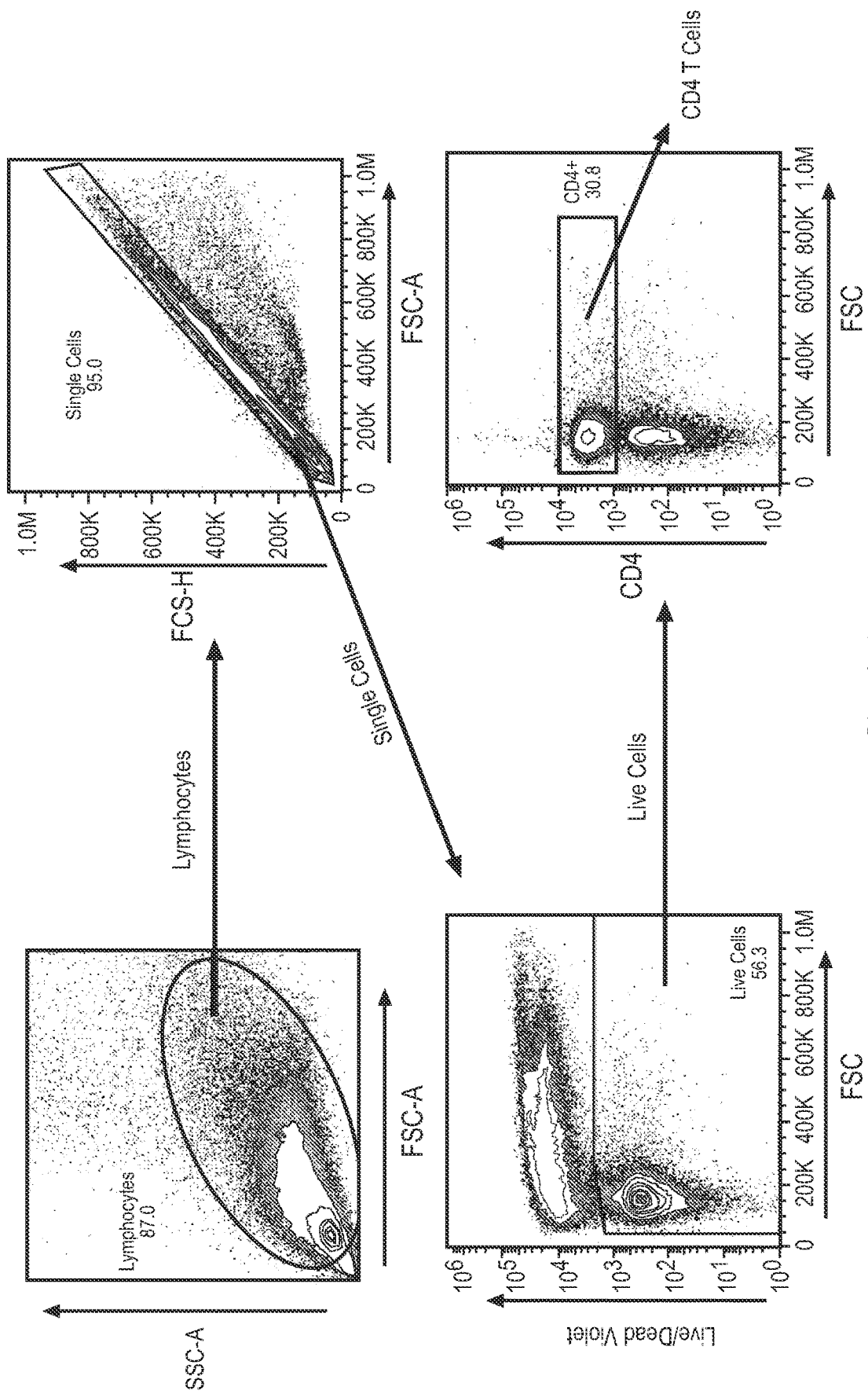

The adaptive immune cascade begins when soluble protein antigens are taken up by Antigen Presenting Cells (APCs) and processed through the Class II antigen presentation pathway. Protein antigens in the Class II presentation pathway are degraded by various proteases found in the Endoplasmic Reticulum. Some of the resulting protein fragments are bound to Class II MHC molecules. Peptide-loaded MHC molecules are trafficked to the cell surface where they are interrogated by CD4+ T cells. Peptide fragments that are capable of binding to an MHC molecule and mediating the cell-to-cell interaction between APCs and circulating T cells are referred to as T cell epitopes. Recognition of these peptide-MHC complexes by CD4+ T cells can lead to either an immune activating or an immune suppressing response based on the phenotype of the responding T cells and the local cytokine/chemokine milieu. In general, engagement between the MHC/peptide complex and the T cell receptor (TCR) of T effector cells leads to activation and the subsequent secretion of pro-inflammatory cytokines such as IL-4, and IFN-γ. On the other hand, the activation of natural T regulatory cells ($T_{Regs}$) leads to the expression of the immune suppressive cytokines IL-10 and TGF-β, among others (Shevach E, (2002), Nat Rev Immunol, 2(6):389-400). These cytokines act directly on nearby effector T cells leading in some cases to anergy or apoptosis. In other cases, regulatory cytokines and chemokines convert effector T cells to T regulatory phenotypes; this process is referred here as "induced" or "adaptive" tolerance. T cell epitopes that are capable of binding to MHC molecules and engaging and/or activating circulating naturally occurring $T_{Regs}$ (in aspects, including natural $T_{Regs}$ and/or adaptive $T_{Regs}$), are referred to as "Tregitopes." In aspects, the instantly disclosed Tregitopes are T cell epitope clusters, which are epitopes capable of binding to multiple MEW alleles and multiple TCRs.

Initial self/non-self discrimination occurs in the thymus during neonatal development where cortical and medullary epithelial cells express specific self-protein epitopes to immature T cells. T cells recognizing self-antigens with high affinity are deleted, but autoreactive T cells with moderate affinity sometimes avoid deletion and can be converted to natural regulatory T cells ($T_{Reg}$) cells. These natural $T_{Reg}$ cells are exported to the periphery and help to control a latent autoimmune response. Natural regulatory T cells are a critical component of immune regulation and self-tolerance.

Self-tolerance is regulated by a complex interplay between T cells, B cells, cytokines and surface receptors. T regulatory immune responses counterbalance T effector immune response to protein antigens (whether self or foreign). A tilt of the balance toward the autoreactive side, either by increasing the number or function of autoreactive T effector cells or by diminishing the number or function of T regulatory cells, is manifested as autoimmunity.

A second form of tolerance occurs in the periphery where mature T cells are converted to an 'adaptive' $T_{Reg}$ phenotype upon activation via their T cell receptor in the presence of IL-10 and TGF-β, which are usually supplied by bystander T regulatory cells. The possible roles for these 'adaptive' $T_{Reg}$ cells include dampening immune response following the successful clearance of an invading pathogen, controlling excessive inflammation caused by an allergic reaction, controlling excessive inflammation caused by low-level or chronic infection, or possibly controlling inflammatory response targeting beneficial symbiotic bacteria and viruses. 'Adaptive' $T_{Regs}$ may also play a role in suppressing immune response targeting human antibodies that have undergone somatic hypermutation (Chaudhry A et al., (2011), Immunity, 34(4):566-78).

$T_{Reg}$ cells are also instrumental in B cell tolerance. B cells express a single low affinity Fc receptor, FcγRIIB on their cell surface (Ravetch J V et al., (1986), Science, 234(4777): 718-25). This receptor contains the immunoreceptor tyrosine-based inhibition motif sequence (ITIM) in its cytoplasmic domain. Co-ligation of FcγRIIB and the B-cell receptor (BCR) by immune complexes act to trigger the tyrosine phosphorylation of the ITIM leading to the recruitment of the inositol phosphatase, SHIP, which inhibits BCR-triggered proliferation by interfering with the activation of MAP kinases and blocks phagocytosis by the dissociation of Burton's tyrosine kinase (Btk) from the cell membrane, which inhibits calcium influx into the cell. FcγRIIB can also induce apoptosis independent of the ITIM. Upon homo-aggregation of FcRIIB by ICs, the association of Btk with the cell membrane is enhanced, thereby triggering an apoptotic response (Pearse R, et al., (1999), Immunity, 10(6): 753-60). Expression of FcγRIIB is highly variable and cytokine dependent. IL-4 and IL-10, which are expressed by activated Th2 and $T_{Reg}$ cells, have been shown to act synergistically to enhance FcγRIIB expression (Joshi T et al., (2006), Mol Immuno., 43(7):839-50), thus aiding in the suppression of a humoral response.

It is possible to exploit Tregitope specific $T_{Reg}$ cells to suppress unwanted immune responses and also to induce adaptive $T_{Reg}$ to co-delivered proteins. This discovery has implications for the design of therapeutic regimens and antigen-specific therapies for transplantation, protein therapeutics, allergy, chronic infection, autoimmunity and vaccine design. Administration of a drug, a protein, or an allergen in conjunction with Tregitopes, including a Tregitope compound or composition of the present disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) can suppress an effector immune response. Tregitopes, including Tregitope compounds and compositions of the present disclosure, can be used to deliberately manipulate the immune system toward tolerance.

The Tregitope compounds and compositions of the present (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) are useful in the selective engagement and activation of regulatory T cells. It is demonstrated herein that certain naturally occurring $T_{Regs}$ (in aspects, including natural $T_{Regs}$ and/or adaptive $T_{Regs}$), can be engaged, activated, and/or applied to the suppression of unwanted immune responses in both systemic and limited, disease-specific contexts.

Despite extensive efforts, with few exceptions, the antigen specificity of natural $T_{Regs}$, and more importantly natural $T_{Regs}$ circulating in clinically significant volumes, is unknown. Presented herein is a demonstration that human immunoglobulins contain T cell epitopes that relate to naturally occurring populations of regulatory T cells (in aspects, including natural $T_{Regs}$ and/or adaptive $T_{Regs}$). In the course of normal immune surveillance, these proteins are taken up by professional APCs, such as dendritic cells or macrophages, and degraded. During the degradation process, some of the epitopes contained in these proteins are bound to MEW molecules, transported to the cell surface presented to regulatory T cells. Those cells, once activated by the APC, release cytokines and chemokines help to suppress autoimmune responses that would otherwise hinder the function of the extracellular proteins.

By using the Tregitope compounds and compositions of the present disclosure (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) to selectively activate naturally occurring $T_{Regs}$ (in aspects, including natural $T_{Regs}$ and/or adaptive $T_{Regs}$), it is herein shown that the Tregitope compositions of the present disclosure can be used to suppress a variety of unwanted immune responses. In its simplest form, systemic application of the Tregitope compositions of the present disclosure can be used as a generalized immune suppressant useful for controlling severe autoimmune reactions such as, for example, MS flare-ups, allergic reactions, transplant reactions, or uncontrolled response to infection.

In a more controlled application, for example but not limited to, topically applied to joints affected by rheumatoid arthritis (RA), the Tregitope compounds and compositions of the present disclosure (including one or more of e.g., a polypeptide ((e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) can be used to suppress localized autoimmune responses. In a targeted application, such as might be achieved through the fusion, bonding or admixture of the Tregitope compounds or compositions of the present disclosure to certain other T cell epitopes, the Tregitope compounds and compositions can suppress highly specific immune reactions to the fused, bonded, or admixed T cell epitopes while leaving the balance of the immune system intact. For example, through the delivery of a Tregitope compound or composition of the present disclosure fused to an autoimmune antigen such as insulin, an allergen such as Brazil nut antigen, or an antigenic protein such as an antibody (which can be IgG, IgM, IgA, IgD or IgE molecules or antigen-specific antibody fragments thereof (including, but not limited to, a Fab, F(ab')$_2$, Fv, disulfide linked Fv, scFv, single domain antibody, closed conformation multispecific antibody, disulfide-linked scfv, diabody) or replacement enzyme, the immune system can be trained to "tolerate" the co-delivered antigen by, e.g., inducing naturally occurring $T_{Regs}$ (in aspects, including natural $T_{Regs}$ and/or adaptive $T_{Regs}$) and/or converting the phenotype of responding effector T cells to that of adaptive regulatory T cells.

As stated above, the Tregitopes of the present disclosure are derived from circulating extracellular proteins, particularly human immunoglobulins. To be useful, these Tregitopes should be true T cell epitopes (i.e., capable of binding to both MEW molecules and TCRs). In aspects, the Tregitopes should be related to a pre-existing population of regulatory T cells that is sufficiently large to have a therapeutic effect. T cell epitope clusters, which are epitopes capable of binding to multiple MEW alleles and multiple TCRs, are key to satisfying this latter qualification.

The instantly disclosed treatments provide the following advantages:
1. Treatment with the Tregitope compositions of the present disclosure is highly antigen specific (e.g., treatment with the Tregitope compositions can, e.g., expand and/or stimulate corresponding naturally occurring $T_{Reg}$ populations (in aspects, including natural $T_{Regs}$ and/or adaptive $T_{Regs}$) in a highly antigen specific manner);
2. An efficient and less expensive treatment regimen when compared to current antigen specific therapies wherein patients are treated over a prolonged period of time with frequent high dose antigen preparations; and
3. A second line of defense when induction of tolerance through high dose therapy fails to induce immune tolerance in the treated patient.

In aspects, the present disclosure is directed to therapeutic Tregitope compounds and compositions (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) that are safely administered to a patient experiencing an autoimmune response. The mechanism of action of the claimed Tregitope compounds and compositions is natural, supporting their efficacy and safety.

In aspects, the present disclosure is directed to Tregitope compounds and compositions (e.g., one or more of: peptides or polypeptides as disclosed herein; concatemeric peptides as disclosed herein; chimeric or fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, recombinant viruses, cells as disclosed herein; and/or pharmaceutical compositions or formulations as disclosed herein) that include one or more of the regulatory Tregitopes disclosed in Table 1, as well as fragments thereof, variants thereof, and fragments of such variants thereof, provided said fragments and/or variants retain MHC binding propensity and/or TCR specificity, and/or retain suppressive or regulatory T cell activity. In certain aspects, the Tregitopes can be capped with an N-terminal acetyl and/or C-terminal amino group.

TABLE 1

| SEQUENCE | SEQUENCE ID NO: |
|---|---|
| KTLYLQMNSLRAEDTAKHYCA | (SEQ ID NO: 1) |
| EEQYQSTYRVVSVLTVLHQDW | (SEQ ID NO: 2) |
| VQPGGSLRLSCAASG | (SEQ ID NO: 3) |
| WVRQAPGKGL | (SEQ ID NO: 4) |
| VRQAPGKGL | (SEQ ID NO: 5) |
| YLQMNSLRAEDTAVY | (SEQ ID NO: 6) |
| KTLYLQMNSLRAEDTAKH | (SEQ ID NO: 7) |
| YLQMNSLRAEDTAKH | (SEQ ID NO: 8) |
| LQSSGLYSLSSVVTVPSSSL | (SEQ ID NO: 9) |
| YNSTYRVVSVLTVLH | (SEQ ID NO: 10) |
| YQSTYRVVSVLTVLH | (SEQ ID NO: 11) |
| FTLTISSLQ | (SEQ ID NO: 12) |
| FYPREAKVQWKVDNALQS | (SEQ ID NO: 13) |
| ETLYLQMNSLRAEDTAVY | (SEQ ID NO: 14) |
| YLQMNSLRAEDT | (SEQ ID NO: 15) |
| KTLYLQMNS | (SEQ ID NO: 16) |
| TLYLQMNSL | (SEQ ID NO: 17) |
| LYLQMNSLR | (SEQ ID NO: 18) |
| YLQMNSLRA | (SEQ ID NO: 19) |
| LQMNSLRAE | (SEQ ID NO: 20) |
| QMNSLRAED | (SEQ ID NO: 21) |
| MNSLRAEDT | (SEQ ID NO: 22) |
| NSLRAEDTA | (SEQ ID NO: 23) |
| SLRAEDTAK | (SEQ ID NO: 24) |
| LRAEDTAKH | (SEQ ID NO: 25) |

TABLE 1-continued

| SEQUENCE | SEQUENCE ID NO: |
|---|---|
| RAEDTAKHY | (SEQ ID NO: 26) |
| AEDTAKHYC | (SEQ ID NO: 27) |
| EDTAKHYCA | (SEQ ID NO: 28) |
| EEQYQSTYR | (SEQ ID NO: 29) |
| EQYQSTYRV | (SEQ ID NO: 30) |
| QYQSTYRVV | (SEQ ID NO: 31) |
| YQSTYRVVS | (SEQ ID NO: 32) |
| QSTYRVVSV | (SEQ ID NO: 33) |
| STYRVVSVL | (SEQ ID NO: 34) |
| TYRVVSVLT | (SEQ ID NO: 35) |
| YRVVSVLTV | (SEQ ID NO: 36) |
| RVVSVLTVL | (SEQ ID NO: 37) |
| VVSVLTVLH | (SEQ ID NO: 38) |
| VSVLTVLHQ | (SEQ ID NO: 39) |
| SVLTVLHQD | (SEQ ID NO: 40) |
| VLTVLHQDW | (SEQ ID NO: 41) |
| VQPGGSLRL | (SEQ ID NO: 42) |
| QPGGSLRLS | (SEQ ID NO: 43) |
| PGGSLRLSC | (SEQ ID NO: 44) |
| GGSLRLSCA | (SEQ ID NO: 45) |
| GSLRLSCAA | (SEQ ID NO: 46) |
| SLRLSCAAS | (SEQ ID NO: 47) |
| LRLSCAASG | (SEQ ID NO: 48) |
| WVRQAPGKG | (SEQ ID NO: 49) |
| VRQAPGKGL | (SEQ ID NO: 50) |
| YLQMNSLRA | (SEQ ID NO: 51) |
| LQMNSLRAE | (SEQ ID NO: 52) |
| QMNSLRAED | (SEQ ID NO: 53) |
| MNSLRAEDT | (SEQ ID NO: 54) |
| NSLRAEDTA | (SEQ ID NO: 55) |
| SLRAEDTAV | (SEQ ID NO: 56) |
| LRAEDTAVY | (SEQ ID NO: 57) |
| KTLYLQMNS | (SEQ ID NO: 58) |
| TLYLQMNSL | (SEQ ID NO: 59) |
| LYLQMNSLR | (SEQ ID NO: 60) |
| YLQMNSLRA | (SEQ ID NO: 61) |
| LQMNSLRAE | (SEQ ID NO: 62) |
| QMNSLRAED | (SEQ ID NO: 63) |
| MNSLRAEDT | (SEQ ID NO: 64) |

TABLE 1-continued

| SEQUENCE | SEQUENCE ID NO: |
|---|---|
| NSLRAEDTA | (SEQ ID NO: 65) |
| SLRAEDTAK | (SEQ ID NO: 66) |
| LRAEDTAKH | (SEQ ID NO: 67) |
| YLQMNSLRA | (SEQ ID NO: 68) |
| LQMNSLRAE | (SEQ ID NO: 69) |
| QMNSLRAED | (SEQ ID NO: 70) |
| MNSLRAEDT | (SEQ ID NO: 71) |
| NSLRAEDTA | (SEQ ID NO: 72) |
| SLRAEDTAK | (SEQ ID NO: 73) |
| LRAEDTAKH | (SEQ ID NO: 74) |
| LQSSGLYSL | (SEQ ID NO: 75) |
| QSSGLYSLS | (SEQ ID NO: 76) |
| SSGLYSLSS | (SEQ ID NO: 77) |
| SGLYSLSSV | (SEQ ID NO: 78) |
| GLYSLSSVV | (SEQ ID NO: 79) |
| LYSLSSVVT | (SEQ ID NO: 80) |
| YSLSSVVTV | (SEQ ID NO: 81) |
| SLSSVVTVP | (SEQ ID NO: 82) |
| LSSVVTVPS | (SEQ ID NO: 83) |
| SSVVTVPSS | (SEQ ID NO: 84) |
| SVVTVPSSS | (SEQ ID NO: 85) |
| VVTVPSSSL | (SEQ ID NO: 86) |
| YNSTYRVVS | (SEQ ID NO: 87) |
| NSTYRVVSV | (SEQ ID NO: 88) |
| STYRVVSVL | (SEQ ID NO: 89) |
| TYRVVSVLT | (SEQ ID NO: 90) |
| YRVVSVLTV | (SEQ ID NO: 91) |
| RVVSVLTVL | (SEQ ID NO: 92) |
| VVSVLTVLH | (SEQ ID NO: 93) |
| YQSTYRVVS | (SEQ ID NO: 94) |
| QSTYRVVSV | (SEQ ID NO: 95) |
| STYRVVSVL | (SEQ ID NO: 96) |
| TYRVVSVLT | (SEQ ID NO: 97) |
| YRVVSVLTV | (SEQ ID NO: 98) |
| RVVSVLTVL | (SEQ ID NO: 99) |
| VVSVLTVLH | (SEQ ID NO: 100) |
| FYPREAKVQ | (SEQ ID NO: 101) |
| YPREAKVQW | (SEQ ID NO: 102) |
| PREAKVQWK | (SEQ ID NO: 103) |
| REAKVQWKV | (SEQ ID NO: 104) |
| EAKVQWKVD | (SEQ ID NO: 105) |
| AKVQWKVDN | (SEQ ID NO: 106) |
| KVQWKVDNA | (SEQ ID NO: 107) |
| VQWKVDNAL | (SEQ ID NO: 108) |
| QWKVDNALQ | (SEQ ID NO: 109) |
| WKVDNALQS | (SEQ ID NO: 110) |
| ETLYLQMNS | (SEQ ID NO: 111) |
| TLYLQMNSL | (SEQ ID NO: 112) |
| LYLQMNSLR | (SEQ ID NO: 113) |
| YLQMNSLRA | (SEQ ID NO: 114) |
| LQMNSLRAE | (SEQ ID NO: 115) |
| QMNSLRAED | (SEQ ID NO: 116) |
| MNSLRAEDT | (SEQ ID NO: 117) |
| NSLRAEDTA | (SEQ ID NO: 118) |
| SLRAEDTAV | (SEQ ID NO: 119) |
| LRAEDTAVY | (SEQ ID NO: 120) |
| YLQMNSLRA | (SEQ ID NO: 121) |
| LQMNSLRAE | (SEQ ID NO: 122) |
| QMNSLRAED | (SEQ ID NO: 123) |
| MNSLRAEDT | (SEQ ID NO: 124) |

Definitions

To further facilitate an understanding of the present invention, a number of terms and phrases are defined below. Unless otherwise defined, all terms (including technical and scientific terms) used herein have the same meaning as commonly understood by one of ordinary skill in the art to which this disclosure belongs. It will be further understood that terms such as those defined in commonly used dictionaries, should be interpreted as having a meaning that is consistent with their meaning in the context of the relevant art and the present disclosure, and will not be interpreted in an idealized or overly formal sense unless expressly so defined herein.

Ranges provided herein are understood to be shorthand for all of the values within the range. For example, a range of 1 to 25 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, or 25, as well as all intervening decimal values between the aforementioned integers such as, for example, 1.1, 1.2, 1.3, 1.4, 1.5, 1.6, 1.7, 1.8, and 1.9. With respect to sub-ranges, "nested sub-ranges" that extend from either end point of the range are specifically contemplated. For example, a nested sub-range of an exemplary range of 1 to 25 may comprise 1 to 5, 1 to 10, 1 to 15, and 1 to 20 in one direction, or 25 to 20, 25 to 15, 25 to 10, and 25 to 5 in the other direction.

As used herein, the term "biological sample" as refers to any sample of tissue, cells, or secretions from an organism.

As used herein, the term "transplantation" refers to the process of taking a cell, tissue, or organ, called a "transplant" or "graft" from one subject and placing it or them into a (usually) different subject. The subject who provides the transplant is called the "donor", and the subject who received the transplant is called the "recipient". An organ or graft transplanted between two genetically different subjects of the same species is called an "allograft". A graft transplanted between subjects of different species is called a "xenograft".

As used herein, the term "medical condition" includes, but is not limited to, any condition or disease manifested as one or more physical and/or psychological symptoms for which treatment and/or prevention is desirable, and includes previously and newly identified diseases and other disorders.

As used herein, the term "immune response" refers to the concerted action of lymphocytes, antigen presenting cells, phagocytic cells, granulocytes, and soluble macromolecules produced by the above cells or the liver (including antibodies, cytokines, and complement) that results in selective damage to, destruction of, or elimination from the human body of cancerous cells, metastatic tumor cells, malignant melanoma, invading pathogens (including a virus), cells or tissues infected with pathogens, or, in cases of autoimmunity or pathological inflammation, normal human cells or tissues. In aspects, an immune response includes a measurable cytotoxic T lymphocyte (CTL) response (e.g., against a virus expressing an immunogenic polypeptide) or a measurable B cell response, such as the production of antibodies, (e.g., against an immunogenic polypeptide). One of ordinary skill would know various assays to determine whether an immune response against a peptide, polypeptide, or related composition was generated, including use of the experiments and assays as disclosed in the Examples herein. Various B lymphocyte and T lymphocyte assays are well known, such as ELISAs, Eli Spot assays, cytotoxic T lymphocyte CTL assays, such as chromium release assays, proliferation assays using peripheral blood lymphocytes (PBL), tetramer assays, and other cytokine production assays. See Benjamini et al. (1991), hereby incorporated by reference.

As used herein, the term "effective amount", "therapeutically effective amount", or the like of a composition, including Tregitope compositions of the present disclosure (including one or more of e.g., a polypeptide (which may be termed herein as "Treg activating regulatory T-cell epitope", "Tregitope", "Tregitope peptide", or "T-cell epitope polypeptide") comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) is a quantity sufficient to achieve a desired therapeutic and/or prophylactic effect, e.g., an amount that results in the prevention of, or a decrease in, the symptoms associated with a disease that is being treated. The amount of a composition of the present disclosure administered to the subject will depend on the type and severity of the disease and on the characteristics of the individual, such as general health, age, sex, body weight and tolerance to drugs. It will also depend on the degree, severity and type of disease. The skilled artisan will be able to determine appropriate dosages depending on these and other factors. The compositions of the present invention can also be administered in combination with each other or with one or more additional therapeutic compounds.

As used herein, the term "regulatory T cell", "Treg" or the like, means a subpopulation of T cells that suppress immune effector function, including the suppression or down regulation of CD4+ and/or CD8+ effector T cell (Teff) induction, proliferation, and/or cytokine production, through a variety of different mechanisms including cell-cell contact and suppressive cytokine production. In aspects, CD4+ Tregs are characterized by the presence of certain cell surface markers including but not limited to CD4, CD25, and FoxP3. In aspects, upon activation, CD4+ regulatory T cells secrete immune suppressive cytokines and chemokines including but not limited to IL-10 and/or TGFβ. CD4+ Tregs may also exert immune suppressive effects through direct killing of target cells, characterized by the expression upon activation of effector molecules including but not limited to granzyme B and perforin. In aspects, CD8+ Tregs are characterized by the presence of certain cell surface markers including but not limited to CD8, CD25, and, upon activation, FoxP3. In aspects, upon activation, regulatory CD8+ T cells secrete immune suppressive cytokines and chemokines including but not limited to IFNγ, IL-10, and/or TGFβ. In aspects, CD8+ Tregs may also exert immune suppressive effects through direct killing of target cells, characterized by the expression upon activation of effector molecules including but not limited to granzyme B and/or perforin.

As used herein, the term "T cell epitope" means an MHC ligand or protein determinant, 7 to 30 amino acids in length, and capable of specific binding to human leukocyte antigen (HLA) molecules and interacting with specific T cell receptors (TCRs). As used herein, in the context of a T cell epitope that is known or determined (e.g. predicted) to engage a T cell, the terms "engage", "engagement" or the like means that when bound to a MHC molecule (e.g. human leukocyte antigen (HLA) molecules), the T cell epitope is capable of interacting with the TCR of the T cell and activating the T cell. Generally, T cell epitopes are linear and do not express specific three-dimensional characteristics. T cell epitopes are not affected by the presence of denaturing solvents. The ability to interact with T cell epitopes can be predicted by in silico methods (De Groot A S et al., (1997), AIDS Res Hum Retroviruses, 13(7):539-41; Schafer J R et al., (1998), Vaccine, 16(19):1880-4; De Groot A S et al., (2001), Vaccine, 19(31):4385-95; De Groot A R et ai,(2003), Vaccine, 21(27-30):4486-504, all of which are herein incorporated by reference in their entirety.

As used herein, the term "T-cell epitope cluster" refers to polypeptide that contains between about 4 to about 40 MHC binding motifs. In particular embodiments, the T-cell epitope cluster contains between about 5 to about 35 MHC binding motifs, between about 8 and about 30 MHC binding motifs; and between about 10 and 20 MHC binding motifs.

As used herein, the term "regulatory T cell epitope" ("Tregitope") refers to a "T cell epitope" that causes a tolerogenic response (Weber C A et al., (2009), Adv Drug Deliv, 61(11):965-76) and is capable of binding to MHC molecules and engaging (i.e. interacting with and activating) circulating naturally occurring Tregs (in aspects, including natural Tregs and/or adaptive Tregs). In aspects, upon activation, CD4+ regulatory T cells secrete immune suppressive cytokines and chemokines including but not limited to IL-10 and/or TGFβ. CD4+ Tregs may also exert immune suppressive effects through direct killing of target cells, characterized by the expression upon activation of effector molecules including but not limited to granzyme B and perforin, leads to the expression of the immune suppressive cytokines including, but not limited to, IL-10 and TGF-β and TNF-α. In aspects, upon activation, regulatory CD8+ T cells secrete immune suppressive cytokines and chemokines including but not limited to IFNγ, IL-10, and/or TGFβ. In aspects, CD8+ Tregs may also exert immune suppressive effects through direct killing of target cells, characterized by the expression upon activation of effector molecules including but not limited to granzyme B and/or perforin. In aspects, the instantly disclosed Tregitopes are T cell epitope clusters, which are epitopes capable of binding to multiple MEW alleles and multiple TCRs.

As used herein, the term "immune stimulating T-cell epitope polypeptide" refers to a molecule capable of inducing an immune response, e.g., a humoral, T cell-based, or innate immune response.

As used herein, the term "B cell epitope" means a protein determinant capable of specific binding to an antibody. B cell epitopes usually consist of chemically active surface groupings of molecules such as amino acids or sugar side chains and usually have specific three-dimensional structural characteristics, as well as specific charge characteristics. Conformational and non-conformational epitopes are distinguished in that the binding to the former but not the latter is lost in the presence of denaturing solvents.

The term "subject" as used herein refers to any living organism in which an immune response is elicited. The term subject includes, but is not limited to, humans, nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be covered.

As used herein, the terms "the major histocompatibility complex (MHC)", "MHC molecules", "MEW proteins" or "HLA proteins" are to be understood as meaning, in particular, proteins capable of binding peptides resulting from the proteolytic cleavage of protein antigens and representing potential T-cell epitopes, transporting them to the cell surface and presenting them there to specific cells, in particular cytotoxic T-lymphocytes or T-helper cells. The major histocompatibility complex in the genome comprises the genetic region whose gene products expressed on the cell surface are important for binding and presenting endogenous and/or foreign antigens and thus for regulating immunological processes. The major histocompatibility complex is classified into two gene groups coding for different proteins, namely molecules of MHC class I and molecules of MEW class II. The molecules of the two MHC classes are specialized for different antigen sources. The molecules of MHC class I present endogenously synthesized antigens, for example viral proteins and tumor antigens. The molecules of MEW class II present protein antigens originating from exogenous sources, for example bacterial products. The cellular biology and the expression patterns of the two MEW classes are adapted to these different roles. MHC molecules of class I consist of a heavy chain and a light chain and are capable of binding a peptide of about 8 to 11 amino acids, but usually 9 or 10 amino acids, if this peptide has suitable binding motifs, and presenting it to cytotoxic T-lymphocytes. The peptide bound by the MHC molecules of class I originates from an endogenous protein antigen. The heavy chain of the MEW molecules of class I is preferably an HLA-A, HLA-B or HLA-C monomer, and the light chain is (β-2-microglobulin. MEW molecules of class II consist of an α-chain and a β-chain and are capable of binding a peptide of about 12 to 25 amino acids if this peptide has suitable binding motifs, and presenting it to T-helper cells. The peptide bound by the MHC molecules of class II usually originates from an extracellular of exogenous protein antigen. The α-chain and the β-chain are in particular HLA-DR, HLA-DQ and HLA-DP monomers.

As used herein, the term "MEW complex" refers to a protein complex capable of binding with a specific repertoire of polypeptides known as HLA ligands and transporting said ligands to the cell surface.

As used herein, the term "MHC Ligand" means a polypeptide capable of binding to one or more specific MEW alleles. The term "HLA ligand" is interchangeable with the term "MHC Ligand". Cells expressing MHC/Ligand complexes on their surface are referred to as "Antigen Presenting Cells" (APCs). Similarly, as used herein, the term "MHC binding peptide" relates to a peptide which binds to an MHC class I and/or an MHC class II molecule. In the case of MHC class I/peptide complexes, the binding peptides are typically 8-10 amino acids long although longer or shorter peptides may be effective. In the case of MHC class II/peptide complexes, the binding peptides are typically 10-25 amino acids long and are in particular 13-18 amino acids long, whereas longer and shorter peptides may also be effective.

As used herein, the term "T Cell Receptor" or "TCR" refers to a protein complex expressed by T cells that is capable of engaging a specific repertoire of MHC/Ligand complexes as presented on the surface of cells, such as antigen presenting cells (APCs).

As used herein, the term "MHC Binding Motif" refers to a pattern of amino acids in a protein sequence that predicts binding to a particular MHC allele.

As used herein, the term "EpiBar™" refers to a 9-mer peptide that is predicted to be reactive to at least four different HLA alleles. A representative example of an immunogenic peptide that contains an EpiBar™ is shown below in FIG. 7. FIG. 7 depicts an example of an EpiBar and the EpiMatrix analysis of a promiscuous influenza epitope. Consider the influenza HA peptide, an epitope known to be promiscuously immunogenic. It scores extremely high for all eight alleles in EpiMatrix. Its cluster score is 18. Cluster scores higher than 10 are considered to be significant. The band-like EpiBar pattern is characteristic of promiscuous epitopes. Results are shown in FIG. 7 for PRYVKQNTL (SEQ ID NO: 125), RYVKQNTLK (SEQ ID NO: 126), YVKQNTLKL (SEQ ID NO: 127), VKQNTLKLA (SEQ ID NO: 128) and KQNTLKLAT (SEQ ID NO: 129). Z score indicates the potential of a 9-mer frame to bind to a given HLA allele. All scores in the top 5% are considered "hits", while non-hits (*) below 10% are masked in FIG. 7 for simplicity.

As used herein, the term "native Fc" refers to a molecule or sequence comprising the sequence of a non-antigen-binding fragment resulting from digestion of whole antibody, whether in monomeric or multimeric form, into which a peptide sequence may be added by insertion into or replacement of a loop region. The original immunoglobulin source of the native Fc is preferably of human origin and may be any of the immunoglobulins, including but not limited to IgG1 and IgG2. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), Nucleic Acids Res. 10: 4071-9). The term "native Fc" as used herein is generic to the monomeric, dimeric, and multimeric forms.

As used herein, the term "Immune Synapse" means the protein complex formed by the simultaneous engagement of a given T cell epitope to both a cell surface MHC complex and TCR.

The term "polypeptide" refers to a polymer of amino acids, and not to a specific length; thus, peptides, oligopeptides and proteins are included within the definition of a polypeptide. As used herein, a polypeptide is said to be "isolated" or "purified" when it is substantially free of cellular material when it is isolated from recombinant and non-recombinant cells, or free of chemical precursors or other chemicals when it is chemically synthesized. A polypeptide (e.g., a polypeptide comprising, consisting of, or consisting essentially of one or more of SEQ ID NOS: 1-124 or variants and fragments thereof, which in aspects may be isolated, synthetic, or recombinant) of the present disclosure, however, can be joined to, linked to, or inserted into another polypeptide (e.g., a heterologous polypeptide) with which it is not normally associated in a cell and still be "isolated" or "purified." As used herein with respect to the one or more Tregitopes of the instant disclosure, the term "heterologous polypeptide" is intended to mean that the one or more Tregitopes is heterologous to, or not included naturally, in the heterologous polypeptide. For example, one or more Tregitopes of the present disclosure (and/or one or more other Tregitopes, such as additional IgG derived Tregitopes as disclosed in U.S. Pat. No. 7,884,184, which is incorporated by reference in its entirety) can be linked to (e.g., fused in-frame, chemically-linked, or otherwise bound) and/or inserted into a heterologous polypeptide (e.g., but not limited to, an antibody (which, in aspects, may be monoclonal, polyclonal, mouse, human, humanized, monospecific, bispecific, glycosylated (e.g., sugar chain-modified), Fc-modified, or antibody-drug conjugate; or an antibody fragment thereof (e.g., Fab, scFv, diabody, sdAb, or tandem scFv); or an antibody of different class or subclass (e.g., IgG (e.g., IgG1, IgG2, IgG3, or IgG4), IgM, IgE, or IgA)). Additionally, one or more Tregitopes of the present disclosure can be joined to, linked to, or inserted into another polypeptide wherein said one or more Tregitopes of the present disclosure is not naturally included in the polypeptide and/or said one or more Tregitopes of the present disclosure is not located at its natural position in the polypeptide. For example, in aspects, the one or more Tregitopes may be inserted into or replace amino acids in a Fc domain as disclosed in U.S. Pat. Nos. 7,442,778, 7,645,861, 7,655,764, 7,655,765, and/or 7,750,128 (each of which are herein incorporated by reference in their entirety). In aspects, the one or more Tregitopes may be covalently bound to one or more internal conjugation site(s) in an Fc domain as disclosed in U.S. Pat. Nos. 8,008,453, 9,114,175, and/or 10,188,740 (each of which are herein incorporated by reference in their entirety). When a polypeptide is recombinantly produced, it can also be substantially free of culture medium, for example, culture medium represents less than about 20%, less than about 10%, or less than about 5% of the volume of the polypeptide preparation.

As used herein, a "concatemeric" peptide or polypeptide refers to a series of at least two peptides or polypeptides linked together. Such linkages may form of string-of-beads design. In aspects, each of the peptides or polypeptides of concatemeric polypeptide may optionally be spaced by one or more linkers, and in further aspects neutral linkers. The term "linker" may refer to a peptide added between two peptide domains such as epitopes or vaccine sequences to connect said peptide domains. In aspects, a linker sequence is used to reduce steric hindrance between each one or more identified peptides of the instant disclosure, is well translated, and supports or allows processing of the each one or more identified polypeptides of the instant disclosure. In aspects, the linker should have little or no immunogenic sequence elements. In aspects, each peptide or polypeptide of the concatemeric polypeptide may optionally have one or more linkers, which may optionally be cleavage sensitive sites, adjacent to their N and/or C terminal end. In such a concatemeric peptide, two or more of the peptides may have a cleavage sensitive site between them. Alternatively two or more of the peptides may be connected directly to one another or through a linker that is not a cleavage sensitive site.

As used herein, the term "pharmaceutically acceptable" refers to approved or approvable by a regulatory agency of the Federal or a state government or listed in the U.S. Pharmacopeia or other generally recognized pharmacopeia for use in animals, including humans.

As used herein, the term "pharmaceutically acceptable excipient, carrier, or diluent" or the like refer to an excipient, carrier, or diluent that can be administered to a subject, together with an agent, and which does not destroy the pharmacological activity thereof and is nontoxic when administered in doses sufficient to deliver a therapeutic amount of the agent.

As used herein, a "free thiol" refers to a thiol side chain of an amino acid optionally in a polypeptide and/or protein, wherein the thiol contains a sulfhydryl group. For example, free thiols are not bound to the side chains of other amino acids through intramolecular or intermolecular disulfide bonds.

As used herein, "functionalities" are groups on blood components, including mobile and fixed proteins, to which reactive groups on modified therapeutic peptides react to form covalent bonds. Functionalities may include hydroxyl groups for bonding to ester reactive groups, thiol groups for bonding to maleimides, imidates and thioester groups; amino groups for bonding to activated carboxyl, phosphoryl or any other acyl groups on reactive groups.

As used herein, "blood components" may be either fixed or mobile. Fixed blood components are non-mobile blood components and include tissues, membrane receptors, interstitial proteins, fibrin proteins, collagens, platelets, endothelial cells, epithelial cells and their associated membrane and membranous receptors, somatic body cells, skeletal and smooth muscle cells, neuronal components, osteocytes and osteoclasts and all body tissues especially those associated with the circulatory and lymphatic systems. Mobile blood components are blood components that do not have a fixed situs for any extended period of time, generally not exceeding one more usually one minute. These blood components are not membrane-associated and are present in the blood for extended periods of time and are present in a minimum concentration of at least μg/ml. Mobile blood components include serum albumin, transferrin, ferritin and immunoglobulins such as IgM and IgG. The half-life of mobile blood components may be at least about 12 hours.

As used herein, the term "purpose built computer program" refers to a computer program designed to fulfill a specific purpose; typically to analyze a specific set of raw data and answer a specific scientific question.

As used herein, the term "z-score" indicates how many standard deviations an element is from the mean. A z-score can be calculated from the following formula. $z=(X-\mu)/\alpha$, where z is the z-score, X is the value of the element, $\mu$ is the population mean, and a is the standard deviation.

As used herein, the singular forms "a," "an," and "the" are intended to include the plural forms, including "at least one," unless the content clearly indicates otherwise. "Or" means "and/or." As used herein, the term "and/or" and "one or more" includes any and all combinations of the associated listed items. For example, the term "one or more" with respect to the "one or more of SEQ ID NOS: 1-124 of the present disclosure" includes any and all combinations of SEQ ID NOS: 1-124. The term "or a combination thereof" means a combination including at least one of the foregoing elements.

The following abbreviations and/or acronyms are used throughout this application:
APC antigen presenting cells
CEF cytomegalovirus, Epstein-Barr virus and influenza virus
CF SE dye carboxyfluorescein succinimidyl ester dye
DMSO dimethyl sulfoxide
DR antibody antigen D related antibody
ELISA enzyme-linked immunosorbent assay
FACS fluorescence-activated cell sortings
Fmoc 9-fluoronyl methoxy carbonyl
FV human coagulation Factor V
FVIII human coagulation Factor VIII
HLA human leukocyte antigen
HPLC high-performance liquid chromatography
IVIG intravenous purified Immunoglobulin G antibody
MFI mean fluorescence index
MHC major histocompatibility complex
PBMC peripheral blood mononuclear cell
PI proliferation index
RPMI Roswell Park Memorial Institute medium
$T_{eff}$ effector T cell
$T_{Reg}$ regulatory T cell
TT tetanus toxoid
UV ultraviolet As used herein, a "variant" peptide or polypeptide (including a variant Tregitope) can differ in amino acid sequence by one or more substitutions, deletions, insertions, inversions, fusions, and truncations or a combination of any of these. In aspects, a variant peptide or polypeptide (including a variant T-cell epitope) can differ in amino acid sequence by one or more substitutions, deletions, insertions, inversions, fusions, and truncations or a combination of any of these provided said variants retain MEW binding propensity and/or TCR specificity, and/or regulatory T cell stimulating or suppressive activity.

As used herein, an "antibody" can take various forms, including, but not limited to, one or more of the following: monoclonal or polyclonal; mouse, human, or humanized; monospecific or bispecific; glycosylated; Fc-modified; antibody-drug conjugate; antibody of different class or subclass, such as IgG (e.g., IgG1, IgG2, IgG3, or IgG4), IgM, IgE, or IgA; and/or antibody fragments or derivatives thereof (e.g., Fab, scFv, diabody, sdAb, or tandem sccFv.

The present disclosure also includes polypeptide fragments of the Tregitopes as described herein. The present disclosure also encompasses fragments of the variants of the Tregitopes described herein, provided said fragments and/or variants at least in part retain MEW binding propensity and/or TCR specificity, and/or regulatory T cell stimulating or suppressive activity.

The present disclosure also provides chimeric or fusion polypeptides (which in aspects may be isolated, synthetic, or recombinant) wherein one or more of the instantly disclosed Tregitopes is a part thereof. In aspects, a chimeric or fusion polypeptide composition comprises one or more polypeptides (Treg activating regulatory T-cell epitope, Tregitope, Tregitope peptide, or T-cell epitope polypeptide) of the instant disclosure linked to a heterologous polypeptide (e.g. but not limited to, monoclonal antibody, polyclonal antibody, mouse antibody, human antibody, humanized antibody, mono specific antibody, bispecific antibody, glycosylated antibody, Fc-modified antibody, or antibody-drug conjugates; an antibody of different class or subclass (e.g., IgG (e.g., IgG1, IgG2, IgG3, IgG4), IgM, IgA, IgD or IgE molecules) or antigen-specific antibody fragments thereof (including, but not limited to, a Fab, F(ab')2, Fv, disulfide linked Fv, scFv, single domain antibody, closed conformation multispecific antibody, disulfide-linked scFv, diabody)). As previously stated, the term "heterologous polypeptide" is intended to mean that the one or more Tregitopes of the instant disclosure (e.g., one or more of SEQ ID NOS: 1-124) are heterologous to, or not included naturally, in the heterologous polypeptide. In aspects, the one or more Tregitopes may be inserted into the heterologous polypeptide (e.g., through mutagenesis or other known means in the art), may be added to the C-terminus (with or without the use of linkers, as is known in the art), and/or added to the N-terminus (with or without the use of linkers, as is known in the art) of the heterologous polypeptide. In aspects, the one or more Tregitopes may be inserted into or replace amino acids in a Fc domain as disclosed in U.S. Pat. Nos. 7,442,778, 7,645,861, 7,655,764, 7,655,765, and/or 7,750,128 (each of which are herein incorporated by reference in their entirety). For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety). In aspects, chimeric or fusion polypeptides comprise one or more Tregitope of the present disclosure operatively linked to a heterologous polypeptide. "Operatively linked" indicates that the polypeptide (e.g., the one or more Treg activating regulatory T-cell epitope, Tregitope, Tregitope peptide, or T-cell epitope polypeptide of the present disclosure) and the heterologous protein are fused in-frame or chemically linked or otherwise bound. For example, in aspects, the one or more Tregitopes may be covalently bound to one or more internal conjugation site(s) in an Fc domain as disclosed in U.S. Pat. Nos. 8,008,453, 9,114,175, and/or 10,188,740 (each of which are herein incorporated by reference in their entirety). In aspects, an isolated, synthetic, or recombinant chimeric or fusion polypeptide composition comprises a polypeptide, said polypeptide having a sequence comprising one or more of SEQ ID NOS: 1-124 of the present disclosure, wherein said one or more of SEQ ID NOS: 1-124 is not naturally included in the polypeptide and/or said of one or more of SEQ ID NOS: 1-124 is not located at its natural position in the polypeptide. In aspects, the one or more of SEQ ID NOS: 1-124 of the present disclosure can be joined, linked to (e.g., fused in-frame, chemically linked, or otherwise bound), and/or inserted into the polypeptide. In aspects, the one or more of SEQ ID NOS: 1-124 of the present disclosure can be joined or linked to (e.g., fused in-frame, chemically-linked, or otherwise bound) to a small molecule, drug, or drag fragment, for example but not limited to, a drug or drug fragment that is binds with high affinity to defined HLAs. In aspects of the above chimeric or fusion polypeptide compositions, the one or more polypeptides (Treg activating regulatory T-cell epitope, Tregitope, Tregitope peptide, or T-cell epitope polypeptide) of the present disclosure have a sequence comprising, consisting of, or consisting essentially of one or more of SEQ ID NOS: 1-124, and optionally 1 to 12 additional amino acids distributed in any ratio on the N terminus and/or C-terminus of the polypeptide of SEQ ID NOS: 1-124.

An "isolated" polypeptide (e.g., an isolated Treg activating regulatory T-cell epitope, Tregitope, Tregitope peptide, or T-cell epitope polypeptide) polypeptide, concatemeric peptide, or chimeric or fusion polypeptide can be purified from cells that naturally express it, purified from cells that have been altered to express it (recombinant), or synthesized using known protein synthesis methods. In one embodiment, a peptide, polypeptide, concatemeric peptide, or chimeric or fusion polypeptide is produced by recombinant DNA or RNA techniques. For example, a nucleic acid molecule encoding the Tregitope is cloned into an expression vector, the expression vector introduced into a host cell and the polypeptide expressed in the host cell. The Tregitope can then be isolated from the cells by an appropriate purification scheme using standard protein purification techniques.

For the purposes of the present disclosure, peptides, polypeptides, concatemeric peptides, or chimeric or fusion polypeptides of the instant disclosure can include, for example, modified forms of naturally occurring amino acids such as D-stereoisomers, non-naturally occurring amino acids; amino acid analogs; and mimetics. Further, in aspects, peptides, polypeptides, concatemeric peptides, or chimeric or fusion polypeptides of the instant disclosure can include retro-inverso peptides of the instantly disclosed peptides, polypeptides, concatemeric peptides, or chimeric or fusion polypeptides of the instant disclosure, provided said retro-inverso peptides, polypeptides, concatemeric peptides, or chimeric or fusion polypeptides of the instant disclosure at least in part retain MHC binding propensity and/or TCR specificity, and/or regulatory T cell stimulating or suppressive activity.

Although any methods and materials similar or equivalent to those described herein can be used in the practice or testing of the present disclosure, the preferred methods and materials are described. Other features, objects, and advantages of the present disclosure will be apparent from the description and the Claims. In the Specification and the appended Claims, the singular forms include plural referents unless the context clearly dictates otherwise. Unless defined otherwise, all technical and scientific terms used herein have the same meaning as commonly understood by one of ordinary skill in the art to which this invention belongs. All references cited herein are incorporated herein by reference in their entirety and for all purposes to the same extent as if each individual publication, patent, or patent application was specifically and individually indicated to be incorporated by reference in its entirety for all purposes.

POLYPEPTIDES, CONCATEMERIC POLYPEPTIDES, and CHIMERIC or FUSION POLYPEPTIDES

In aspects, the present disclosure provides Tregitope compounds and compositions, including polypeptides (Treg activating regulatory T-cell epitope, Tregitope, Tregitope peptide, or T-cell epitope polypeptide, which in aspects may be isolated, synthetic, or recombinant) as disclosed herein; nucleic acids, expression cassettes, plasmids, expression vectors, recombinant viruses, or cells (all of which in aspects may be isolated, synthetic, or recombinant) as disclosed herein; isolated, synthetic, or recombinant chimeric or fusion polypeptide compositions as disclosed herein; and/or pharmaceutical compositions or formulations as disclosed herein. In aspects, the Tregitope compositions include one or more of the regulatory Tregitopes of Table 1 (including fragments thereof, variants thereof, and fragments of such variants thereof, provided said fragments and/or variants retain MHC binding propensity and/or TCR specificity, and/or regulatory T cell stimulating or suppressive activity.). In certain aspects, the Tregitopes can be capped with an N-terminal acetyl and/or C-terminal amino group.

In one aspect, the present disclosure provides a novel class of T cell epitopes (which may be isolated, synthetic, or recombinant), termed 'Tregitopes', which comprise a peptide or polypeptide chain derived from common human proteins. Tregitopes of the present disclosure are highly conserved among known variants of their source proteins (e.g., present in more than 10% of known variants). Tregitopes of the present disclosure comprise at least one putative T cell epitope as identified by EpiMatrix™ analysis. EpiMatrix™ is a proprietary computer algorithm developed by EpiVax (Providence, Rhode Island), which is used to screen protein sequences for the presence of putative T cell epitopes. Input sequences are parsed into overlapping 9-mer frames where each frame overlaps the last by 8 amino acids. Each of the resulting frames is then scored for predicted binding affinity with respect to a panel of eight common Class II HLA alleles (DRB1*0101, DRB1*0301, DRB1*0401, DRB1*0701, DRB1*0801, DRB1*1101, DRB1*1301, and DRB1*1501). Raw scores are normalized against the scores of a large sample of randomly generated peptides. The resulting "Z" score is reported. In aspects, any 9-mer peptide with an allele-specific EpiMatrix™ Z-score in excess of 1.64, theoretically the top 5% of any given sample is considered a putative T cell epitope.

Peptides containing clusters of putative T cell epitopes are more likely to test positive in validating in vitro and in vivo assays. The results of the initial EpiMatrix™ analysis are further screened for the presence of putative T cell epitope "clusters" using a second proprietary algorithm known as Clustimer™ algorithm. The Clustimer™ algorithm identifies sub-regions contained within any given amino acid sequence that contains a statistically unusually high number of putative T cell epitopes. Typical T-cell epitope "clusters" range from about 9 to roughly 30 amino acids in length and, considering their affinity to multiple alleles and across multiple 9-mer frames, can contain anywhere from about 4 to about 40 putative T cell epitopes. Each epitope cluster identified an aggregate EpiMatrix™ score is calculated by summing the scores of the putative T cell epitopes and subtracting a correcting factor based on the length of the candidate epitope cluster and the expected score of a randomly generated cluster of the same length. EpiMatrix™ cluster scores in excess of +10 are considered significant. In aspects, the Tregitopes of the instant disclosure contain several putative T cell epitopes forming a pattern known as a T cell epitope cluster. FIGS. 7-9 show exemplary EpiMatrix reports.

Many of the most reactive T cell epitope clusters contain a feature referred to as an "EpiBar™." As described previously, an EpiBar™ is a single 9-mer frame that is predicted to be reactive to at least four different HLA alleles. In aspects, the Tregitopes of the present disclosure can comprise one or more EpiBars™.

The JanusMatrix system (EpiVax, Providence, Rhode Island) useful for screening peptide sequences for cross-conservation with a host proteome. JanusMatrix is an algorithm that predicts the potential for cross-reactivity between peptide clusters and the host genome or proteome, based on conservation of TCR-facing residues in their putative MHC ligands. The JanusMatrix algorithm first considers all the predicted epitopes contained within a given protein sequence and divides each predicted epitope into its constituent agretope and epitope. Each sequence is then screened against a database of host proteins. Peptides with a compatible MHC-facing agretope (i.e., the agretopes of both the input peptide and its host counterparty are predicted to bind the same MHC allele) and exactly the same TCR-facing epitope are returned. The JanusMatrix Homology Score suggests a bias towards immune tolerance. In the case of a therapeutic protein, cross-conservation between autologous human epitopes and epitopes in the therapeutic may increase the likelihood that such a candidate will be tolerated by the human immune system. In the case of a vaccine, cross-conservation between human epitopes and the antigenic epitopes may indicate that such a candidate utilizes immune camouflage, thereby evading the immune response and making for an ineffective vaccine. When the host is, for example, a human, the peptide clusters are screened against human genomes and proteomes, based on conservation of TCR-facing residues in their putative HLA ligands. The peptides are then scored using the JanusMatrix Homology Score. In aspects, peptides with a JanusMatrix Homology Score above 3.0 indicate high tolerogenicity potential and as such may be very useful Tregitopes of the present disclosure.

FIG. 11 is the overview of JanusMatrix results for identified the Tregitopes of SEQ ID NOS: 1-15 of the instant disclosure. FIG. 12 is the JanusMatrix report for the Tregitope of SEQ ID NO: 1 and the 9-mers contained within SEQ ID NO: 1, including SEQ ID NOS: 16-28. FIG. 13 is the JanusMatrix report for the Tregitope of SEQ ID NO: 10 and the 9-mers contained within SEQ ID NO: 10, including SEQ ID NOS: 87-93. FIG. 14 is the JanusMatrix report for the Tregitope of SEQ ID NO: 11 and the 9-mers contained within SEQ ID NO: 11, including SEQ ID NOS: 94-100. FIG. 15 is the JanusMatrix report for the Tregitope of SEQ ID NO: 12. *Count of HUMAN JanusMatrix matches found in the search database. FIG. 16 is the JanusMatrix report for the Tregitope of SEQ ID NO: 13 and the 9-mers contained within SEQ ID NO: 13, including SEQ ID NOS: 101-110. FIG. 17 is the JanusMatrix report for the Tregitope of SEQ ID NO: 14 and the 9-mers contained within SEQ ID NO: 14, including SEQ ID NOS: 111-120. *Count of HUMAN JanusMatrix matches found in the search database. FIG. 18 is the JanusMatrix report for the Tregitope of SEQ ID NO: 15 and the 9-mers contained within SEQ ID NO: 15, including SEQ ID NOS: 121-124. FIG. 19 is the JanusMatrix report for the Tregitope of SEQ ID NO: 10 and the 9-mers contained within SEQ ID NO: 2, including SEQ ID NOS: 29-41. *Count of HUMAN JanusMatrix matches found in the search database. FIG. 20 is the JanusMatrix report for the Tregitope of SEQ ID NO: 3 and the 9-mers contained within SEQ ID NO: 3, including SEQ ID NOS: 42-48. FIG. 21 is the JanusMatrix report of SEQ ID NO: 4 and the 9-mers contained within SEQ ID NO: 4, including SEQ ID NOS: 49-50. *Count of HUMAN JanusMatrix matches found in the search database. FIG. 22 is the JanusMatrix report for the Tregitope of SEQ ID NO: 50. FIG. 23 is the JanusMatrix report for the Tregitope of SEQ ID NO: 6 and the 9-mers contained within SEQ ID NO: 6, including SEQ ID NOS: 51-57. FIG. 24 is the JanusMatrix report for the Tregitope of SEQ ID NO: 10 and the 9-mers contained within SEQ ID NO: 7, including SEQ ID NOS: 58-67. FIG. 25 is the JanusMatrix report for the Tregitope of SEQ ID NO: 8 and the 9-mers contained within SEQ ID NO: 8, including SEQ ID NOS: 68-74. FIG. 26 is the JanusMatrix report for the Tregitope of SEQ ID NO: 9 and the 9-mers contained within SEQ ID NO: 9, including SEQ ID NOS: 87-93. For each of FIGS. 11-26, * is the count of HUMAN JanusMatrix matches found in the search database. With respect to a given EpiMatrix Hit (a 9-mer contained within the input sequence which is predicted to bind to a specific allele), a Janus Matrix match is a 9-mer derived from the search database (e.g., the human genome) which is predicted to bind to the same allele as the EpiMatrix Hit and shares TCR facing contacts with the EpiMatrix Hit. Further, the Janus Homology Score**represents the average depth of coverage in the search database for each EpiMatrix hit in the input sequence. For example, an input peptide with eight EpiMatrix hits, all of which have one match in the search database, has a Janus Homology Score of 1. An input peptide with four EpiMatrix Hits, all of which have two matches in the search database, has a Janus Homology Score of 2. The JanusMatrix Homology Score considers all constituent 9-mers in any given peptide, including flanks.

In aspects, Tregitopes of the present disclosure bind to at least one and preferably two or more common HLA class II molecules with at least a moderate affinity (e.g., in aspects, <1000 µM $IC_{50}$, <500 µM $IC_{50}$, <400 µM $IC_{50}$, <300 µM $IC_{50}$, or <200 µM $IC_{50}$ in HLA binding assays based on soluble HLA molecules). In aspects, Tregitopes of the present disclosure are capable of being presented at the cell surface by APCs in the context of at least one and, in other aspects, two or more alleles of the HLA. In this context, the Tregitope-HLA complex can be recognized by naturally occurring $T_{Regs}$ (in aspects, including natural $T_{Regs}$ and/or adaptive $T_{Regs}$) having TCRs that are specific for the Tregitope-HLA complex and circulating in normal control subjects. In aspects, the recognition of the Tregitope-HLA complex can cause the matching regulatory T cell to be activated and to secrete regulatory cytokines and chemokines.

In aspects, the present disclosure is directed to a polypeptide (which may be termed herein as "Treg activating regulatory T-cell epitope", "Tregitope", "Tregitope peptide", or "T-cell epitope polypeptide") having a sequence comprising, consisting of, or consisting essentially of one or more of SEQ ID NOS: 1-124 (and fragments and variants thereof). The phrase "consisting essentially of" is intended to mean that a polypeptide according to the present disclosure, in addition to having the sequence according to any of SEQ ID NOS: 1-124 or a variant thereof, contains additional amino acids or residues that may be present at either terminus of the peptide and/or on a side chain that are not necessarily forming part of the peptide that functions as an MHC ligand and provided they do not substantially impair the activity of the peptide to function as a Tregitope. In aspects, the peptides or polypeptides of the instant disclosure can be either in neutral (uncharged) or salt forms, and may be either free of or include modifications such as glycosylation, side chain oxidation, or phosphorylation. In certain aspects, such polypeptides can be capped with an N-terminal acetyl and/or C-terminal amino group.

In aspects, the instant disclosure is directed to a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124. In aspects, the instant disclosure is directed to a peptide or polypeptide have a core amino acid sequence comprising, consisting of, or consisting essentially of one or more peptides or polypeptides having an amino acid sequence of SEQ ID NOS: 1-124, and optionally having extensions of 1 to 12 amino acids on the C-terminal and/or the N-terminal of the core amino acid sequence, wherein the overall number of these flanking amino acids is 1 to 12, 1 to 3, 2 to 4, 3 to 6, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to or 10 to 12, wherein the flanking amino acids can be distributed in any ratio to the C-terminus and the N-terminus (for example all flanking amino acids can be added to one terminus, or the amino acids can be added equally to both termini or in any other ratio). In aspects, the instant disclosure is directed to a peptide or polypeptide having a core sequence comprising, consisting of, or consisting essentially of one or more peptides or polypeptides having an amino acid sequence of SEQ ID NOS: 1-124 (and/or fragments and variants thereof), optionally with extensions of 1 to 12 amino acids on the C-terminal and/or the N-terminal, wherein the overall number of these flanking amino acids is 1 to 12, 1 to 3, 2 to 4, 3 to 6, 1 to 10, 1 to 8, 1 to 6, 2 to 12, 2 to 10, 2 to 8, 2 to 6, 3 to 12, 3 to 10, 3 to 8, 3 to 6, 4 to 12, 4 to 10, 4 to 8, 4 to 6, 5 to 12, 5 to 10, 5 to 8, 5 to 6, 6 to 12, 6 to 10, 6 to 8, 7 to 12, 7 to 10, 7 to 8, 8 to 12, 8 to 10, 9 to 12, 9 to 10, or 10 to 12, wherein the flanking amino acids can be distributed in any ratio to the C-terminus and the N-terminus (for example all flanking amino acids can be added to one terminus, or the amino acids can be added equally to both termini or in any other ratio), provided that the polypeptide with the flanking amino acids is still able to bind to a same HLA molecule (i.e., retain MHC binding propensity) as said polypeptide core sequence without said flanking amino acids. In aspects, said polypeptide with the flanking amino acids is still able to bind to a same HLA molecule (i.e., retain MHC binding propensity) and/or retain the same TCR specificity, and/or retain regulatory T cell stimulating or suppressive activity, as said polypeptide core sequence without said flanking amino acids. In aspects, said flanking amino acid sequences are those that also flank the peptides or polypeptides included therein in the naturally occurring protein, e.g., in an IgG antibody. In aspects, the extension(s) may serve and be designed to improve the biochemical properties of the peptides or polypeptides (e.g., but not limited to, solubility or stability) or to improve the likelihood for efficient proteasomal processing of the peptide. In aspects, said flanking amino acid sequences as described herein may serve as a MEW stabilizing region. The use of a longer peptide may allow endogenous processing by patient cells and may lead to more effective antigen presentation and induction of T cell responses. In aspects, the peptides or polypeptides can be in either neutral (uncharged) or salt forms, and may be either free of or include modifications such as glycosylation, side chain oxidation, or phosphorylation. In certain aspects, such polypeptides can be capped with an N-terminal acetyl and/or C-terminal amino group.

In aspects, the instant disclosure is directed to a polypeptide comprising an amino acid sequence having at least 75%, 80%, 85%, 90%, or 95% homology to any one of SEQ ID NOS: 1-124 (and/or fragments thereof), wherein said polypeptide is still able to bind to a same HLA molecule (i.e., retain MHC binding propensity) and/or retain the same TCR specificity, and/or retain regulatory T cell stimulating or suppressive activity.

In aspects, the present disclosure is directed to a concatemeric polypeptide or peptide that comprises at one or more of the instantly-disclosed polypeptides or peptides (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) linked, fused, or joined together (e.g., fused in-frame, chemically linked, or otherwise bound) to an additional peptide or polypeptide. Such additional peptide or polypeptide may be one or more of the instantly disclosed polypeptides or peptides, or may be an additional peptide or polypeptide of interest. In aspects a concatemeric peptide is composed of 3 or more, 4 or more, 5 or more 6 or more 7 or more, 8 or more, 9 or more of the instantly-disclosed peptides or polypeptides. In other aspects, the concatemeric peptides or polypeptides include 1000 or more, 1000 or less, 900 or less, 500 or less, 100 or less, 75 or less, or less, 40 or less, 30 or less, 20 or less or 100 or less peptide epitopes. In yet other embodiments, a concatemeric peptide has 3-100, 5-100, 10-100, 15-100, 20-100, 25-100, 30-100, 35-100, 40-100, 45-100, 50-100, 55-100, 60-100, 65-100, 70-100, 75-100, 80-100, 90-100, 5-50, 10-50, 15-20-50, 25-50, 30-50, 35-50, 40-50, 45-50, 100-150, 100-200, 100-300, 100-400, 100-500, 50-500, 50-800, 50-1,000, or 100-1,000 of the instantly disclosed peptides or polypeptides linked, fused, or joined together. It should be understood that the present disclosure also relates to nucleic acids (e.g., RNA mRNA, DNA, cDNA) encoding such concatemeric peptides. Each peptide or polypeptide of the concatemeric polypeptide may optionally have one or more linkers, which may optionally be cleavage sensitive sites, adjacent to their N and/or C terminal end. Such suitable linkers and cleavage sensitive sites, including AAY cleavage motifs or a poly GS linker which may be include on the N terminus of the C-terminal element, are known in the art. In such a concatemeric peptide, two or more of the peptide epitopes may have a cleavage sensitive site between them. Alternatively, two or more of the peptide epitopes may be connected directly to one another or through a linker that is not a cleavage sensitive site. In aspects, such linker is antigenically neutral, and the liker is preferably less than the length of a peptidyl backbone of 9 amino acids linearly arranged. In aspects, linker length is the length of a peptidyl backbone of between 2 and 8 amino acids, linearly arranged. In aspects, the spacer is unable to hydrogen bond in any spatially distinct manner to other distinct elements of the enhancing hybrid peptide.

In aspects, and with respect to antigenically neutral linker elements, various chemical groups may be incorporated as linkers instead of amino acids. Examples are described in U.S. Pat. No. 5,910,300, the contents of which are incorporated herein by reference. In aspects, a linker may be comprised of an aliphatic chain optimally interrupted by heteroatoms, for example a C2-C6 alkylene, or =N—(CH2) 2-6-N=. Alternatively, a spacer may be composed of alternating units, for example of hydrophobic, lipophilic, aliphatic and aryl-aliphatic sequences, optionally interrupted by heteroatoms such as O, N, or S. Such components of a spacer are preferably chosen from the following classes of compounds: sterols, alkyl alcohols, polyglycerides with varying alkyl functions, alkyl-phenols, alkyl-amines, amides, hydroxyphobic polyoxyalkylenes, and the like. Other examples are hydrophobic polyanhydrides, polyorthoesters, polyphosphazenes, polyhydroxy acids, polycaprolactones, polylactic, polyglycolic polyhydroxy-butyric acids. A linker may also contain repeating short aliphatic chains, such as polypropylene, isopropylene, butylene, isobutylene, pentamethlyene, and the like, separated by oxygen atoms.

Additional peptidyl sequences which can be used in as possible linkers are described in U.S. Pat. No. 5,856,456, the contents of which are incorporated herein by reference. In one embodiment, a linker has a chemical group incorporated within which is subject to cleavage. Without limitation, such a chemical group may be designed for cleavage catalyzed by a protease, by a chemical group, or by a catalytic monoclonal antibody. In the case of a protease-sensitive chemical group, tryptic targets (two amino acids with cationic side chains), chymotryptic targets (with a hydrophobic side chain), and cathepsin sensitivity (B, D or S) are favored. The term 'tryptic target' is used herein to describe sequences of amino acids which are recognized by trypsin and trypsin-like enzymes. The term 'chymotryptic target' is used herein to describe sequences of amino acids which are recognized by chymotrypsin and chymotrypsin-like enzymes. In addition, chemical targets of catalytic monoclonal antibodies, and other chemically cleaved groups are well known to persons skilled in the art of peptide synthesis, enzymatic catalysis, and organic chemistry in general, and can be designed into the hybrid structure and synthesized, using routine experimental methods.

In aspects, a concatemeric polypeptide of the instant disclosure is produced using the EpiAssembler System (EpiVax). The EpiAssembler system is useful for assembling overlapping epitopes to Immunogenic Consensus Sequences (ICS). EpiAssembler is an algorithm that optimizes the balance between pathogen and population coverage. EpiAssembler uses the information from the sequences produced by Conservatrix and EpiMatrix to form highly immunogenic consensus sequences.

In aspects of above-described concatemeric peptides or polypeptides, the concatemeric peptides or polypeptides may be isolated, synthetic, or recombinant. In aspects, the concatemeric peptides or polypeptides can be in either neutral (uncharged) or salt forms, and may be either free of or include modifications such as glycosylation, side chain oxidation, or phosphorylation. In certain aspects, the concatemeric polypeptides can be capped with an N-terminal acetyl and/or C-terminal amino group.

As used herein, two polypeptides (or a region of the polypeptides) are substantially homologous or identical when the amino acid sequences are at least about 45-55%, typically at least about 70-75%, more typically at least about 80-85%, more typically greater than about 90%, and more typically greater than 95% or more homologous or identical. To determine the percent homology or identity of two amino acid sequences, or of two nucleic acid sequences, the sequences are aligned for optimal comparison purposes (e.g., gaps can be introduced in the sequence of one polypeptide or nucleic acid molecule for optimal alignment with the other polypeptide or nucleic acid molecule). The amino acid residues or nucleotides at corresponding amino acid positions or nucleotide positions are then compared. When a position in one sequence is occupied by the same amino acid residue or nucleotide as the corresponding position in the other sequence, then the molecules are homologous at that position. As is known in the art, the percent identity between the two sequences is a function of the number of identical positions shared by the sequences, taking into account the number of gaps, and the length of each gap, which need to be introduced for optimal alignment of the two sequences. Sequence homology for polypeptides is typically measured using sequence analysis software. As used herein, amino acid or nucleic acid "homology" is equivalent to amino acid or nucleic acid "identity". In aspects, the percent homology between the two sequences is a function of the number of identical positions shared by the sequences (e.g., percent homology equals the number of identical positions/total number of positions×100).

In aspects, the present disclosure also encompasses polypeptides having a lower degree of identity but having sufficient similarity so as to perform one or more of the same functions performed by a polypeptide of the instant disclosure (e.g., a polypeptide having a sequence comprising, consisting of, or consisting essentially of one or more of SEQ ID NOS: 1-124 and/or fragments and variants thereof, and optionally 1 to 12 additional amino acids distributed in any ratio on the N terminus and/or C-terminus of the polypeptide of SEQ ID NOS: 1-124; and concatemeric peptides as disclosed herein). Similarity is determined by conserved amino acid substitution. Such substitutions are those that substitute a given amino acid in a polypeptide by another amino acid of like characteristics. Conservative substitutions are likely to be phenotypically silent. Typically seen as conservative substitutions are the replacements, one for another, among the aliphatic amino acids Ala, Val, Leu, Met, and Ile; interchange of the hydroxyl residues Ser and Thr, exchange of the acidic residues Asp and Glu, substitution between the amide residues Asn and Gln, exchange of the basic residues His, Lys and Arg and replacements among the aromatic residues Trp, Phe and Tyr. Guidance concerning which amino acid changes are likely to be phenotypically silent are found (Bowie J U et al., (1990), Science, 247 (4948):130610, which is herein incorporated by reference in its entirety).

In aspects, a variant polypeptide can differ in amino acid sequence by one or more substitutions, deletions, insertions, inversions, fusions, and truncations or a combination of any of these. Variant polypeptides can be fully functional (e.g., retain MHC binding propensity and/or TCR specificity, and/or retain regulatory T cell stimulating or suppressive activity) or can lack function in one or more activities. Fully functional variants typically contain only conservative variation or variation in non-critical residues or in non-critical regions; in this case, typically MHC contact residues provided MHC binding is preserved. Functional variants can also contain substitution of similar amino acids that result in no change or an insignificant change in function (e.g., retain MHC binding propensity and/or TCR specificity, and/or retain regulatory T cell stimulating or suppressive activity). Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region; in this case, typically TCR contact residues. In aspects, a variant and/or a homologous polypeptide retains the desired regulatory T cell stimulating or suppressive activity of the instant disclosure. Alternatively, such substitutions can positively or negatively affect function to some degree. Non-functional variants typically contain one or more non-conservative amino acid substitutions, deletions, insertions, inversions, or truncation or a substitution, insertion, inversion, or deletion in a critical residue or critical region; in this case, typically TCR contact residues.

In aspects, functional variants of a polypeptide having a sequence (or a core sequence) comprising, consisting of, or consisting essentially of one or more of SEQ ID NOS: 1-124 as disclosed herein may contain one or more conservative substitutions, and in aspects one or more non-conservative substitutions, at amino acid residues which are not believed to be essential for functioning (with amino acid residues considered being essential for functioning, including, e.g., retain MHC binding propensity and/or TCR specificity, and/or retain regulatory T cell stimulating or suppressive activity) of the instantly-disclosed polypeptides. For example, in aspects, a variant polypeptide having a sequence (or a core sequence) comprising, consisting of, or consisting essentially of one or more of SEQ ID NOS: 1-124, or fragments thereof as disclosed herein, or a concatemeric peptide as disclosed herein, may contain one or more conservative substitutions (and in aspects, a nonconservative substitution) in one or more HLA contact residues, provided HLA binding is preserved. WIC binding assays are well known in the art. In aspects, such assays may include the testing of binding affinity with respect to WIC class I and class II alleles in in vitro binding assays, with such binding assays as are known in the art. Examples include, e.g., the soluble binding assays as disclosed in U.S. Pat. No. 7,884,184 or PCT/US2020/020089, both of which are herein incorporated by reference in their entireties. Additionally, in aspects, a fully functional variant polypeptide having a sequence (or a core sequence) comprising, consisting of, or consisting essentially of one or more of SEQ ID NOS: 1-124 as disclosed herein do not contain mutations at one or more critical residues or regions, such as TCR contact residues.

In aspects, the TCR-binding epitope (which can be referred to as TCR binding residues, TCR facing epitope, TCR facing residues, or TCR contacts) for a 9-mer identified epitope (which may be a 9-mer fragment of one or more of SEQ ID NOS: 1-124 as disclosed herein or a 9-mer fragment of a concatemeric peptide as disclosed herein) that bind to a MHC class II molecule are at position 2, 3, 5, 7, and 8 of the identified epitope, while the MHC-binding agretope (which can be referred to as WIC contacts, MHC facing residues, WIC-binding residues, or WIC-binding face) for a 9-mer identified epitope (which may be a 9-mer fragment of one or more of SEQ ID NOS: 1-124 as disclosed herein or a 9-mer fragment of a concatemeric peptide as disclosed herein) that bind to a WIC class II molecule are at position 1, 4, 6, and 9, both as counted from the amino terminal.

In aspects, the TCR binding epitope for a 9-mer identified epitope (which may be a 9-mer fragment of one or more of SEQ ID NOS: 1-124 or as disclosed herein or a 9-mer fragment of a concatemeric peptide) that binds to a MHC class I molecule are at position 4, 5, 6, 7, and 8 of the identified epitope, while the MHC binding agretope for a 9-mer identified epitope (which may be a 9-mer fragment of one or more of SEQ ID NOS: 1-124 as disclosed herein or a 9-mer fragment of a concatemeric peptide as disclosed herein) that bind to a MHC class I molecule are at position 1, 2, 3, and 9, both as counted from the amino terminal.

In aspects, the TCR binding epitope for a 10-mer identified epitope that bind to a MHC class I molecule are at position 4, 5, 6, 7, 8, and 9 of the identified epitope (which may be a 10-mer fragment of one or more of SEQ ID NOS: 1-124 as disclosed herein, or a 10-mer fragment of a concatemeric peptide as disclosed herein, or a 10-mer peptide containing a 9-mer of one or more of SEQ ID NOS: 1-124), while the MHC binding agretope for a 10-mer identified epitope (which may be a 10-mer fragment of one or more of SEQ ID NOS: 1-124 as disclosed herein, or a 10-mer fragment of a concatemeric peptide as disclosed herein, or a 10-mer peptide containing a 9-mer of one or more of SEQ ID NOS: 1-124) that bind to a MHC class I molecule are at position 1, 2, 3, 9, and 10, both as counted from the amino terminal.

In aspects, the TCR-binding epitope for a 9-mer identified epitope (which may be a 9-mer fragment of one or more of SEQ ID NOS: 1-124 as disclosed herein or a 9-mer fragment of a concatemeric peptide as disclosed herein) that bind to a MHC class II molecule are at any combination of residues at positions 2, 3, 5, 7, and 8 (e.g., but not limited to, positions 3, 5, 7 and 8; positions 2, 5, 7, and 8; positions 2, 3, 5, and 7, etc.) of the identified epitope, while the MHC binding agretope for a 9-mer identified epitope (which may be a 9-mer fragment of one or more of SEQ ID NOS: 1-124 as disclosed herein or a 9-mer fragment of a concatemeric peptide as disclosed herein) is the complementary face to the TCR facing residues, both as counted from the amino terminal.

In aspects, the TCR binding epitope for 9-mer identified epitope (which may be a 9-mer fragment of one or more of SEQ ID NOS: 1-124 as disclosed herein or a 9-mer fragment of a concatemeric peptide as disclosed herein) that bind to a MHC class I molecule are at positions 4, 5, 6, 7, and 8; 1, 4, 5, 6, 7 and 8; or 1, 3, 4, 5, 6, 7, and 8 of the identified epitope, while the MHC binding agretope for a 9-mer identified epitope (which may be a 9-mer fragment of one or more of SEQ ID NOS: 1-124 as disclosed herein or a 9-mer fragment of a concatemeric peptide as disclosed herein) is the complementary face to the TCR facing residues, both as counted from the amino terminal.

In aspects, the TCR-binding epitope for a 10-mer identified epitope (which may be a 10-mer fragment of one or more of SEQ ID NOS: 1-124 as disclosed herein, or a 10-mer fragment of a concatemeric peptide as disclosed herein, or a 10-mer peptide containing a 9-mer of one or more of SEQ ID NOS: 1-124) that bind to a MHC class I molecule are at any combination of residues at positions 1, 3, 4, 5, 6, 7, 8, and 9 of the identified epitope, while the MHC binding agretope for a 10-mer identified epitope (which may be a 10-mer fragment of one or more of SEQ ID NOS: 1-124 as disclosed herein or a 10-mer fragment of a concatemeric peptide as disclosed herein, or a 10-mer peptide containing a 9-mer of one or more of SEQ ID NOS: 1-124) is the complementary face to the TCR facing residues, both as counted from the amino terminal.

Based on the above, it should be understood that in aspects in which one or more 9-mers and/or 10-mer epitopes are contained within a longer polypeptide and are predicted to bind one or more Class I or Class II MHC molecules and are occurring in close proximity to each other in a naturally occurring sequence (e.g., wherein position 1 of each pair of binding 9-mers and/or 10-mers fall within, e.g., 3 amino acids of each other), such epitopes may be combined to form an epitope cluster. In a given cluster, any given amino acid may be, with respect to a given 9-mer epitope or 10-mer epitope, MHC facing and, with respect to another 9-mer epitope, TCR facing.

In aspects, the present disclosure also includes fragments of the instantly-disclosed polypeptides and concatemeric polypeptides. In aspects, the present disclosure also encompasses fragments of the variants of the instantly-disclosed polypeptides and concatemeric polypeptides as described herein. In aspects, as used herein, a fragment comprises at least about nine contiguous amino acids. In aspects, the present disclosure also encompasses fragments of the variants of the T-cell epitopes described herein. Useful fragments (and fragments of the variants of the polypeptides and concatemeric polypeptides described herein) include those that retain one or more of the biological activities, particularly: MHC binding propensity and/or TCR specificity, and/or retain regulatory T cell stimulating or suppressive activity. Biologically active fragments are, for example, about 9, 10, 11, 12, 1, 14, 15, 16, 20, 25, 30, 40, 50, 60, 70, 80, 90, 100 or more amino acids in length, including any value or range therebetween. Fragments can be discrete (not fused to other amino acids or polypeptides) or can be within a larger polypeptide. Several fragments can be comprised within a single larger polypeptide. In aspects, a fragment designed for expression in a host can have heterologous pre- and pro-polypeptide regions fused to the amino terminus of the polypeptide fragment and an additional region fused to the carboxyl terminus of the fragment.

In aspects, the instantly disclosed polypeptides and concatemeric polypeptides of the present disclosure can include allelic or sequence variants ("mutants") or analogs thereof, or can include chemical modifications (e.g., pegylation, glycosylation). In aspects, a mutant retains the same function, particularly WIC binding propensity and/or TCR specificity, and/or retain regulatory T cell stimulating or suppressive activity. In aspects, a mutant can provide for enhanced binding to WIC molecules. In aspects, a mutant can lead to enhanced binding to TCRs. In another instance, a mutant can lead to a decrease in binding to WIC molecules and/or TCRs. Also contemplated is a mutant that binds, but does not allow signaling via the TCR.

The manner of producing the polypeptides of the present disclosure will vary widely, depending upon the nature of the various elements comprising the molecule. For example, an isolated polypeptide can be purified from cells that naturally express it, purified from cells that have been altered to express it (recombinant), or synthesized using known protein synthesis methods. The synthetic procedures may be selected so as to be simple, provide for high yields, and allow for a highly purified stable product. For example, polypeptides of the instant disclosure can be produced either from a nucleic acid disclosed herein, or by the use of standard molecular biology techniques, such as recombinant techniques, mutagenesis, or other known means in the art. An isolated polypeptide can be purified from cells that naturally express it, purified from cells that have been altered to express it (recombinant), or synthesized using known protein synthesis techniques. In aspects, a polypeptide of the instant disclosure is produced by recombinant DNA or RNA techniques. In aspects, a polypeptide of the instant disclosure can be produced by expression of a recombinant nucleic acid of the instant disclosure in an appropriate host cell. For example, a nucleic acid molecule encoding the polypeptide is cloned into an expression cassette or expression vector, the expression cassette or expression vector introduced into a host cell and the polypeptide expressed in the host cell. The polypeptide can then be isolated from the cells by an appropriate purification scheme using standard protein purification techniques. Alternatively a polypeptide can be produced by a combination of ex vivo procedures, such as protease digestion and purification. Further, polypeptides of the instant disclosure can be produced using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety).

In aspects, one or more peptides or polypeptides of the instant disclosure (e.g., but not limited to, a peptide or polypeptide comprising, consisting, or consisting essentially of an amino acid sequence of SEQ ID NOS. 1-124 (and/or fragments or variants thereof), and optionally 1 to 12 additional amino acids distributed in any ratio on the N terminus and/or C-terminus of the polypeptide of SEQ ID NOS. 1-124, as well as the concatemeric polypeptides disclosed herein) may be joined to, linked to (e.g., fused in-frame, chemically linked, or otherwise bound), and/or inserted into a heterologous polypeptide (e.g. but not limited to, e.g. monoclonal antibody, polyclonal antibody, mouse antibody, human antibody, humanized antibody, mono specific antibody, bispecific antibody, glycosylated antibody, Fc-modified antibody, or antibody-drug conjugates; an antibody of different class or subclass (e.g., IgG (e.g., IgG1, IgG2, IgG3, IgG4), IgM, IgA, IgD or IgE molecules) or antigen-specific antibody fragments thereof (including, but not limited to, a Fab, F(ab')2, Fv, disulfide linked Fv, scFv, single domain antibody, closed conformation multispecific antibody, disulfide-linked scFv, diabody))). As previously described, with respect to the one or more Tregitopes of the instant disclosure, the term "heterologous polypeptide" is intended to mean that the one or more Tregitopes of the instant disclosure are heterologous to, or not included naturally, in the heterologous polypeptide. In aspects, one or more of the instantly-disclosed polypeptides (Tre g activating regulatory T-cell epitopes, Tregitopes, or T-cell epitope polypeptides) may be inserted into the heterologous polypeptide (e.g., through recombinant techniques, mutagenesis, or other known means in the art), may be added to the C-terminus (with or without the use of linkers, as is known in the art), and/or added to the N-terminus (with or without the use of linkers, as is known in the art) of the heterologous polypeptide. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety). In aspects, the one or more Tregitopes may be inserted into or replace amino acids in a Fc domain as disclosed in U.S. Pat. Nos. 7,442,778, 7,645,861, 7,655,764, 7,655,765, and/or 7,750,128 (each of which are herein incorporated by reference in their entirety). In aspects, chimeric or fusion polypeptides comprise one or more of the instantly-disclosed polypeptides of the present disclosure operatively linked to a heterologous polypeptide. "Operatively linked" indicates that the one or more of the instantly-disclosed polypeptides and the heterologous protein are fused in-frame or chemically linked or otherwise bound. For example, in aspects, the one or more of the instantly-disclosed polypeptides may be covalently bound to one or more internal conjugation site(s) in an Fc domain as disclosed in U.S. Pat. Nos. 8,008,453, 9,114,175, and/or 10,188,740 (each of which are herein incorporated by reference in their entirety). In aspects, the one or more peptides or polypeptides of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124, as well as the concatemeric polypeptides disclosed herein) may be joined to, linked to (e.g., fused in-frame, chemically linked, or otherwise bound), and/or inserted into a heterologous polypeptide as a whole, although it may be made up from a joined to, linked to (e.g., fused in-frame, chemically linked, or otherwise bound), and/or inserted amino acid sequence, together with flanking amino acids of the heterologous polypeptide. In aspects, the one or more peptides or polypeptides of the instant disclosure can be joined or linked to (e.g., fused in-frame, chemically-linked, or otherwise bound) to a small molecule (e.g., albumin or other known carriers and proteins), drug, or drag fragment, for example but not limited to, a drug or drug fragment that is binds with high affinity to defined HLAs. In aspects, the peptides or polypeptides can be in either neutral (uncharged) or salt forms, and may be either free of or include modifications such as glycosylation, side chain oxidation, or phosphorylation. In certain aspects, the peptides or polypeptides can be capped with an n-terminal acetyl and/or c-terminal amino group.

In aspects, the present disclosure is directed to polypeptide (which, in aspects, may be an isolated, synthetic, or recombinant) having a sequence comprising one or more of SEQ ID NOS: 1-124 (and/or fragments or variants thereof), and optionally 1 to 12 additional amino acids distributed in any ratio on the N terminus and/or C-terminus of the polypeptide of SEQ ID NOS. 1-124, wherein said one or more of SEQ ID NOS: 1-124 is not naturally included in the polypeptide and/or said one or more of SEQ ID NOS: 1-124 is not located at its natural position in the polypeptide. In aspects, one or more Tregitopes of the instant disclosure having a sequence comprising one or more of SEQ ID NOS: 1-124 (and/or fragments or variants thereof), and optionally 1 to 12 additional amino acids distributed in any ratio on the N terminus and/or C-terminus of the polypeptide of SEQ ID NOS. 1-124, may also be fused to or inserted internally within (e.g., but not limited to, by site directed mutagenesis or other recombinant techniques) an antibody (e.g., but not limited to, monoclonal antibody, polyclonal antibody, mouse antibody, human antibody, humanized antibody, monospecific antibody, bispecific antibody, glycosylated antibody, Fc-modified antibody, antibody of different classes or subclasses (e.g., IgG (such as IgG1, IgG2, IgG3, or IgG4), IgM, IgE, or IgA), or antibody-drug conjugate) or fragment thereof (e.g., but not limited to, Fab scFv, diabody, sdAb, tandem scFv), such as in instances where the Tregitope is not located in its natural position within the antibody or fragment thereof or where the antibody or fragment thereof is missing such a Tregitope (e.g., if a particular antibody or fragment thereof has a mutated or missing corresponding section). In aspects, said insertion of the one or more regulatory T cell epitopes into the antibody or fragment thereof comprises insertion of all or some of the amino acids of the one or more regulatory T cell epitopes (e.g., inserting the entire sequence of the Tregitope or a fragment thereof). In aspects, said insertion of the one or more regulatory T cell epitopes into the antibody or fragment thereof comprises insertion of some or all of the amino acids of the one or more regulatory T cell epitopes and removing one or more amino acids at the site of insertion of the regulatory T cell epitope amino acids. In aspects, said insertion of the one or more regulatory T cell epitopes into the antibody or fragment thereof comprises mutating the sequence of the antibody or fragment thereof to include the one or more regulatory T cell epitopes (for example, but not limited to, introduction one or more point mutations into the antibody or fragment thereof by site-directed mutagenesis or other recombinant techniques). In aspects, said insertion of the one or more regulatory T cell epitopes into the antibody or fragment, which in aspects will introduce the one or more regulatory T cell epitope sequences, such that the previous immunogenicity of the sequence is decreased and the tolerogenicity of the new sequence is enhanced. In aspects, the number of said added one or more amino acids at the site of insertion of the regulatory T cell epitope amino acids need not correspond to the number of amino acids deleted from the sequence of the antibody or fragment thereof. In aspects in which the one or more regulatory T cell epitopes are inserted or fused into a particular antibody (e.g., a human IgG or fragment thereof) that has a mutated or missing corresponding section for which the Tregitope might be normally found, said insertion or fusion is at the site within antibody where the Tregitope would normally be present. In aspects, said insertion of one or more regulatory T cell epitopes into the antibody or fragment thereof results in decreasing the immunogenicity of the antibody or fragment thereof.

In aspects, the Tregitope compositions of the present disclosure comprise one or more Tregitopes incorporated as an internal sequence into an Fc domain as disclosed in U.S. Pat. Nos. 7,442,778, 7,645,861, 7,655,764, 7,655,765, and/or 7,750,128 (each of which are herein incorporated by reference in their entirety). Such an internal sequence may be added by insertion (i.e., between amino acids in the previously existing Fc domain) or by replacement of amino acids in the previously existing Fc domain (i.e., removing amino acids in the previously existing Fc domain and adding peptide amino acids). In the latter case, the number of peptide amino acids added need not correspond to the number of amino acids removed from the previously existing Fc domain; for example and not by way of limitation, in aspects, the compositions may comprise an added internal sequence of 9-21 amino acids, with a sequence of 1-21 amino acids removed from the native Fc domain. In aspects, the one or more Tregitopes are inserted at or replace (e.g., full or partial replacement) one or more preferred internal sites in the Fc domain as disclosed in U.S. Pat. Nos. 7,442,778, 7,645,861, 7,655,764, 7,655,765, and/or 7,750,128.

For example, in aspects, a polypeptide has a sequence comprising one or more of SEQ ID NOS: 1, 3-8, 14-15, 16-28, 42-74, and 111-124 (and fragments or variants thereof), and optionally 1 to 12 additional amino acids distributed in any ratio on the N terminus and/or C-terminus of the polypeptide of SEQ ID NOS: 1, 3-8, 14-15, 16-28, 42-74, and 111-124, wherein said polypeptide does not comprise an antibody heavy chain variable region. In aspects, if a polypeptide does comprise an antibody heavy chain variable region then said one or more of SEQ ID NOS: 1, 3-8, 14-15, 16-28, 42-74, and 111-124 (and fragments or variants thereof), and optionally 1 to 12 additional amino acids distributed in any ratio on the N terminus and/or C-terminus of the polypeptide of SEQ ID NOS: 1, 3-8, 14-15, 16-28, 42-74, and 111-124, is not located in its natural position in the antibody heavy chain variable region. In aspects, one or more Tregitopes having a sequence comprising SEQ ID NOS: 1, 3-8, 14-15, 16-28, 42-74, and 111-124 (and fragments or variants thereof)), and optionally 1 to 12 additional amino acids distributed in any ratio on the N terminus and/or C-terminus of the polypeptide of SEQ ID NOS: 1, 3-8, 14-15, 16-28, 42-74, and 111-124, may also be fused to or inserted internally within (e.g., but not limited to, using immune engineering techniques such as but not limited to, site directed mutagenesis or other recombinant techniques) an antibody heavy chain variable region or fragment thereof, such as in instances where the Tregitope is not located in its natural position within the antibody heavy chain variable region or fragment thereof or where the antibody heavy chain variable region or fragment thereof (is missing such a Tregitope (e.g., if a particular antibody heavy chain variable region or fragment thereof has a mutated or missing corresponding section).

In aspects, a polypeptide has a sequence comprising one or more of SEQ ID NOS: 2, 9-11, 29-41, and 75-100, (and fragments or variants thereof), and optionally 1 to 12 additional amino acids distributed in any ratio on the N terminus and/or C-terminus of the polypeptide of SEQ ID NOS: 2, 9-11, 29-41, and 75-100, wherein said polypeptide does not comprise an antibody heavy chain constant region. In aspects, if a polypeptide does comprise an antibody heavy chain constant region then said one or more of SEQ ID NOS: 2, 9-11, 29-41, and 75-100 (and fragments or variants thereof), and optionally 1 to 12 additional amino acids distributed in any ratio on the N terminus and/or C-terminus of the polypeptide of SEQ ID NOS: 2, 9-11, 29-41, and 75-100, is not located in its natural position of the antibody heavy chain constant region. In aspects, one or more Tregitopes having a sequence comprising SEQ ID NOS: 2, 9-11, 29-41, and 75-100 (and fragments or variants thereof), and optionally 1 to 12 additional amino acids distributed in any ratio on the N terminus and/or C-terminus of the polypeptide of SEQ ID NOS: 2, 9-11, 29-41, and 75-100, may also be fused to or inserted internally within (e.g., but not limited to, using immune engineering techniques such as but not limited to, site directed mutagenesis or other recombinant techniques) an antibody heavy chain constant region or fragment thereof, such as in instances where the Tregitope is not located in its natural position within the antibody heavy chain constant region or fragment thereof or where the antibody heavy chain constant region or fragment thereof is missing such a Tregitope (e.g., if a particular antibody heavy chain constant region or fragment thereof has a mutated or missing corresponding section).

In aspects, a polypeptide (which may be an isolated, synthetic, or recombinant) has a sequence comprising SEQ ID NO: 12 (and fragments or variants thereof), and optionally 1 to 12 additional amino acids distributed in any ratio on the N terminus and/or C-terminus of the polypeptide of SEQ ID NO: 12, wherein said polypeptide does not comprise an antibody light chain variable region. In aspects, if a polypeptide does comprise an antibody light chain variable region, then said SEQ ID NO: 12 (and fragments or variants thereof), and optionally 1 to 12 additional amino acids distributed in any ratio on the N terminus and/or C-terminus of the polypeptide of SEQ ID NO: 12, is not located at its natural position of the antibody light chain variable region. In aspects, one or more Tregitopes having a sequence comprising SEQ ID NO: 12 (and fragments or variants thereof), and optionally 1 to 12 additional amino acids distributed in any ratio on the N terminus and/or C-terminus of the polypeptide of SEQ ID NO: 12, may also be fused to or inserted internally within (e.g., but not limited to, using immune engineering techniques such as site directed mutagenesis or other recombinant techniques) an antibody light chain variable region or fragment thereof, such as in instances where the Tregitope is not located in its natural position within the antibody light chain variable region or fragment thereof or where the antibody light chain variable region or fragment thereof is missing such a Tregitope (e.g., if a particular antibody light chain variable region or fragment thereof has a mutated or missing corresponding section).

In aspects, a polypeptide (which may be an isolated, synthetic, or recombinant) has a sequence comprising one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, wherein said polypeptide does not comprise an antibody light chain constant region. In aspects, if a polypeptide does comprise an antibody light chain constant region, then said one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, is not located at its natural position of the antibody light chain constant region. In aspects, one or more Tregitopes having a sequence comprising one or more of SEQ ID NOS: 13 and 101-110 (and fragments or variants thereof), and optionally 1 to 12 additional amino acids distributed in any ratio on the N terminus and/or C-terminus of the polypeptide of SEQ ID NOS: 13 and 101-110, may also be fused to or inserted internally within (e.g., but not limited to, using immune engineering techniques such as site directed mutagenesis or other recombinant techniques) an antibody light chain constant region or fragment thereof, such as in instances where the Tregitope is not located in its natural position within the antibody light chain constant region or fragment thereof or where an antibody light chain constant region or fragment thereof is missing such a Tregitope (e.g., if a particular antibody light chain variable region or fragment thereof has a mutated or missing corresponding section).

For the above examples, said insertion of the one or more regulatory T cell epitopes into the antibody or fragment thereof comprises insertion of all or some of the amino acids of the one or more regulatory T cell epitopes (e.g., inserting the entire sequence of the Tregitope or a fragment thereof). In aspects, said insertion of the one or more regulatory T cell epitopes into the antibody or fragment thereof comprises insertion of some or all of the amino acids of the one or more regulatory T cell epitopes and removing one or more amino acids at the site of insertion of the regulatory T cell epitope amino acids. In aspects, said insertion of the one or more regulatory T cell epitopes into the antibody or fragment thereof comprises mutating the sequence of the antibody or fragment thereof to include the one or more regulatory T cell epitopes (for example, but not limited to, introduction one or more point mutations into the antibody or fragment thereof by site-directed mutagenesis or other recombinant techniques). In aspects, said insertion of the one or more regulatory T cell epitopes into the antibody or fragment, which in aspects will introduce the one or more regulatory T cell epitope sequences, such that the previous immunogencity of the sequence is decreased and the tolerogenicity of the new sequence is enhanced. In aspects, the number of said added one or more amino acids at the site of insertion of the regulatory T cell epitope amino acids need not correspond to the number of amino acids deleted from the sequence of the antibody or fragment thereof. In aspects in which the one or more regulatory T cell epitopes are inserted or fused into a particular antibody (e.g., a human IgG or fragment thereof) that has a mutated or missing corresponding section for which the Tregitope might be normally found, said insertion or fusion is at the site within the subject's own antibody where the Tregitope would normally be present. In aspects, said insertion of one or more regulatory T cell epitopes into the antibody or fragment thereof results in decreasing the immunogenicity of the antibody or fragment thereof.

In aspects, the Tregitope compositions of the present disclosure comprise a Tregitope peptide as described herein (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) that is modified by attaching a reactive moiety to the Tregitope peptide to create a modified Tregitope peptide, wherein the reactive moiety of the modified Tregitope peptide is capable of forming a bond with a reactive functionality on a blood component, wherein upon formation of a bond between the reactive moiety of the Tregitope peptide and the reactive functionality on the blood component, a Tregitope-blood component conjugate is formed, as disclosed in U.S. Pat. Nos. 6,849,714, 6,887,470, 7,256,253, and 7,307,148 (each of which are herein incorporated by reference in their entirety). In aspects, the Tregitope in the Tregitope-blood component conjugate retains all or most of its original biologic activity. In aspects, the bond formed between the reactive moiety of the one or more modified Tregitope peptides and the blood component is a covalent bond. In aspects, the Tregitope peptide sequence is independently selected from SEQ ID NOS: 1-124, and optionally 1 to 12 additional amino acids distributed in any ratio on the N-terminus and/or C-terminus of the polypeptide of SEQ ID NOS: 1-124.

Tregitope-blood component conjugates can extend the half-life of the modified polypeptides comprising Tregitopes in vivo, protect the modified polypeptides comprising Tregitopes from rapid proteolytic degradation, protect the modified polypeptides comprising Tregitopes from rapid clearance from circulation and/or rapid kidney excretion, allow for wide distribution of Tregitope-blood component conjugates throughout the body of a subject, aid in delivery of modified polypeptides comprising Tregitopes to appropriate immune cells (such as macrophages and APCs), allow the modified polypeptides comprising Tregitopes to be processed by the endocytic pathway of certain immune cells (such as macrophages and APCs), and/or aid in the presentation of modified polypeptides comprising Tregitopes as an antigen by said immune cells.

In aspects, the Tregitope-blood component conjugates comprise a blood component which acts as a carrier protein (e.g., albumin), and further comprise a modified polypeptide, said modified polypeptide comprising one or more regulatory T cell epitopes (termed "Tregitopes"). The modified polypeptide comprises a reactive moiety that is attached to the polypeptide, with the reactive moiety being capable of forming a bond (e.g., a covalent linkage) with a reactive functionality on the blood component. Tregitope-blood component conjugates may be formed by modifying a polypeptide comprising a Tregitope by attaching a reactive moiety to the polypeptide to create a modified polypeptide, then forming a bond between reactive moiety of the modified polypeptide with a reactive functionality on a blood component, as disclosed in U.S. Pat. Nos. 6,849,714, 6,887,470, 7,256, 253, and 7,307,148, herein incorporated by reference in their entireties. In aspects of above-described Tregitope-blood component conjugates and modified polypeptides comprising Tregitopes, the Tregitope-blood component conjugates and modified polypeptides comprising Tregitopes may be isolated, synthetic, or recombinant.

In aspects, the blood components of the Tregitope-blood component conjugates may be either fixed or mobile, as disclosed in U.S. Pat. Nos. 6,849,714, 6,887,470, 7,256,253, and 7,307,148. Fixed blood components are non-mobile blood components and include tissues, membrane receptors, interstitial proteins, fibrin proteins, collagens, platelets, endothelial cells, epithelial cells and their associated membrane and membranous receptors, somatic body cells, skeletal and smooth muscle cells, neuronal components, osteocytes and osteoclasts and all body tissues, especially those associated with the circulatory and lymphatic systems. Mobile blood components are blood components that do not have a fixed situs for any extended period of time, generally not exceeding 5, more usually one minute. These blood components are not membrane-associated and are present in the blood for extended periods of time and are present in a minimum concentration of at least 0.1 µg/ml. Mobile blood components include serum albumin, transferrin, ferritin and immunoglobulins such as IgM and IgG. The half-life of mobile blood components is at least about 12 hours. In aspects of the Tregitope-blood component conjugates, the blood component is albumin, such as serum albumin, human serum albumin, recombinant albumin, and recombinant human serum albumin. Albumin is a preferred blood component because it contains an Fc neonatal binding domain that will carry the Tregitope-albumin conjugate into the appropriate cells, such as macrophages and APCs. Further, albumin contains a cysteine at amino acid 34 (Cys34) (the location of the amino acid in the amino acid sequence of human serine albumin), containing a free thiol with a pKa of approximately 5, which may serve as a preferred reactive functionality of albumin. Cys34 of albumin is capable of forming a stable thioester bond with maleimidopropionamido (MPA), which is a preferred reactive moiety of a modified Tregitope peptide.

In aspects, reactive functionalities on the blood component of the Tregitope-blood component conjugates or on the blood components that are capable of forming a conjugate with the instantly-disclosed modified polypeptides are groups on blood components, including mobile and fixed proteins, to which reactive groups on modified therapeutic peptides react to form covalent bonds. As disclosed in U.S. Pat. Nos. 6,849,714, 6,887,470, 7,256,253, and 7,307,148, such functionalities usually include hydroxyl groups for bonding to ester reactive groups, thiol groups for bonding to maleimides, imidates and thioester groups; amino groups for bonding to activated carboxyl, phosphoryl or any other acyl groups on reactive groups. In aspects, the reactive functionality of the blood component is an amino group, a hydroxyl group, or a thiol group. In aspects, the reactive functionality of the blood component is a component of a side group of an amino acid in a polypeptide and/or protein, wherein the reactive functionality is near the surface of the polypeptide and/or protein. In aspects, the reactive functionality of the blood component is a thiol group of a free cysteine residue of a proteinaceous blood component. In aspects, the reactive functionality is a free thiol group of the cysteine at amino acid 34 ($Cys^{34}$) of serine albumin. In aspects, the reactive functionality of the blood component is a thiol with a pKa of approximately 5 in a physiological environment, such as plasma. In aspects, the reactive functionality of the blood component is a thiol with a pKa of approximately 5.5 in a physiological environment, such as plasma. In aspects, the reactive functionality of the blood component is a thiol with a pKa of 3-7 in a physiological environment, such as plasma. In aspects, the reactive functionality of the blood component is a thiolate anion. In aspects, the reactive functionality is a thiolate anion of the cysteine at amino acid 34 (Cys') of serine albumin.

In aspects, the modified polypeptides of the Tregitope-blood component conjugates and the modified polypeptides used to form the Tregitope-blood component conjugates comprise a reactive moiety that is attached to the polypeptide, with the reactive moiety being capable of forming a bond (e.g., a covalent linkage) with a reactive functionality on the blood component. In aspects, the reactive group is capable of reacting with an amino group, a hydroxyl group, or a thiol group on blood component to form a covalent bond therewith. In aspects, the reactive moiety is placed at a site such that when the modified polypeptide is bonded to the blood component, the modified peptide retains a substantial proportion of the parent compound's activity. In aspects, the reactive moiety may be a succinimidyl or maleimido group. In aspects, the reactive moiety may be attached to an amino acid positioned in the less therapeutically active region of amino acids of the polypeptide to be modified. In aspects, the reactive moiety is attached to the amino terminal amino acid of the modified polypeptide. In aspects, the reactive moiety is attached to the carboxy terminal amino acid of the modified polypeptide. In aspects, the reactive moiety is attached to an amino acid positioned between the amino terminal amino acid and the carboxy terminal amino acid of the modified polypeptide. In aspects, the reactive group may be attached to the polypeptide (to be modified) either via a linking group, or optionally without using a linking group. Further, one or more additional amino acids (e.g., one or more lysines) may be added to the polypeptide to facilitate the attachment of the reactive group. Linking groups are chemical moieties that link or connect reactive groups of blood components to polypeptides comprising one or more Tregitopes. Linking groups may comprise one or more alkyl groups, alkoxy group, alkenyl group, alkynyl group or amino group substituted by alkyl groups, cycloalkyl group, polycyclic group, aryl groups, polyaryl groups, substituted aryl groups, heterocyclic groups, and substituted heterocyclic groups. Linking groups may also comprise poly ethoxy aminoacids such as AEA ((2-amino)ethoxy acetic acid) or a preferred linking group AEEA ([2-(2-amino)ethoxy)]ethoxy acetic acid). In aspects, linking groups may comprise a polyethyleneglycol linker (e.g., but not limited to, PEG2 or PEG12).

As should be understood, modified polypeptides may be administered in vivo such that conjugation with blood components occurs in vivo, or they may be first conjugated to blood components in vitro and the resulting peptidase-stabilized polypeptide administered in vivo. Further, as disclosed in in U.S. Pat. Nos. 6,849,714, 6,887,470, 7,256,253, and 7,307,148, a peptidase-stabilized polypeptide is a modified polypeptide that has been conjugated to a blood component via a covalent bond formed between the reactive group of the modified peptide and the functionalities of the blood component, with or without a linking group. Such reaction is preferably established by covalent bonding of a polypeptide modified with a maleimide link (e.g. prepared from GMBS, MPA or other maleimides) to a thiol group on a mobile blood protein such as serum albumin or IgG. Peptidase-stabilized polypeptides are more stable in the presence of peptidases in vivo than a non-stabilized peptide. A peptidase-stabilized therapeutic peptide generally has an increased half-life of at least 10-50% as compared to a non-stabilized peptide of identical sequence. Peptidase-stability is determined by comparing the half-life of the unmodified therapeutic peptide in serum or blood to the half-life of a modified counterpart therapeutic peptide in serum or blood. Half-life is determined by sampling the serum or blood after administration of the modified and non-modified peptides and determining the activity of the peptide. In addition to determining the activity, the length of the therapeutic peptide may also be measured.

In aspects, the modified polypeptides of the Tregitope-blood component conjugates and the modified polypeptides used to form the Tregitope-blood component conjugates comprise one or more Tregitopes as disclosed herein. In aspects, the one or more Tregitopes of the modified polypeptides have a sequence comprising, consisting of, or consisting essentially of one or more of SEQ ID NOS: 1-124 (and fragments and variants thereof) as essentially disclosed herein. In aspects, the one or more Tregitopes of the modified polypeptide may optionally have one or more linkers, which may optionally be cleavage sensitive sites, adjacent to their N and/or C terminal end. In such a modified polypeptide, two or more of the Tregitopes may have a cleavage sensitive site between them. Alternatively, two or more of the Tregitopes may be connected directly to one another or through a linker that is not a cleavage sensitive site. In aspects, the modified polypeptide comprising the one or more Tregitopes and/or the Tregitopes contained therein can be in either neutral (uncharged) or salt forms, and may be either free of or include modifications such as glycosylation, side chain oxidation, or phosphorylation. In certain aspects, the modified polypeptide comprising the one or more Tregitopes peptides or polypeptides can be capped with an N-terminal acetyl and/or C-terminal amino group. In aspects, the one or more Tregitopes included in the modified polypeptide can be capped with an N-terminal acetyl and/or C-terminal amino group.

In aspects, the blood component that forms the Tregitope-blood component conjugate with the modified Tregitope is albumin. In aspects, the reactive functionality of the blood component is an amino group, a hydroxyl group, or a thiol group. In aspects, the reactive functionality of the blood component is a component of a side group of an amino acid in a polypeptide and/or protein, wherein the reactive functionality is near the surface of the polypeptide and/or protein. In aspects, the reactive functionality of the blood component is a thiol group of a free cysteine residue of a proteinaceous blood component. In aspects, the reactive functionality is a free thiol group of the cysteine at amino acid 34 ($Cys^{34}$) of serine albumin. In aspects, the reactive functionality of the blood component is a thiol with a pKa of approximately 5 in a physiological environment, such as plasma. In aspects, the reactive functionality of the blood component is a thiol with a pKa of approximately 5.5 in a physiological environment, such as plasma. In aspects, the reactive functionality of the blood component is a thiol with a pKa of 3-7 in a physiological environment, such as plasma. In aspects, the reactive functionality of the blood component is a thiolate anion. In aspects, the reactive functionality is a thiolate anion of the cysteine at amino acid 34 ($Cys^{34}$) of serine albumin.

In aspects, the reactive moiety of the modified Tregitope peptide is a soft electrophile. In aspects, the reactive moiety of the modified Tregitope peptide is an electrophile that is selective for thiols. In a preferred embodiment, the reactive moiety attached to the Tregitope to create the modified Tregitope peptide is maleimide. In aspects, the reactive moiety is maleimide propionic acid. In a preferred embodiment, the reactive moiety attached of the modified Tregitope peptide is maleimide, the blood component is albumin, and the reactive functionality on the albumin is a free thiol or thiolate anion of $Cys^{34}$ of albumin. When the reactive moiety of the modified Tregitope peptide a maleimide, the blood component is albumin, and the reactive functionality of the albumin is a free thiol or thiolate anion of Cys$^{34}$ of albumin, a stable thioester linkage between the maleimide group and the sulfhydryl is formed which cannot be cleaved under physiological conditions. In aspects, the modified Tregitope peptide contains a linker, wherein the reactive moiety is attached to the Tregitope peptide through the linker. In aspects, the modified Tregitope peptide binds to the blood component in a 1:1 molar ratio.

The manner of producing the modified Tregitope peptides of the present disclosure will vary widely, depending upon the nature of the various elements comprising the molecule. The synthetic procedures may be selected so as to be simple, provide for high yields, and allow for a highly purified stable product. Normally, the reactive moiety will be created as the last stage, for example, with a carboxyl group, esterification to form an active ester will be the last step of the synthesis.

In aspects, the present disclosure is also directed to a method of synthesizing the modified Tregitope peptide, as disclosed in U.S. Pat. Nos. 6,849,714, 6,887,470, 7,256,253, and 7,307,148. In aspects, the method comprises the following steps. In the first step, the one or more Tregitope sequence of the polypeptide can be made as essentially disclosed herein. In the second step, if the polypeptide does not contain a cysteine, then the polypeptide may be synthesized from the carboxy terminal amino acid and the reactive moiety is added to the carboxy terminal amino acid. Alternatively, a terminal lysine (or one or more lysines) may added to the carboxy terminal amino acid and the reactive moiety is added to the terminal lysine. In the third step, if the polypeptide contains only one cysteine, then the cysteine is reacted with a protective group prior to addition of the reactive moiety to an amino acid in a less therapeutically active region of the polypeptide. In the fourth step, if the polypeptide contains two cysteines as a disulfide bridge, then the two cysteines are oxidized and the reactive moiety is added to the amino terminal amino acid, or to the carboxy terminal amino acid, or to an amino acid positioned between the carboxy terminal amino acid and the amino terminal amino acid of the polypeptide. In the fifth step, if the polypeptide contains more than two cysteines as disulfide bridges, the cysteines are sequentially oxidized in the disulfide bridges and the peptide is purified prior to the addition of the reactive moieties to the carboxy terminal amino acid.

In aspects, the present disclosure is also directed to a method of synthesizing the Tregitope-blood component conjugate. In a first step, reactive maleimidopropionamido (MPA) is added via an N-terminal lysine on the polypeptide comprising one or more Tregitopes to create a modified polypeptide. In aspects, one or more lysines are present on the N-terminus of the polypeptide, optionally present at the N-terminus of a Tregitope sequence selected from the group of SEQ. ID NOS: 1-124 as disclosed herein. Optionally, polyethyleneglycol linker, such as PEG2 or PEG12, is present between the one or more lysines and a Tregitope sequence, or at the N-terminus of a Tregitope sequence. In aspects, a lysosomal cleavage site, such as a Cathepsin B site, optionally consisting (sequentially from N-terminus to C-terminus) of valine and citrulline, is present between the PEG2 or PEG12 moiety and the Tregitope sequence. The lysosomal cleavage site (such as Cathepsin B site) may be incorporated to provide a lysosomal protease site, allowing the Tregitope to be released into the lysosomal compartment. In aspects, lysosomal cleavage site (such as Cathepsin B site) is present to provide a lysosomal protease site, allowing the Tregitope to be released into cells, preferably into the early endosome. In a preferred embodiment, the lysosomal cleavage site (such as Cathepsin B site) is present to provide a lysosomal protease site, allowing the Tregitope to be released into cells, such as into a membrane-enclosed vesicle (such as the early endosome, late endosome, or lysosome), such that the Tregitope may be processed for antigen presentation. In aspects, the Tregitope is presented as antigen by immune cells, such as macrophages or antigen-presenting cells, preferably presented as an MEW class II antigen. In aspects, a lysosomal cleavage site, such as a Cathepsin B site, optionally consisting (sequentially from N-terminus to C-terminus) of valine and citrulline, is present between the PEG2 moiety and the Tregitope sequence, and/or between one or more Tregitopes. In aspects, one or more Tregitopes may be present on the construct, optionally more proximate to the C-terminus than the linker. In aspects, one or more lysosomal cleavage sites are present between multiple Tregitopes (for example, such that a single lysosomal cleavage site separates two Tregitopes, or such that one lysosomal cleavage site is present between a first and second Tregitope, and another lysosomal cleavage site is present between a second and third Tregitope, and so on). In aspects, a norleucine (Nle) residue is present at the C-terminus as a means to quantitate the amount of Tregitope peptide incorporated into the final Tregitope-blood component conjugate, for example for evaluation by mass spectrometry. In aspects, the C-terminus of the polypeptide is capped with a c-terminal amino group. In a second step, a maleimide-based chemistry is used to covalently link the modified polypeptide to a blood component, preferably serum albumin, in a 1:1 molar ratio. The second step may be performed in vivo or ex vivo, as described further below and in the examples of the present disclosure.

In aspects, the formation of the Tregitope-blood component conjugate protects the Tregitope, when present in vivo, from rapid degradation by peptidases, rapid clearance from circulation, and/or rapid kidney excretion. In aspects, the formation of the Tregitope-blood component conjugate significantly extends the half-life of the Tregitope in vivo. In aspects, the formation of the Tregitope-blood component conjugate allows wide distribution of the Tregitope-blood component conjugate throughout the body of a subject. In aspects, the Tregitope-blood component conjugate does not cross the blood-brain barrier when present in the plasma of a subject. In aspects, the Tregitope-blood component conjugate aid in delivery of Tregitopes to appropriate immune cells, such as macrophages and/or antigen-presenting cells (APCs). In aspects, upon delivery of Tregitopes to appropriate immune cells, such as macrophages and/or APCs, the Tregitopes are encompassed in a membrane-bound vesicle, preferably a vesicle in the endocytic pathway such as an early endosome, late endosome, or lysosome. In aspects, the Tregitopes, once processed by the appropriate immune cells, such as macrophages and/or APCs, are presented as WIC class II antigens.

In aspects, the Tregitope in the Tregitope-blood component conjugate has a plasma half-life in vivo of up to 12 hours. In aspects, the Tregitope in the Tregitope-blood component conjugate has a plasma half-life in vivo of up to 1 day. In aspects, the Tregitope in the Tregitope-blood component conjugate has a plasma half-life in vivo of up to 40-48 hours. In aspects, the Tregitope in the Tregitope-blood component conjugate has a plasma half-life in vivo of up to 60 hours. In aspects, the Tregitope in the Tregitope-blood component conjugate has a plasma half-life in vivo of up to 15 days.

In aspects, the modified polypeptide comprising one or more Tregitopes is administered to a subject, wherein upon administration, the modified polypeptide reacts in vivo with a reactive functionality of a circulating blood component. In aspects, the peptide is administered to a human subject, and the blood component is human albumin, preferably the circulating albumin of the human subject.

In aspects, the modified polypeptides used to form the Tregitope-blood component conjugates is capable of forming a bond ex vivo with a reactive functionality on a blood component, wherein upon formation of a bond between the reactive moiety of the modified polypeptide and the reactive functionality on the blood component, a Tregitope-blood component conjugate is formed, as disclosed in U.S. Pat. Nos. 6,849,714, 6,887,470, 7,256,253, and 7,307,148. In aspects, the modified polypeptide as disclosed herein is configured to covalently attach to a reactive functionality of a blood component outside of the body. In aspects, the blood component is albumin. In aspects, the blood component is selected from the group of recombinant albumin, human recombinant albumin, and albumin from a genomic source.

In aspects, the present disclosure is also directed to an ex vivo method of synthesizing the modified Tregitope peptide and the Tregitope-blood component conjugate, as disclosed in U.S. Pat. Nos. 6,849,714, 6,887,470, 7,256,253, and 7,307,148. In aspects, the modified polypeptide as disclosed herein is added to blood, serum or saline solution containing human serum albumin to permit covalent bond formation between the modified therapeutic peptide and the blood component. In aspects, the polypeptide comprising one or more Tregitopes as disclosed herein is modified with maleimide and it is reacted with serum albumin in saline solution. In aspects, once the modified polypeptide has reacted with the blood component, to form a Tregitope-blood component conjugate, the conjugate may be administered to the subject. In aspects, after the modified polypeptide has reacted with the blood component to form the conjugate, but before the conjugate is administered to the subject, the conjugate may be separated from non-conjugated blood components in the reaction mixture. In aspects, conjugate may be separated from non-conjugated blood components in the reaction mixture by separating substances on the basis of the varying strengths of their hydrophobic interactions with hydrophobic ligands immobilized to an uncharged matrix. In aspects, the uncharged matrix may be a hydrophobic solid support, wherein the support comprises a column containing a hydrophobic resin such as, but not limited to, octyl sepharose, phenyl sepharose and butyl sepharose. In aspects, this technique may be performed with moderately high concentrations of salts ($\approx$1M) in the start buffer (salt promoted adsorption). Elution is achieved by a linear or stepwise decrease in salt concentration. The type of ligand, the degree of substitution, the pH and the type and concentration of salt used during the adsorption stage have a profound effect on the overall performance (e.g., selectivity and capacity) of an HIC matrix (Hydrophobic Interaction Chromatography matrix).

The solvent is one of the most important parameters that influence capacity and selectivity in HIC (Hydrophobic Interaction Chromatography). In general, the adsorption process is more selective than the desorption process. It is therefore important to optimize the start buffer with respect to pH, type of solvent, type of salt and concentration of salt. The addition of various "salting-out" salts to the sample promotes ligand-protein interactions in HIC. As the concentration of salt is increased, the amount of bound protein increases up to the precipitation point for the protein. Each type of salt differs in its ability to promote hydrophobic interactions.

Increasing the salting-out effect strengthens the hydrophobic interactions, whereas increasing the chaotropic effect weakens them. Examples of salts with high salting-out effects, in order from greater salting-out effect to smaller salting-out effect, include: $PO_4^{3-}$, $SO_4^{2-}$, $CH_3COO^-$, $Cl^-$, $Br^-$, $NO_3^-$, $ClO_4^-$, $I^-$, and $SCN^-$. Examples of salts with high chaotropic effects, in order from greater chaotropic effect to smaller chaotropic effect, include: $NH_4^+$, $Rb^+$, $K^+$, $Na^+$, $Cs^+$, $Li^+$, $Mg^{2+}$, and $Ba^{2+}$. The most commonly used salts for HIC are ammonium sulfate (($NH_4)_2SO_4$), sodium sulfate (($Na)_2SO_4$)), magnesium sulfate ($MgSO_4$), sodium chloride (NaCl), potassium chloride (KCl), and ammonium acetate ($CH_3COONH_4$).

Protein binding to HIC adsorbents is promoted by moderate to high concentrations of "salting-out" salts, most of which also have a stabilizing influence on protein structure due to their preferential exclusion from native globular proteins, i.e. the interaction between the salt and the protein surface is thermodynamically unfavorable. The salt concentration should be high enough (e.g. 500-1000 mM) to promote ligand-protein interactions yet below that which causes precipitation of the protein in the sample. In the case of albumin, the salt concentration should be kept below 3M (moles per liter). The principle mechanism of salting-out consists of the salt-induced increase of the surface tension of water (Melander and Horvath, 1977). Thus, a compact structure becomes energetically more favorable because it corresponds to smaller protein-solution interfacial area. Under these conditions, for example buffer composed of $SO_4^{2-}$, $PO_4^{2-}$ or $CH_3COO^-$ with any counter ion, these salts exhibit their salting-out effect upon essentially all conjugated albumin described herein in a manner different to non-conjugated albumin (e.g., mercaptalbumin and albumin capped with cysteine), thus enabling a consistent chromatographic separation between conjugated albumin versus non-conjugated albumin. Thus, lower concentrations of salt are required to promote interactions between ligand and conjugated albumin than between ligand and non-conjugated albumin. This chromatographic separation is essentially independent of (a) the sequence of albumin (e.g. human, mouse, rat, etc.), (b) the source of albumin (i.e. plasma derived or recombinant), (c) the molecular weight of the conjugated modified Tregitope, (d) the position of the reactive moiety within the structure of the molecule, (e) the peptide sequence or chemical structure of the molecule, and (f) the three-dimensional structure of the conjugated molecule (e.g. linear versus loop structure).

In aspects, the salt of the aqueous buffer has a sufficient salting-out effect. In aspects, for providing a sufficient salting out effect, the salt may be phosphate, sulfate and acetate. In aspects, the selection of the cation of the buffer is can be selected, without limitation, from the group consisting of $NH_4^+$, $R^+$, $K^+$, $Na^+$, $Cs^+$, $Li^+$, $Mg^{2+}$ and $Ba^{2+}$. In aspects, the aqueous buffer may be selected from the group of ammonium phosphate, ammonium sulfate and magnesium phosphate. In aspects, the buffer pH is between 3.0 and 9.0; more preferably between 6.0 and 8.0, and even more preferably, the pH is 7.0. In aspects, the buffer and the hydrophobic solid support are at room temperature (about 25° C.) or at 4° C. or in between.

In aspects, the present disclosure also provides chimeric or fusion polypeptide compositions. In aspects, the present disclosure provides chimeric or fusion polypeptide compositions (which in aspects may be isolated, synthetic, or recombinant) wherein one or more of the instantly disclosed Tregitopes is a part thereof. In aspects, a chimeric or fusion polypeptide composition comprises one or more polypeptides (Treg activating regulatory T-cell epitope, Tregitope, Tregitope peptide, or T-cell epitope polypeptide) of the present disclosure joined to, linked to (e.g., fused in-frame, chemically linked, or otherwise bound), and/or inserted into a heterologous polypeptide (e.g., but not limited to, a heterologous antibody (which can be IgG, IgM, IgA, IgD or IgE molecules or antigen-specific antibody fragments thereof (including, but not limited to, a Fab, F(ab')$_2$, Fv, disulfide linked Fv, scFv, single domain antibody, closed conformation multispecific antibody, disulfide-linked scfv, diabody)). As previously described, with respect to the one or more Tregitopes of the instant disclosure, the term "heterologous polypeptide" is intended to mean that the one or more Tregitopes of the instant disclosure are heterologous to, or not included naturally, in the heterologous polypeptide. In aspects, one or more of the instantly-disclosed polypeptides ($T_{reg}$ activating regulatory T-cell epitopes, Tregitopes, or T-cell epitope polypeptides) may be inserted into the heterologous polypeptide (e.g., through recombinant techniques, mutagenesis, or other known means in the art), may be added to the C-terminus (with or without the use of linkers, as is known in the art), and/or added to the N-terminus (with or without the use of linkers, as is known in the art) of the heterologous polypeptide. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety)..

In aspects of the above isolated, synthetic, or recombinant chimeric or fusion polypeptide compositions, the one or more polypeptides (Treg activating regulatory T-cell epitope, Tregitope, Tregitope peptide, or T-cell epitope polypeptide) of the present disclosure have a sequence comprising, consisting of, or consisting essentially of one or more of SEQ ID NOS: 1-124. In aspects of the instantly disclosed chimeric or fusion polypeptide compositions, the one or more polypeptides comprise, consist, or consist essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124. In aspects of the chimeric or fusion polypeptide compositions, the one or more Tregitopes as disclosed herein may be joined to, linked to (e.g., fused in-frame, chemically-linked, or otherwise bound), and/or inserted into a heterologous polypeptide as a whole, although it may be made up from a joined to, linked to (e.g., fused in-frame, chemically-linked, or otherwise bound), and/or inserted amino acid sequence, together with flanking amino acids of the heterologous polypeptide. In aspects, a chimeric or fusion polypeptide composition comprises a polypeptide, said polypeptide having a sequence comprising one or more of SEQ ID NOS: 1-124 (and/or fragments or variants thereof, and optionally 1 to 12 additional amino acids distributed in any ratio on the N terminus and/or C-terminus of the polypeptide of SEQ ID NOS: 1-124) of the present disclosure, wherein said one or more of SEQ ID NOS: 1-124 is not naturally included in the polypeptide and/or said of one or more of SEQ ID NOS: 1-124 is not located at its natural position in the polypeptide. In aspects, the one or more Tregitopes of the present disclosure can be joined, linked to (e.g., fused in-frame, chemically linked, or otherwise bound), and/or inserted into the polypeptide. In aspects, chimeric or fusion polypeptide compositions comprise one or more of the instantly disclosed Tregitopes operatively linked to a heterologous polypeptide having an amino acid sequence not substantially homologous to the Tregitope. In aspects, the chimeric or fusion polypeptide does not affect function of the Tregitope per se. For example, the fusion polypeptide can be a GST-fusion polypeptide in which the Tregitope sequences are fused to the C-terminus of the GST sequences. Other types of fusion polypeptides include, but are not limited to, enzymatic fusion polypeptides, for example beta-galactosidase fusions, yeast two-hybrid GAL fusions, poly-His fusions and Ig fusions. Such fusion polypeptides, particularly poly-His fusions or affinity tag fusions, can facilitate the purification of recombinant polypeptide. In certain host cells (e.g., mammalian host cells), expression and/or secretion of a polypeptide can be increased by using a heterologous signal sequence. Therefore, in aspects, the chimeric or fusion polypeptide contains a heterologous signal sequence at its N-terminus. In aspects of the above chimeric or fusion polypeptide compositions, the heterologous polypeptide or polypeptide comprises a biologically active molecule. In aspects, the biologically active molecule is selected from the group consisting of an immunogenic molecule, a T cell epitope, a viral protein, and a bacterial protein. In aspects, the one or more of Tregitopes of the present disclosure can be joined or linked to (e.g., fused in-frame, chemically linked, or otherwise bound) to a small molecule, drug, or drug fragment. For example, one or more of SEQ ID NOS: 1-124 (and/or fragments or variants thereof, and optionally 1 to 12 additional amino acids distributed in any ratio on the N terminus and/or C-terminus of the polypeptide of SEQ ID NOS: 1-124) of the present disclosure can be joined or linked to (e.g., fused in-frame, chemically linked, or otherwise bound) a drug or drug fragment that is binds with high affinity to defined HLAs. In aspects of the above-described chimeric or fusion polypeptide compositions, the chimeric or fusion polypeptide compositions can be recombinant, isolated, and/or synthetic.

A chimeric or fusion polypeptide composition can be produced by standard recombinant DNA or RNA techniques as are known in the art. For example, DNA or RNA fragments coding for the different polypeptide sequences may be ligated together in-frame in accordance with conventional techniques. In another embodiment, the fusion gene can be synthesized by conventional techniques including automated DNA synthesizers. Alternatively, polymerase chain reaction (PCR) amplification of nucleic acid fragments can be carried out using anchor primers which give rise to complementary overhangs between two consecutive nucleic acid fragments which can subsequently be annealed and re-amplified to generate a chimeric nucleic acid sequence (Short Protocols in Molecular Biology: A Compendium of Methods from Current Protocols in Molecular Biology, (2 ND, 1992), FM Asubel et al. (eds), Green Publication Associates, New York, NY (Publ), ISBN: 9780471566355, which is herein incorporated by reference in its entirety). Further, one or more polypeptides (Treg activating regulatory T-cell epitope, Tregitope, Tregitope peptide, or T-cell epitope polypeptide) of the present disclosure (e.g., one or more Tregitopes of the present disclosure having a sequence comprising, consisting of, or consisting essentially of one or more of SEQ ID NOS: 1-124) can be inserted into a heterologous polypeptide, inserted into a non-naturally occurring position of a polypeptide, or inserted into a polypeptide that does not include the Tregitope through recombinant techniques, synthetic polymerization techniques, mutagenesis, or other standard techniques known in the art. For example, protein engineering by mutagenesis can be performed using site-directed mutagenesis techniques, or other mutagenesis techniques known in the art (see e.g., James A. Brannigan and Anthony J. Wilkinson., 2002, Protein engineering 20 years on. Nature Reviews Molecular Cell Biology 3, 964-970; Turanli-Yildiz B. et al., 2012, Protein Engineering Methods and Applications, intechopen.com, which are herein incorporated by reference in their entirety). As explained previously, in aspects, the one or more Tregitopes may be inserted into or replace amino acids in a Fc domain as disclosed in U.S. Pat. Nos. 7,442,778, 7,645,861, 7,655,764, 7,655,765, and/or 7,750,128 (each of which are herein incorporated by reference in their entirety). In aspects, the one or more Tregitopes may be covalently bound to one or more internal conjugation site(s) in an Fc domain as disclosed in U.S. Pat. Nos. 8,008,453, 9,114,175, and/or 10,188,740 (each of which are herein incorporated by reference in their entirety).

In aspects, the polypeptides, concatemeric polypeptides, and chimeric or fusion polypeptides can be purified to homogeneity or partially purified. It is understood, however, that preparations in which the T-cell epitope compounds and compositions are not purified to homogeneity are useful. The critical feature is that the preparation allows for the desired function of the composition, even in the presence of considerable amounts of other components. Thus, the present disclosure encompasses various degrees of purity. In one embodiment, the language "substantially free of cellular material" includes preparations of the polypeptides, concatemeric polypeptides, and chimeric or fusion polypeptides having less than about 30% (by dry weight) other proteins (e.g., contaminating protein), less than about 20% other proteins, less than about 10% other proteins, less than about 5% other proteins, less than about 4% other proteins, less than about 3% other proteins, less than about 2% other proteins, less than about 1% other proteins, or any value or range therebetween.

In aspects, when a polypeptide, concatemeric polypeptide, and chimeric or fusion polypeptide of the present disclosure is recombinantly produced, the composition can also be substantially free of culture medium, for example, culture medium represents less than about 20%, less than about 10%, or less than about 5% of the volume of the polypeptides, concatemeric polypeptides, and chimeric or fusion polypeptides preparation. The language "substantially free of chemical precursors or other chemicals" includes preparations of the polypeptides, concatemeric polypeptides, and chimeric or fusion polypeptides in which it is separated from chemical precursors or other chemicals that are involved in the T-cell epitope's synthesis. The language "substantially free of chemical precursors or other chemicals" can include, for example, preparations of the polypeptides, concatemeric polypeptides, and chimeric or fusion polypeptides having less than about 30% (by dry weight) chemical precursors or other chemicals, less than about 20% chemical precursors or other chemicals, less than about 10% chemical precursors or other chemicals, less than about 5% chemical precursors or other chemicals, less than about 4% chemical precursors or other chemicals, less than about 3% chemical precursors or other chemicals, less than about 2% chemical precursors or other chemicals, or less than about 1% chemical precursors or other chemicals.

In aspects, the present disclosure also includes pharmaceutically acceptable salts of the Regulatory T-cell epitope compounds and compositions (including one or more of e.g., peptides or polypeptides as disclosed herein; concatemeric peptides as disclosed herein; chimeric or fusion polypeptide compositions as disclosed herein (which in aspects may be isolated, synthetic, and/or recombinant). "Pharmaceutically acceptable salt" means a salt that is pharmaceutically acceptable and that possesses the desired pharmacological activity of the parent peptide or polypeptide (e.g., peptides, polypeptides, concatemeric peptides, and/or chimeric or fusion polypeptides as disclosed herein). As used herein, "pharmaceutically acceptable salt" refers to derivative of the instantly-disclosed polypeptides, concatemeric polypeptides, and/or chimeric or fusion polypeptides, wherein such compounds are modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroiodic, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Nucleic Acids

In aspects, the present disclosure also provides for nucleic acids (e.g., DNAs (including cDNA, RNAs (such as, but limited to mRNA), vectors, viruses, or hybrids thereof, all of which may be isolated, synthetic, or recombinant) that encode in whole or in part one or more one or more peptides, polypeptides, concatemeric peptides, and/or chimeric or fusion polypeptides of the present disclosure as described herein. In aspects, the nucleic acid further comprises, or is contained within, an expression cassette, a plasmid, and expression vector, or recombinant virus, wherein optionally the nucleic acid, or the expression cassette, plasmid, expression vector, or recombinant virus is contained within a cell, optionally a human cell or a non-human cell, and optionally the cell is transformed with the nucleic acid, or the expression cassette, plasmid, expression vector, or recombinant virus. In aspects, cells are transduced, transfected, or otherwise engineered to contain within one or more of e.g., polypeptides of the present disclosure; isolated, synthetic, or recombinant nucleic acids, expression cassettes, plasmids, expression vectors, or recombinant viruses as disclosed herein; and/or isolated, synthetic, or recombinant chimeric or fusion polypeptide compositions as disclosed herein. In aspects, the cell can be a mammalian cell, bacterial cell, insect cell, or yeast cell. In aspects, the nucleic acid molecules of the present disclosure can be inserted into vectors and used, for example, as expression vectors or gene therapy vectors. Gene therapy vectors can be delivered to a subject by, e.g., intravenous injection, local administration (U.S. Pat. No. 5,328,470) or by stereotactic injection (Chen S H et al., (1994), Proc Natl Acad Sci USA, 91(8):3054-7, which are herein incorporated by reference in their entirety). Similarly, the nucleic acid molecules of the present disclosure can be inserted into plasmids. The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. Such pharmaceutical compositions can be included in a container, pack, or dispenser together with instructions for administration. In aspects of the above nucleic acids (e.g., DNAs, RNAs, vectors, viruses, or hybrids thereof) that encode in whole or in part at least one or more peptides, polypeptides, concatemeric peptides, and/or chimeric or fusion polypeptides as described herein, the nucleic acids encode one or more peptides or polypeptides of the instant disclosure as described above (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 41-124; as well as the concatemeric peptides as disclosed herein. In aspects, the present disclosure is directed to a vector comprising a nucleic acid of the present disclosure encoding one or more polypeptides of the present disclosure or chimeric or fusion polypeptide composition of the present disclosure. In aspects, the present disclosure is directed to a cell comprising a vector of the present disclosure. In aspects, the cell can be a mammalian cell, bacterial cell, insect cell, or yeast cell.

The nucleic acid of the instant disclosure may be DNAs (including but not limited to cDNA) or RNAs (including but not limited to mRNA), single- or double-stranded. The nucleic acid is typically DNA or RNA (including mRNA). The nucleic acid may be produced by techniques well known in the art, such as synthesis, or cloning, or amplification of the sequence encoding the immunogenic polypeptide; synthesis, or cloning, or amplification of the sequence encoding the cell membrane addressing sequence; ligation of the sequences and their cloning/amplification in appropriate vectors and cells. The nucleic acids provided herein (whether RNAs, DNAs, vectors, viruses or hybrids thereof) that encode in whole or in part one or more peptides, polypeptides, concatemeric peptides, and/or chimeric or fusion polypeptides as described herein can be isolated from a variety of sources, genetically engineered, amplified, synthetically produced, and/or expressed/generated recombinantly. Recombinant polypeptides generated from these nucleic acids can be individually isolated or cloned and tested for a desired activity. Any recombinant expression system can be used, including e.g. in vitro, bacterial, fungal, mammalian, yeast, insect or plant cell expression systems. In aspects nucleic acids provided herein are synthesized in vitro by well-known chemical synthesis techniques (as described in, e.g., Adams (1983) J. Am. Chem. Soc. 105: 661; Belousov (1997) Nucleic Acids Res. 25:3440-3444; Frenkel (1995) Free Radic. Biol. Med. 19:373-380; Blommers (1994) Biochemistry 33:7886-7896; Narang (1979) Meth. Enzymol. 68:90; Brown (1979) Meth. Enzymol. 68:109; Beaucage (1981) Tetra. Lett. 22:1859; U.S. Pat. No. 4,458,066, all of which are herein incorporated by reference in their entirety). Further, techniques for the manipulation of nucleic acids provided herein, such as, e.g., subcloning, labeling probes (e.g., random-primer labeling using Klenow polymerase, nick translation, amplification), sequencing, hybridization and the like are well described in the scientific and patent literature (see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993), all of which are herein incorporated by reference in their entirety).

A further object of the present disclosure relates to a nucleic acid molecule encoding one or more peptides, polypeptides, concatemeric peptides, and/or chimeric or fusion polypeptides as described herein. The nucleic acid may be used to produce the one or more peptides, polypeptides, concatemeric peptides, and/or chimeric or fusion polypeptides as described herein in vitro or in vivo, or to produce cells expressing the polypeptide on their surface, or to produce vaccines wherein the active agent is the nucleic acid or a vector containing the nucleic acid. The nucleic acid may be, e.g., DNA, cDNA, PNA, CNA, RNA, either single- and/or double-stranded, or native or stabilized forms of polynucleotides as are known in the art.

As previously mentioned, the nucleic acid molecules according to the present disclosure may be provided in the form of a nucleic acid molecule per se such as naked nucleic acid molecules; a plasmid, a vector; virus or host cell, etc., either from prokaryotic or eukaryotic origin. Vectors include expression vectors that contain a nucleic acid molecule of the invention. An expression vector capable of expressing a polypeptide can be prepared. Expression vectors for different cell types are well known in the art and can be selected without undue experimentation. Generally, the (e.g., cDNA, or RNA, including mRNA) is inserted into an expression vector, such as a plasmid, in proper orientation and correct reading frame for expression. If necessary, the DNA (e.g., cDNA, or RNA, including mRNA) may be linked to the appropriate transcriptional and translational regulatory control nucleotide sequences recognized by the desired host (e.g., bacteria), although such controls are generally available in the expression vector. The vector is then introduced into the host bacteria for cloning using standard techniques. The vectors of the present invention may, for example, comprise a transcriptional promoter, and/or a transcriptional terminator, wherein the promoter is operably linked with the nucleic acid molecule, and wherein the nucleic acid molecule is operably linked with the transcription terminator. One or more peptides or polypeptides of the present disclosure may be encoded by a single expression vector. Such nucleic acid molecules may act as vehicles for delivering peptides/polypeptides to the subject in need thereof, in vivo, in the form of, e.g., DNA/RNA vaccines.

In aspects, the vector may be a viral vector comprising a nucleic acid as defined above. The viral vector may be derived from different types of viruses, such as, Swinepox, Fowlpox, Pseudorabies, Aujezky's virus, *salmonella*, vaccinia virus, BHV (Bovine Herpes Virus), HVT (Herpes Virus of Turkey), adenovirus, TGEV (Transmissible Gastroenteritidis Coronavirus), Erythrovirus, and SIV (Simian Immunodeficiency Virus). Other expression systems and vectors may be used as well, such as plasmids that replicate and/or integrate in yeast cells.

The instant disclosure also relates to a method for preparing a peptide, polypeptide, concatemeric peptide, and/or chimeric or fusion polypeptide of the instant disclosure, the method comprising culturing a host cell containing a nucleic acid or vector as defined above under conditions suitable for expression of the nucleic acid and recovering the polypeptide. As indicated above, the proteins and peptides may be purified according to techniques known per se in the art.

Pharmaceutical Compositions and Formulations

In aspects, the Tregitope compounds and compositions of the present disclosure (including one or more of e.g., polypeptides as disclosed herein; concatemeric peptides as disclosed herein; chimeric of fusion polypeptide compositions as disclosed herein; nucleic acids as disclosed herein, including nucleic acids encoding such peptides, polypeptides, concatemeric peptides, or chimeric of fusion polypeptide compositions as disclosed herein; expression cassettes, plasmids, expression vectors, and recombinant viruses, or cells as disclosed herein; hereafter referred to as "T-cell epitope compounds and compositions of the present disclosure") may be comprised in a pharmaceutical composition or formulation. In aspects, the instantly-disclosed pharmaceutical compositions or formulations generally comprise a Tregitope compound or composition of the present disclosure and a pharmaceutically acceptable carrier, excipient, and/or adjuvant. In aspects, the instantly-disclosed pharmaceutical compositions or formulations may further comprise diluents, adjuvants, freeze drying stabilizers, wetting or emulsifying agents, pH buffering agents, gelling or viscosity enhancing additives, and preservatives, depending on the route of administration. In aspects, said pharmaceutical compositions are suitable for administration. Pharmaceutically acceptable carriers and/or excipients are determined in part by the particular composition being administered, as well as by the particular method used to administer the composition. Accordingly, there is a wide variety of suitable formulations of pharmaceutical compositions for administering the instantly disclosed Tregitope compositions (see, e.g., Remington's Pharmaceutical Sciences, (18 w Ed, 1990), Mack Publishing Co., Easton, PA Publ)). In aspects, the pharmaceutical compositions are generally formulated as sterile, substantially isotonic, and in full compliance with all Good Manufacturing Practice (GMP) regulations of the U.S. Food and Drug Administration.

The terms "pharmaceutically-acceptable," "physiologically-tolerable," and grammatical variations thereof, as they refer to compositions, carriers, excipients, and reagents, are used interchangeably and represent that the materials are capable of administration to or upon a subject without the production of undesirable physiological effects to a degree that would prohibit administration of the composition. For example, "pharmaceutically-acceptable excipient" means, for example, an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous. A person of ordinary skill in the art would be able to determine the appropriate timing, sequence and dosages of administration for particular Tregitope compounds and compositions of the present disclosure. The dosage of the Tregitope compounds and compositions of the present disclosure will depend on the species, breed, age, size, treatment history, and health status of the animal (e.g., human) to be treated, as well as the route of administration, e.g., subcutaneous, intradermal, oral intramuscular or intravenous administration. The Tregitope compounds and compositions of the instant disclosure can be administered as single doses or in repeated doses. The Tregitope compounds and compositions of the instant disclosure can be administered alone, or can be administered simultaneously or sequentially administered with one or more further compositions, such as other porcine immunogenic or vaccine compositions. Where the compositions are administered at different times, the administrations may be separate from one another or overlapping in time.

Examples of pharmaceutically acceptable carriers, excipients or diluents include, but are not limited to, demineralized or distilled water; saline solution; vegetable based oils such as peanut oil, *arachis* oil, safflower oil, olive oil, cottonseed oil, maize oil, sesame oil, or coconut oil; silicone oils, including polysiloxanes, such as methyl polysiloxane, phenyl polysiloxane and methylphenyl polysolpoxane; volatile silicones; mineral oils such as light liquid paraffin oil, or heavy liquid paraffin oil; squalene; cellulose derivatives such as methylcellulose, ethylcellulose, carboxymethylcellulose, carboxymethylcellulose sodium salt, or hydroxypropyl methylcellulose; lower alkanols, for example ethanol or isopropanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrrolidone; agar; carrageenan; gum tragacanth or gum acacia; and petroleum jelly. Typically, the carrier or carriers will form from 10% to 99.9% by weight of the vaccine composition and may be buffered by conventional methods using reagents known in the art, such as sodium hydrogen phosphate, sodium dihydrogen phosphate, potassium hydrogen phosphate, potassium dihydrogen phosphate, a mixture thereof, and the like.

In aspects, preferred examples of such carriers or diluents include, but are not limited to, water, saline, Ringer's solutions, dextrose solution, and 5% human serum albumin. Liposomes and non-aqueous vehicles such as fixed oils can also be used. The use of such media and compounds for pharmaceutically active substances is well known in the art. Except insofar as any conventional media or compound is incompatible with the Tregitope compounds and compositions of the present disclosure and as previously described above, use thereof in the compositions is contemplated. Supplementary active compounds can also be incorporated into the compositions.

Examples of adjuvants include, but are not limited to, oil in water emulsions, aluminum hydroxide (alum), immunostimulating complexes, non-ionic block polymers or copolymers, cytokines (like IL-1, IL-2, IL-7, IFN-α, IFN-γ, etc.), saponins, monophosphoryl lipid A (MLA), muramyl dipeptides (MDP) and the like. Other suitable adjuvants include, for example, aluminum potassium sulfate, heat-labile or heat-stable enterotoxin(s) isolated from *Escherichia coli*, cholera toxin or the B subunit thereof, diphtheria toxin, tetanus toxin, pertussis toxin, Freund's incomplete or complete adjuvant, etc. Toxin-based adjuvants, such as diphtheria toxin, tetanus toxin and pertussis toxin may be inactivated prior to use, for example, by treatment with formaldehyde. Further adjuvants may include, but are not limited to, poly-ICLC, 1018 ISS, aluminum salts, Amplivax, AS 15, BCG, CP-870,893, CpG7909, CyaA, dSLIM, GM-CSF, IC30, IC31, Imiquimod, ImuFact IMP321, IS Patch, ISS, ISCOMATRTX, Juvlmmune, LipoVac, MF59, monophosphoryl lipid A, Montanide IMS 1312, Montanide ISA 206, Montanide ISA 50V, Montanide ISA-51, OK-432, OM-174, OM-197-MP-EC, ONTAK, PEPTEL, vector system, PLGA microparticles, resiquimod, SRL172, Virosomes and other Virus-like particles, YF-17D, VEGF trap, R848, beta-glucan, Pam3Cys, and Aquila's QS21 stimulon. In aspects of the pharmaceutical compositions or vaccines as disclosed herein, the adjuvant comprises poly-ICLC. The TLR9 agonist CpG and the synthetic double-stranded RNA (dsRNA) TLR3 ligand poly-ICLC are two of the most promising vaccine adjuvants currently in clinical development. In preclinical studies, poly-ICLC appears to be the most potent TLR adjuvant when compared to LPS and CpG. This appears due to its induction of pro-inflammatory cytokines and lack of stimulation of IL-10, as well as maintenance of high levels of co-stimulatory molecules in DCs. Poly-ICLC is a synthetically prepared double-stranded RNA consisting of polyI and polyC strands of average length of about 5000 nucleotides, which has been stabilized to thermal denaturation and hydrolysis by serum nucleases by the addition of polylysine and carboxymethylcellulose. The compound activates TLR3 and the RNA helicase-domain of MDA5, both members of the PAMP family, leading to DC and natural killer (NK) cell activation and mixed production of type I interferons, cytokines, and chemokines.

Examples of freeze-drying stabilizer may be for example carbohydrates such as sorbitol, mannitol, starch, sucrose, dextran or glucose, proteins such as albumin or casein, and derivatives thereof.

In aspects, Tregitope compounds and compositions of the present disclosure are formulated to be compatible with its intended route of administration. The Tregitope compounds and compositions of the present disclosure can be administered by parenteral, topical, intravenous, oral, subcutaneous, intra-arterial, intradermal, transdermal, rectal, intracranial, intrathecal, intraperitoneal, intranasal; vaginally; intramuscular route or as inhalants. In aspects, Tregitope compositions of the present disclosure can be injected directly into a particular tissue where deposits have accumulated, e.g., intracranial injection. In other aspects, intramuscular injection or intravenous infusion may be used for administration of Tregitope compounds and compositions of the present disclosure. In some methods, T-cell epitope compounds and compositions of the present disclosure are administered as a sustained release composition or device, such as but not limited to a Medipad™ device. In aspects, T-cell epitope compounds and compositions of the present disclosure are administered intradermally, e.g., by using a commercial needle-free high-pressure device such as Pulse NeedleFree technology (Pulse 50TM Micro Dose Injection System, Pulse NeedleFree Systems; Lenexa, KS, USA). In aspects, said commercial needle-free high-pressure device (e.g., Pulse NeedleFree technology) confers one or more of the following benefits: non-invasive, reduces tissue trauma, reduces pain, requires a smaller opening in the dermal layer to deposit the composition in the subject (e.g., only requires a micro skin opening), instant dispersion of the composition, better absorption of the composition, greater dermal exposure to the composition, and/or reduced risk of sharps injury.

In aspects, Tregitope compounds and compositions of the present disclosure can optionally be administered in combination with other agents that are at least partly effective in treating various medical conditions as described herein. For example, in the case of administration into the central nervous system of a subject, Tregitope compositions of the present disclosure can also be administered in conjunction with other agents that increase passage of the agents of the invention across the blood-brain barrier.

In aspects, solutions or suspensions used for parenteral, intradermal, or subcutaneous application can include, but are not limited to, the following components: a sterile diluent such as water for injection, saline solution, fixed oils, polyethylene glycols, glycerine, propylene glycol or other synthetic solvents; antibacterial compounds such as benzyl alcohol or methyl parabens; antioxidants such as ascorbic acid or sodium bisulfite; chelating compounds such as ethylenediaminetetraacetic acid (EDTA); buffers such as acetates, citrates or phosphates, and compounds for the adjustment of tonicity such as sodium chloride or dextrose. The pH can be adjusted with acids or bases, such as hydrochloric acid or sodium hydroxide. Examples of excipients can include starch, glucose, lactose, sucrose, gelatin, malt, rice, flour, chalk, silica gel, water, ethanol, DMSO, glycol, propylene, dried skim milk, and the like. The composition can also contain pH buffering reagents, and wetting or emulsifying agents.

In aspects, the parenteral preparation can be enclosed in ampoules, disposable syringes or multiple dose vials made of glass or plastic.

In aspects, pharmaceutical compositions or formulations suitable for injectable use include sterile aqueous solutions (where water-soluble) or dispersions and sterile powders for the extemporaneous preparation of sterile injectable solutions or dispersion. For intravenous administration, suitable carriers include physiological saline, bacteriostatic water, Cremophor ELTM (BASF, Parsippany, NJ) or phosphate buffered saline (PBS). In all cases, the composition is sterile and should be fluid to the extent that easy syringeability exists. It is stable under the conditions of manufacture and storage and is preserved against the contaminating action of microorganisms such as bacteria and fungi. In aspects, formulations including a Tregitope compound and composition of the present disclosure may include aggregates, fragments, breakdown products and post-translational modifications, to the extent these impurities bind HLA and present the same TCR face to cognate T cells they are expected to function in a similar fashion to pure Tregitopes. The carrier can be a solvent or dispersion medium containing, e.g., water, ethanol, polyol (e.g., glycerol, propylene glycol, and liquid polyethylene glycol, and the like), and suitable mixtures thereof. The proper fluidity can be maintained, e.g., by the use of a coating such as lecithin, by the maintenance of the required particle size in the case of dispersion and by the use of surfactants. Prevention of the action of microorganisms can be achieved by various antibacterial and antifungal compounds, e.g., parabens, chlorobutanol, phenol, ascorbic acid, thimerosal, and the like. In many cases, it will be preferable to include isotonic compounds, e.g., sugars, polyalcohols such as manitol, sorbitol, and sodium chloride in the composition. Prolonged absorption of the injectable compositions can be brought about by including in the composition a compound that delays absorption, e.g., aluminum monostearate and gelatin.

In aspects, sterile injectable solutions can be prepared by incorporating the Tregitope compounds and compositions of the present disclosure in the required amount in an appropriate solvent with one or a combination of ingredients enumerated above, as required, followed by filtered sterilization. Generally, dispersions are prepared by incorporating the binding agent into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof. Further, Tregitope compounds and compositions of the present disclosure can be administered in the form of a depot injection or implant preparation that can be formulated in such a manner as to permit a sustained or pulsatile release of the active ingredient.

In aspects, oral compositions generally include an inert diluent or an edible carrier and can be enclosed in gelatin capsules or compressed into tablets. In aspects, for the purpose of oral therapeutic administration, the binding agent can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding compounds, and/or adjuvant materials can be included as part of the composition. In aspects, the tablets, pills, capsules, troches and the like can contain any of the following ingredients, or compounds of a similar nature: a binder such as microcrystalline cellulose, gum tragacanth or gelatin; an excipient such as starch or lactose, a disintegrating compound such as alginic acid, Primogel or corn starch; a lubricant such as magnesium stearate or Sterotes; a glidant such as colloidal silicon dioxide; a sweetening compound such as sucrose or saccharin; or a flavoring compound such as peppermint, methyl salicylate or orange flavoring.

For administration by inhalation, Tregitope compounds and compositions of the present disclosure can be delivered in the form of an aerosol spray from pressured container or dispenser that contains a suitable propellant, e.g., a gas such as carbon dioxide, or a nebulizer.

In aspects, systemic administration of the Tregitope compounds and compositions of the present disclosure can also be by transmucosal or transdermal means. For transmucosal or transdermal administration, penetrants appropriate to the barrier to be permeated are used in the formulation. Such penetrants are generally known in the art, and include, e.g., for transmucosal administration, detergents, bile salts, and fusidic acid derivatives. Transmucosal administration can be accomplished through the use of nasal sprays or suppositories. For transdermal administration, the Tregitope compounds and compositions may be formulated into ointments, salves, gels, or creams, and applied either topically or through transdermal patch technology as generally known in the art.

In aspects, the Tregitope compounds and compositions of the present disclosure can also be prepared in the form of suppositories (e.g., with conventional suppository bases such as cocoa butter and other glycerides) or retention enemas for rectal delivery.

In aspects, the Tregitope compounds and compositions of the present disclosure are prepared with carriers that protect the Tregitope compounds and compositions against rapid elimination from the body, such as a controlled-release formulation, including implants and microencapsulated delivery systems. Biodegradable, biocompatible polymers can be used, such as, for example, ethylene vinyl acetate, polyanhydrides, polyglycolic acid, collagen, polyorthoesters, and polylactic acid. Methods for preparation of such formulations will be apparent to those skilled in the art. The materials can also be obtained commercially, e.g., from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art (U.S. Pat. No. 4,522,811, which is herein incorporated by reference in its entirety). In aspects, the Tregitope compounds and compositions of the present disclosure can be implanted within or linked to a biopolymer solid support that allows for the slow release of the Tregitope compounds and compositions to the desired site.

In aspects, it is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of binding agent calculated to produce the desired therapeutic effect in association with the required pharmaceutical carrier. The specification for the dosage unit forms of the instant disclosure are dictated by and directly dependent on the unique characteristics of the binding agent and the particular therapeutic effect to be achieved, and the limitations inherent in the art of compounding such Tregitope compounds and compositions for the treatment of a subject.

In aspects, the one or more of the Tregitope compounds and compositions as disclosed herein can also be administered to the patient by ex vivo pulsing of isolated dendritic cells (DC) with Tregitopes, followed by reinfusion of the pulsed cells into the patient. These can be prepared according to methods known to those skilled in the art (Butterfield, (2013), Front Immunol, 4:454 and Dissanayake et al., (2014), PLoS One, 9(3)1-10). These reinfusions may be administered by the above methods and compositions.

In aspects of a pharmaceutical composition as described herein, the composition may comprise at least 2, at least 3, at least 4, at least 5, at least 6, at least 7, at least 8, at least 9, at least at least 11, at least 12, at least 13, at least 14, at least 15, at least 16, at least 17, at least 18, at least 19, or at least 20 of the instantly-disclosed peptides or polypeptides (including concatemeric polypeptides) or nucleic acids encoding such peptides or polypeptides (including concatemeric polypeptides). For example, in aspects, a pharmaceutical composition can comprise at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, or at least 20 peptides or polypeptides (including up to 40 peptides or polypeptides), including any value or range therebetween, comprising, consisting of, or consisting essentially of one or more peptides or polypeptides having an amino acid sequence comprising, consisting of, or consisting essentially of one or more of SEQ ID NOS: 1-124 and/or fragments and variants thereof, and optionally 1 to 12 additional amino acids distributed in any ratio on the N terminus and/or C-terminus of the polypeptide of SEQ ID NOS: 1-124; concatemeric peptides as disclosed herein; and nucleic acids (e.g., RNA mRNA, DNA, cDNA) encoding such peptides, polypeptides, or concatemeric peptides, and/or fragments and variants thereof, as described herein.

In aspects, the Tregitope compounds and compositions of the present disclosure (including one or more of e.g., polypeptides (which may be termed herein as "Treg activating regulatory T-cell epitope", "Tregitope", or "T-cell epitope polypeptide") having a sequence comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) are combined in admixture with an antigen, allergen, or a therapeutic protein. Such compositions are useful in methods of inducing tolerance to the antigen, allergen, or a therapeutic protein in a subject in need thereof, wherein local delivery of the admixture with an antigen, allergen, or a therapeutic protein results in increased tolerance to the antigen or allergen in the subject, and delivered with an appropriate excipient resulting in induced tolerance to the antigen, allergen, or a therapeutic protein. This combination may be administered with the Tregitope compounds and compositions of the present disclosure bound either covalently or non-covalently, or they may be administered as an admixture, or a branched or chemically-link preparation. Such compositions are useful in methods of inducing tolerance to an antigen or allergen or a therapeutic protein. For example, such composition are useful in a subject in need thereof, wherein local delivery of the admixture with an antigen or allergen or therapeutic protein results in increased tolerance to the antigen or allergen or therapeutic protein in the subject, and delivered with an appropriate excipient resulting in induced tolerance to the antigen or allergen or therapeutic protein.

Methods of Use

Stimulating regulatory T cells with Tregitope compounds and compositions of the present disclosure (including one or more of e.g., polypeptides (which may be termed herein as "Treg activating regulatory T-cell epitope", "Tregitope", or "T-cell epitope polypeptide") having a sequence comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124) as disclosed herein; nucleic acids, expression cassettes, plasmids, expression vectors, recombinant viruses, or cells (all of which in aspects may be isolated, synthetic, or recombinant) as disclosed herein; chimeric or fusion polypeptide compositions as disclosed herein (which in aspects may be isolated, synthetic, or recombinant); and/or pharmaceutical compositions or formulations as disclosed herein) can stimulate, induce, and/or expand corresponding naturally occurring $T_{Reg}$ populations (in aspects, including natural $T_{Regs}$ and/or adaptive $T_{Regs}$) and in aspects results in increased secretion of one or more of the following cytokines and chemokines: IL-10, IL-35, TGF-β, TNF-α and MCP1. This increased secretion of regulatory cytokines and chemokines is a hallmark of regulatory T cells. In aspects, stimulation can result in the increased expression of IL-2Rα by corresponding naturally occurring $T_{Reg}$ populations (in aspects, including natural $T_{Regs}$ and/or adaptive $T_{Regs}$) and deprivation of IL-2 to effector T cells. In further aspects, stimulation can result in increased perforin granzyme by corresponding naturally occurring $T_{Reg}$ populations (in aspects, including natural $T_{Regs}$ and/or adaptive $T_{Regs}$), which allows for such Treg populations to kill T effector cells and other immune stimulatory cells. In even further aspects, such stimulation can result in the generation of immune suppressive adenosine by corresponding naturally occurring $T_{Reg}$ populations (in aspects, including natural $T_{Regs}$ and/or adaptive $T_{Regs}$). In other aspects, such stimulation can result in corresponding naturally occurring $T_{Reg}$ populations (in aspects, including natural $T_{Regs}$ and/or adaptive $T_{Regs}$) binding to and removing costimulatory molecules on dendritic cells, resulting the inhibition of dendritic cell function. Further, in aspects, such stimulation can result in $T_{Reg}$ induced upregulation of checkpoint molecules on dendritic cells and other cell populations, e.g., but not limited to endothelial cells, by corresponding naturally occurring $T_{Reg}$ populations (in aspects, including natural $T_{Regs}$ and/or adaptive $T_{Regs}$). In additional aspects, such stimulation can result in $T_{reg}$ stimulation of B-regulatory cells. B-regulatory cells ("B-regs") are cells that are responsible for the anti-inflammatory effect, which is characterized by the expression of CD1d, CD5, and the secretion of IL-10. B-regs are also identified by expression of Tim-1 and can be induced through Tim-1 ligation to promote tolerance. The ability of being B-regs was shown to be driven by many stimulatory factors such as toll-like receptors, CD40-ligand and others. However, full characterization of B-regs is ongoing. B-regs also express high levels of CD25, CD86, and TGF-β. The increased secretion of such regulatory cytokines and chemokines by regulatory T cells, as well as other activities described above, are hallmarks of regulatory T cells. In aspects, regulatory T cells activated by the Tregitope compositions of the present disclosure may express a CD4+CD25+FOXP3 phenotype. In aspects, regulatory T cells activated by the Tregitope compositions of the present disclosure may express a CD4+CD25+Foxp3+ phenotype. Regulatory T cells activated by the Tregitope compounds and compositions of the present disclosure directly suppress T-effector immune responses ex vivo as measured by decreased antigen-specific Th1- or Th2-associated cytokine levels, principally INF-γ, IL-4, and IL-5, and by decreased proliferation and/or effector function of antigen-specific T effector cells as measured by CFSE dilution and/or cytolytic activity. In aspects, regulatory T cells activated by the Tregitope compounds and compositions of the present disclosure directly suppress T effector immune responses in vivo, as measured by decreased antigen-specific Th1- or Th2-associated cytokine levels (as measured by Elisa assay), decreased antigen-specific T effector cell levels (as measured by EliSpot assay), decreased cytolytic activity, and/or decreased antibody titers for protein antigens.

In aspects, natural regulatory T cells activated by the Tregitope compounds and compositions of the present disclosure stimulate the development of adaptive $T_{Reg}$ cells. In aspects, co-incubating peripheral T cells with the Tregitope compounds and compositions of the present disclosure in the presence of antigen results in the expansion of antigen-specific CD4+/CD25+ T cells, upregulates the expression of the Foxp3 gene or Foxp3 protein in those cells and suppresses the activation of antigen-specific T effector cells in vitro. In aspects, the Tregitope compounds and compositions of the present disclosure may result in the activation and/or expansion of T regulatory type 1 (Tr1) cells. Tr1 cells have strong immunosuppressive capacity in several immune-mediated diseases (Roncarolo and Battaglia, 2007, Nat Rev Immunol 7, 585-598; Roncarolo et al., 2011, Immunol Rev 241, 145-163; Pot et al., 2011, Semin Immunol 23, 202-208). The secretion of high levels of IL-10, and the killing of myeloid antigen-presenting cells (APCs) via Granzyme B are the main mechanisms of Tr1-mediated suppression (Groux et al., 1997, Nature 389, 737-742; Magnani et al., 2011 Eur J Immunol 41, 1652-1662). Tr1 cells are distinguished from T helper ($T_H$)1, $T_H$2, and $T_H$17 cells by their unique cytokine profile and the regulatory function. Tr1 cells have been shown secrete higher levels of IL-10 than IL-4 and IL-17, the hallmark cytokines of $T_H$2 and $T_H$17 cells, respectively. Tr1 cells can also secrete low levels of IL-2 and, depending on the local cytokine milieu, can produce variable levels of IFN-γ, together, the key $T_H$1 cytokines (Roncarolo et al., 2011, Immunol Rev 241, 145-163). FOXP3 is not a biomarker for Tr1 cells since its expression is low and transient upon activation. IL-10-producing Tr1 cells express ICOS (Haringer et al., 2009, J Exp Med 206, 1009-1017) and PD-1 (Akdis et al., 2004, J Exp Med 199, 1567-1575), but these markers are not specific (Maynard et al., 2007, Nat Immunol 8, 931-941). CD49b, the α2 integrin subunit of the very-late-activation antigen (VLA)-2, has been proposed as a marker for IL-10-producing T cells (Charbonnier et al., 2006, J Immunol 177, 3806-3813); but it is also expressed by human $T_H17$ cells (Boisvert et al., 2010, Eur J Immunol 40, 2710-2719). Moreover, murine CD49b+ T cells secrete IL-10 (Charbonnier et al., 2006, J Immunol 177, 3806-3813) but also pro-inflammatory cytokines (Kassiotis et al., 2006, J Immunol 177, 968-975). Lymphocyte activation gene-3 (LAG-3), a CD4 homolog that binds with high affinity to MHC class II molecules, is expressed by murine IL-10-producing $CD4^+$ T cells (Okamura et al., 2009, Proc Natl Acad Sci USA 106, 13974-13979), but also by activated effector T cells (Workman and Vignali, 2005, J Immunol 174, 688-695; Bettini et al., 2011, J Immunol 187, 3493-3498; Bruniquel et al., 1998, Immunogenetics 48, 116-124; Lee et al., 2012, Nat Immunol 13, 991-999) and by $FOXP3^+$ regulatory T cells (Tregs) (Camisaschi et al., 2010, J Immunol 184, 6545-6551). It was recently shown that human Tr1 cells express CD226 (DNAM-1), which is involved in the specific killing of myeloid APCs (Magnani et al., 2011 Eur J Immunol 41, 1652-1662). In further aspects, Tregitope compounds and compositions of the present disclosure may result in the activation and/or expansion of TGF-β secreting Th3 cells, regulatory NKT cells, regulatory $CD8^+$ T cells, double negative regulatory T cells. "Th3 cells" refer to cells having the following phenotype $CD4^+FoxP3^+$ and capable of secreting high levels TGF-β upon activation, amounts of IL-4 and IL-10 and no IFN-γ or IL-2. These cells are TGF-β derived. "Regulatory NKT cells" refers to cells having the following phenotype at rest $CD161^+CD56^+CD16^+$ and a Vα24/Vβ11 TCR. "Regulatory CD8+ T cells" refers to cells having the following phenotype at rest $CD8^+CD122^+$ and capable of secreting highs levels of IL-10 upon activation. "Double negative regulatory T cells" refers to cells having the following phenotype at rest $TCRαβ^+CD4^-CD8^-$.

In aspects, the Tregitope compounds and compositions of the present disclosure are useful for regulating immune response to monoclonal antibodies, protein therapeutics, self-antigens promoting autoimmune response, allergens, transplanted tissues, and in other applications where tolerance is the desired outcome.

In aspects, the Tregitope compounds and compositions of the present disclosure can bind MHC class II molecules, engage TCR in context of MHC class II molecules and activate naturally occurring $T_{Regs}$ (in aspects, including natural $T_{Regs}$ and/or adaptive $T_{Regs}$).

Suppressing an Immune Response in a Subject in Need Thereof. In aspects, the present disclosure is directed to a method of stimulating, inducing, and/or expanding regulatory T-cells by administering or introducing or contacting with an amino acid sequence of SEQ ID NOS: 1-124 or a fragment or variant thereof, either directly or through introduction of a nucleic acid encoding such and providing or allowing for transcription and translation thereof.

In aspects, the present disclosure is directed to a method of stimulating, inducing, and/or expanding regulatory T-cells (e.g., naturally occurring $T_{Regs}$ (in aspects, including natural $T_{Regs}$ and/or adaptive $T_{Regs}$)) to suppress an immune response in a subject in need thereof by administering to the subject a therapeutically effect amount of a Tregitope compound or composition of the present disclosure. In aspects, the immune response is the result of one or more therapeutic treatments with at least one therapeutic protein, treatment with a vaccine (particularly in situations in which an adverse event results from the vaccination), or treatment with at least one antigen. In another aspect, the administration of a Tregitope compound or composition of the present disclosure shifts one or more antigen presenting cells to a regulatory phenotype, one or more dendritic cells to a regulatory phenotype, decreases CD11c and HLA-DR expression in the dendritic cells or other antigen presenting cells.

In aspects, the present disclosure is directed to a method for repressing/suppressing an immune response in a subject, comprising administering a therapeutically effective amount of Tregitope compound or composition of the present disclosure, wherein the Tregitope compound or composition represses/suppresses the immune response. In aspects, the Tregitope compound or composition represses/suppresses an innate immune response. In aspects, the Tregitope compound or composition represses/suppresses an adaptive immune response. In aspects, the Tregitope compound or composition represses/suppresses an effector T cell response. In aspects, the Tregitope compound or composition represses/suppresses a memory T cell response. In aspects, the Tregitope compound or composition represses/suppresses helper T cell response. In aspects, the Tregitope compound or composition represses/suppresses B cell response. In aspects, the Tregitope compound or composition represses/suppresses an NKT cell response.

In aspects, the present disclosure is directed to a method of suppressing an immune response, specifically an antigen-specific immune response in a subject, through the administration of a therapeutically effective amount of a Tregitope compound or composition of the present disclosure, wherein said Tregitope compound or composition activates naturally occurring $T_{Regs}$ (in aspects, including natural $T_{Regs}$ and/or adaptive $T_{Regs}$, and in aspects $CD4^+/CD25^+/FoxP3^+$ regulatory T-cells) or suppresses the activation of $CD4^+$ T-cells, the proliferation of $CD4^+$ and/or $CD8^+$ T-cells, and/or suppresses the activation or proliferation of β-cells or NKT Cells. In aspects, a Tregitope compound or composition of the present disclosure may be either covalently bound, non-covalently bound, or in admixture with a specific target antigen. In particular aspects, one or more of e.g., polypeptides (Treg activating regulatory T-cell epitope, Tregitope, Tregitope peptide, or T-cell epitope polypeptide, which in aspects may be isolated, synthetic, or recombinant) and/or chimeric or fusion polypeptide compositions of the presently disclosed Tregitope compounds or compositions may be either covalently bound, non-covalently bound, or in admixture with a specific target antigen. In aspects, an administered Tregitope compound or composition of the present disclosure that is covalently bound, non-covalently bound, or in admixture with a specific target antigen results in the diminution of immune response against the target antigen.

In aspects, the target antigen may be an autologous protein or protein fragment. In aspects, the target antigen may be an allergen. In aspects, the target antigen may be an allogenic protein or protein fragments. In aspects, the target antigen may be a biologic medicine or fragments thereof. In aspects, the suppressive effect is mediated by natural $T_{Regs}$. In aspects, the suppressive effect is mediated by an adaptive $T_{Regs}$. In aspects, the one or more Tregitopes included in the Tregitope compounds or compositions of the present disclosure suppresses an effector T cell response. In aspects, the one or more Tregitopes of the presently disclosed Tregitope compounds or compositions suppresses an innate immune response. In aspects, the one or more Tregitopes of the presently disclosed Tregitope compounds or compositions suppresses an adaptive immune response. In aspects, the one or more Tregitopes of the presently disclosed Tregitope compounds or compositions suppresses helper T cell response. In aspects, the one or more Tregitopes of the presently disclosed Tregitope compounds or compositions suppresses a memory T cell response. In aspects, the one or more Tregitopes of the presently disclosed Tregitope compounds or compositions suppresses a β cell response. In aspects, the one or more Tregitopes of the presently disclosed Tregitope compounds or compositions suppresses a NKT cell response.

Designing Small Molecule Therapeutics. In one aspect, the present disclosure provides methods of using a Tregitope compound or composition of the present disclosure for the purpose of designing small molecule therapeutics. In one aspect, Tregitope-specific T cells are stimulated three times with pools of small molecule mixtures at a concentration of 1 μg/ml and autologous dendritic cells (DC) at 2-week intervals, followed by stimulation with heterologous DC and antigens. T cells ($1.25 \times 10^5$) and DC ($0.25 \times 10^5$) are added per well in round-bottom, 96-well plates. T cell medium is made by supplementing 500 ml of RPMI medium 1640 with 50 ml of FCS (HyClone Laboratories, Inc., Logan, UT), penicillin, and streptomycin (GIBCO Laboratories, Gaithersburg, MD); 20 mM Hepes (GIBCO); and 4 ml 1 N NaOH solution. The IL-2 concentration is initially 0.1 nM and gradually is increased to 1 nM during subsequent rounds of stimulation. T cell clones are derived by limiting dilution by using $0.6 \times 10^5$ Epstein—Barr virus-transformed B cells (100 Gray) and $1.3 \times 10^5$ heterologous peripheral blood mononuclear cells (33 Gray) as feeder cells and 1 μg/ml Difco™ phytohemagglutinin (Bacterius Ltd, Houston, TX) in medium containing 2 nM IL-2. Small molecules pools that stimulate the Tregitope specific T cells are then tested as individual molecules.

Cloning T Cell Receptors. In aspects, the present disclosure provides methods of using a Tregitope compound or composition of the present disclosure for the purpose of cloning T cell receptors. Cloning of Tregitope-specific T cells can be conducted by techniques known to one of skill in the art. For example, isolated PBMCs are stimulated with Tregitopes at 10 μg/ml RPMI media containing 20% HSA. IL-2 is added (10 U/ml final concentration) every other day starting on day 5. T cells are stained with tetramer pools on day 11 or 12. For each pool, $2-3 \times 10$ 5 cells are incubated with 0.5 mg of PE-labeled tetramer in 50 ml of culture medium (10 mg/ml) at 37° C. for 1 to 2 h, and then stained with anti-CD4-FITC (BD PharMingen™, San Diego, CA) for 15 min at room temperature. Cells are washed and analyzed with a Becton Dickinson FACSCalibur™ flow cytometer (Becton Dickinson, San Jose, CA). Tetramers loaded with the corresponding single peptides are generated for those pools that give positive staining, and analysis is done on day 14 or 15. Cells that are positive for a particular tetramer are single-cell sorted into 96-well U-bottom plates by using a Becton Dickinson FACSVantage™ (San Jose, CA) on the same or following day. Sorted cells are expanded with $1.5-3 \times 10^5$ unmatched, irradiated (5000 rad) PBMC per well as feeders with 2.5 mg/ml PHA and 10 U/ml IL-2 added 24 h later. Specificity of cloned T cells is confirmed by staining with tetramers (loaded with cognate peptide or control peptide, HA307-319) and T cell proliferation assays with 10 mg/ml of specific peptide (Novak E J et al., J Immunol, 166(11):6665-70). In aspects, total RNA is extracted with an RNeasy Mini Kit (Qiagene, Hilden, D E) from the Tregitope specific T cell lines generated as described above. One microgram of total RNA is used to clone the TCR cDNAs by a rapid amplification of cDNA end (RACE) method using aGeneRacer® kit (Invitrogen, Carlsbad, C A). Before synthesizing the single-strand cDNA, the RNA is de-phosphorylated, de-capped, and ligated with an RNA oligonucleotide according to the instruction manual of 5' RACE GeneRacer® kit. SuperScript II RT® (Life Technologies Corp, Carlebad, C A) and GeneRacer® Oligo-dT are used for reverse transcription of the RNA Oligo-ligated mRNA to single-strand cDNAs. 5' RACE is performed by using GeneRacer® 5' (GeneRacer® Kit) as 5' primer and gene-specific primer TCRCAR (5'-GTT AAC TAG TTC AGC TGG ACC ACA GCC GCA GC-3'; SEQ ID NO: 130) or TCRCB1R (5'-CGG GTT AAC TAG TTC AGA AAT CCT TTC TCT TGA CCA TGG C-3'; SEQ ID NO: 131), or TCRCBR2 (5'-CTA GCC TCT GGA ATC CTT TCT CTT G-3; SEQ ID NO: 132) as 3' primers for TCR a, (31, or (32 chains, respectively. The polymerase chain reaction (PCR) products are cloned into pCR2.1 TOPO vector (Invitrogen, Carlsbad, C A) and then transformed into One Shot TOP10 Competent *Escherichia coli* (Invitrogen, Carlsbad, C A). Plasmid DNAs are prepared from 96 individual clones from each construct for TCRα, 131, and 132 chains. Full-length insert of all the plasmids is sequenced to determine the vα/vβ usage (Zhao Y et al., (2006), J Immunother, 29(4): 398-406, herein incorporated by reference in its entirety).

Methods of Preventing or Treating a Medical Condition. The present disclosure is directed to, for example methods of preventing or treating one or more medical conditions in a subject comprising administering a Tregitope compound or composition of the present disclosure and preventing or treating the medical condition in a subject by said step of administering. The medical condition can be, for example, primary immunodeficiencies, immune-mediated thrombocytopenia, Kawasaki disease, hematopoietic stem cell transplantation in patients older than 20 years, chronic B-cell lymphocytic leukemia, and pediatric HIV type 1 infections. Specific examples include: (Hematology) aplastic anemia, pure red cell aplasia, Diamond-Blackfan anemia, autoimmune hemolytic anemia, hemolytic disease of the newborn, acquired factor VIII inhibitors, acquired von Willebrand disease, immune-mediated neutropenia, refractoriness to platelet transfusion, neonatal alloimmune/autoimmune thrombocytopenia, posttransfusion purpura, thrombotic thrombocytopenia purpura/hemolytic uremic syndrome; Infectious diseases, solid organ transplantation, surgery, trauma, burns, and HIV infection; (Neurology) epilepsy and pediatric intractable Guillain-Barre syndrome, chronic inflammatory demyelinating polyneuropathy, myasthenia gravis, Lambert-Eaton myasthenic syndrome, multifocal motor neuropathy, multiple sclerosis; (Obstetrics) recurrent pregnancy loss; (Pulmonology) asthma, chronic chest symptoms, rheumatology, rheumatoid arthritis (adult and juvenile), systemic lupus erythematosus, systemic vasculitides, dermatomyositis, polymyositis, inclusion-body myositis, wegener granulomatosis; (Miscellaneous) adrenoleukodystrophy, amyotrophic lateral sclerosis, Behcet syndrome, acute cardiomyopathy, chronic fatigue syndrome, congenital heart block, cystic fibrosis, autoimmune blistering dermatosis, diabetes mellitus, acute idiopathic dysautonomia, acute disseminated encephalomyelitis, endotoxemia, hemolytic transfusion reaction, hemophagocytic syndrome, acute lymphoblastic leukemia, lower motor neuron syndrome, multiple myeloma, human T-cell lymphotrophic virus-1-associated myelopathy, nephritic syndrome, membranous nephropathy, nephrotic syndrome, euthyroid ophthalmopathy, opsoclonus-myoclonus, recurrent otitis media, paraneoplastic cerebellar degeneration, paraproteinemic neuropathy, parvovirus infection (general), polyneuropathy, organomegaly, endocrinopathy, M-protein, and skin changes (POEMS) syndrome, progressive lumbosacral plexopathy, lyme radiculoneuritis, Rasmussen syndrome, Reiter syndrome, acute renal failure, thrombocytopenia (nonimmune), streptococcal toxic shock syndrome, uveitis, and Vogt-Koyanagi-Harada syndrome.

In a particular aspect, the present disclosure is directed to, for example, methods of treating allergy, autoimmune disease, transplant-related disorders such as graft versus host disease, enzyme or protein deficiency disorders, hemostatic disorders (e.g., Hemophilia A, B, or C), cancers (particularly tumor associated autoimmunity), infertility, or infections (viral, bacterial, or parasitic). The Tregitope compounds or compositions of the present disclosure can be used with in conjunction with other proteins or compounds used for treating a subject with a medical condition in order to reduce adverse events or enhance the efficacy of the co-administered compound.

Application to Allergy. Allergen-specific regulatory T cells play an important role in controlling the development of allergy and asthma. Naturally occurring $T_{Regs}$ (in aspects, including natural $T_{Regs}$ and/or adaptive $T_{Regs}$, and in aspects $CD4^+/CD25^+/FoxP3^+$ regulatory T-cells) have been shown to inhibit the inappropriate immune responses involved in allergic diseases. A number of recent studies indicate that regulatory T cells play an important role in controlling the overdevelopment of T-helper type 2 biased immune responses in susceptible individuals, not only in animal models, but in humans as well. Recent studies indicate that $T_{regs}$ also suppress T cell co-stimulation by the secretion of TGF-β and IL-10, suggesting an important role of $T_{regs}$ in the regulation of allergic disorders. Impaired expansion of natural or adaptive regulatory T cells leads to the development of allergy, and treatment to induce allergen-specific $T_{regs}$ would provide curative therapies for allergy and asthma. One strategy for both the prevention and therapy of asthma is the induction of $T_{regs}$. Animals can be protected from developing asthma by immune stimulation leading to Th1 or $T_{reg}$ responses. Accordingly, Tregitope compounds or compositions of the present disclosure are useful in methods for the prevention or treatment of allergy and/or asthma. As such, in aspects, the present disclosure is directed to a method of preventing or treating allergy and/or asthma in a subject, the method comprising administering a therapeutically-effective amount of a Tregitope compound or composition of the present disclosure, and preventing or treating allergy and/or asthma in a subject by said step of administering.

Application to Transplantation. The Tregitope compounds and compositions of the present disclosure are useful to induce tolerance during the transplantation process, by promoting the development of cells that specifically down regulate immune responses against donor cells. Induction of Ag-specific $T_{Reg}$ cells for treating organ-specific autoimmunity is an important therapeutic development, avoiding generalized immune suppression. In murine models of bone marrow transplantation, $T_{Regs}$ promote donor bone marrow engraftment and decrease the incidence and severity of graft versus host disease without abrogating the beneficial graft versus tumor immunologic effect. These findings, in concert with observations that $T_{Regs}$ in mice and humans share phenotypic and functional characteristics, have led to active investigations into the use of these cells to decrease complications associated with human hematopoietic cell transplantation. An imbalance of $T_{Regs}$ and effector T cells contributes to the development of graft versus host disease, however, the mechanisms of immunoregulation, in particular, the allorecognition properties of $T_{Regs}$, their effects on and interaction with other immune cells, and their sites of suppressive activity, are not well understood.

Accumulating evidence from both humans and experimental animal models has implicated the involvement of $T_{Regs}$ in the development of graft versus host disease (GVHD). The demonstration that $T_{Regs}$ can separate GVHD from graft versus tumor (GVT) activity suggests that their immunosuppressive potential could be manipulated to reduce GVHD without detrimental consequence on GVT effect. Although a variety of T lymphocytes with suppressive capabilities have been reported, the two best-characterized subsets are the naturally arising, intrathymic-generated $T_{Regs}$ (natural $T_{Regs}$) and the peripherally generated, inducible $T_{Regs}$ (inducible $T_{Regs}$). Accordingly, Tregitope compositions of the present disclosure are useful in methods for inducing tolerance during the transplantation process. As such, in aspects, the present disclosure is directed to a method of inducing tolerance during the transplantation process in a subject, the method comprising administering a therapeutically-effective amount of a Tregitope compound or composition of the present, and inducing tolerance during the transplantation process in a subject by said step of administering.

Application as a Tolerizing Agent and to Autoimmunity. In aspects, Tregitope compounds and compositions of the present disclosure can be used as a tolerizing agents for immunogenic compounds (protein therapeutics) (Weber C A et al., (2009), Adv Drug Deliv, 61(11):965-76). This discovery has implications for the design of protein therapeutics. Thus, administration of an immunogenic compound (e.g., protein therapeutic, such as but not limited to antibody (e.g., monoclonal antibody), autologous cytokine, or foreign protein) in conjunction with a Tregitope composition of the present disclosure suppresses adverse T effector immune responses. In vivo, $T_{Regs}$ act through dendritic cells to limit autoreactive T-cell activation, thus preventing their differentiation and acquisition of effector functions. By limiting the supply of activated pathogenic cells, $T_{Regs}$ prevent or slow down the progression of autoimmune diseases. This protective mechanism appears, however, insufficient in autoimmune individuals, likely because of a shortage of $T_{Regs}$ cells and/or the development and accumulation of $T_{Reg}$-resistant pathogenic T cells over the long disease course. Thus, restoration of self-tolerance in these patients may require purging of pathogenic T cells along with infusion of $T_{Regs}$ with increased ability to control ongoing tissue injury. Organ-specific autoimmune conditions, such as thyroiditis and insulin-dependent diabetes mellitus have been attributed to a breakdown of this tolerance mechanism (Mudd P A et al., (2006), Scand J Immunol, 64(3):211-8). Accordingly, Tregitope compounds and compositions of the present disclosure are useful in methods for the prevention or treatment of autoimmunity. As such, in aspects, the present disclosure is directed to a method of preventing or treating autoimmunity in a subject, the method comprising administering a therapeutically-effective amount of a Tregitope compound or composition of the present disclosure, and preventing and/or treating autoimmunity in a subject by said step of administering.

Application to Diabetes. Type 1 (juvenile) diabetes is an organ-specific autoimmune disease resulting from destruction of insulin-producing pancreatic beta-cells. In non-diabetics, islet cell antigen-specific T cells are either deleted in thymic development or are converted to T regulatory cells that actively suppress effector responses to islet cell antigens. In juvenile diabetics and in the NOD mouse model of juvenile diabetes, these tolerance mechanisms are missing.

In their absence, islet cell antigens are presented by human leukocyte antigen (HLA) class I and II molecules and are recognized by CD8(+) and CD4(+) auto-reactive T cells. Destruction of islet cells by these auto-reactive cells eventually leads to glucose intolerance. Co-administration of Tregitopes and islet cell antigens leads to the activation of naturally occurring T regulatory cells and the conversion of existing antigen specific effector T cell to a regulatory phenotype. In this way, deleterious autoimmune response is redirected leading to the induction of antigen-specific adaptive tolerance. Modulation of autoimmune responses to autologous epitopes by induction of antigen-specific tolerance can prevent ongoing beta-cell destruction. Accordingly, Tregitope compounds and compositions of the present disclosure are useful in methods for the prevention or treatment of diabetes. As such, in aspects, the present disclosure is directed to a method of preventing or treating diabetes in a subject, the method comprising administering a therapeutically-effective amount of Tregitope compound or composition of the present disclosure, and preventing and/or treating diabetes in a subject by said step of administering.

Application to Hepatitis B (HBV) infection. Chronic HBV is usually either acquired (by maternal fetal transmission) or can be a rare outcome of acute HBV infection in adults. Acute exacerbations of chronic hepatitis B (CH—B) are accompanied by increased cytotoxic T cell responses to hepatitis B core and e antigens (HBcAg/HBeAg). In a recent study, the SYFPEITHI T cell epitope mapping system was used to predict MHC class II-restricted epitope peptides from the HBcAg and HbeAg (Feng I C et al., (2007), J Biomed Sci, 14(1):43-57). MHC class II tetramers using the high scoring peptides were constructed and used to measure $T_{Reg}$ and CTL frequencies. The results showed that $T_{Reg}$ cells specific for HBcAg declined during exacerbations accompanied by an increase in HBcAg peptide-specific cytotoxic T cells. During the tolerance phase, FOXp3-expressing $T_{Reg}$ cell clones were identified. These data suggest that the decline of HbcAg $T_{Reg}$ T cells accounts for the spontaneous exacerbations on the natural history of chronic hepatitis B virus infection. Accordingly, Tregitope compounds and compositions of the present disclosure are useful in methods for the prevention or treatment of chronic hepatitis B viral infection. As such, in aspects, the present disclosure is directed to a method of preventing or treating a viral infection (e.g., HBV infection) in a subject, the method comprising administering a therapeutically-effective amount of a Tregitope compound or composition of the present disclosure, and preventing and/or treating said viral infection in a subject by said step of administering.

Application to SLE. A $T_{Reg}$ epitope that plays a role in Systemic Lupus Erythematosus (SLE) or Sjögren's syndrome has been defined. This peptide encompasses residues 131-151 (RIHMVYSKRSGKPRGYAFIEY; SEQ ID NO: 133) of the spliceosome protein. Binding assays with soluble HLA class II molecules and molecular modeling experiments indicated that the epitope behaves as promiscuous epitope and binds to a large panel of human DR molecules. In contrast to normal T cells and T cells from non-lupus autoimmune patients, PBMCs from 40% of randomly selected lupus patients contain T cells that proliferate in response to peptide 131-151. Alteration of the ligand modified the T cell response, suggesting that several populations of T cells responding to this peptide exist, among which may be $T_{Reg}$ cells. T regulatory epitopes have also been defined in Sjögren's syndrome. Accordingly, Tregitope compounds or compositions of the present disclosure administered in combination with SEQ ID NO: 133 are useful in methods for the prevention or treatment of SLE. As such, in aspects, the present disclosure is directed to a method of preventing or treating SLE in a subject, the method comprising administering a therapeutically-effective amount of a Tregitope compound or composition of the present disclosure in combination with SEQ ID NO: 133, and preventing and/or treating SLE in a subject by said step of administering.

Application to Autoimmune Thyroiditis. Autoimmune Thyroiditis is a condition that occurs when antibodies arise to self-thyroid peroxidase and/or thyroglobulin, which cause the gradual destruction of follicles in the thyroid gland. HLA DR5 is closely associated with the disease. Accordingly, Tregitope compounds or compositions of the present disclosure administered in combination with thyroid peroxidase and/or thyroglobulin TSHR or portions thereof are useful in methods for the prevention or treatment of autoimmune thyroiditis. As such, in aspects, the present disclosure is directed to a method of preventing or treating autoimmune thyroiditis in a subject, the method comprising administering a therapeutically-effective amount of a Tregitope compound or composition of the present disclosure in combination with thyroid peroxidase and/or thyroglobulin TSHR or portions thereof, and preventing and/or treating autoimmune thyroiditis in a subject by said step of administering. In further aspects, Tregitope compositions of the present disclosure administered in combination with TSHR or other Graves' disease antigens or portions thereof are useful in methods for the prevention or treatment of Grave's disease. Graves' disease is an autoimmune disorder that is characterized by antibodies to self-thyroid stimulating hormone receptor (TSHR) leading to leading to hyperthyroidism, or an abnormally strong release of hormones from the thyroid gland. Several genetic factors can influence susceptibility to Graves' disease. Females are much more likely to contract the disease than males; White and Asian populations are at higher risk than black populations and HLA DRB1-0301 is closely associated with the disease. As such, in aspects, the present disclosure is directed to a method of preventing or treating Grave's disease in a subject, the method comprising administering a therapeutically-effective amount of a Tregitope compound or composition of the present disclosure in combination with TSHR or other Graves' disease antigens or portions thereof, and preventing and/or treating Grave's disease in a subject by said step of administering.

Ex Vivo Expansion and/or Stimulation of T-Regulatory Cells Using Tregitope Compositions. In aspects, the present disclosure provides ex vivo methods for the expansion of regulatory T-cells. In one embodiment, the invention provides a method of expanding regulatory T-cells in a biological sample, the method comprising: (a) providing a biological sample from a subject; (b) isolating regulatory T-cells from the biological sample; and contacting the isolated regulatory T-cells with an effective amount of a Tregitope compound or composition of the present disclosure under conditions wherein the T-regulatory cells increase in number to yield an expanded regulatory T-cells, thereby expanding the regulatory T-cells in the biological sample. In aspects, the method further comprises the step of administration of the expanded regulatory T-cells to a subject. In aspects, the subject administered the expanded regulatory T-cells is the same individual from which the original biological sample was obtained, e.g., by autologous transplantation of the expanded Tregitope (Ruitenberg J J et al., (2006), BMC Immunol, 7:11).

In aspects, the present disclosure provides ex vivo methods for stimulation of regulatory T-cells in a biological sample, the method comprising: (a) providing a biological sample from a subject; and (b) isolating regulatory T-cells from the biological sample; and contacting the isolated regulatory T-cells with an effective amount of a Tregitope compound or composition of the present disclosure under conditions wherein the T-regulatory cells are stimulated to alter one or more biological function, thereby stimulating the regulatory T-cells in the biological sample. In aspects, the method further comprises the step of administration of the stimulated regulatory T-cells to a subject. In aspects, the subject to which the stimulated regulatory T-cells are administered is the same subject from which the original biological sample was obtained, e.g., by autologous transplantation of the expanded Tregitope.

Ex Vivo Pulsing of Antigen Presenting Cells using Tregitope Compositions. In aspects, the present disclosure provides ex vivo methods for antigen presenting cells (e.g., dendritic cells, macrophages, etc.) in a biological sample, the method comprising: (a) providing a biological sample from a subject; and (b) isolating antigen presenting cells from the biological sample; and contacting the isolated antigen presenting with an effective amount of a Tregitope compound or composition of the present disclosure under conditions wherein the antigen presenting cells are stimulated to alter one or more biological function (e.g., to present the Tregitopes and/or skew the antigen presenting cells to a be tolerogenic (which, in aspects, can further include cytokine treatment of the antigen presenting cells to induce such a tolerogenic state), thereby stimulating the antigen presenting cells in the biological sample. In aspects, the method further comprises the step of administration of the stimulated antigen presenting cells to a subject. In aspects, the subject to which the stimulated antigen presenting cells are administered is the same subject from which the original biological sample was obtained, e.g., by autologous transplantation of the stimulated antigen presenting cells.

In Vitro Uses of Tregitope Compositions. In aspects, the present disclosure provides the use of a Tregitope compound or composition of the present disclosure as reagents in the study of regulatory T-cell function in in vitro studies and experimental models.

Methods of Immune Engineering. In aspects, the present disclosure is directed to a methods of immune engineering, including removal or insertion of one or more Tregitopes of the instant disclosure, from or into a polypeptide, such as an antibody or fragment thereof.

For example, in aspects the present disclosure is directed to a method for enhancing the immunogenicity of a compound or composition comprising an antibody or fragment thereof, which may be particularly useful when an antibody or fragment thereof serves as a vaccine delivery vector for antigen targeting to antigen presenting cells, such as dendritic cells. In aspects, said method comprises identification and removal of one or more regulatory T cell epitopes (e.g., a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) from said antibody or fragment thereof. In aspects, the one or more regulatory T cell epitopes of the antibody or fragment thereof are identified by EpiMatrix and JanusMatrix analysis, such as is described herewithin (for example, in section (1) of the exemplification). In aspects, the one or more regulatory T cell epitopes of an antibody (or fragment thereof) vaccine delivery vector (such as DEC-205) can suppress an antigen-specific immune response to a delivered antigen, and removal of said one or more regulatory T cell epitopes can allow for diminution of tolerogenicity and stimulation of a strong antigen-specific immune response against the delivered antigen. In aspects, said removal comprises modifying those Tregitopes such that they no longer bind to MHC molecules or no longer retain MHC binding propensity, no longer retain the same TCR specificity, and/or no longer retain Tregitope or suppressive activity. In aspects, said removal of the one or more regulatory T cell epitopes from the vaccine delivery vector comprises deletion of all or some of the amino acids of the one or more regulatory T cell epitopes. In aspects, said removal of the one or more regulatory T cell epitopes from the vaccine delivery vector comprises deletion of some or all of the amino acids of the one or more regulatory T cell epitopes and adding one or more amino acids at the site of deletion of the regulatory T cell epitope amino acids. In aspects, said removal of the one or more regulatory T cell epitopes from the vaccine delivery vector comprises mutating the one or more regulatory T cell epitopes (for example, but not limited to, introduction one or more point mutations into the one or more regulatory T cell epitopes by site-directed mutagenesis or other recombinant techniques). In aspects, said removal of the one or more regulatory T cell epitopes from the vaccine delivery vector comprises introducing one or more amino acids into the one or more regulatory T cell epitope sequences, which in aspects will disrupt the one or more regulatory T cell epitope sequences, such that the previous tolerogenicity of the sequence is removed. In aspects, the number of said added one or more amino acids at the site of removal need not correspond to the number of amino acids deleted from the previously existing regulatory T cell epitope amino acids. In aspects, said removal of one or more regulatory T cell epitopes from the antibody or fragment thereof results in enhancing the immunogenicity of the vaccine delivery vector or target antigen of the vaccine delivery vehicle or vector. In aspects, said removal of one or more regulatory T cell epitopes from the vaccine delivery vector results in a heightened antigen-specific immune response to the vaccine delivery vector or target antigen of the vaccine delivery vehicle or vector. In aspects, the vaccine delivery vector can comprise an antibody, including but not limited to a monoclonal antibody, a polyclonal antibody, a mouse antibody, a human antibody, a humanized antibody, a monospecific antibody, a bispecific antibody, a glycosylated antibody, an Fc-modified antibody, an antibody-drug conjugate, an antibody of a different class of subclass (e.g., IgG (e.g., IgG1, IgG2, IgG3, or IgG4), IgM, IgE, or IgA), or fragments or antigen-specific antibody fragments thereof (including, but not limited to, a Fab, F(ab')$_2$, Fv, disulfide linked Fv, scFv, single domain antibody, closed conformation multispecific antibody, disulfide-linked scfv, diabody). In aspects, the one or more regulatory T cell epitopes have a sequence comprising, consisting of, or consisting essentially of one or more of SEQ ID NOS: 1-124.

Additionally, the present disclosure is directed to a method for decreasing the immunogenicity and/or increasing tolerogenicity of an antibody or fragment thereof, which may be particularly useful when an antibody or fragment thereof serves as a therapeutic protein. In aspects, said method comprises insertion of one or more regulatory T cell epitopes (e.g., a peptide or polypeptide comprising, consisting of, or consisting essentially of one or more peptides or polypeptides having an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) into said antibody or fragment thereof. In aspects, the one or more regulatory T cell epitopes of the antibody or fragment suppress an antigen-specific immune response against the antibody or fragment thereof. In aspects, said one or more regulatory T cell epitopes may be fused to or inserted internally within (e.g., but not limited to, site directed mutagenesis or other recombinant techniques) an antibody or fragment thereof, such as in instances where the Tregitope is not located in its natural position within the antibody or fragment thereof or wherein the antibody or fragment thereof is missing such a Tregitope (e.g., if a particular antibody or fragment thereof has a mutated or missing corresponding section). In aspects, said insertion of the one or more regulatory T cell epitopes into the antibody or fragment thereof comprises insertion of all or some of the amino acids of the one or more regulatory T cell epitopes. In aspects, said insertion of the one or more regulatory T cell epitopes into the antibody or fragment thereof comprises insertion of some or all of the amino acids of the one or more regulatory T cell epitopes and removing one or more amino acids at the site of insertion of the regulatory T cell epitope amino acids. In aspects, said insertion of the one or more regulatory T cell epitopes into the antibody or fragment thereof comprises mutating the sequence of the antibody or fragment thereof to include the one or more regulatory T cell epitopes (for example, but not limited to, introduction one or more point mutations into the antibody or fragment thereof by site-directed mutagenesis or other recombinant techniques). In aspects, said insertion of the one or more regulatory T cell epitopes into the antibody or fragment, which in aspects will introduce the one or more regulatory T cell epitope sequences, such that the previous immunogenicity of the sequence is decreased and the tolerogenicity of the new sequence is enhanced. In aspects, the number of said added one or more amino acids at the site of insertion of the regulatory T cell epitope amino acids need not correspond to the number of amino acids deleted from the sequence of the antibody or fragment thereof. In aspects, said insertion of one or more regulatory T cell epitopes into the antibody or fragment thereof results in decreasing the immunogenicity of the antibody or fragment thereof. In aspects, said insertion of one or more regulatory T cell epitopes into the antibody or fragment thereof results in a increasing the tolerogenicity of the antibody or fragment thereof. In aspects, one or more Tregitopes may be incorporated as an internal sequence into an Fc domain as disclosed in U.S. Pat. Nos. 7,442,778, 7,645,861, 7,655,764, 7,655,765, and/or 7,750,128 (each of which are herein incorporated by reference in their entirety). Such an internal sequence may be added by insertion (i.e., between amino acids in the previously existing Fc domain) or by replacement of amino acids in the previously existing Fc domain (i.e., removing amino acids in the previously existing Fc domain and adding peptide amino acids). In the latter case, the number of peptide amino acids added need not correspond to the number of amino acids removed from the previously existing Fc domain; for example, in aspects, the compositions may comprise an added internal sequence of 9-15 amino acids, with a sequence of 1-21 amino acids removed from the native Fc domain. In aspects, the antibody or fragment thereof can comprise, but is not limited to, a monoclonal antibody, a polyclonal antibody, a mouse antibody, a human antibody, a humanized antibody, a monospecific antibody, a bispecific antibody, a glycosylated antibody, an Fc-modified antibody, an antibody-drug conjugate, an such as antibody of a different class of subclass (e.g., IgG (e.g., IgG1, IgG2, IgG3, or IgG4), IgM, IgE, or IgA) molecules, or antigen-specific antibody fragments thereof (including, but not limited to, a Fab, $F(ab')_2$, Fv, disulfide linked Fv, scFv, single domain antibody, closed conformation multispecific antibody, disulfide-linked scfv, diabody). In aspects, the one or more regulatory T cell epitopes have a sequence comprising, consisting of, or consisting essentially of one or more of SEQ ID NOS: 1-124.

For example, in aspects, one or more Tregitopes of the instant disclosure having a sequence comprising one or more of SEQ ID NOS: 1-124 (and fragments or variants thereof), and optionally 1 to 12 additional amino acids distributed in any ratio on the N-terminus and/or C-terminus of the polypeptide of SEQ ID NOS: 1-124), may be fused to or inserted internally within (e.g., but not limited to, site directed mutagenesis or other recombinant techniques) a human IgG or fragment thereof, such as in instances where the Tregitope is not located in its natural position within the human IgG or fragment thereof or where the human IgG or fragment thereof (such as a subject's own human IgG or fragment thereof) is missing such a Tregitope (e.g., if a particular human IgG or fragment thereof has a mutated or missing corresponding section). As described previously, a Tregitope comprising one or more of SEQ ID NOS: 1, 3-8, 14-15, 16-28, 42-74, and 111-124 may be fused to or inserted internally within a polypeptide, e.g., a polypeptide that does not comprise a human IgG heavy chain variable region. In aspects, if a polypeptide does comprise a human IgG heavy chain variable region (such as a human IgG antibody or fragment thereof), then said one or more of SEQ ID NOS: 1, 3-8, 14-15, 16-28, 42-74, and 111-124 may be fused to or inserted internally within (e.g., but not limited to, site directed mutagenesis or other recombinant techniques) a human IgG heavy chain variable region or fragment thereof, such as in instances where the Tregitope is not located in its natural position within the a human IgG heavy chain variable region or fragment thereof or where the human IgG heavy chain variable region or fragment thereof is missing such a Tregitope (e.g., if a particular a human IgG heavy chain variable region or fragment thereof has a mutated or missing corresponding section). In aspects, a Tregitope comprising one or more of SEQ ID NOS: 2, 9-11, 29-41, and 75-100 may be fused to or inserted internally within a polypeptide, e.g., a polypeptide that does not comprise a human IgG heavy chain constant region. In aspects, if a polypeptide does comprise a human IgG heavy chain constant region (such as a human IgG antibody or fragment thereof), then said one or more of SEQ ID NOS: 2, 9-11, 29-41, and 75-100 may be fused to or inserted internally within (e.g., but not limited to, site directed mutagenesis or other recombinant techniques) a human IgG heavy chain constant region or fragment thereof, such as in instances where the Tregitope is not located in its natural position within the human IgG heavy chain constant region or fragment thereof or where the human IgG heavy chain constant region or fragment thereof is missing such a Tregitope (e.g., if a particular a human IgG heavy chain constant region or fragment thereof has a mutated or missing corresponding section). In aspects, a Tregitope comprising one or more of SEQ ID NO: 12 may be fused to or inserted internally within a polypeptide, e.g., a polypeptide that does not comprise a human IgG light chain variable region. In aspects, if a polypeptide does comprise a human IgG light chain variable region (such as a human IgG antibody or fragment thereof), then said one or more of SEQ ID NO: 12 may be fused to or inserted internally within (e.g., but not limited to, site directed mutagenesis or other recombinant techniques) a human IgG light chain variable region or fragment thereof, such as in instances where the Tregitope is not located in its natural position within the human IgG light chain variable region or fragment thereof or where the human IgG light chain variable region or fragment thereof is missing such a Tregitope (e.g., if a particular a human IgG light chain variable region or fragment thereof has a mutated or missing corresponding section). In aspects, a Tregitope comprising one or more of SEQ ID NOS: 13 and 101-110 may be fused to or inserted internally within a polypeptide, e.g., a polypeptide that does not comprise a human IgG light chain constant region. In aspects, if a polypeptide does comprise a human IgG light chain constant region (such as a human IgG antibody or fragment thereof), then said one or more of SEQ ID NOS: 13 and 101-110 may be fused to or inserted internally within (e.g., but not limited to, site directed mutagenesis or other recombinant techniques) a human IgG light chain constant region or fragment thereof, such as in instances where the Tregitope is not located in its natural position within the human IgG light chain constant region or fragment thereof or where the human IgG light chain constant region or fragment thereof is missing such a Tregitope (e.g., if a particular a human IgG light chain constant region or fragment thereof has a mutated or missing corresponding section).

Kits. The methods described herein can be performed, e.g., by utilizing pre-packaged kits comprising at least one Tregitope compound or composition of the present disclosure which can be conveniently used, e.g., in clinical settings to treat subjects exhibiting symptoms or family history of a medical condition described herein. In one embodiment, the kit further comprises instructions for use of the at least one Tregitope compound or composition of the instant disclosure to treat subjects exhibiting symptoms or family history of a medical condition described herein.

Aspects

A 1st aspect is directed to a polypeptide consisting of an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A 2nd aspect is directed to a polypeptide consisting essentially of an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A 3rd aspect is directed to a polypeptide comprising an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A 4th aspect is directed to a polypeptide according to any one of aspects 1-3, wherein said variant or fragment of an amino acid sequence selected from the group consisting of SEQ ID NOS: 1-124 retains MHC binding propensity and TCR specificity, and/or retains regulatory T cell stimulating or suppressive activity.

A $5^{th}$ aspect is directed to a polypeptide consisting of an amino acid sequence having at least 75%, 80%, 85%, 90%, or 95% homology to any one of SEQ ID NOS: 1-124, and fragments thereof, wherein said polypeptide retains MHC binding propensity and the same TCR specificity, and/or retains regulatory T cell stimulating or suppressive activity.

A $6^{th}$ aspect is directed to a polypeptide consisting essentially of an amino acid sequence having at least 75%, 80%, 85%, 90%, or 95% homology to any one of SEQ ID NOS: 1-124, and fragments thereof, wherein said polypeptide retains MHC binding propensity and the same TCR specificity, and/or retains regulatory T cell stimulating or suppressive activity.

A $7^{th}$ aspect is directed to a polypeptide comprising an amino acid sequence having at least 75%, 80%, 85%, 90%, or 95% homology to any one of SEQ ID NOS: 1-124, and fragments thereof, wherein said polypeptide retains MHC binding propensity and the same TCR specificity, and/or retains regulatory T cell stimulating or suppressive activity.

An 8th aspect is directed to a polypeptide according to any one of aspects 1-7, wherein said polypeptide has one or more conservative substitutions compared to the polypeptide.

A 9th aspect is directed to a polypeptide according to aspect 8, wherein said polypeptide retains MHC binding propensity and TCR specificity, and/or retains regulatory T cell stimulating or suppressive activity.

A $10^{th}$ aspect is directed to a polypeptide composition comprising one or more T-cell epitope polypeptides linked to a heterologous polypeptide, wherein the T-cell epitope polypeptide is a polypeptide according to any one of aspects 1-9.

An $11^{th}$ aspect is directed to a polypeptide composition according to aspect 10, wherein the T-cell epitope polypeptide is linked to the N-terminus of the heterologous polypeptide.

An 12th aspect is directed to a polypeptide composition according to any one or aspects wherein the T-cell epitope polypeptide is linked to the C-terminus of the heterologous polypeptide.

A $13^{th}$ aspect is directed to a polypeptide composition according to any one or aspects 10-12, wherein the heterologous polypeptide comprises a biologically active molecule and wherein the biologically active molecule is selected from the group consisting of an immunogenic molecule, a T-cell epitope, a viral protein, and a bacterial protein.

A 14th aspect is directed to a polypeptide composition according to any one or aspects 10-13, wherein the heterologous polypeptide is operatively linked to the T-cell epitope polypeptide.

A $15^{th}$ aspect is directed to a nucleic acid encoding a polypeptide consisting of an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A $16^{th}$ aspect is directed to a nucleic acid encoding a polypeptide consisting essentially of an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A $17^{th}$ aspect is directed to a nucleic acid encoding a polypeptide comprising an amino acid sequence selected from the group consisting of SEQ ID NOS: 1-124, and/or fragments and variants thereof, and optionally 1 to 12 additional amino acids distributed in any ratio on the N terminus and/or C-terminus of the polypeptide of SEQ ID NOS: 1-124.

A $18^{th}$ aspect is directed to a nucleic acid of any one of aspects 8-10, wherein said fragment or variant of the nucleic acid encoding a polypeptide comprising an amino acid sequence selected from the group consisting of SEQ ID NOS: 1-124 encodes a polypeptide that retains regulatory T cell stimulating or suppressive activity.

A 19th aspect is directed to a plasmid comprising a nucleic acid of any one of aspects 15-18.

A 20$^{th}$ aspect is directed to a vector comprising a nucleic acid according to any one of aspects 15-18.

A 21$^{st}$ aspect is directed to a pharmaceutical composition comprising a polypeptide according to any one of aspects 1-14 and a pharmaceutically-acceptable carrier and/or excipient.

A 22$^{nd}$ aspect is directed to a pharmaceutical composition comprising a nucleic acid according to any one of aspects 15-18 and a pharmaceutically-acceptable carrier and/or excipient.

A 23$^{rd}$ aspect is directed to a pharmaceutical composition comprising a plasmid according to aspect 19 and a pharmaceutically-acceptable carrier and/or excipient.

A 24$^{th}$ aspect is directed to a pharmaceutical composition comprising a vector according to aspect 20 and a pharmaceutically-acceptable carrier and/or excipient.

A 25$^{th}$ aspect is directed to a method for suppressing an immune response in a subject in need thereof, the method comprising administering to the subject a therapeutically effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24.

A 26$^{th}$ aspect is directed to a method of inducing regulatory T-cells to suppress immune response in a subject comprising administrating to the subject a therapeutically effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24.

A 27$^{th}$ aspect is directed to a method for stimulating regulatory T-cells in a subject in need thereof, the method comprising administering to the subject a therapeutically effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24.

A 28$^{th}$ aspect is directed to a method suppressing an antigen-specific immune response in a subject in need thereof, the method comprising administering to the subject a therapeutically effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24.

A 29$^{th}$ aspect is directed to a method according to any one of aspects 25-28, wherein the administration of the Tregitope composition activates CD4$^{+}$/CD25$^{+}$/FoxP3$^{+}$ regulatory T-cells.

A 30$^{th}$ aspect is directed to a method according to any one of aspects 25-28, wherein the administration of the Tregitope composition suppresses activation of CD4+ T-cells.

A 31$^{st}$ aspect is directed to a method according to any one of aspects 25-28, wherein the administration of the Tregitope composition suppresses activation or proliferation of CD4$^{+}$ effector T—cells and/or CD8$^{+}$ effector T-cells.

A 32$^{nd}$ aspect is directed to a method according to any one of aspects 25-28, wherein the administration of the Tregitope composition suppresses activation or proliferation of B-cells.

A 33$^{rd}$ aspect is directed to a method according to any one of aspects 25-28, wherein the subject suffers from an allergy, an autoimmune disease, a transplant related disorder, an enzyme or protein deficiency disorder, or a blood clotting disorder.

A 34$^{th}$ aspect is directed to a method according to any one of aspects 25-28, wherein the immune response is a result of one or more therapeutic treatments select from the group consisting of, treatment with at least one therapeutic protein, treatment with a vaccine, and treatment with at least one antigen A 35$^{th}$ aspect is directed to a method according to any one of aspects 25-28, wherein the administration of the pharmaceutical Tregitope composition shifts one or more antigen presenting cells to a regulatory phenotype.

A 36$^{th}$ aspect is directed to a method according to any one of aspects 25-28, wherein the administration of the regulatory T-cell epitope shifts one or more dendritic cells to a regulatory phenotype.

A 37$^{th}$ aspect is directed to a method according to any one of aspects 25-28, wherein the administration of the pharmaceutical Tregitope composition shifts one or more dendritic cells to a regulatory phenotype.

A 38$^{th}$ aspect is directed to a method according to any one of aspects 25-28, wherein the regulatory phenotype is characterized by a decrease in CD11c and HLA-DR expression in the dendritic cells or other antigen presenting cells.

A 39$^{th}$ aspect is directed to a method according to any one of aspects 25-28, wherein the administration of the regulatory T-cell epitope shifts one or more T cells to a regulatory phenotype.

A 40$^{th}$ aspect is directed to a method according to any one of aspects 25-28, wherein the administration of the regulatory T-cell epitope shifts one or more CD4+ T cells to a regulatory phenotype.

A 41$^{st}$ aspect is directed to a method according to any one of aspects 25-28, wherein the administration of the regulatory T-cell epitope shifts one or more CD8+ T cells to a regulatory phenotype.

A 42$^{nd}$ aspect is directed to a method according to any one of aspects 25-28, wherein the administration of the regulatory T-cell epitope shifts one or more B cells to a regulatory phenotype.

A 43$^{rd}$ aspect is directed to a method for expanding a population of regulatory T cells of a patient, comprising:
 (a) providing a biological sample obtained from a subject; and
 (b) isolating regulatory T-cells from the biological sample; and contacting the isolated regulatory T-cells with an effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24 under conditions wherein the T-regulatory cells increase in number to yield an expanded regulatory T-cell composition, thereby expanding the regulatory T-cells in the biological sample; and
 (c) returning said increased number of regulatory T cells to said patient.

A 44th aspect is directed to a method for stimulating regulatory T cells in a biological sample, comprising:
(a) providing a biological sample obtained from a subject;
(b) isolating regulatory T-cells from the biological sample; and contacting the isolated regulatory T-cells with an effective amount of one or more of a polypeptide according to any one of aspects 1-14, a nucleic acid according to any one of aspects 15-18, a plasmid according to aspect 19, a vector according to aspect 20, or a pharmaceutical composition according to any one of aspects 21-24 under conditions wherein the T-regulatory cells are stimulated to alter one or more biological function, thereby stimulating the regulatory T-cells in the biological sample.

Exemplification

The examples that follow are not to be construed as limiting the scope of the invention in any manner. In light of the present disclosure, numerous embodiments within the scope of the claims will be apparent to those of ordinary skill in the art.

(1) In-Silico Identification of a Tregitope Compound or Composition

T cells specifically recognize epitopes presented by antigen presenting cells (APCs) in the context of MHC (Major Histocompatibility Complex) Class II molecules. These T-helper epitopes can be represented as linear sequences comprising 7 to 30 contiguous amino acids that fit into the MHC Class II binding groove. A number of computer algorithms have been developed and used for detecting Class II epitopes within protein molecules of various origins (De Groot A S et al., (1997), AIDS Res Hum Retroviruses, 13(7):539-41; Schafer J R et al., (1998), Vaccine,16(19):1880-4; De Groot A S et al., (2001), Vaccine, 19(31):4385-95; De Groot A S et al., (2003), Vaccine, 21(27-30):4486-504). These "in silica" predictions of T-helper epitopes have been successfully applied to the design of vaccines and the de-immunization of therapeutic proteins, e.g., antibody-based drugs, Fc fusion proteins, anticoagulants, blood factors, bone morphogenetic proteins, engineered protein scaffolds, enzymes, growth factors, hormones, interferons, interleukins, and thrombolytics (Dimitrov D S, (2012), Methods Mol Biol, 899:1-26).

The EpiMatrix™ system (EpiVax, Providence, Rhode Island) is a set of predictive algorithms encoded into computer programs useful for predicting class I and class II HLA ligands and T cell epitopes. The EpiMatrix™ system uses 20×9 coefficient matrices in order to model the interaction between specific amino acids (20) and binding positions within the HLA molecule (9). In order to identify putative T cell epitopes resident within any given input protein, the EpiMatrix™ System first parses the input protein into a set of overlapping 9-mer frames where each frame overlaps the last by eight amino acids. Each frame is then scored for predicted affinity to one or more common alleles of the human HLA molecule; typically DRB1*0101, DRB1*0301, DRB1*0401, DRB1*0701, DRB1*0801, DRB1*1101, DRB1*1301, and DRB1*1501 (Mack et al., (2013), Tiss Antig, 81(4):194-203). Briefly, for any given 9-mer peptide specific amino acid codes (one for each of 20 naturally occurring amino acids) and relative binding positions (1-9) are used to select coefficients from the predictive matrix. Individual coefficients are derived using a proprietary method similar to, but not identical to, the pocket profile method first developed by Sturniolo (Sturniolo T et al., 1999, Nat Biotechnol, 17(6):555-61). Individual coefficients are then summed to produce a raw score. EpiMatrix™ raw scores are then normalized with respect to a score distribution derived from a very large set of randomly generated peptide sequences. The resulting "Z" scores are normally distributed and directly comparable across alleles.

EpiMatrix™ peptide scoring. It was determined that any peptide scoring above 1.64 on the EpiMatrix™ "Z" scale (approximately the top 5% of any given peptide set) has a significant chance of binding to the MHC molecule for which it was predicted. Peptides scoring above 2.32 on the scale (the top 1%) are extremely likely to bind; most published T cell epitopes fall within this range of scores. Previous studies have also demonstrated that EpiMatrix™ accurately predicts published WIC ligands and T cell epitopes.

Identification of promiscuous T cell Epitope Clusters. Potential T cell epitopes are not randomly distributed throughout protein sequences but instead tend to "cluster." T cell epitope "clusters" range from 9 to roughly 30 amino acids in length and, considering their affinity to multiple alleles and across multiple frames, contain anywhere from 4 to 40 binding motifs. Following epitope mapping, the result set produced by the EpiMatrix™ algorithm is screened for the presence of T cell epitope clusters and EpiBars™ by using a proprietary algorithm known as Clustimer™. Briefly, the EpiMatrix™ scores of each 9-mer peptide analyzed are aggregated and checked against a statistically derived threshold value. High scoring 9mers are then extended one amino acid at a time. The scores of the extended sequences are then re-aggregated and compared to a revised threshold value. The process is repeated until the proposed extension no longer improves the overall score of the cluster. Tregitope(s) identified in the present studies were identified by the Clustimer-™ algorithm as T cell epitope clusters. They contain significant numbers of putative T cell epitopes and EpiBars™ indicating a high potential for MHC binding and T cell reactivity.

Identification of tolerogenic T cell Epitope Clusters. The JanusMatrix system (EpiVax, Providence, Rhode Island) useful for screening peptide sequences for cross-conservation with a host proteome. JanusMatrix is an algorithm that predicts the potential for cross-reactivity between peptide clusters and the host genome or proteome, based on conservation of TCR-facing residues in their putative MHC ligands. The JanusMatrix algorithm first considers all the predicted epitopes contained within a given protein sequence and divides each predicted epitope into its constituent agretope and epitope. Each sequence is then screened against a database of host proteins. Peptides with a compatible MHC-facing agretope (i.e., the agretopes of both the input peptide and its host counterparty are predicted to bind the same MHC allele) and exactly the same TCR-facing epitope are returned. The JanusMatrix Homology Score suggests a bias towards immune tolerance. In the case of a therapeutic protein, cross-conservation between autologous human epitopes and epitopes in the therapeutic may increase the likelihood that such a candidate will be tolerated by the human immune system. In the case of a vaccine, cross-conservation between human epitopes and the antigenic epitopes may indicate that such a candidate utilizes immune camouflage, thereby evading the immune response and making for an ineffective vaccine. When the host is, for example, a human, the peptide clusters are screened against human genomes and proteomes, based on conservation of TCR-facing residues in their putative HLA ligands. The peptides are then scored using the JanusMatrix Homology Score. In aspects, peptides with a JanusMatrix Homology Score above 3.0 indicate high tolerogenicity potential and as such may be very useful Tregitopes of the present disclosure.

Example 1. Identification of a Tregitope Composition

The results of in-silico analysis, using the methods as previously described, are presented in FIGS. 8-9 for SEQ ID NOS: 7 and 14, respectively, and FIGS. 11-26.

FIG. 8 depicts the EpiMatrix analysis of SEQ ID NO: 7. Results are shown for KTLYLQMNS (SEQ ID NO: 16), TLYLQMNSL (SEQ ID NO: 17), LYLQMNSLR (SEQ ID NO: 18), YLQMNSLRA (SEQ ID NO: 19), LQMNSLRAE (SEQ ID NO: 20), QMNSLRAED (SEQ ID NO: 21), MNSLRAEDT (SEQ ID NO: 22), NSLRAEDTA (SEQ ID NO 23), SLRAEDTAK (SEQ ID NO 24), and LRAEDTAKH (SEQ ID NO 25). Z score indicates the potential of a 9-mer frame to bind to a given HLA allele. All scores in the top 5% are considered "hits", while non-hits (*) below 10% are masked in FIG. 8 for simplicity.

FIG. 9 depicts the EpiMatrix analysis of SEQ ID NO: 14. Results are shown for ETLYLQMNS (SEQ ID NO: 111), TLYLQMNSL (SEQ ID NO: 112), LYLQMNSLR (SEQ ID NO: 113), YLQMNSLRA (SEQ ID NO: 114), LQMNSLRAE (SEQ ID NO: 115), QMNSLRAED (SEQ ID NO: 116), MNSLRAEDT (SEQ ID NO: 117), NSLRAEDTA (SEQ ID NO 118), SLRAEDTAV (SEQ ID NO 119), AND LRAEDTAVY (SEQ ID NO 120). Z score indicates the potential of a 9-mer frame to bind to a given HLA allele. All scores in the top 5% are considered "hits", while non-hits (*) below 10% are masked in FIG. 9 for simplicity.

FIG. 11 is the overview of JanusMatrix results for identified the Tregitopes of SEQ ID NOS: 1-15 of the instant disclosure. FIG. 12 is the JanusMatrix report for the Tregitope of SEQ ID NO: 1 and the 9-mers contained within SEQ ID NO: 1, including SEQ ID NOS: 16-28. FIG. 13 is the JanusMatrix report for the Tregitope of SEQ ID NO: 10 and the 9-mers contained within SEQ ID NO: 10, including SEQ ID NOS: 87-93. FIG. 14 is the JanusMatrix report for the Tregitope of SEQ ID NO: 11 and the 9-mers contained within SEQ ID NO: 11, including SEQ ID NOS: 94-100. FIG. 15 is the JanusMatrix report for the Tregitope of SEQ ID NO: 12. FIG. 16 is the JanusMatrix report for the Tregitope of SEQ ID NO: 13 and the 9-mers contained within SEQ ID NO: 13, including SEQ ID NOS: 101-110. FIG. 17 is the JanusMatrix report for the Tregitope of SEQ ID NO: 14 and the 9-mers contained within SEQ ID NO: 14, including SEQ ID NOS: 111-120. FIG. 18 is the JanusMatrix report for the Tregitope of SEQ ID NO: 15 and the 9-mers contained within SEQ ID NO: 15, including SEQ ID NOS: 121-124. FIG. 19 is the JanusMatrix report for the Tregitope of SEQ ID NO: 10 and the 9-mers contained within SEQ ID NO: 2, including SEQ ID NOS: 29-41. FIG. 20 is the JanusMatrix report for the Tregitope of SEQ ID NO: 3 and the 9-mers contained within SEQ ID NO: 3, including SEQ ID NOS: 42-48. FIG. 21 is the JanusMatrix report for the Tregitope of SEQ ID NO: 4 and the 9-mers contained within SEQ ID NO: 4, including SEQ ID NOS: 49-50. *Count of HUMAN JanusMatrix matches found in the search database. FIG. 22 is the JanusMatrix report for the Tregitope of SEQ ID NO: 50. FIG. 23 is the JanusMatrix report for the Tregitope of SEQ ID NO: 6 and the 9-mers contained within SEQ ID NO: 6, including SEQ ID NOS: 51-57. FIG. 24 is the JanusMatrix report for the Tregitope of SEQ ID NO: 10 and the 9-mers contained within SEQ ID NO: 7, including SEQ ID NOS: 58-67. FIG. 25 is the JanusMatrix report for the Tregitope of SEQ ID NO: 8 and the 9-mers contained within SEQ ID NO: 8, including SEQ ID NOS: 68-74. FIG. 26 is the JanusMatrix report for the Tregitope of SEQ ID NO: 9 and the 9-mers contained within SEQ ID NO: 9, including SEQ ID NOS: 87-93. For each of FIGS. 11-26, * is the count of HUMAN JanusMatrix matches found in the search database. With respect to a given EpiMatrix Hit (a 9-mer contained within the input sequence which is predicted to bind to a specific allele), a Janus Matrix match is a 9-mer derived from the search database (e.g., the human genome) which is predicted to bind to the same allele as the EpiMatrix Hit and shares TCR facing contacts with the EpiMatrix Hit. Further, the Janus Homology Score**represents the average depth of coverage in the search database for each EpiMatrix hit in the input sequence. For example, an input peptide with eight EpiMatrix hits, all of which have one match in the search database, has a Janus Homology Score of 1. An input peptide with four EpiMatrix Hits, all of which have two matches in the search database, has a Janus Homology Score of 2. The JanusMatrix Homology Score considers all constituent 9-mers in any given peptide, including flanks.

(2) Methods for the Assessment of Tregitope Binding to Soluble MHC.

Synthesis of peptides. The Tregitopes of the present disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124, can be produced by direct chemical synthesis or by recombinant methods (J Sambrook et al., Molecular Cloning: A Laboratory Manual, ($2^{ED}$, 1989), Cold Spring Harbor Laboratory Press, Cold Springs Harbor, NY (Publ)). Every peptide undergoes rigorous quality control characterization before release to determine purity, mass, and correct sequence. Peptides are assessed for purity by reversed phase high-pressure liquid chromatography (RP-HPLC). Peptides are≥90% pure, and each preparation undergoes Amino Acid Analysis to ensure that the equivalent molar amounts are used in assays for consistency and reproducibility between different lots of peptides, and will allow for reliable comparison studies between peptide efficacy. Peptides are also assessed for mass and correct sequence using tandem mass spectrometry and MS CheckT analysis. In certain aspects, the Tregitopes are capped with an n-terminal acetyl and/or c-terminal amino group. HPLC, mass spectrometry and UV scan (ensuring purity, mass and spectrum, respectively) analysis of the selected Tregitopes indicated≥80% purity.

HLA Binding Assay. Binding activity was analyzed at EpiVax (Providence, Rhode Island) and is conducted for any Tregitope disclosed herein (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124. The binding assay used (Steere A C et al., (2006), J Exp Med, 2003(4):961-71) yields an indirect measure of peptide-MHC affinity. Soluble HLA molecules are loaded onto a 96-well plate with the unlabeled experimental Tregitopes and labeled control peptide. Once the binding mixture reaches steady equilibrium (at 24 hours), the HLA-Tregitope complexes are captured on an ELISA plate coated with anti-human DR antibody and are detected with a Europium-linked probe for the label (PerkinElmer, Waltham, M A). Time-resolved fluorescence measuring bound labeled control peptide is assessed by a SpectraMax® M5 unit (Spectramax, Radnor, PA). Binding of experimental Tregitopes is expressed as the percent inhibition of the labeled control peptide (experimental fluorescence/control fluorescence multiplied by 100). The percent inhibition values for each experimental Tregitope (across a range of molar concentrations) is used to calculate the concentration at which it inhibits 50% of the labeled control Tregitope's specific binding, i.e., the Tregitope's $IC_{50}$.

Select experimental Tregitope (e.g., SEQ ID NO: 14) was solvated in DMSO. The diluted Tregitope (SEQ ID NO: 14) was then mixed with binding reagents in aqueous buffering solution, yielding a range of final concentrations from 100,000 nM down to 100 nM. Tregitope (SEQ ID NO: 14) was then assayed against a panel of eight common Class II HLA alleles: DRB1*0101, DRB1*0301, DRB1*0401, DRB1*0701, DRB1*0801, DRB1*1101, DRB1*1301, and DRB1 *1501. From the percent inhibition of labeled control peptide at each concentration, $IC_{50}$ values were derived for each Tregitope (SEQ ID NO: 14)/allele combination using linear regression analysis.

In this assay, the experimental Tregitopes are considered to bind with very high affinity if they inhibit 50% of control peptide binding at a concentration of 100 nM or less, high affinity if they inhibit 50% of control peptide binding at a concentration between 100 nM and 1,000 nM, and moderate affinity if they inhibit 50% of control peptide binding at a concentration between 1,000 nM and 10,000 nM. Low affinity peptides inhibit 50% of control peptide binding at concentrations between 10,000 nM and 100,000 nM. Peptides that fail to inhibit at least 50% of control peptide binding at any concentration below 100,000 nM and do not show a dose response are considered non-binders (NB).

Example 2. Peptide Characterization by Binding to HLA Class II Molecules

Soluble MHC binding assays are performed on any of the instantly disclosed Tregitopes (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124. Soluble MEW binding assays were performed on selected Tregitopes (e.g. Tregitope (SEQ ID NO: 14)) of the instant disclosure according to the methods described previously. $IC_{50}$ values (nM) were derived from a six-point inhibition curve.

A summary of HLA binding results for Tregitopes (SEQ ID NO: 14) is presented in FIG. 1A. EpiMatrix™ Predictions, calculated $IC_{50}$ values, and results classifications are reported for each Tregitope and HLA allele. FIGS. 1B-C shows the binding curves for certain Tregitopes against the selected Class II HLA alleles. FIG. 1B summarizes the results for HLA DRB1 *0801 assay, while FIG. 1C summarizes the results for the HLA DRB1 *1501 assay. It is expected that other Tregitopes of the instant disclosure (e.g., SEQ ID NOS: 1-13 and 15-124) will demonstrate similar results.

(3) Methods for Assessing the Phenotype of Peptide-Exposed APC

Surface expression of Class II HLA (HLA-DR) and CD86 by professional antigen presenting cells (APCs) is one way APCs modulate T cell response. Expression of Class II HLA surface marker has been previously demonstrated for down-regulated in response to Tregitopes, and in particular to, the control Tregitope 167 (21s t Century Biochemicals, Marlboro, M A). Additionally, reduced expression of surface marker CD86 correlates positively with enhanced $T_{Reg}$ function (Zheng Y et al., J Immunol, 2004, 172(5):2778-84). In this assay, candidate Tregitopes, including the selected Tregitopes, are tested for their ability to down-regulate the expression of Class II HLA and the co-stimulatory molecule CD86 on the surface of professional APCs, specifically dendritic cells.

Tregitopes of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124, are individually tested for regulatory potential using a proprietary APC phenotyping assay previously developed at EpiVax (EpiVax, Providence, Rhode Island). Previously harvested and frozen PBMC are thawed and suspended in chRPMI by conventional means. HLA typing is conducted on small, extracted samples of cellular material. On assay day 0, $0.5 \times 10^6$ cells are extracted, are screened for the presence of surface marker CD11c (a marker specific to dendritic cells) and are analyzed for the presence of surface markers HLA-DR and CD86 by flow cytometry. The remaining cells are plated ($4.0 \times 10^6$ cell per ml in chRPMI plus 800 ul media) and are stimulated (501.1 g/mL) with one of the selected peptides or positive and negative controls including buffer only (negative control), Tregitope 167 (positive control) (21s t Century Biochemicals, Marlboro, MA), Flu-HA 306-318 (negative control) (21 ST Century Biochemicals, Marlboro, MA) and Ova 323-339 (negative control) (21s t Century Biochemicals, Marlboro, MA). Plated cells are incubated for seven days at 37° C. On assay day 7, incubated cells are screened by flow cytometry for the presence of surface marker CD11c. CD11c positive cells are then analyzed for the presence of surface markers HLA-DR and CD86. The experimental peptides are tested in samples drawn from five different human donors.

Leukocyte Reduction Filters are obtained from the Rhode Island Blood Center (Providence, RI) to filter white blood cells from whole blood obtained from healthy donors. After the whole blood is run through the filters, the filters are flushed in the opposite direction to push collected white blood cells out of the filter. The white blood cells are isolated using a conventional Ficoll™ separation gradient (GE Healthcare). The collected white blood cells are thereafter frozen for future use. When needed for use in an assay, the frozen white blood cells are thawed using conventional methods. For the GvHD studies discussed below, PBMCs are obtained (e.g., from HemaCare, Van Nuys, CA) and the experiments are performed.

Exposure to putative Tregitopes on the phenotypes of dendritic cells is measured by multiple means. First, for each experimental condition, dot-plots, contrasting surface expression of CD11c and HLA-DR, are produced. Dot-plots of cells exposed to all control and experimental peptides are overlaid onto dot-plots produced from control cells exposed to only the culture media. The overlay provides an effective method to visually observe shifts in HLA-DR distribution between Tregitope stimulated and unstimulated CD11c-high cells (data not shown). Observed shifts in the distribution of HLA-DR is reported as a qualitative measure. Next, the change in intensity of HLA-DR expression for the CD11c-high segment of each dot-plot is calculated. Percent change in intensity of HLA-DR expression equals Mean Florescence Index (MFI) of HLA-DR expression for peptide exposed cells minus MFI of HLA-DR expression for media exposed cells divided by MFI of HLA-DR expression for media exposed cells, times 100 ($^{HLA-DR}$ $MFI_{peptide}{}^{HLA-DR}MFI_{media}/{}^{HLA-DR}MFI_{media}*100)$. Next, the percent change in the percentage of HLA-DR-low cells present among the CD11c high population is calculated for each peptide relative to media control. Percent change in the percentage of HLA-DR-low cells is calculated, and equals the percent of HLA-DR-low for peptide exposed cells minus the percent of HLA-DR-low for media exposed cells divided by percent of HLA-DR-low for media exposed cells times 100 $({}^{HLA-DR-low}\%_{peptide}-{}^{HLA-DR-low}\%_{media}/{}^{HLA-DR-low}\%_{media}*100)$. In this assay, a negative change in observed HLA-DR WWI and a positive change in percentage of HLA-DR-low cells present in the CD11c-high population indicates reduced expression of HLA and a shift to a regulatory APC phenotype.

A similar process is used to assess the impact Tregitope exposure on surface expression of CD86, which is a costimulatory molecule known to promote T cell activation. First, for each experimental condition, dot plots contrasting surface expression of CD11c and CD86 is produced. Dot plots of cells exposed to all control and experimental Tregitopes is overlaid onto dots plots produced from control cells exposed to only the culture media. The overlay provides an effective method to visually observe shifts in CD86 distribution between Tregitope stimulated and unstimulated CD11c-high cells. Observed shifts in the distribution of CD86 is reported as a qualitative measure. Next, the change in intensity of CD86-high expression for the CD11c-high segment of each dot plot is calculated. Percent change in intensity of CD86-high expression equals Mean Florescence Index (MFI) of CD86 expression for peptide exposed cells minus MFI of CD86-high expression for media exposed cells divided by WWI of CD86 expression for media exposed cells, times 100 $({}^{CD86-high}MFI_{peptide}-{}^{CD86-high}MFI_{media}{}^{CD86-high}\%_{media}*100)$. Next, the percent change in the percentage of CD86-low cells present among the CD11c high population is calculated. Percent change in the percentage of CD86-high cells equals the percent of CD86-high for peptide exposed cells minus the percent of CD86-high for media exposed cells divided by percent of CD86-high for media exposed cells, times 100 $({}^{CD86-low}\%_{peptide}-{}^{CD86-low}\%_{media}/{}^{CD86-low}\%_{media}*100)$. In this assay, a negative change in observed CD86 WWI and a positive change in percentage of CD86-low cells present in the CD11c-high population indicates reduced expression of CD86 and a shift to a regulatory APC phenotype.

Example 3. Characterization of Peptide Exposed APC

Dendritic cell phenotyping assays are performed on Tregitopes of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) according to the methods described previously.

Dot plots representing the surface expression of CD11 vs HLA-DR analyzed on assay day 7 across the five donors in the presence of various peptide stimulants is prepared. It is expected that downward movement of the CD11c+/HLA-DR+ population is apparent in the samples treated with the Tregitopes of the instant disclosure as compared to media control indicating an acquired regulatory phenotype.

Dot plots representing the surface expression of CD11c vs CD86 analyzed on assay day 7 across the five donors in the presence of various peptide stimulants. It is expected that an increase in CD86-low cells present in the samples treated with Tregitopes of the instant disclosure as compared to media control, which indicates a shift to the acquired regulatory phenotype. It is further expected that exposure to claimed Tregitopes results in decreased expression of HLA-DR in all subjects that are tested.

(4) Methods for Assessing Peptide Effects on Proliferation of Regulatory T Cells Previous studies performed by EpiVax (Providence, RI) demonstrated increased proliferation of regulatory T cells following exposure to known Tregitope including positive control Tregitope 167 (SEQ ID NO: 134, PAVLQSSGLYS-LSLSSVVTVPSSSLGTQ, $21^{st}$ Century Biochemicals, Marlboro, MA). Tregitopes of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124), are tested for their ability to induce proliferation among CD4+ CD25+ FoxP3+ regulatory T cells. In this assay, candidate Tregitopes, including the Tregitopes of the instant disclosure (e.g., SEQ ID NO: 7), are tested for their ability to induce proliferation among CD4+CD25+ FoxP3+ regulatory T cells. Previously harvested and frozen PBMC are thawed and suspended in conditioned chRPMI ($3.3 \times 10^6$ cells/mL) by conventional means. Table 2 shows that the donors evaluated represent a diversity of HLA DRB1 supertypes. Cells are stained with CFSE (Cat #: 65-0850-84, Affymetrix, Santa Clara, CA) and plated at 300,000 cells per well. Plates are incubated overnight (37° C. in 5% $CO_2$). Each well contains 200 of media. In an exemplary experiment, on assay day 1, SEQ ID NO: 7 is reconstituted in sterile DMSO yielding a final stock concentration of 10 mg/mL. Previous titration experiments performed at EpiVax (EpiVax, Providence, Rhode Island) have established that stimulation with 0.5 µg/ml Tetanus Toxoid (TT) (Astarte Biologics, Bothell, WA) elicits a measurable CD4+ effector memory T cells response in PBMC drawn from healthy control donors (Rhode Island Blood Center, Providence, RI). Tetanus Toxoid stock (100 µg/mL) (Astarte Biologics, Bothell, WA) is diluted in conditioned chRPMI yielding a working concentration of 1 ug/mL (2x concentration). Plated cells (in 100 µL media) are then stimulated with either 100 µL of conditioned chRPMI (negative control), 100 µL Tetanus Toxoid solution (2x solution, positive control) (Astarte Biologics, Bothell, WA), 100 µL of a dilution of 2991 µL Tetanus Toxoid solution plus 9 µL SEQ ID NO: 7 solution, 100 µL of a dilution of 2997 µL Tetanus Toxoid solution plus 3 µL SEQ ID NO: 7 solution, or 100 µL of a dilution of 6998.2 µL Tetanus Toxoid solution plus 1.8 µL SEQ ID NO: 7 solution. All plates are then incubated for six additional days. On assay day five, 100 µL of supernatant is removed from each well and replaced with freshly conditioned chRPMI (for no TT control wells), or 100 µl of media with 2X TT (1 mg/mL) for the wells originally incubated with TT alone or TT+Tregitope. No extra Tregitope is added.

TABLE 2

The panel of donors include HLA Supertypes DRB1 8010, *0401, *0701, *0801, *1101, and *1501.

| Donor | Age | Gender | HLA Haplotype 1 | HLA Haplotype 2 |
|---|---|---|---|---|
| Donor A | 43 | F | DRB1*1104 | DRB1*1301 |
| Donor B | 57 | M | DRB1*0801 | DRB1*1102 |
| Donor C | 18 | M | DRB1*0101 | DRB1*0701 |
| Donor D | 40 | F | DRB1*0401 | DRB1*1503 |

Figure 2B:
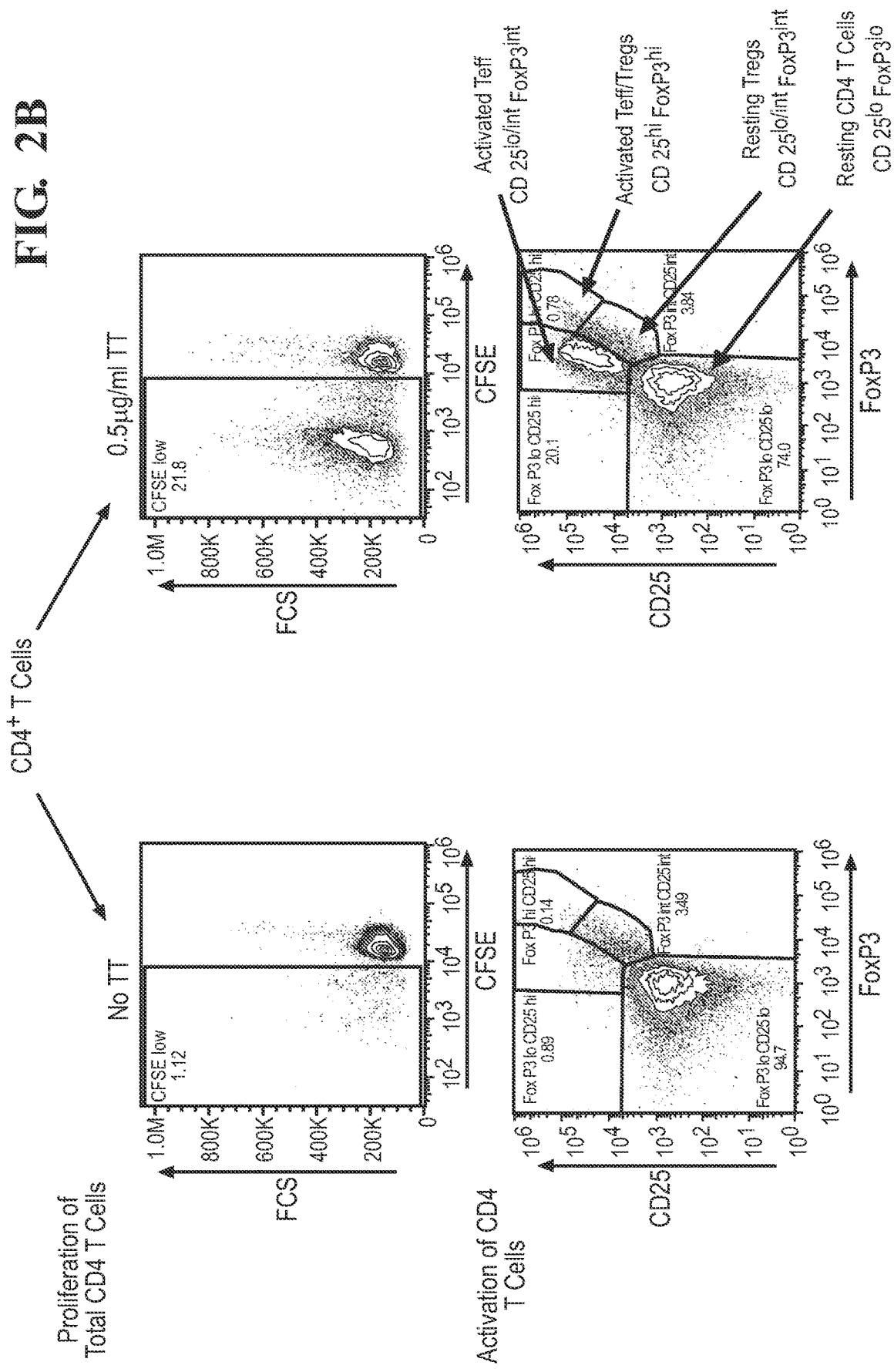

Highly activated regulatory T cells displaying elevated levels of FoxP3, CD25, Granzyme B and proliferation are selected. The gating strategy for highly activated regulatory T cells and CD4+ effector T cells is shown in FIGS. 2A-C(which depict a representative result). As shown in FIG. 2A, cells are first gated to eliminate aggregates and dead cells, and live cells are gated for CD4+ T cells and all subsequent analysis is done on this population. CD4+ T cells are gated for elevated CD25, FoxP3, and low CFSE (proliferation) (FIG. 2B). FIG. 2B shows the results of a representative assay with no added TT (left side), of a representative assay with 0.5 µg/ml TT (right side). FIG. 2C shows representative results of such an assay and depicts that proliferating and activated CD4+ T cell populations are highly correlated.

Example 4. Tregitopes Induce a Population of Highly Proliferative, Activated Regulatory T Cells Regulatory T cell proliferation assays are performed on the Tregitopes of the present disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) according to the methods described previously. It is expected that such data will demonstrate that the Tregitopes of the present disclosure strongly induces a population of highly proliferative, activated regulatory T cells.

(5) Methods for Assessing Peptide Effects on Proliferation of CD4+ Effector T Cells CD4+ effector memory T cells contained within PBMC cell populations can be induced to proliferate in response to stimulation with known T cell epitopes.

The purpose of this experiment is to establish the ability of Tregitopes of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) to suppress the proliferation of antigen stimulated CD4+ effector memory T cells by either direct (engagement and activation of $T_{Reg}$) or indirect (modulation of APC phenotype) means. For the initial and exemplary study, SEQ ID NO: 7 was tested. (FIGS. 3-6).

Previous studies performed by EpiVax (Providence, RI) demonstrated increased proliferation of regulatory T cells following exposure to known Tregitope including positive control Tregitope 167 (SEQ ID NO: 134, 21s t Century Biochemicals, Marlboro, MA). In this assay, candidate Tregitopes, including the Tregitopes of the instant disclosure (e.g., SEQ ID NO: 7), are tested for their ability to induce proliferation among CD4+CD25+ FoxP3+ regulatory T cells. Previously harvested and frozen PBMC are thawed and suspended in conditioned chRPMI ($3.3 \times 10^6$ cells/mL) by conventional means. Table 2 shows that the donors evaluated represent a diversity of HLA DRB1 supertypes. Cells are stained with CFSE (Cat #: 65-0850-84, Affymetrix, Santa Clara, CA) and plated at 300,000 cells per well. Plates are incubated overnight (37° C. in 5% $CO_2$). Each well contains 200 µL of media. On assay day 1, SEQ ID NO: 7 is reconstituted in sterile DMSO yielding a final stock concentration of 10 mg/mL. Previous titration experiments performed at EpiVax (EpiVax, Providence, Rhode Island) have established that stimulation with 0.5 µg/ml Tetanus Toxoid (TT) (Astarte Biologics, Bothell, WA) elicits a measurable CD4+ effector memory T cells response in PBMC drawn from healthy control donors (Rhode Island Blood Center, Providence, RI). Tetanus Toxoid stock (100 µg/mL) (Astarte Biologics, Bothell, WA) is diluted in conditioned chRPMI yielding a working concentration of 1 ug/mL (2x concentration). Plated cells (in 100 µL media) are then stimulated with either 100 µL of conditioned chRPMI (negative control), 100 µL Tetanus Toxoid solution (2x solution, positive control) (Astarte Biologics, Bothell, WA), 100 µL of a dilution of 2991 µL Tetanus Toxoid solution plus 9 µL SEQ ID NO: 7 solution, 100 µL of a dilution of 2997 µL Tetanus Toxoid solution plus 3 µL SEQ ID NO: 7 solution, or 100 µL of a dilution of 6998.2 µL Tetanus Toxoid solution plus 1.8 µL SEQ ID NO: 7 solution. All plates are then incubated for six additional days. On assay day five, 100 µL of supernatant is removed from each well and is replaced with freshly conditioned chRPMI (for no TT control wells), or 10011.1 of media with 2X TT (1 mg/mL) for the wells originally incubated with TT alone or TT+Tregitope. No extra Tregitope is added.

On assay day seven, cells are removed from incubation. As shown in FIG. 2A, cells are first gated to eliminate aggregates and dead cells, and live cells are gated for CD4+ T cells and all subsequent analysis is done on this population. CD4+ T cells are gated for elevated CD25, FoxP3, and low CFSE (proliferation) (FIG. 2B). The activated Teffector population is identified as the CD4+/CD25-high/FoxP3-intermediate ($CD4^+/CD25^{hi}/FoxP3^{int}$) (FIG. 2B). Proliferation of CD4+/Foxp3-low/CD25-high ($CD4^+/Foxp3^{lo}/CD25^{hi}$) T cells is estimated from the dilution of the CFSE stain (Cat #: 65-0850-84, Affymetrix, Santa Clara, CA) and % proliferation is determined by the CFSE-low (CFSE 10) population (FIG. 2C).

Figure 4A:
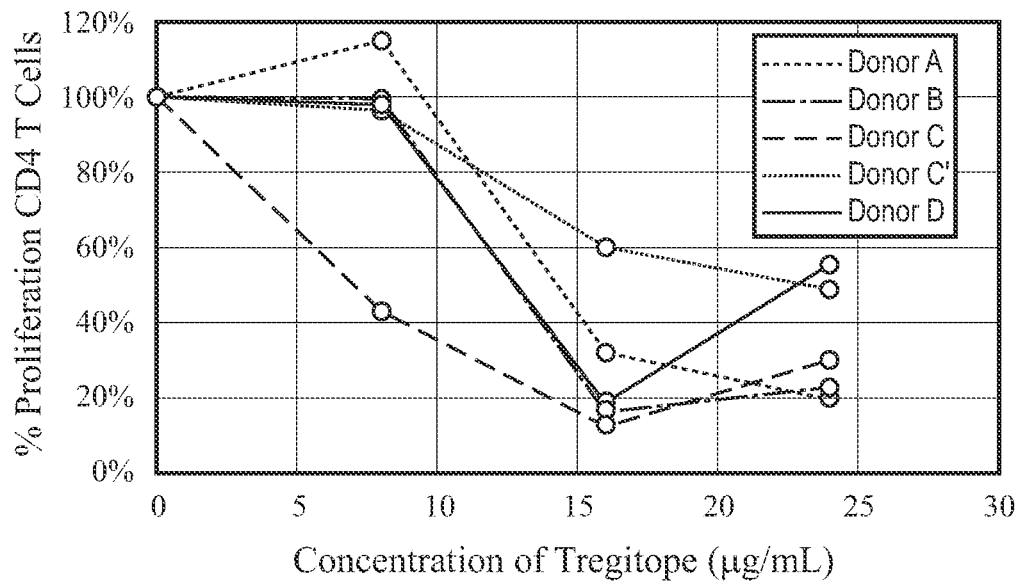
Figure 4B:
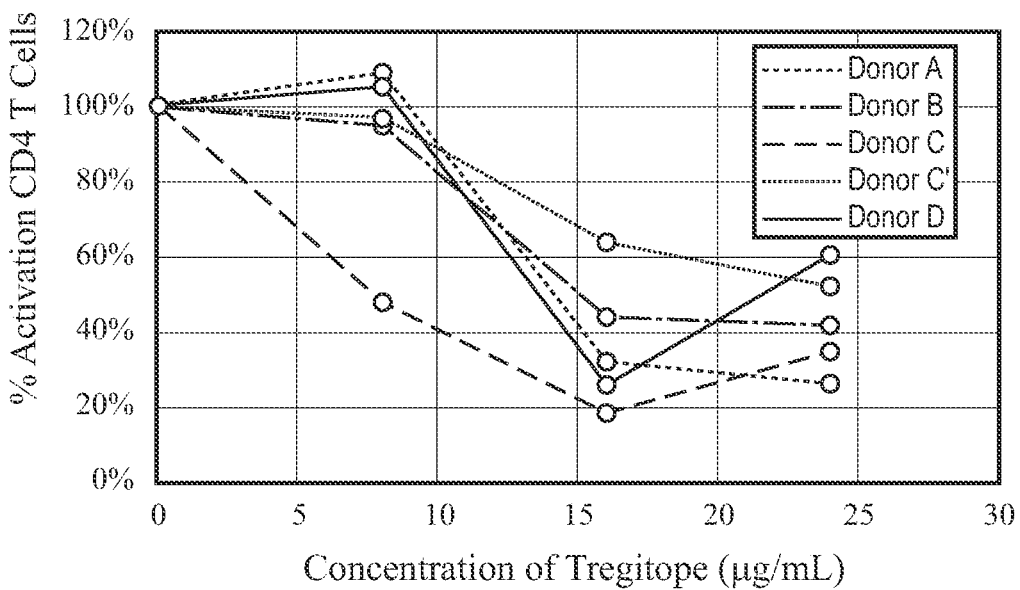
Figure 10:
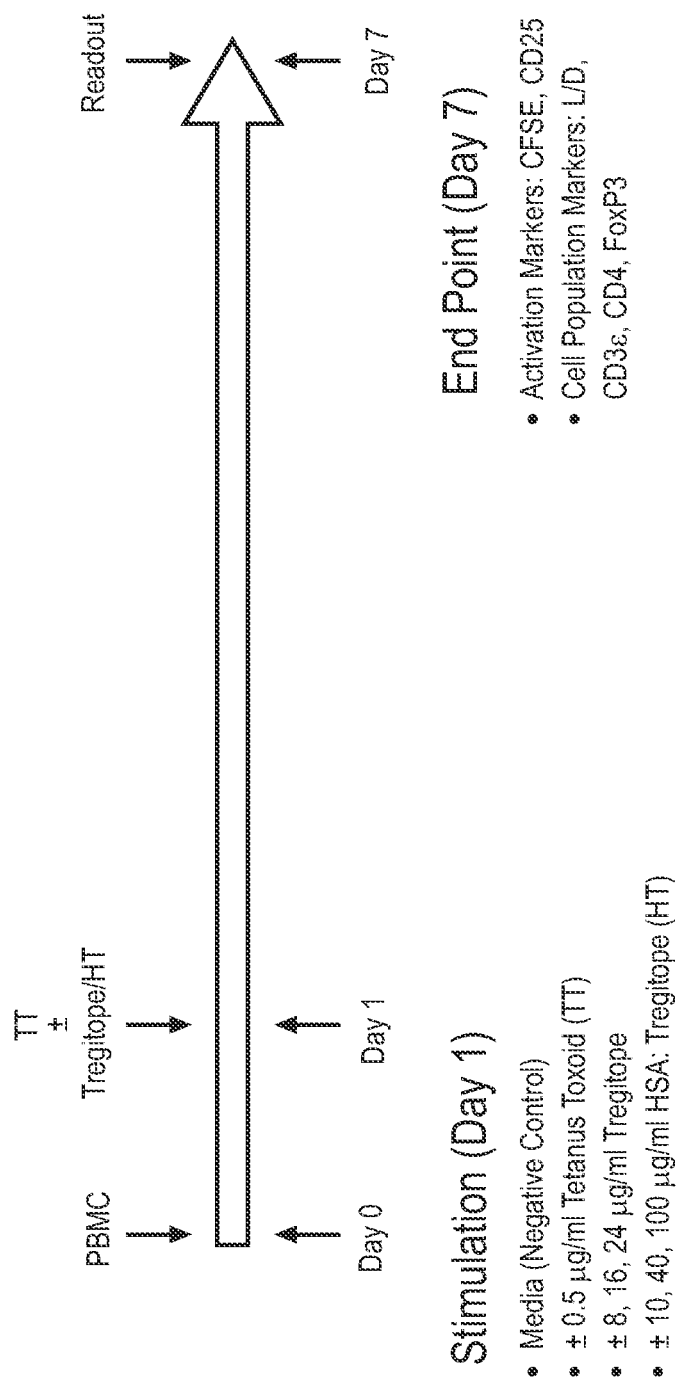
FIG. 10 shows an experimental design for a TTBSA assay evaluating the efficacy of Tregitope-albumin delivery vehicles.

Example 5. Peptide SEQ ID NO: 7 Suppressed Proliferation and Activation of CD4+ Effector T Cells The change in activation (FIG. 3, right panel—showing absolute values with media only controls subtracted; FIG. 4, right panel—showing normalized values with media only controls subtracted; FIG. 5, right panel,— showing absolute values with media only controls not subtracted; and FIG. 6, right panel—showing normalized values with media only controls not subtracted) and proliferation (FIG. 3, left panel—showing absolute values with media only controls subtracted; FIG. 4, left panel—showing normalized values with media only controls subtracted; FIG. 5, left panel,—showing absolute values with media only controls not subtracted; and FIG. 6, left panel—showing normalized values with media only controls not subtracted) of CD4+ effector cells when the proliferation stimulant (Tetanus Toxoid) is co-delivered with SEQ ID NO: 7 is measured and the proliferative response of CD4+ T cells, comprised mainly of T effector memory cells, is characterized.

T cell proliferation assays are performed on the Tregitopes of the present disclosure according to the methods described previously. FIGS. 3-6 shows that, in the various donors disclosed in Table 2, peptide SEQ ID NO: 7 strongly suppressed a population of activated effector CD4+ T cells (CD4+/CD25-high/FoxP3-intermediate, shown as CD4+/CD25 hi/FoxP3$^{int}$) reacting to Tetanus Toxoid in a dose-dependent manner.

(6) Methods for Assessing Peptide Effects on CD8+ Effector T Cells.

We have previously shown that CD8+ effector memory T cells contained within PBMC cell populations can be induced to proliferate in response to stimulation with known class I T cell epitopes. The results of this assay establish the ability of the instantly-disclosed Tregitopes (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) to suppress the proliferation of antigen stimulated CD8+T effector memory T cells by either direct (engagement and activation of $T_{Reg}$) or indirect (modulation of APC phenotype) means.

T cell proliferation assays are performed on the Tregitopes of the present disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) according to the methods described previously. PBMCs from two healthy donors are thawed and suspended in conditioned chRPMI (3.3×10$^6$ cells/mL) by conventional means. Cells are stained with CFSE (Cat #: 65-0850-84, Affymetrix, Santa Clara, CA) and plated at 300,000 cells per well. Plates are incubated overnight (37° C. in 5% CO$_2$). On assay day 1, Tregitopes of the instant disclosure are reconstituted in sterile DMSO yielding a final stock concentration of 20 mg/mL. Intermediate solutions of Tregitopes of the instant disclosure at twice the final concentration in chRPMI are prepared as described previously. Final concentration of Tregitopes of the instant disclosure are tested from 2.5, 5, 10 and 20 µg/ml. As a CD8+ stimulating antigen, the CEF peptide pool, which consists of 23 MHC class I restricted viral epitopes derived from human cytomegalovirus, Epstein-Barr virus, and influenza virus, are used. CEF peptides are added to the wells (data shown for 2 µg/mL) with cells and media (control) or a Tregitope of the instant disclosure at 0, 1, 2 or 4 µg/ml. All plates are incubated for six additional days. On assay day 5, 100 µL of supernatant is removed from each well and is replaced with freshly conditioned chRPMI.

Conventional methods are used to stain cells for live/dead marker, extracellular markers CD4, CD8a and CD25, CD127, CD45RA and CCR7, and intracellular marker FoxP3. After FACS analysis, cells are gated to eliminate aggregates and dead cells. On the live cells population, CD8a and CD4 cells are gated separately and each population is analyzed for proliferation (CF SE low population) or activation (CD25-high/FoxP3 low/intermediate, shown as FoxP3int_lo CD25hi) as explained previously.

Example 6. Tregitopes of the Instant Disclosure Suppress Proliferation of CD8+ Effector T Cells The potential inhibition of CD8+ T cell response by Tregitopes of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) when PBMC from healthy donors are stimulated with CEF peptides mixture is tested. It is expected that Tregitopes of the instant disclosure strongly inhibit the CD8+ T cell proliferative response to CEF peptides, as well as activation, in a dose-dependent manner.

(7) Methods for Assessing Peptide Effects on Immune Response (GvHD)

Bone marrow transplant is a procedure whereby unhealthy bone marrow is replaced with donated healthy bone marrow. Bone marrow transplants can be used to treat patients with life-threatening blood cancers like leukemia (Vincente D et al., (2007), Bone Marrow Transplant, 40(4): 349-54), diseases which result in bone marrow failure like aplastic anemia (Champlin R E et al., (2007), Blood, 109 (10):4582-5), and other immune system or genetic diseases (Chinen J and Bucley RH, (2010), J Allergy Clin Immunol, 125(2 Suppl 2):5324-35). Graft versus host disease (GvHD) is known as a major complication in bone marrow transplantation and is characterized by immediate and high mortality after onset (Lee S J et al., (2003), Biol Blood Marrow Transplant, 9(4):215-33). In GvHD, severe tissue damage is caused by donor lymphocytes as they make their way from transplanted donor tissue to HLA-mismatched recipient tissues. Symptoms include severe damage in various organs such as skin, lungs, liver and intestines caused by infusion in the recipient (Goker H et al., (2001), Exp Hematol, 29(3):259-77).

It was previously observed by EpiVax (Providence, RI) that transplantation of human peripheral blood mononuclear cells (PBMCs) (obtained from leukopaks (Hemacare, Van Nuys, CA)) into an immune deficient mouse causes a GvHD-like syndrome resulting in death by 20-50 days. In this model, T cells contained within the transplanted PBMC infiltrate the host mouse's skin, liver, intestine, lungs and kidneys causing severe damage and ultimately death. Immunodeficient mouse strain NOD-scid IL-2Rγ$^{null}$ (NSG-Jax stock #005557) (The Jackson Laboratory, Bar Harbor, ME) mice and transplants of human PBMC are used to assess the impact of Tregitopes of the instant disclosure on the progression of GvHD. On assay day—1, mice are be grouped by weight into matched treatment and control groups and are then irradiated with 100 cGy from an X-ray irradiator source (Lifespan Hospital, Providence, RI). After 6 hours of irradiation, mice subjects receive 10 million hPBMCs IV via the tail vein. Some mice receive irradiation, but no PBMCs (Group 8 in Table 3). Starting on assay day 0 and continuing through assay day 25, subject mice are dosed according to schedule outlined in Table 2.

Clinical observations, including weight loss, posture, activity, and appearance of hair coat and skin, are made three times per week. A subject mouse is euthanized if it exhibited a>20% weight loss from the starting date or exhibits a combination of the following clinical signs: (i) a 10-20% weight loss from the starting date (ii) coldness to touch (iii) lethargy with a hunched posture and scruffy coat.

TABLE 3

Experimental groups and dosing schedule for GVHD study

| Group | Mice | PBMC | Test Articles | Dose amount | Dosing frequency |
|---|---|---|---|---|---|
| 1 | 3 | + | PBS (disease control) | 300 µl PBS | Days 0, 2, 4, 7, 10, 15, 20, 25 |
| 2 | 10 | + | PBS + DMSO (vehicle) | 0.5% DMSO | Days 0, 2, 4, 7, 10, 15, 20, 25 |
| 6 | 10 | + | A Tregitope of the instant disclosure | 20 µg | Days 0, 2, 4, 7, 10, 15, 20, 25 |
| 7 | 7 | + | IVIG (positive control) | 50 mg | Days 0, 7, 14, 21, 28 |
| 8 | 3 | − | None (control group) | NA | |

Example 7. Tregitopes of the Instant Disclosure Inhibit the Development of GvHD in Xenogenic GvHD Model The transplantation of human lymphocytes into immunodeficient mice and subsequent treatment with a Tregitope of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) enables the assessment of the Tregitope of the instant disclosure on immune function in this in vivo model. Tregitopes of the instant disclosure are expected to suppress T-cell activation, thus slowing the progression of the disease. The main evaluation criteria to be used to evaluate is survival of the test subjects. A delay in the development of GvHD for the group treated with Tregitope of the instant disclosure is expected to be observed as suggested by the Kaplan-Meiers Survival Curve. Treatment with a Tregitope of the instant disclosure is expected to result in extended survival relative to negative controls and a positive control IVIG.

Example 8. Generation of a FVIII-Tregitope Construct

Fusion of a Tregitope with an immunogenic protein can lead to the induction of peripheral tolerance of the immunogenic protein. Clotting Factor VIII is immunogenic in people with severe hemophilia A. In one exemplary method of producing such constructs, chimeric constructs comprised of the coding sequence of Factor VIII and Tregitope are produced (Sambrook et al., Molecular Cloning: A Laboratory Manual, 2 ed., Cold Spring Harbor Laboratory Press, (1989)). Briefly, the Factor VIII coding region fused at the carboxy-terminus and/or amino-terminus to a Tregitope is generated by annealing overlapping oligos and sub-cloned into an expression plasmid. A Tregitope may also be inserted into Factor VIII, e.g. by mutagenesis (i.e., site-directed mutagenesis). The plasmids are transfected into DG44 CHO cells and stable transfectants selected. The chimeric protein is purified over an immunoaffinity column and evaluated for tolerogenicity. Tables 3 and 4 illustrate exemplary embodiments of such proteins (e.g., a chimeric protein). While Tables 4 and 5 depict Factor VIII fused with SEQ ID NO:1, it should be understood that such constructs could include one or more polypeptides (Treg activating regulatory T-cell epitope, Tregitope, Tregitope peptide, or T-cell epitope polypeptide) of the present disclosure included therein, having a sequence comprising, consisting of, or consisting essentially of one or more of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124).

TABLE 4

Factor VIII-Tregitope: SEQ ID NO: 135 (Tregitope bold)

MQIELSTCFFLCLLRFCFSATRRYYLGAVELSWDYMQSDLGELPVDARFP
PRVPKSFPFNTSVVYKKTLFVEFTDHLFNIAKPRPPWMGLLGPTIQAEVY
DTVVITLKNMASHPVSLHAVGVSYWKASEGAEYDDQTSQREKEDDKVFPG
GSHTYVWQVLKENGPMASDPLCLTYSYLSHVDLVKDLNSGLIGALLVCRE
GSLAKEKTQTLHKFILLLFAVFDEGKSWHSETKNSLMQDRDAASARAWPKM
HTVNGTVNRSLPGLIGCHRKSVYWHVIGMGTTPEVHSIFLEGHTFLVRNH
RQASLEISPITFLTAQTLLMDLGQFLLFCHISSHQHDGMEAYVKCDSCPE
EPQLRMKNNEEAEDYDDDLTDSEMDVVRFDDDNSPSFIQIRSVAKKHPKT
WVHYIAAEEEDWDYAPLVLAPDDRSYKSQYLNNGPQRIGRKYKKVRFMAY
TDETFKTREAIQHESGILGPLLYGEVGDTLLIIFKNQASRPYNIYPHGIT
DVRPLYSRRLPKGVKHLKDFPILPGEIFKYKWTVTVEDGPTKSDPRCLTR
YYSSFVNMERDLASGLIGPLLICYKESVDQRGNQIMSDKRNVILFSVFDE
NRSWYLTENIQRFLPNPAGVQLEDPEFQASNIMHSINGYVFDSLQLSVCL
HEVAYWYILSIGAQTDFLSVFFSGYTFKHKMVYEDTLTLFPFSGETVFMS
MENPGLWILGCHNSDFRNRGMTALLKVSSCDKNTGDYYEDSYEDISAYLL
SKNNAIEPRSFSQNSRHPSTRQKQFNATTIPENDIEKTDPWFAHRTPMPK
IQNVSSSDLLMLLRQSPTPHGLSLSDLQEAKYETFSDDPSPGAIDSNNSL
SEMTHFRPQLHHSGDMVFTPESGLQLRLNEKLGTTAATELKKLDFKVSST
SNNLISTIPSDNLAAGTDNTSSLGPPSMPVHYDSQLDTTLFGKKSSPLTE
SGGPLSLSEENNDSKLLESGLMNSQESSWGKNVSSTESGRLFKGKRAHGP
ALLTKDNALFKVSISLLKTNKTSNNSATNRKTHIDGPSLLIENSPSVWQN
ILESDTEFKKVTPLIHDRMLMDKNATALRLNHMSNKTTSSKNMEMVQQKK
EGPIPPDAQNPDMSFFKMLFLPESARWIQRTHGKNSLNSGQGPSPKQLVS
LGPEKSVEGQNFLSEKNKVVVGKGEFTKDVGLKEMVFPSSRNLFLTNLDN
LHENNTHNQEKKIQEEIEKKETLIQENVVLPQIHTVTGTKNFMKNLFLLS
TRQNVEGSYDGAYAPVLQDFRSLNDSTNRTKKHTAHFSKKGEEENLEGLG
NQTKQIVEKYACTTRISPNTSQQNFVTQRSKRALKQFRLPLEETELEKRI
IVDDTSTQWSKNMKHLTPSTLTQIDYNEKEKGAITQSPLSDCLTRSESIP
QANRSPLPIAKVSSFPSIRPIYLTRVLFQDNSSNLPAASYRKKDSGVQES
SHFLQGAKKNNLSLAILTLEMTGDQREVGSLGTSATNSVTYKKVENTVLP
KPDLPKTSGKVELLPKVHIYQKDLFPTETSNGSPGHLDLVEGSLLQGTEG
AIKWNEANRPGKVPFLRVATESSAKTPSKLLDPLAWDNHYGTQIPKEEWK
SQEKSPEKTAFKKKDTILSLNACESNHAIAAINEGQNKPEIEVTWAKQGR

TABLE 4-continued

| Factor VIII-Tregitope: SEQ ID NO: 135 (Tregitope bold) |
|---|
| TERLCSQNPPVLKRHQREITRTTLQSDQEEIDYDDTISVEMKKEDFDIYD |
| EDENQSPRSFQKKTRHYFIAAVERLWDYGMSSSPHVLRNRAQSGSVPQFK |
| KVVFQEFTDGSFTQPLYRGELNEHLGLLGPYIRAEVEDNIMVTFRNQASR |
| PYSFYSSLISYEEDQRQGAEPRKNFVKPNETKTYFWKVQHHMAPTKDEFD |
| CKAWAYFSDVDLEKDVHSGLIGPLLVCHTNTLNPAHGRQVTVQEFALFFT |
| IFDETKSWYFTENMERNCRAPSNIQMEDPTFKENYRFHAINGYIMDTLFG |
| LVMAQDQRIRWYLLSMGSNENIHSIHFSGHVFTVRKKEEYKMALYNLYPG |
| VFETVEMLPSKAGIWRVECLIGEHLHAGMSTLFLVYSNKCQTPLGMASGH |
| IRDFQITASGQYGQWAPKLARLHYSGSINAWSTKEPFSWIKVDLLAPMII |
| HGIKTQGARQKFSSLYISQFIIMYSLDGKKWQTYRGNSTGTLMVFFGNVD |
| SSGIKHNIFNPPIIAR YIRLHPTHYSIRSTLRMELMGCDLNSCSMPLGME |
| SKAISDAQITASSYFTNMFATWSPSKARLHLQGRSNAWRPQVNNPKEWLQ |
| VDFQKTMKVTGVTTQGVKSLLTSMYVKEFLISSSQDGHQWTLFFQNGKVK |
| VFQGNQDSFTPVVNSLDPPLLTRYLRIHPQSWVHQIALRMEVLGCEAQDL |
| YKTLYLQMNSLRAEDTAKHYCA |

TABLE 5

| Factor VIII-Tregitope: SEQ ID NO: 136 (Tregitope bold) |
|---|
| KTLYLQMNSLRAEDTAKHYCAQIELSTCFFLCLLRFCFSATRRYYLGAVE |
| LSWDYMQSDLGELPVDARFP |
| PRVPKSFPFNTSVVYKKTLFVEFTDHLFNIAKPRPPWMGLLGPTIQAEVY |
| DTVVITLKNMASHPVSLHAVGVSYWKASEGAEYDDQTSQREKEDDKVFPG |
| GSHTYVWQVLKENGPMASDPLCLTYSYLSHVDLVKDLNSGLIGALLVCRE |
| GSLAKEKTQTLHKFILLFAVFDEGKSWHSETKNSLMQDRDAASARAWPKM |
| HTVNGTVNRSLPGLIGCHRKSVYWHVIGMGTTPEVHSIFLEGHTFLVRNH |
| RQASLEISPITFLTAQTLLMDLGQFLLFCHISSHQHDGMEAYVKCDSCPE |
| EPQLRMKNNEEAEDYDDDLTDSEMDVVRFDDDNSPSFIQIRSVAKKHPKT |
| WVHYIAAEEEDWDYAPLVLAPDDRSYKSQYLNNGPQRIGRKYKKVRFMAY |
| TDETFKTREAIQHESGILGPLLYGEVGDTLLIIFKNQASRPYNIYPHGIT |
| DVRPLYSRRLPKGVKHLKDFPILPGEIFKYKWTVTVEDGPTKSDPRCLTR |
| YYSSFVNMERDLASGLIGPLLICYKESVDQRGNQIMSDKRNVILFSVFDE |
| NRSWYLTENIQRFLPNPAGVQLEDPEFQASNIMHSINGYVFDSLQLSVCL |
| HEVAYWYILSIGAQTDFLSVFFSGYTFKHKMVYEDTLTLFPFSGETVFMS |
| MENPGLWILGCHNSDFRNRGMTALLKVSSCDKNTGDYYEDSYEDISAYLL |
| SKNNAIEPRSFSQNSRHPSTRQKQFNATTIPENDIEKTDPWFAHRTPMPK |
| IQNVSSSDLLMLLRQSPTPHGLSLSDLQEAKYETFSDDPSPGAIDSNNSL |
| SEMTHFRPQLHHSGDMVFTPESGLQLRLNEKLGTTAATELKKLDFKVSST |
| SNNLISTIPSDNLAAGTDNTSSLGPPSMPVHYDSQLDTTLFGKKSSPLTE |

TABLE 5-continued

| Factor VIII-Tregitope: SEQ ID NO: 136 (Tregitope bold) |
|---|
| SGGPLSLSEENNDSKLLESGLMNSQESSWGKNVSSTESGRLFKGKRAHGP |
| ALLTKDNALFKVSISLLKTNKTSNNSATNRKTHIDGPSLLIENSPSVWQN |
| ILESDTEFKKVTPLIHDRMLMDKNATALRLNHMSNKTTSSKNMEMVQQKK |
| EGPIPPDAQNPDMSFFKMLFLPESARWIQRTHGKNSLNSGQGPSPKQLVS |
| LGPEKSVEGQNFLSEKNKVVVGKGEFTKDVGLKEMVFPSSRNLFLTNLDN |
| LHENNTHNQEKKIQEEIEKKETLIQENVVLPQIHTVTGTKNFMKNLFLLS |
| TRQNVEGSYDGAYAPVLQDFRSLNDSTNRTKKHTAHFSKKGEEENLEGLG |
| NQTKQIVEKYACTTRISPNTSQQNFVTQRSKRALKQFRLPLEETELEKRI |
| IVDDTSTQWSKNMKHLTPSTLTQIDYNEKEKGAITQSPLSDCLTRSESIP |
| QANRSPLPIAKVSSFPSIRPIYLTRVLFQDNSSNLPAASYRKKDSGVQES |
| SHFLQGAKKNNLSLAILTLEMTGDQREVGSLGTSATNSVTYKKVENTVLP |
| KPDLPKTSGKVELLPKVHIYQKDLFPTETSNGSPGHLDLVEGSLLQGTEG |
| AIKWNEANRPGKVPFLRVATESSAKTPSKLLDPLAWDNHYGTQIPKEEWK |
| SQEKSPEKTAFKKKDTILSLNACESNHAIAAINEGQNKPEIEVTWAKQGR |
| TERLCSQNPPVLKRHQREITRTTLQSDQEEIDYDDTISVEMKKEDFDIYD |
| EDENQSPRSFQKKTRHYFIAAVERLWDYGMSSSPHVLRNRAQSGSVPQFK |
| KVVFQEFTDGSFTQPLYRGELNEHLGLLGPYIRAEVEDNIMVTFRNQASR |
| PYSFYSSLISYEEDQRQGAEPRKNFVKPNETKTYFWKVQHHMAPTKDEFD |
| CKAWAYFSDVDLEKDVHSGLIGPLLVCHTNTLNPAHGRQVTVQEFALFFT |
| IFDETKSWYFTENMERNCRAPSNIQMEDPTFKENYRFHAINGYIMDTLFG |
| LVMAQDQRIRWYLLSMGSNENIHSIHFSGHVFTVRKKEEYKMALYNLYPG |
| VFETVEMLPSKAGIWRVECLIGEHLHAGMSTLFLVYSNKCQTPLGMASGH |
| IRDFQITASGQYGQWAPKLARLHYSGSINAWSTKEPFSWIKVDLLAPMII |
| HGIKTQGARQKFSSLYISQFIIMYSLDGKKWQTYRGNSTGTLMVFFGNVD |
| SSGIKHNIFNPPIIARYIRLHPTHYSIRSTLRMELMGCDLNSCSMPLGME |
| SKAISDAQITASSYFTNMFATWSPSKARLHLQGRSNAWRPQVNNPKEWLQ |
| VDFQKTMKVTGVTTQGVKSLLTSMYVKEFLISSSQDGHQWTLFFQNGKVK |
| VFQGNQDSFTPVVNSLDPPLLTRYLRIHPQSWVHQIALRMEVLGCEAQDL |
| Y |

Example 9. Generation of an Enhanced Vaccine Delivery Vehicle

Fc binding to Fc receptors enhances uptake in antigen presenting cells presentation to T and B lymphocytes. The Tregitopes of SEQ ID NOS: 1-124 are located within IgG molecules and act to deliver suppressive signals. More particularly, SEQ ID NOS: 1, 3-8, 14-15, 16-28, 42-74, and 111-124 are located within the human IgG heavy chain variable region, SEQ ID NOS: 2, 9-11, 29-41, and 75-100 are located within the human IgG heavy chain constant region, SEQ ID NO: 12 is located within the human IgG light chain variable region, and SEQ ID NOS: 13 and 101-110 are located within the human IgG light chain constant region. The modification of IgG (or antigen-specific antibody fragments thereof (including, but not limited to, a Fab, F(ab')2, Fv, disulfide linked Fv, scFv, single domain antibody, closed conformation multispecific antibody, disulfide-linked scfv, diabody)) so that one or more of SEQ ID NOS: 1-124 contained therein no longer binds to MHC molecules and/or regulatory T cells which allows for efficient targeting of vaccine candidates while avoiding suppressive effects. Modifications to decrease binding of Tregitopes to MHC molecules are useful. Table 6 illustrates such a modification. Chimeric constructs comprised of various proteins or epitope pseudo-proteins of interest and a Tregitope modified lgG Fc are designed (Sambrook et al., Molecular Cloning: A Laboratory Manual, 2 ed., Cold Spring Harbor Laboratory Press, (1989)). Briefly, the protein or epitope pseudo-protein of interest is generated by annealing overlapping oligos and sub-cloned into a Tregitope modified Fc fusion expression plasmid. The plasmids are transfected into DG44 CHO cells and stable transfectants selected. The chimeric protein homodimers are purified over a protein A column and evaluated for immunogenicity. Table 6 illustrates one exemplary embodiment of a chimeric protein where the pseudo-protein of interest is a string of immunogenic T cell epitopes (in this example, derived from the Epstein Barr Virus (EBV)) fused to a modified Fc protein in which a Tregitope has been modified to no longer bind MHC class II molecules and cannot stimulate natural regulatory T cells. EBV-Tregitope modified Fc SEQUENCE (Kb SIGNAL SEQUENCE) in Table 6 is designated as underlined text. The Tregitope is designated as bold text. The Tregitope modified amino acids are designated as shaded text. The human Fc region is designated as italicized text. While Table 4 and 5 depict Factor VIII fused with SEQ ID NO:1, it should be understood that such constructs could include one or more polypeptides (Treg activating regulatory T-cell epitope, Tregitope, Tregitope peptide, or T-cell epitope polypeptide) of the present disclosure included therein, having a sequence comprising, consisting of, or consisting essentially of one or more of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124).

body, closed conformation multispecific antibody, disulfide-linked scfv, diabody)) by insertion or fusion of one or more Tregitopes of SEQ ID NOS: 1-124, thereby enhancing binding of modified IgG or fragments thereof to WIC molecules and regulatory T cells allows for suppression of immunostimulatory effects. The modification of an antibody, such as an IgG molecule or fragment thereof (e.g., if a particular antibody or fragment thereof has a mutated or missing corresponding section) by insertion or fusion of one or more Tregitopes of SEQ ID NOS: 1-124 (and fragments or variants thereof, is useful. Table 7 illustrates one exemplary embodiment of a Tregitope (SEQ ID NO:29) inserted or fused to a human IgG1 Fc protein. The Tregitope is designated as bold text. The human Fc region is designated as italicized text. While Table 7 depicts insertion of SEQ ID NO:29, it should be understood that such constructs could include insertion of one or more polypeptides (Treg activating regulatory T-cell epitope, Tregitope, Tregitope peptide, or T-cell epitope polypeptide) of the present disclosure included therein, having a sequence comprising, consisting of, or consisting essentially of one or more of SEQ ID NOS: 1-124 (and/or fragments or variants thereof), and optionally 1 to 12 additional amino acids distributed in any ratio on the N terminus and/or C-terminus of the polypeptide of SEQ ID NOS: 1-124).

TABLE 7

Tregitope modified Fc SEQUENCE (SEQ ID NO: 138)

dkthtcppcpapellggpsvflfppkpkdtlmisrtpevtcvvvdvshe dpevkfnwyvdgvevhnaktkpreeqqdwlngkeykckvsnkalpapie ktiskakgqprepqvytlppsrdelteegyqstyrknqvsltclvkgfy psdiavewesngqpennyktppvldsdgsfflyskltvdksrwqqgnv fscsvmhealhnhytqkslslspg SEQ ID NO: 138

(8) Generation of Tregitope-Blood Component Conjugates

Fusion of a Tregitope with a blood component conjugate, such as albumin, are useful as a carrier protein for Tregitope payload. Tregitope-blood component conjugates can extend the half-life of Tregitopes in vivo, protect Tregitopes from

TABLE 6

EBV-T-regitope modified Fc SEQUENCE (SEQ ID NO: 137)

<u>mvpctllllaaalaptqtraenkggdqgpplmtdggggpgpgplssslglallllllallfwlyivmsdwtggallvlysfa</u>

<u>lmliiiiliififrrdllcplgalcilllmitlllialwnlhgqalflgivlfifgcllvlgiwiyllemlwrlgatiwqllafflaffldli</u>

<u>lliialylqqnwwtllvdllwlllflailiwmyyhgqrhsdehhhddslphgpgpggprhrdgvrrpqkrpscigckgpg</u>

<u>pgiaeglrallarshvertgpgpgagvfvyggsktslynlrrgtalaigpgpgtslynlrrgtalaipqcrltplsrlgpgpgre</u>

<u>sivcyfmvflqthifaevlgpgpgaikdlvmtkpaptcnirvgpgpggpqrrggdnhgrg</u>x*dkthtcppcpapellggp*

*svflfppkpkdtlmisrtpevtcvvvdvshedpevkfnwyvdgvevhnaktkpree*qns*nasvltvlhqdwlngke*

*ykckvsnkalpapiektiskakgqprepqvytlppsrdeltknqvsltclvkgfypsdiavewesngqpennykttppvlds*

*dgsfflyskltvdksrwqqgnvfscsvmhealhnhytqkslslspx* SEQ ID NO: 137

Example 10. Insertion of a Tregitope into Fc

The modification of IgG (or antigen-specific antibody fragments thereof (including, but not limited to, a Fab, F(ab')₂, Fv, disulfide linked Fv, scFv, single domain anti-rapid proteolytic degradation, protect Tregitopes from rapid clearance from circulation and/or rapid kidney excretion, allow for wide distribution of Tregitope-blood component conjugates throughout the body of a subject, aid in delivery of Tregitopes to appropriate immune cells (such as macrophages and APCs), allow the Tregitopes to be processed by the endocytic pathway of certain immune cells (such as macrophages and APCs), and aid in the presentation of Tregitopes as an antigen by said immune cells.

Tregitope-blood component conjugates may be formed by modifying a Tregitope peptide of the instant disclosure (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) by attaching a reactive moiety to the Tregitope peptide to create a modified Tregitope peptide, then forming a bond between reactive moiety of the modified Tregitope peptide with a reactive functionality on a blood component, as disclosed in U.S. Pat. Nos. 6,849,714, 6,887,470, 7,256,253, and 7,307,148. Albumin is a preferred blood component because it contains an Fc neonatal binding domain that will carry the Tregitope-albumin conjugate into the appropriate cells, such as macrophages and APCs. Further, albumin contains a cysteine at amino acid 34 ($Cys^{34}$) (the location of the amino acid in the amino acid sequence of human serine albumin), containing a free thiol with a pKa of approximately 5, which may serve as a preferred reactive functionality of albumin. $Cys^{34}$ of albumin is capable of forming a stable thioester bond with maleimidopropionamido (MPA), which is a preferred reactive moiety of a modified Tregitope peptide. The stable thioester bond between albumin and the Tregitope peptide modified with MPA cannot be cleaved under physiological conditions.

The Tregitope peptide may be as disclosed herein, and in certain aspects is preferably selected from SEQ ID NOS: 1-124, or a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124. One or more lysines may be present on the N-terminus of the Tregitope peptide, such as, but not limited to, added onto to the N-terminus of peptides selected from SEQ ID NOS: 1-124. A linker, such as a polyethylene glycol linker (e.g., PEG2 or PEG12), is present between the one or more lysines and the Tregitope sequence, or at the N-terminus of a Tregitope sequence. In aspects, a lysosomal cleavage site, such as a Cathepsin B site, optionally consisting (sequentially from N-terminus to C-terminus) of valine and citrulline, is present between the PEG2 moiety and the Tregitope sequence. A maleimide-based chemistry may be used to covalently link the modified Tregitope peptide to a blood component, preferably serum albumin, in a 1:1 molar ratio. Linking the modified Tregitope peptide to a blood component may be performed in vivo or ex vivo.

Cathepsin B is the first described member of the family of lysosomal cysteine proteases. Cathepsin B possesses both endopeptidase and exopeptidase activities, in the latter case acting as a peptidyldipeptidase. Cathepsin B was been included in the Tregitope peptide design to facilitate the proper cleavage of the Tregitope from Albumin once it is in the lysosomal compartment in the antigen presenting cells. The Valine-Citrulline is a cathepsin B cleavage site that has been previously used successfully and has been FDA approved in Antibody Drug conjugate (e.g., monomethyl auristatin E (MMAE) conjugate in the drug brentuximab vedotin). Our interest in incorporating the site is to provide cleavage sites that would allow the proper cleavage of the Tregitope from the human serum albumin for efficient MHC class II presentation once it is in the APC. EpiVax sought to determine whether the incorporation of the cathepsin B site is essential to the design of the Tregitope composition.

Example 11. Generation of a Tregitope-Albumin Conjugate by Ex Vivo Conjugation

Standard Fmoc (9-fluorenylmethoxycarbonyl) solid-phase peptide synthesis chemistry was used for peptide synthesis. Synthesis was performed on Intavis™ Multi-Pep™ automated peptide synthesizers. Amino acids are added stepwise to the growing peptide chain (C-terminus to N-terminus; right to left), while attached to an insoluble polystyrene resin support. Amino acid building blocks, protected at their amino terminus by an Fmoc group, were coupled to the growing chain after activation of the carboxylic acid terminus via one or more condensation reagents (e.g., Hexafluorophosphate Azabenzotriazole Tetramethyl Uronium (HATU), 0-(1H-6-Chlorobenzotriazole-1-yl)-1,1,3,3-tetramethyluronium hexafluorophosphate (HCTU)). The reaction by-products at each addition are removed by solvent washing (6X, Dimethylformamide (DMF)). Following each coupling and capping step, the Fmoc is removed via piperidine deprotection of the peptide resin (performed 2x; 20% in DMF volume/volume with HOBt to suppress Asp dehydration), the resin washed with DMF 6x, and the next amino acid added. A Cathepsin B cleavage site was incorporated at the N-terminus of the Tregitope sequence.

For a PEG2 construct ("PEG2" or "P2"), after the desired Tregitope peptide was completed a PEG2 moiety was added to the N-terminus, followed by the addition of 4 lysines to the N-terminus. The PEG2 and Lysines were incorporated to provide a potential docking area for the Cathepsin B. Additionally, the PEG2 and lysines (via the primary amine on the lysine side-chain) would increase the solubility of the final construct. The composition of the PEG2 construct is shown in Table 8 (below).

TABLE 8

| PEG2 construct composition |
|---|
| HSA (Cys 34)-Maleimide linkage-KKKK-Peg2-Val-Cit (CatB cleavage site)_Tregitope_Nle |

For a PEG12 construct ("PEG12" or "P12"), two additions of a PEG6 were added after the Tregitope peptide synthesis. In this case, no lysines were added. Increasing the PEG length also provided a docking region for Cathepsin B and improved the solubility of the Tregitope. The composition of the PEG2 construct is shown Table 9 (below).

TABLE 9

| PEG12 construct composition |
|---|
| HSA (Cys 34)-Maleimide linkage-Peg12-Val-Cit (CatB cleavage site)_Tregitope_Nle |

Subsequently, a small amount of the peptide constructs were removed from the resin and the peptide sample cleaved and deprotected by treatment with trifluoroacetic acid (TFA. 92.5% v/v) in the presence of TIS (triisopropylsilane, 5%) and water (2.5%) to scavenge side-chain protecting groups. Each crude, linear, peptide (~3-5 mg) was purified by preparative reversed phased HPLC (Gilson) using a 20 mm×50 mm YMC C18, 5 μm, Hydrosphere column. The peptides were purified to ≥90% purity (determined via analytical HPLC) and the mass verified utilizing an ABI-SCIEX QSTAR XL Pro Qo-TOF mass spectrometer prior to the Cathepsin B evaluation. The remaining peptides (PEG2-Tregitope and PEG12-Tregitope) was left on the resin for the addition of 3-maleimidoproprionic acid (MPA) at a later time.

Recombinant human Cathepsin B (catalog 953-CY of R&D Systems™) was used to evaluate the cleavage of the Val-Cit site engineered into the Tregitope peptide. The activity assay protocol was used according to the R&D Systems™'s recommendations with final assay conditions of 0.01 μg of rhCathepsin B and 10 uM of peptide substrate. After incubation of Cathepsin B with purified peptides (at RT for 15 min). The peptide was evaluated by mass spec using the Qstar XL Pro™. It was determined that the PEG2 peptide did not have successful cleavage, and further modification of the Cathepsin B protocol did not produce successful cleavage. For the PEG12 product, successful cleavage was demonstrated.

After evaluation of the cleavage of the Val-Cit site by Cathepsin B, the reactive moiety of 3-maleimidoproprionic acid (MPA) was added to the N-terminus of the PEG2 and PEG12 peptides. Similar, to the amino acid building blocks, the MPA is protected by an Fmoc group, and coupled to the growing chain after activation of the carboxylic acid terminus. The final MPA-Tregitope constructs were removed from the resin and the peptide sample was cleaved and deprotected by treatment with trifluoroacetic acid (TFA. 92.5% v/v) in the presence of TIS (triisopropylsilane, 5%) and water (2.5%). Each crude, linear, peptide (~20 mg) was purified by preparative reversed phased HPLC (Gilson™) using a 20 mm×50 mm YMC C18, 5 μm, Hydrosphere column. The MPA-peptides were purified to ≥90% purity (determined via analytical HPLC) and the mass verified utilizing an ABI-SCIEX QSTAR XL Pro™ Qo-TOF mass spectrometer, as shown in FIGS. 10-13. A total of 15 mg of the MPA-P2 and MPA-P12 Tregitopes was used in the subsequent conjugation to rHSA (Albucult-Novozyme™) to construct the final preformed HSA-Tregitope conjugate.

Ellman's Reagent (5,5'-dithio-bis-[2-nitrobenzoic acid]) was used to estimate sulfhydryl groups in a sample by comparing to a standard curve of a sulfhydryl-containing compound such as cysteine. Ellman's test was performed on rHSA (Sigma™, Albucult®) at multiple concentrations to ensure the accuracy of the analysis. Ellman's reagent (Sigma™), rHSA from Sigma™ lot RF-009 was evaluated for free cysteine that would be available for conjugation with the maleimide. We estimated that 78% of the rHSA had free cysteine available, as shown in Table (below).

After the conjugation step, the HSA-conjugate was then dialyzed into PBS (pH 7.0) first at room temperature for 2 hours, followed by two changes to fresh PBS at 4° C. for 18-24h. This process removed excess peptide from the HSA and HSA-Tregitope conjugate preparation.

The Ellman's test was performed on each conjugate to demonstrate conjugation of the peptide via the rHSA free Cysteine, and determine the efficiency of conjugation in the reaction. The HSA-conjugation preparation did not remove the reduced HSA (mercaptabumin), inherent in the preexisting preparation (~22% of the HAS pre-conjugation). The remaining unreacted HSA was determined to be 14% for the HSA-MPA P2-Tregitope construct, meaning after conjugation with the maleimide-Tregitope 14% of the free cysteine remained. Thus, ~64% of total rHSA preparation was reacted with the MPA P2-Tregitope peptide.

(9) Methods for Assessing Effect of Tregitope-Blood Component Conjugates on Immune Cells A maleimide-based chemistry may be used to covalently link a Tregitope (e.g., but not limited to, a peptide or polypeptide comprising, consisting, or consisting essentially of an amino acid sequence of SEQ ID NOS: 1-124 (and/or fragments or variants thereof), and optionally 1 to 12 additional amino acids distributed in any ratio on the N-terminus and/or C-terminus of the polypeptide of SEQ ID NOS: 1-124) payload to recombinant HSA (rHSA) in a 1:1 stoichiometry. Maleimido-propionamido (MPA) forms a stable thiol ester conjugate with the available free Cys34 in HSA. HSA leverages the neonatal receptor (FcRn) recycling pathway, increasing the half-life of any conjugated payload, and potentially decreasing the need for repeat dosing. rHSA is also known to deliver conjugated payloads to the lymph nodes and is endocytosed by dendritic cells and other antigen presenting cells that express FcRn.

EpiVax designed an rHSA-Tregitope conjugate to contain cleavage sites between the Tregitopes. The cleavage sites are specific for an early endosomal protease, which enable the Tregitopes to be liberated from the rHSA molecule, increasing the efficiency of MHC class II presentation on the cell surface. The long and substantiated history of this FDA-Approved rHSA conjugation chemistry approach, as well as its successful manufacturing history, support its selection for delivery of our T1D payload.

Once Tregitope-blood component conjugates are formed, for example as described herein, the Tregitope-blood com-

TABLE 10

Estimation of free cysteine in rHSA samples

| Grams rHSA | Moles huHSA | O.D. 412 | Concentration | Moles | Moles huHSA per mole free cysteine | % free cysteine |
|---|---|---|---|---|---|---|
| 0.001 | 1.50376E−08 | 0.059 | 4.1696E−06 | 1.16749E−08 | 1.29 | 77.64 |
| 0.002 | 3.00752E−08 | 0.12 | 8.4806E−06 | 2.37456E−08 | 1.27 | 78.95 |

Peptide was solubilized in dH20, rHSA added (15 mg/ml) and 100 mM Phosphate buffer added to give a final pH of 8. The peptide is added in a 10X molar excess to the HSA. Peptide/HSA was incubated at room temperature for 2h followed by incubation at 4° C. for approximately 24-30 hours.

ponent conjugates may be evaluated for their effectiveness in inhibiting effector T-cells and activating regulatory T-cells and their proliferation, for example in comparison with Tregitope peptides alone. Further, the Tregitope-blood component conjugates may be evaluated for their capacity to induce immune tolerance against certain antigens

Example 12. Evaluation of the Inhibitory Effect of Tregitope-Albumin Delivery Vehicle To determine the inhibitory effect of the Tregitope delivery vehicle, healthy donor PBMCs are used in a tetanus toxoid bystander suppression assay (TTBSA), and analysis is done on CD4 T-cell proliferation, activation of T cells, frequencies of T effector and T regulatory cells to determine the ratio of Treg/Teff, as is displayed in FIG. 10.

So as to optimize the best combination of Tregitopes for translation to the clinic, the effect of combinations of Tregitopes for their ability to synergistically suppress effector T-cell responses in vitro is analyzed. To facilitate these comparisons, a high throughput in vitro assay is developed using human donor peripheral blood mononuclear cells (PBMCs). This assay, referred to as the Tetanus Toxoid Bystander Suppression Assay (TTBSA), takes advantage of the ability of $T_{regs}$ to suppress T memory cells specific to Tetanus that are elicited in individuals with a history of Tetanus toxoid (TT) vaccination.

At day 0, PBMCs are incubated and stained with Carboxyfluorescein succinimidyl ester (CFSE) dye. At day 1, cells are stimulated with by adding media, Tetanus Toxoid, and either: 8, 6, or 24 μg/mL of a Tregitope; or 10, 40, or 100 μg/mL of a Tregitope-albumin conjugate. Tetanus Toxoid is used at a final concentration of 0.5 μg/ml, where the concentration is methodically titrated and optimized to measure the inhibitory capacity of Tregitopes. Negative controls, including media-only, are included. At day 7, L/D cell population marker, extracellular stain, and intracellular stain are added to the cells. At day 8, a readout is taken. Cell sorting assays for analysis of activation markets (e.g., CFSE, CD25) and cell population markets (e.g., L/D, CD2c, CD4, and FoxP3) are performed.

Incubation of donor PBMCs with TT stimulates expansion of T effector cells. Tregitopes are added to PBMC in vitro with TT, and activate $CD25^{hi}FoxP3^{hi}$ regulatory T cells suppressing expansion of TT-specific T effector cells. Tregitopes significantly inhibit the proliferation (as is measured by CFSE dilution) and activation (as is measured by CD25 expression) of CD4+T effector cells in a dose dependent manner, and also slightly expand $T_{regs}$ ($CD25^+/FoxP3^+/CD127^{lo}$), which is suggested by an increase in the ratio of Treg/Teff cells. A reduction of effector T cell proliferation is a direct consequence of the activation of T regulatory cells and/or the conversion of TT-specific T effector to Treg, for example as is supported by the induction of Treg in vivo.

Using the TTBSA, each of a number of available Tregitopes individually and in pairwise combinations is examined for their potential to suppress CD4+ T cell proliferation. The most promising IgG-Tregitope peptides are selected for further testing. A certain Tregitope, Tregitope A, is the single Tregitope has the most suppressive activity in the TTBSA as compared to the other single Tregitopes. Combining Tregitope A with Tregitope C, an even greater suppressive effect on TT-specific T cell proliferation is observed. Conjugating A+C to rHSA improves their efficacy in vitro.

Thus, using TTBSA, it is shown that HSA-Tregitope conjugates inhibit CD4+ T cell proliferation and activation, and increase the ratio of Treg cells to Teff cells.

Example 13. Evaluation of the Effectiveness of Preformed Conjugate HSA-Tregitope Therapeutics and Maleimide-Tregitope Peptide Therapeutics The effect on the response to OVA immunization of preformed conjugate HSA-Tregitope therapeutics and a free-maleimide-Tregitope peptide is evaluated. The latter free-maleimide peptide forms a conjugation in vivo after injection via the reactive maleimide group to the free-Cys34 of the subject's endogenous HSA. 5 mgs of the MPA-P2 and MPA-P12 is used as free-MPA-Tregitope, with the unconjugated HSA in the sample being accounted for by calculating the molar ratio of conjugated to unconjugated HSA.

Mice (female C57BL/6) are immunized s.c. with 50 mg ovalbumin (OVA) on day 0 (CFA) and day 14 (IFA). The preformed HSA conjugate treatments is administered with the OVA in CFA on day 0. Test groups include OVA/HSA-P2-high and OCA/HSA-P2-low. Per injection OVA is and HSA at 800 and HSA-P2H(high) conjugation is at 825 μg (~20 μg Tregitope). HSA-P2L(low) conjugation is at 100 μg (~3.7 μg Tregitope). Four control groups include PBS only, PBS/OVA, HSA/OVA, and Tregitope/OVA. A last arm is included to evaluate the utility of the free-maleimide Tregitope peptide and is administered by IV into tail vein. There are five mice per group.

Mice are sacrificed on Day 17. Upon sacrifice, cardiac bleeds and spleens are harvested for each animal. IFNγ/IL2 fluorospot assays, IFNγ/IL17 fluorospot assays, CD4 T cell proliferation, and T cell characterization are performed on the splenocytes stimulated with OVA. PHA is used as a positive control stimulation for spleen cell assays. All of the wells in PHA stimulation are confluent. An acceptance criteria is used wherein SFC (spot forming cells) after stimulation must be greater than 50 spots/$10^6$ over negative control (media wells) and must also have a stimulation index greater than 2. According to both the IFNγ/IL2 fluorospot and IFNγ/IL17 fluorospot assays, IFNγ production is inhibited by treatment, and the HSA-only control group is inhibited less compared than the treatment groups.

For T-cell proliferation and characterization assays, splenocyte samples are evaluated for induction of FoxP3 expression in TCR Tg cells and for the suppression of OVA specific T cell proliferation (in response to OVA peptide in vitro) by CFSE dilution. To detect $FoxP3^+$ Tregs, a single-cell suspension of draining lymph nodes is incubated with 2.4G2 mAb (anti-CD16/32, ATCC) for 15 minutes to block FcR then is stained with anti CD3, CD4, CD25 and anti-clonotypic KJ1-26 for 40 minutes at 4° C. KJ1-26 is specific for clonotypic TCR expressed by DO11.10 transgenic mice. Cells are then be permeabilized and stained for FoxP3 nuclear expression and acquired on a Thermo Attune NxT Autosampler™ for FACS analysis. The $CD4^+CD25^+FoxP3^+KJ1-26^+$ live cell gate population is established to determine the number and proportion of OVA-Specific T regulatory cells compared to PBS or HSA alone.

Antigen-specific T cell proliferation is evaluated by CFSE dilution. Draining lymph nodes are harvested, are stained with cell proliferation dye CFSE, and a single-cell suspension is prepared at $2\times10^6$ cells/mL. Cells are added to 96-well plates at 100 μL per well in the presence of 10 μg/ml concentration of OVA 323-339 (New England Peptide, Gardner, MA, USA). Cells are stimulated for 72 hours and harvested for staining with CD3α, CD4, CD8, CD54RA, CCR7, CD25, CD127, IFNγ HLA-II, CD69, CD154, IL-17, IL-21 for 40 minutes at 4° C. Cells are be fixed, permeabilized and stained for FoxP3 expression and analyzed by flow cytometry. An increase of OVA-specific $KJ1-26^+CD4^+CD25^+FoxP3^+$ adaptive (converted) T regulatory cells in mice treated with free maleimide-Tregitopes and HSA-Tregitope conjugates as compared to mice treated with rHSA is observed. Free maleimide-Tregitopes and HSA- Tregitope conjugates more effectively reduce OVA-specific proliferation of KJ1-26$^+$CD4$^+$ T effector cells as compared to rHSA alone.

Anti-OVA antibodies in serum from the bleeds harvested on day 17 are evaluated in serum by ELISA, including a serial dilution plot and a standard ELISA to determine antibody concentrations. Mice treated with HSA-conjugates and free maleimide have lower serum antibody titers compared to no treatment, as indicated by absorbance at different dilutions, as well as comparison of absorbance over a standard curve.

EQUIVALENTS

While the instant disclosure has been described in connection with the specific embodiments thereof, it will be understood that it is capable of further modification. Furthermore, this application is intended to cover any variations, uses, or adaptations of the invention, including such departures from the present disclosure as come within known or customary practice in the art to which the invention pertains, and as fall within the scope of the appended claims.

What is claimed is:

1. A method of inducing regulatory T-cells to suppress immune response in a subject comprising administrating to the subject a therapeutically effective amount of a T-cell epitope composition, wherein the T-cell epitope composition comprises one or more isolated T-cell epitope polypeptides, wherein at least one isolated T-cell epitope polypeptide consists of the amino acid sequence of SEQ ID NO: 7.

2. The method of claim 1, wherein the T-cell epitope composition further comprises at least one isolated T-cell epitope polypeptide consisting of an amino acid sequence selected from the group consisting of SEQ ID NOS: 1-6 and 8-124.

3. The method of claim 1, wherein the T-cell epitope composition further comprises an effective amount of one or more antigens and/or allergens.

4. The method of claim 1, wherein the immune suppressive effect is mediated by natural regulatory T cells.

5. The method of claim 1, wherein the immune suppressive effect is mediated by adaptive regulatory T-cells.

6. The method of claim 1, wherein the T-cell epitope composition suppresses an effector T-cell response.

7. The method of claim 6, wherein the T-cell epitope composition suppresses a cytokine secretion of effector T-cells.

8. The method of claim 1, wherein the T-cell epitope composition suppresses a helper T-cell response.

9. The method of claim 1, wherein the T-cell epitope composition suppresses a B-cell response.

\* \* \* \* \*